US007590493B2

(12) United States Patent
Mendrick et al.

(10) Patent No.: US 7,590,493 B2
(45) Date of Patent: *Sep. 15, 2009

(54) METHODS FOR DETERMINING HEPATOTOXINS

(75) Inventors: Donna Mendrick, Gaithersburg, MD (US); Mark Porter, Gaithersburg, MD (US); Kory Johnson, Gaithersburg, MD (US); Brandon Higgs, Gaithersburg, MD (US); Arthur Castle, Gaithersburg, MD (US); Michael Elashoff, Gaithersburg, MD (US)

(73) Assignee: Ocimum Biosolutions, Inc., Indianapolis, IN (US)

( * ) Notice: Subject to any disclaimer, the term of this patent is extended or adjusted under 35 U.S.C. 154(b) by 484 days.

This patent is subject to a terminal disclaimer.

(21) Appl. No.: 11/059,535

(22) Filed: Feb. 17, 2005

(65) Prior Publication Data

US 2007/0043515 A1    Feb. 22, 2007

Related U.S. Application Data

(60) Division of application No. 10/060,087, filed on Jan. 31, 2002, now abandoned, and a continuation-in-part of application No. 09/917,800, filed on Jul. 31, 2001, now abandoned.

(60) Provisional application No. 60/331,273, filed on Nov. 13, 2001, provisional application No. 60/303,459, filed on Jul. 9, 2001, provisional application No. 60/298,884, filed on Jun. 19, 2001, provisional application No. 60/297,457, filed on Jun. 13, 2001, provisional application No. 60/295,798, filed on Jun. 6, 2001, provisional application No. 60/292,336, filed on May 22, 2001, provisional application No. 60/290,645, filed on May 15, 2001, provisional application No. 60/290,029, filed on May 11, 2001, provisional application No. 60/244,880, filed on Nov. 2, 2000, provisional application No. 60/222,040, filed on Jul. 31, 2000.

(51) Int. Cl.
G06F 19/00 (2006.01)
(52) U.S. Cl. .............................. 702/19; 435/6; 700/30; 702/22; 707/104.1
(58) Field of Classification Search ..................... None
See application file for complete search history.

(56) References Cited

U.S. PATENT DOCUMENTS

| 5,811,231 | A | 9/1998 | Farr et al. |
| 5,858,659 | A | 1/1999 | Sapolsky et al. |
| 6,132,969 | A | 10/2000 | Stoughton et al. |
| 6,153,421 | A | 11/2000 | Yanagi et al. |
| 6,203,987 | B1 | 3/2001 | Friend et al. |
| 6,218,122 | B1 | 4/2001 | Friend et al. |
| 6,228,589 | B1 | 5/2001 | Brenner et al. |
| 6,365,352 | B1 | 4/2002 | Yerramilli et al. |
| 6,372,431 | B1 | 4/2002 | Cunningham et al. |
| 6,403,778 | B1 | 6/2002 | Cunningham et al. |
| 6,421,612 | B1 | 7/2002 | Agrafiotis et al. |
| 6,461,807 | B1 | 10/2002 | Friend et al. |
| 2001/0039006 | A1 | 11/2001 | Snodgrass |
| 2001/0049139 | A1 | 12/2001 | Lagasse et al. |
| 2002/0119462 | A1 | 8/2002 | Mendrick et al. |
| 2002/0142284 | A1 | 10/2002 | Raha et al. |
| 2003/0028327 | A1 | 2/2003 | Brunner et al. |
| 2003/0124552 | A1 | 7/2003 | Lindemann et al. |
| 2003/0154032 | A1 | 8/2003 | Pittman et al. |

FOREIGN PATENT DOCUMENTS

| WO | WO 93/01205 | 1/1993 |
| WO | WO 94/17208 | 4/1994 |
| WO | WO 97/13877 | 4/1997 |
| WO | WO 99/27090 | 6/1999 |
| WO | WO 99/43345 | 9/1999 |
| WO | WO 99/58670 | 11/1999 |
| WO | WO 00/12760 | 9/2000 |
| WO | WO 01/25473 | 4/2001 |
| WO | WO 01/32928 | 5/2001 |

OTHER PUBLICATIONS

"Nephrotoxic" definition, Merriam-Webster online dictionary, 2005, on the world wide web at http://www.m-w.com/cgi-bin/dictionary?book=Dictionary&va=nephrotoxic, 2 pages.
Aardema and MacGregor, Mutation Res., 499:13-25, (2002).
Adamson & Harman et al., Biochem. Pharmacol., 45: 2289-2294 (1993).
Affymetrix Rat Toxicology U34 Datasheet, released Aug. 1999.
Afshari et al., Cancer Res., 59: 4759-4760 (1999).
Agha et al., Lipid Peroxidation and Lysosomal Integrity ; 31., 279-285 (1995).
Ahotupa et al., Carcinogenesis., 15: 863-868 (1994).
Ala-Kokko, et al., Biochem J., 244:75-79, (1987).
Al-Bayati & Stohs, Arch. Environ. Contam. Toxicol., 20: 361-365 (1991).
Allan et al., J. Biol. Chem., 276:27272-27280 (2001).
Amelsen, Jean Claude., Setting death in motion, vol., (1998).
Andersen & Barton, Environ. Health Perspect., 106: 349-355 (1998).
Anderson et al., Toxicol. Appl. Pharmacol., 137: 75-89 (1996).
Anderson, Steven P., Hepatic Expression of Acute-Phase Protein, 26: 226-238 (1999).

(Continued)

Primary Examiner—Carolyn L. Smith
(74) Attorney, Agent, or Firm—Cooley Godward Kronish LLP

(57) ABSTRACT

The present invention is based on the elucidation of the global changes in gene expression and the identification of toxicity markers in tissues or cells exposed to a known toxin. The genes may be used as toxicity markers in drug screening and toxicity assays. The invention includes a database of genes characterized by toxin-induced differential expression that is designed for use with microarrays and other solid-phase probes.

10 Claims, No Drawings

OTHER PUBLICATIONS

Andersson et al; Anthraquinone-induced cell injury; 135: 11-20 (1999).
Anton et al., Cell Biochem. Biophys., 32: 27-36 (2000) Abstract only.
Arano et al., Arzneim-Forsch./Drug, 46 : 398-400 (1996).
Atchison et al., Digestive Dis. Sci., 45: 614-620 (2000).
Bajgar et al., Neurochem. Int., 24: 555-558 (1994).
Baker et al., Chem. Res. Toxicol., 14(9): 1218-1231 (2001).
Bandara, et al., Toxicol. Sci., 73:195-206, (2003).
Barner & Gray, Ann. Pharmacother., 32: 70-77 (1998).
Bartosiewicz et al., J. Pharmacol. Exp. Ther., 297: 895-905 (2001).
Beck et al, Arch. Toxicol., 64: 210-217 (1990).
Becker et al., Alzheimer Dis. Assoc. Disord., 10: 124-131 (1996).
Bedard et al., Antimicrob Agents Chemother., 43: 557-567 (1999).
Bedossa et al., Hepatology, 19: 1262-1271 (1994).
Beierschmitt, William P., Induction of Hepatic Microsomal Drug-Metabolizing;, 15-21, 2001.
Belury et al., Toxicol. Appl. Pharmacol., 151: 254-261 (1998).
Berbner et al., "induction of cytochrome P450 1A and NDA damage in isolated rainbow trout (Onchorhynchus mykiss) hepatocytes by 2, 3, 7, 8-tetrachlorodibenzo p-dioxin," Biomarkers 4: 214-228 (1999).
Bergeron et al., Xenobiotica, 28: 303-312 (1998).
Berndt et al., Proc. Natl. Acad. Sci. U.S.A.., 95: 12556-12561 (1998).
Birge et al., Toxicol. Appl. Pharmacol., 105: 472-482 (1990).
Bissig et al., "Functional expression cloning of the canalicular sulfate transport system of rat hepatocytes," J Biol Chem 269(4):3017-3021, 1994.
Boelsterli et al., Cell Biol. Toxicol., 3: 231-250 (1987).
Boess, et al., Toxicological Sciences, 73:386-402, (2003).
Bogdan, "Human carbon catabolite repressor protein (CCR4)-associative factor 1: cloning, expression and characterization of its interaction with the B-cell translocation protein BTG1," Biochem. J. 336:471-481 (1998).
Boon, et al., Proc. Natl. Acad. Sci. USA, 99(17):11287-11292, (2002).
Boorman et al., "Toxicogenomics, Drug Discovery, and the Pathologist," Toxicologic Pathology 30(1):15-27 (2002).
Bort et al., J. Pharmacol. Exp. Ther., 288: 65-72 (1999).
Bosio and Borlak, Innovations in Pharmaceutical Technology, 65-75, 2001.
Bouchard et al., Liver, 13: 193-202 (1993).
Bramow, Stephan, et al., Pharmacol. & Toxicol., 89:133-139, (2001).
Browne, et al., Targets, 1(2):59-65, (2002).
Bruck et al., Dig. Dis. Sci., 44: 1228-1235 (1999).
Bulera, S.J., et al., Hepatology, 33:1239-1258, (2001).
Burchiel et al., Toxicol. Sci., 59: 193-195 (2001).
Burczynski & Penning, Cancer Res., 60: 908-915 (2000) Abstract only.
Burczynski (Editor), "An Introduction to Toxicogenomics," Wyeth Research, Andover, MA, CRC Press pp. 226-259, (Pub. 2003).
Burczynski et al., Toxicol. Sci., 58: 399-415 (2000).
Burris, Hicken and Farr, Genetic Engineering News, May 1, 1999, pp. 42-43, (1999).
Bursch et al., Arch. Toxicol., 69: 253-258 (1995).
Buttar et al., Toxicology., 6: 9-20 (1976).
Butterworth et al., Cancer Res., 49: 1075-1084 (1989).
Cadet, et al., Synapset, 44:211-226 (2002).
Cai et al., J. Med. Chem., 41: 1970-1979 (1998).
Calabrese et al., J. Amer. College Toxicol., 15: 62-69 (1996).
Castell et al., Cell Biol. Toxicol., 13: 331-338 (1997).
Castle, A., et al., "Apex Necrosis," Soc. Of Tox. Mtg. (2004).
Castle, A., et al., "Effects of Multiple Cardiac Apex Necrosis Agents on Genome Wide Expression," Soc. Of Tox. Mtg. (2003) Abstract only.
Castle, A.L., et al., "Liver Toxicity Prediction and Classification Using Microarray Data: . . . ," Soc. Of Tox. Mtg., (2002).
Castle, Carver & Mendrick, Drug Disc. Today, 7(13):728-736, (2002).
Chan et al., Proc. Natl. Acad. Sci. U.S.A.., 98: 4611-4616 (2001).
Chanda et al., Hepatology, 21: 477-486 (1995).
Chen et al., J. Biol. Chem.., 275: 22619-22622 (2000).
Chen et al., J. Environ. Pathol. Toxicol. Oncol., 14: 83-99 (1995) Abstract only.
Chen, et al., Mol. Carcinog. 30:79-87, (2001).
Chisholm et al., Am. J. Physiol., 276: G1165-G1173 (1999).
Chou et al., Proc. Natl. Acad. Sci. U.S.A.., 98: 8113-8118 (2001).
Christian et al., Toxicol. Appl. Pharmacol., 82: 239-255 (1986).
Clive et al., Fundam. Appl. Toxicol., 3: 587-602 (1983).
Coles et al., Arch. Biochem. Biophys., 264: 253-260 (1988).
Conforti et al., Agents Actions, 40: 176-180 (1993).
Coni et al., Hepatology, 17: 1109-1116 (1993).
Copenhagen et al., Journal of Hepatology; 30: 1 pg. (1999).
Corell et al., Acta Pharmacol. Toxicol. (Copenh), 45: 232-239 (1979).
Corton & Stauber, Toxicol. Sci., 58: 217-219 (2000).
Corton et al., Biochimie., 79: 151-162 (1997).
Corton et al., Cancer Lett., 134: 61-71 (1998).
Corton et al., Cancer Lett., 137: 9-15 (1999).
Corton et al., Mol. Pharmacol., 54: 463-473 (1998).
Cronin, M.T.D., IL Farmaco, 56:149-151, (2001).
Crosby et al., Toxicol. Appl. Pharmacol., 169: 205-221 (2000).
Cunningham et al., Ann. N.Y. Acad. Sci., 919: 52-67 (2000).
Cunningham, M.J., J. of Pharmacol. And Toxicol. Methods, 44:291-300, (2000).
Cutler, P., et al., Electrophoresis, 20:3647-3658, (1999).
D'Mello et al., Exp. Toxicol. Pathol., 51: 549-553 (1999).
Daniels, K., "Toxicogenomics: Database Construction, Predictive Modeling & Biomarker Discovery," U.S. Army—7th Annual Health Protection Conf. (2004) Abstract only.
Daniels, K., "Toxicogenomics: The Application of Gene Expression in Transforming Toxicology Screening," U.S. Army Center for Health Promotion & Preventive Medicine Seminar, (2004).
Database Geneseq [online], "Sindbis virus genomic cDNA PCR primer SEQ ID No. 3," Database Accession No. AAZ92894, retrieved from EBI Accession No. GSN:AAZ92894 (2000).
Database Geneseq 'Online!, "Reverse transcription primer used in cDNA analysis technique," Database Accession No. AAQ75569, retrieved from EBI Accession No. GSN:AAQ75569 (1995).
Davila et al., Toxicology., 57: 267-286 (1989).
Davis et al., Cancer Res., 60: 2887-2891 (2000).
De Fabiani et al., J. Biol. Chem., 276: 30708-30716 (2001).
Del Giudice et al., IL Farmaco., 51: 693-698 (1996).
Delaney & Timbrell, Xenobiotica, 25: 1399-1410 (1995).
Demeule, Brossard and Beliveau, Am. J. Physiol. Renal Physiol. 277:F832-F840, (1999).
Diel et al., J. Steroid Biochem. Mol. Biol., 73: 1-10 (2000).
Diez-Fernandez, et al., Biochem. Pharmacol., 51:1159-1163, (1996).
Dodds & Rivory, Mol. Pharmacol., 56: 1346-1353 (1999).
Dos Santos et al., J. Am. Soc. Nephrol., 8: 361-367 (1997).
Duivenvoorden et al., Biochem. Biophys. Res. Commun., 215(2):598-605 (1995).
Dutar et al., Brain Res., 527: 32-40 (1990).
Eadie et al., Med. Toxicol. Adverse Drug Exp., 3: 85-106 (1988).
Eikmans, et al., Kidney Int'l, 62:1125-1135, (2002).
Eldridge et al., Carcinogenesis, 11: 2245-2251 (1990).
Ellis & Isaacs, Cancer Res., 45: 6041-6050 (1985).
Emmison et al., Biochim. Biophys. Acta, 1083: 147-152 (1991).
Enomoto et al., Toxicol. Sci., 59: 169-177 (2001).
Evans & Relling, Science, 286:487-491, (1991).
Falzon et al., Br. J. Exp. Pathol., 66: 527-534 (1985).
Fan & Rozman, Toxicol. Lett., 75: 209-216 (1995).
Fan et al., J. Biol. Chem., 271: 24698-24710 (1996).
Farag & Hassib, Clin. Sci. (Lond), 84: 387-390 (1993).
Farghali et al., Methods Find. Exp. Clin. Pharmacol., 6: 449-454 (1984).
Farr & Dunn, Toxicol. Sci., 50: 1-9 (1999).
Farr et al., "Concise review: gene expression applied to toxicology," Toxicol Sci 50(1):1-9, 1999.
Fernandez-Tome & Sterin-Speziale, Pharmacology, 48: 341-348 (1994).
Ficazzola et al., Carcinogenesis, 22: 1271-1279 (2001).
Fielden & Zacharewski, Toxicol. Sci., 60: 6-10 (2001).
Fitten et al., J. Gerontol., 42: 681-685 (1987).
Forestier et al., Biochem. Biophys. Res. Commun., 225: 377-383 (1996).

Fracasso et al., Agents Actions, 22: 3-4 (1987).
Fracasso et al., Agents Actions, 31: 313-316 (1990).
Frazier JM, Predictive Toxicodynamics: Empirical/mechanistic approaches. Toxicology in Vitro, 1997. pp. 465-472, vol. 11.
Froesch et al., J. Biol. Chem., 274: 6469-6475 (1999).
Frueh et al., Mol. Pharmacol., 51: 363-399 (1997).
Fulgencio et al., Biochem. Pharmacol., 62: 439-446 (2001).
Furr, Ann. N.Y. Acad. Sci., 761: 79-96 (1995).
Furr, Eur. Urol., 29: 83-95 (1996).
Gallagher, et al., Toxicol. And Appl. Pharmacol. 134:81-91, (1995).
Ganem & Jefcoate, Toxicol. Appl. Pharmacol., 150: 68-75 (1998).
Garcia-Allan et al., J. Biochem. Mol. Toxicol., 14: 65-72 (2000).
Geiger et al., Agents Actions, 38: Spec No. C69-72 (1993) Abstract only.
GenBank Accession No. AA799479 (Apr. 30, 1998).
GenBank Accession No. AA891812 (Jan. 25, 1999).
GenBank Accession No. AI177366 (Jan. 20, 1999).
GenBank Accession No. L23413, Bissig et al., "Rattus norvegicus sulfate anion transporter (sat-1) mRNA," Apr. 12, 1994.
GenBank Accession No. L26268, Raburn et al., "Rattus norvegicus anti-proliferative factor (BTGI) mRNA," Jan. 26, 1996.
GenBank Accession No. M25823 (Apr. 27, 1993).
Genes on Clontech Atlas Human Stress/Toxicology Array from e-mail/ website dated Oct. 29, 1998.
Gerhold et al., Physiol. Genomics, 5: 161-170 (2001).
Ghatineh & Timbrell, Biochem. Soc. Trans., 18: 1217-1218 (1990).
Ghatineh et al., Arch. Toxicol., 66: 660-668 (1992).
Gobe, G., et al., J. Am. Soc. Nephrol., 11:454-467, (2000).
Goll et al., Toxicol. Appl. Pharmacol., 160: 21-32 (1999).
Golub et al., "Molecular Classification of Cancer: Class Discovery and Class Prediction by gene Expression monitoring," Science 285:531-537 (1999).
Gombar et al. Assesment of Developmental Toxicity Potential of Chemicals by Quantitative Structure-Toxicity Relationship Models, Chemosphere, 1995, vol. 31, No. 1, pp. 2499-2510.
Gomez-Lechon, et al., Toxicol. Sciences, 65:299-308, (2002).
Gooderham et al., "Molecular and genetic toxicology of 2-amino-1-methyl-6-phenylimidazo[4,5-*b*]pyridine (Ph1P)," Mutation Research 506-507:91-99 (2001).
Gram & Bentsen, Acta Neurol. Scand. Suppl., 97: 81-90 (1983).
Greaves et al., Cancer Res., 53: 3919-3924 (1993).
Green et al., Toxicol. Appl. Pharmacol., 76: 139-149 (1984).
Grigg, Environmental Health Inst. to use gene chips to evaluate chemicals for potential harm to humans NEIHS, Feb. 29, 2000, entire document.
Guardavaccaro et al., Mol. Cell. Biol., 20: 1797-1815 (2000).
Guarner et al., Liver, 5: 35-39 (1985) Abstract only.
Hamada et al., Hepatology, 21: 1455-1464 (1995).
Hamada et al., J. Hepatol., 30: 807-818 (1999).
Hamadah, et al., Toxicol. Sciences, 67:232-240, (2002).
Hamaya, Y., et al., Anesth. Analg., 90:1177-1183, (2000).
Hargus et al., Chem. Res. Toxicol., 7: 575-582 (1994).
Hargus et al., Chem. Res. Toxicol., 8: 993-996 (1995).
Harries et al., Toxicol. In Vitro, 15: 399-405 (2001).
Harris et al., "Comparison of basal gene expression profiles and effects of hepatocarcinogens on gene expression in cultured primary human hepatocytes and HepG2 cells," Mutation Research 539:79-99 (2004).
Hartmann, et al., J. of Pharma. And Experim. Therap., 303:273-281, (2002).
Hartung & Wendel, Biochem. Pharmacol., 42: 1129-1135 (1991).
Hasegawa et al., Gan to Kagaku Ryoho 30:325-333 abstract (2003).
Hassett et al., Biochem. Pharmacol., 55: 1059-1069 (1998) Abstract only.
Hayashi et al., Biochim. Biophys. Acta., 879: 140-148 (1986) Abstract only.
He et al., J. Biol. Chem., 276: 20858-20865 (2001).
He, et al., J. Clin. Invest., 108: 1321-1330 (2001).
Hellriegel et al., Biochem. Pharmacol., 52: 1561-1568 (1996).
Henger and Kretzler, et al., Kidney Int'l, 65:904-917, (2004).
Hessel et al., Braz J. Med. Biol. Res., 29: 793-796 (1996).
Hewitt, et al., J. Am. Soc. Nephrol. 15:1677-1689, (2004) Abstract only.

Higgs, B., et al., "Effects of Rat Gender and Strain on Elucidating Liver Toxicity," Soc. OfTox. Mtg., (2003) Abstract only.
Hildebrand et al., Arch. Toxicol., 73: 233-245 (1999) Abstract only.
Hillstrom et al., Proc. Soc. Exp. Biol. Med., 200: 122-126, 1992.
Hissink et al., Chem. Res. Toxicol., 9: 1249-1256 (1996).
Hoebe et al., Vet. Q., 22: 21-25 (2000) Abstract only.
Hogstrand et al., "Application of genomics and proteomics for study of the integrated response to zinc exposure in a non-model fish species, the rainbow trout," Comparative Biochemistry and Physiology Part B 133:523-535 (2002).
Hogue, Chemical and Engineering News, 79: 33-34 (2001).
Hoshi et al., Jpn. J. Pharmacol., 50: 289-293 (1989).
Huang, et al., Toxicol. Sciences, 63:196-207, (2001).
Hunter et al., Br. J. Pharmacol., 98: 79-86 (1989).
Hwang, et al., Biochem. And Biophys. Res. Commun., 146(I):87-93, (1987).
Iida, et al., Carcinogenesis, 24(4):757-770, (2003).
Inohara et al., EMBO J., 17: 2526-2533 (1998).
International Search Report in Applicant's corresponding PCT application, WO 02/095000 A3, published Nov. 28, 2002.
International Search Report in Applicants' PCT Application No. PCT/US01/23872, Mar. 21, 2003.
International Search Report in Applicants' PCT Application No. PCT/US05/34780, Mar. 30, 2006.
International Search Report in Applicants' PCT Application No. PCT/US04/39593, Mar. 8, 2006.
International Search Report in Applicants' PCT Application No. PCT/US05/11532, mailed Sep. 13, 2006.
Iredale et al., J. Clin. Invest., 102: 538-549 (1998).
Irizarry et al. (2003), "Summaries of Affymetrix GeneChip probe level data," Nucl Acids Res 31(4):e15, 8 pp.
Iswaran et al., J. Toxicol. Sci., 22 75-88 (1997).
Itoh et al., Behav. Brain Res., 83: 165-167 (1997).
Itoh et al., Eur. J. Pharmacol., 322: 11-19 (1997).
Izumi et al., J. Biol. Chem., 272: 7381-7389 (1997).
Jaeschke, et al., Toxicol. Sciences, 65: 166-176 (2002).
Jakubczak et al., An Oncolytic Adenovirus Selective for Retinoblastoma Tumor Suppressor Protein Pathway-Defective Tumors, Cancer Research, Apr. 1, 2003, vol. 63, pp. 1490-1499.
Jansen, Muller, and Sturm, Hepatology, 34(6):1067-1074 (2001).
Jean et al., Toxicol. Lett., 95: 155-163 (1998).
Jenner & Timbrell, Arch. Toxicol., 68: 349-357 (1994).
Jeon et al., Toxicol. Appl. Pharmacol., 144: 27-35 (1997).
Johnson and McMillian, 23rd Annual Mtg. Of the Amer. College of Toxicology, p. 532 (2002).
Johnson and Wolfgang, Current Topics in Med. Chem., 1(4):233-245, (2001).
Johnson, K., et al., "Predictive Modeling of Hepatotoxicants Using Microarrays and a Linear Discrinimant Modeling Approach," ISMB Conf., Aug. 2002, (2002).
Johnston & Kroening, Pharmacol. Toxicol., 83: 231-239 (1998).
Jover et al., Toxic in Vitro., 6: 47-52 (1992).
Kanaji et al., J. Cell Biol., 151: 277-288 (2000).
Kannan et al., Oncogene., 20: 2225-2234 (2001).
Karam & Ghanayem, Carcinogenesis, 18: 2077-2083 (1997).
Kasper & Mueller, Carcinogenesis, 17: 2271-2274 (1996).
Kawamoto, et al., Gene, 174:151-158 (1996).
Kesterson et al., Hepatology, 4: 1143-1152 (1984).
Kikuchi et al., Gene Expressions and Activities of Protein Phosphatases 1 alpha, 2A and 2C in Hepatocarcinogenesis and Regeneration After Partial Hepatectomy, Cancer Detection and Prevention, 1997, vol. 21 (1), pp. 36-43.
Kim & Ziegler, Drug Metab. Dispos., 28: 1003-1006 (2000).
Kim et al., Drug Metab. Dispos., 26: 66-72 (1998).
Kim et al., Toxicol. Appl. Pharmacol., 102: 34-39 (1990).
Kim et al., Toxicology and Applied Pharmacology 176:118-126 (2001).
Kinbara et al., Scand. J. Gastroenterol., 32: 947-952 (1997).
Kingsley et al., Epilepsia, 21: 699-704 (1980).
Kingsley et al., J. Clin. Pharmacol., 23: 178-185 (1983).
Knapp et al., Am. J. Vet. Res., 56: 801-805 (1995).
Kocarek et al., Mol. Pharmacol., 54: 474-84 (1998).
Koga et al., Fukuoka Igaku Zasshi, 82: 197-206 (1991).

Kondo et al., Cancer Res., 50: 6222-6228 (1990).
Kongo et al., Toxicol. Lett., 105: 103-110 (1999).
Konstandi et al., "Stress-mediated modulation of B(alpha)P-induced hepatic CYP1A1: role of catecholamines," Chemico-Biological Interactions 147:abstract, (2004).
Koopen et al., Hepatology 27: 537-545 (1998).
Koopen et al., J. Lipid. Res., 40: 100-108 (1999).
Kossor et al., Biochem. Pharmacol., 46: 2061-2066 (1993).
Kossor et al., Fundam. Appl. Toxicol., 26: 51-62 (1995).
Kossor et al., Toxicol. Appl. Pharmacol., 119: 108-114 (1993).
Kretz-Rommel & Boelsterli, Toxicol. Appl. Pharmacol., 120: 155-161 (1993).
Kurota and Yamaguchi, Molec. And Cell. Biochem., 151:55-60, (1995).
Kwak et al., Mol. Med., 7: 135-145 (2001).
Kwon, et al., Am. J. Physiol. Renal Physiol. 279:F552-F564, (2000).
Lake et al., Toxicology., 131: 9-20 (1998).
Lake et al., Hepatic Effects of Phthalate Esters and Related., 67: pp. 283-290, (1986).
Lake, Annu. Rev. Pharmacol. Toxicol., 35: 483-507 (1995).
Lang et al., Alcohol Clin. Exp. Res., 22: 823-829 (1998).
Larsen & Jefcoate, Arch. Biochem. Biophys., 321: 467-476 (1995).
Lashkari et al., PNAS 94:13057-13062, (1997).
Laskin et al., Hepatology, 21: 1045-1050 (1995).
Lauredo et al., J. Appl. Physiol., 85: 2298-2304 (1998).
Lazartigues et al., Eur. J. Pharmacol., 361: 61-71 (1998).
LeBlank, G., et al., Cancer Research, 52:540-547, (1992).
Lecureur, V., et al., Toxicology, 153:203-219, (2000).
Lee et al., J. Pharm. Pharmacol., 52: 341-355 (2000).
Lees et al., Lipids, 30: 221-226 (1995).
Leifeld, et al., Amer. J. of Pathol., 154(6):1711-1720, (1999).
Lewis et al., Hepatology, 2: 870-873 (1982).
Li et al., Zhonghua Gan Zang Bing Za Zhi, 9: 103-104 (2001).
Liang et al., Zhonghua Gan Zang Bing Za Zhi, 7: 72-73 (1999).
Liu et al., Infect. Immun., 66: 5089-5098 (1998).
Liu et al., Mol. Cell. Biol., 20: 6105-6113 (2000).
Liu et al., Proc. Natl. Acad. Sci. U.S.A.., 98: 6192-6197 (2001).
Liu et al., Shock, 14: 361-365 (2000).
Lock et al., Toxicol. Lett., 10: 427-435 (1982).
Lorenzini et al., Carcinogenesis, 17: 1323-1329 (1996).
Lovett, Science, 289: 536-537 (2000).
Lubman, et al., "What do the FDA and Pharma Companies Think of Toxicogenomics" (2002).
Lugovskoy et al., Cell, 99: 747-755 (1999).
Luhe, A., et al., Toxicol. Sciences, 73:315-328, (2003).
Lullmann & Lullmann-Rauch, Toxicol. Appl. Pharmacol., 61: 138-146 (1981).
MacGregor, et al., Toxicol. Sciences, 59:17-36, (2001).
Mahnke et al., Arch. Biochem. Biophys., 337: 62-68 (1997).
Mann, Toxicol. Pathol., 25: 72-79 (1997).
Manoukian & Carson, Drug Saf., 15: 64-71 (1996).
Marketing Materials, "Symposium on Toxicogenomics Launches New National Academics Program," Emerging Issues, 2:1-7, (2003).
Markovich et al., "Heavy metals mercury, cadmium, and chromium inhibit the activity if the mammalian liver and kidney sulfate transporter sat-1," Toxicol. Appl. Pharmacol. 154:181-187 (1999).
Martelli et al., J. Pharmacol. Exp. Ther., 273: 113-120 (1995).
Masubuchi et al., J. Pharmacol. Exp. Ther., 287: 208-213 (1998).
Masubuchi et al., J. Pharmacol. Exp. Ther., 292: 982-987 (2000).
Mattes, W., & Orr, M., "Concordance of Toxicogenomic Predictions and Mechanistic Analysis for compounds Tested in Both Rat Liver and Primary Rat Hepatocytes," LabFusion 2004 Presentation, (2004).
Mattes, W., et al., "Cross-Species Analysis of Phenobarbital-Induced Gene Expression Changes in Dog and Rat," Soc. Of Toxicol. Mtg. 2003, (2003) Abstract only.
Mattes, W., et al., "Cross-Species Analysis of Phenobarbital-Induced Gene Expression Changes in Dog and Rat," Soc. Of Toxicol. Mtg. 2004, (2004).
Mayeux & Sano, N. Engl. J. Med., 341: 1670-1679 (1999).
Mayol et al., Carcinogenesis., 13: 2381-2388 (1992).
Maziasz et al., Toxicol. Appl. Pharmacol., 110: 365-373 (1991).
McKillop et al., Xenobiotica., 28: 465-478 (1998).

MDS Pharma Services Marketing Materials,"Pharmotif Solutions: Smart Decisions in Discovery and New Applications for Existing Drugs," 1-6, (2003).
Mendrick, D.L., ToxExpress, FDA-DIA Pharmacogenomics Workshop May 2002, (2002).
Mendrick, D., "Discovery of Relevant biomarkers for Nonclinical and Clinical Applications," American College of Toxicology Mtg. Nov. 8, 2004, (2004).
Mendrick, D., "Rold of Gene Expression Studies in Nonclinical Toxicogenomics," PhRMA/FDA Genomics (Microarray) Biostatistics Workshop, (2004).
Mendrick, D.L., et al., "Using Gene Markers Identified From a Large Database Built with Primary Rat Hepatocytes for Prediction of Human Hepatotoxicity," Society of Toxicology Mtg, (2002).
Mendrick, D.L., et al., Cross compound predictions and pathway analysis using gene expression profiles from acetaminophen or carbon tetrachloride, two structurally distinct liver toxicants, Society of Toxicology Mtg., (2002).
Mendrick 1, Cysteine Protease Inhibitor (2004).
Mendrick, Extracellular Matrix Protein Dermatopontin., (2004).
Mendrick., Chemokine (2004).
Mendrick., Lipid Transporter (2004).
Mendrick., "General Biological Findings for 80 Genes" (2004).
Mendrick, "Genomic Search for Candidate Biomarkers" (2004).
Menegazzi et al., Hepatology, 25: 585-592 (1997).
Meneses-Lorente, et al., Chem. Res. Toxicol., 16(9):A-H, 1070-1077), (2003).
Metz & Ritter, J. Biol. Chem., 237: 5607-5614 (1998).
Metz et al., Mol. Pharmacol., 58: 319-327 (2000).
Meyer, K., et al., Carcinogenesis, 24(5):975-984, (2003).
Milam and Byard, Toxicol. Appl. Pharmacol., 79: 342-347 (1985).
Minamide et al., J. Pharm. Sci., 87: 640-646 (1998).
Mino et al., J. Histochem. Cytochem., 46: 1151-1160 (1998).
Miracle et al., The Path from Molecular Indicators of Exposure., 12 : 457-462 (2003).
Mitchell & Acosta, J. Toxicol. Environ. Health, 7: 83-92 (1981).
Mitchell et al., Ann. Intern. Med., 84: 181-192 (1976).
Monteith et al., Drug Chem. Toxicol., 19: 71-84 (1996).
Moore et al., Fundam. Appl. Toxicol., 3: 560-568 (1983).
Moran et al., Immunopharmacology, 12: 245-250 (1986).
Morgan, K.T., et al., Toxicol. Pathol., 30(4):435-451, (2002).
Morigasaki et al., Biochem. Biophys. Res. Commun., 273: 261-266 (2000).
Morooka et al., J. Biol. Chem.., 270: 30084-30092 (1995).
Motoki et al., Cancer Lett., 135: 145-150 (1999).
Nakamura, et al., Clinical Immun. And Immunopath., 66(1):33-42, (1993).
Newsholms, et al., Electrophoresis, 21:2122-2128, (2000).
Nguyen et al. (2002), "Tumor classification by partial least squares using microarray gene expression data," Bioinformatics 18(1):39-50.
Nicholls-Grzemski et al., Toxicol. Sci., 56: 220-228 (2000).
Nims et al., Carcinogenesis., 8: 67-71 (1987).
Nordberg & Svensson, Drug Saf., 19: 465-480 (1998).
Nuwaisyr et al., "Microarrays and toxicology: the advent of toxicogenomics," Molecular Carcinogenesis 24(3):153-159, 1999.
Nuwaysir, et al., Cancer Research, 56:3704-3710, (1996).
Oberhammer et al., Hepatology, 23: 329-337 (1996).
O'Brien, et al., Toxicol. And Appl. Pharma., 171:27-37, (2001).
Ohta et al., Biochem. J., 324: 777-782 (1997).
Olden & Guthrie, Mutation Research, 473:3-10, (2001).
Olson et al., Fundam. Appl. Toxicol., 22: 631-630 (1994).
Omiecinski et al., Mol. Pharmacol., 38: 462-470 (1990).
Omiecinski, et al., Toxicol. Sciences, 48: 151-156, (1999).
Omogbai et al., Drug Chem. Toxicol., 22: 629-242 (1999).
Ono et al., Biol. Pharm. Bull., 18: 1779-1783 (1995) Abstract only.
Ono et al., Chem. Pharm. Bull. (Tokyo), 43: 1492-1496 (1995).
Orr, M., et al., Concordance of Toxicogenomic Predictions and Mechanistic Analysis for Compounds Tested in Both Rat Liver and Primary Rat Hepatocytes, Soc. Of Toxicol. Mtg., (2004).
Orr, M., et al., "Cross-species Comparisons—Human and Rat," Soc. Of Toxicol. Mtg., (2004).

Orr, M.S., et al., "Microarray Analysis of NRF2 Pathway and Novel Co-Regulated Genes Induced by Acetaminophen," Soc. Of Toxicol. Mtg., (2002).
Orr, M.S., et al., "Predicting Toxicity in Two distinct Sections of the Kidney via Microarray Analysis," Soc. Of Toxicol. Mtg., (2002).
Orr, M, et al. "Challenges and Limitations of Gene Expression Profiling" 60: 6-10 (2001).
Orr, Michael, "Comparison of Liver Gene Dysregulation" 21: 253-262 (2002).
Orsler et al., Toxicol. Sci., 47: 203-210 (1999).
Outinen et al., Blood, 94: 959-967 (1999).
Owen et al., Biochem. J., 348 Pt 3: 607-614 (2000).
Panduro et al., Nephron, 65: 100-107 (1993).
Park & Pirmohamed, Toxicol. Lett., 120: 281-291 (2001).
Park et al., Pharmacol. Ther., 68: 385-424 (1995).
Passreiter et al., J. Cell Biol., 141: 373-383 (1998).
Peng et al., JBC 271(6): 3324-3327 (1996).
Pennie & Kimber, Toxicology in Vitro, 16:319-326, (2002).
Pennie, et al., Toxicol. Lett., 120: 353-358 (2001).
Pennie, et al., Toxicol. Sci. 54: 277-283 (2000).
Pennie, Toxicol. Lett., 112-113: 473-477 (2000).
Perrone et al., Toxicol. Appl. Pharmacol., 150: 277-286 (1998).
Petricoin III, et al., Nature Genetics Supp., 32:474-479, (2002).
Pfeffer et al., J Immunology 153(4):1789-1797 (1994).
Pischedda et al., Proc. Natl. Acad. Sci. U.S.A., 92: 3511-3515 (1995).
Plant, N., et al., Toxicol. And Applied Pharma., 183:127-134, (2002).
Pohl et al., Arthritis Rheum., 37: 1557 (1994).
Pollenz et al., Toxicol. Sci., 42: 117-128 (1998).
Porter, M. et al., "Determination of Biological Replicate Number for Rat and Human Microarray-Based Predictive and Mechanistic Assays," Soc. Of Toxicol. Mtg., (2003) Abstract only.
Porter, M., et al., "Effects of Hydration, Fasting, and Anesthesia on Baseline Gene Expression," Soc. Of Toxicol. Mtg., (2003) Abstract only.
Porter, M., et al., "Liver Effects at the Gene Expression Level of Food-Tasting, Water Deprivation, and Anesthetic Agent Administration in Untreated Rats," Soc. Of Toxicol. Mtg., (2003) Abstract only.
Porter, M.W., et al., "Comparison of Microarray Data Generated from the Same RNA at 19 Different Processing Sites," Soc. Of Toxicol. Mtg., (2002).
Porter, Mark, "Comparison of Microarray data Generated from the same RNA at 15 Different Processing Sites," Soc. Of Toxicol. Mtg. Oct. 2003, Abstract only.
Poyet & Labrie, Mol. Cell. Endocrinol., 42: 283-288 (1985).
Prevot et al. J. Biol. Chem., 276: 9640-9648 (2001).
Pumford et al., Drug Metab. Rev., 29: 39-57 (1997).
Raats, et al., Am. J. Pathol. 156:1749-1765, (2000).
Raburn et al., "Stage-specific expression of B Cell Translocation Gene 1 in rat testis," Endocrinology 136(12):5769-5777, 1995.
Raburn et al., Endocrinology 136(12):5769-5777, 1995. Abstract only.
Rajeski, David, "Exploring the Genomics Frontier," Risk Policy Report, pp. 1-5, (2002).
Ratanasavanh et al., Xenobiotica., 18: 765-771 (1988).
Ray & Jena, Arch. Toxicol., 73: 594-606 (2000).
Raychaudhuri et al., "Basic microarray analysis: grouping and feature reduction," Trends Biotechnol. 19:189-193 (2001).
Raymond et al., J. Toxicol. Environ. Health, 51: 463-476 (1997).
Reilly et al., Biochem. Biophys. Res. Commun., 282: 321-328 (2001).
Rejeski D., Exploring the Genomics Frontier, Aug. 20, 2002.
Reuter et al., Life Sci., 55: 1-8 (1994).
Rice et al., Carcinogenesis., 15: 395-402 (1994).
Rich et al., Nature, 407: 777-783 (2000).
Richert, L., et al., Toxicol. And Appl. Pharmacol., 191:130-146, (2003).
Riekkinen et al., Eur. J. Pharmacol., 322: 1-9 (1997).
Riekkinen et al., Eur. J. Pharmacol., 323: 11-19 (1997).
Riendeau et al., Br. J. Pharmacol., 121: 105-117 (1997).
Rininger et al., Biochem. Pharmacol., 52: 1749-1755 (1996).
Rininger et al., Drug Discov. Today, 5: 560-568 (2000).
Roberts et al., Toxicol. Appl. Pharmacol., 135: 192-199 (1995).
Rockett & Dix, Environ. Health Perspect., 107: 681-685 (1999).
Rodi et al., Toxicol. Pathol., 27: 107-110 (1999) Abstract only.
Rodrigues & Machinist, Toxicol. Appl. Pharmacol., 137: 193-201 (1996).
Ronchetti et al., "Robust Linear Model Selection by Cross-Validation," J. Am. Statistical Assoc. 92:1017-1023 (1997).
Ruepp et al., Toxicol. Sci., 65: 135-150 (2002).
Runge-Morris et al., Drug Metab. Dispos., 26: 795-801 (1998).
Rusyn, et al., Cancer Research, 64:1050-1057. (2004).
Sachidanandam et al., Nature, 409: 928-933 (2001).
Safe, Annu. Rev. Pharmacol. Toxicol., 38: 121-158 (1998).
Salter and Nilsson, Drug Disc. and Dev., 6(1):117-122 (2003).
Sanz, et al., British J. of Cancer, 75(4):487-492, (1997).
Scales & Timbrell, J. Toxicol. Environ. Health, 10:941-953 (1982).
Scali et al., Pharmacol. Res., 36: 463-469 (1997).
Scassa et al., Exp. Cell Res., 244: 460-469 (1998) Abstract only.
Schiaffonati & Tiberio, Liver, 17: 183-191 (1997) Abstract only.
Schiller et al., Toxicol. Appl. Pharmacol., 81: 356-361 (1985).
Schilter, B. et al. Activation of cytochrome P450 gene expression in rat brain by phenobarbital-like inducers. J Pharmacol Exp Ther 294(3):916-22 (Sep. 2000). Abstract only.
Schiodt et al., N. Engl. J. Med., 337: 1112-1117 (1997).
Scholer et al., Am. J. Med., 80: 34-38 (1986).
Schulte-Hermann et al., Cancer Res., 48: 2462-2468 (1988).
Schuppe-Koistinen, et al., Toxicology, 179:197-219, (2002).
Seefeld et al., Arch. Environ. Contam. Toxicol., 9: 317-327 (1980).
Sendo et al., Chem. Pharm. Bull. (Tokyo), 32: 795-796 (1984).
Servais & Galand, Cell Biol. Int Rep., 16: 319-328 (1992).
Shankar, K., et al., "PPAR-a Mediates Diabetes-Induced Resistance Against Acetaminophen Hepatotoxicity. . . .," Ann. Mtg. Of the Amer. College of Toxicol., p. 526 (2002) Abstract only.
Shannon et al., J. Pharmacol. Exp. Ther., 255: 1071-1077 (1990).
Shao, "Linear Model Selection by Cross-Validation," J. Am. Statistical Assoc. 88:486-494 (1993).
Shervington, Biochem: Mol. Biol. Int., 45: 303-313 (1998) Abstract only.
Shiota et al., Res. Commun. Mol. Pathol. Pharmacol., 94: 141-146 (1996).
Shultz et al., Toxicol. Appl. Pharmacol., 154: 84-96 (1999) Abstract only.
Sidhu & Omiecinski, J. Biochem. Mol. Toxicol., 13: 1-9 (1999) Abstract only.
Sidhu & Omiecinski, J. Biol. Chem., 273: 4769-4775 (1998) Abstract only.
Sidhu et al., Arch. Biochem. Biophys., 301: 103-113 (1993).
Simmons, P.T. & Portier, C.J., Carcinogenesis, 23(6):903-905, (2002).
Sinz & Woolf, Biochem. Pharmacol., 54: 425-427 (1997).
Skouteris and McMenamin, Biochem. J., 281: 729-733 (1992).
Skrtic et al., J. Hepatol., 27: 903-911 (1997).
Smith, Trends Pharmacol. Sci., 22: 281-285 (2001).
Snape et al., Neuropharmacology, 38: 181-193 (1999).
Soffers, A.E.M.F., et al., Toxic. In Vitro, 15:539-551 (2001).
Somani & Dube, Int. J. Clin. Pharmacol. Ther. Toxicol., 27: 367-387 (1989).
Somani, Biopharm. Drug Dispos., 10: 187-203 (1989).
Soni et al., Regul. Toxicol. Pharmacol., 29: 165-174 (1999).
Sprankle, C., et al., Cancer Letters, 101:97-106, (1996).
Stachlewitz et al., J. Pharmacol. Exp. Ther., 282: 1591-1599 (1997).
Steiner, et al., Environ. Health Perspect., 112(12):1236-1247, (2004).
Stohs et al., Biochem. Biophys. Res. Commun., 111:854-859 (1983).
Su, et al., Proc. Natl. Acad. Sci. USA, 99(17):11181-11186, (2002).
Seürmen & Eryèurek, Toxicology, 75: 63-69 (1992) Abstract only.
Suter, et al., "Toxicogenomics: Correlation of acetaminophen-induced hepatoxicity with gene expression using DNA microarrays," Soc. Of Toxicogenomics Mtg., (2000).
Sutter, et al., Mol. Cancer Therapeutics, 1:1283-1292, (2002).
Suzuki and Sudo, Japan J. Pharmacol., 49:43-51, (1989).
Tamura et al., Toxicology, 63: 199-213 (1996) Abstract only.
Tao, et al., Experimental Hermatology, 31:251-260 (2003).
Tarloff et al., Fundam. Appl. Toxicol., 30: 13-22 (1996).
Tenniswood et al., Mol. Cell. Endocrinol., 37: 153-158 (1984).
Thomas, R.S., et al., Molecular Pharmacol., 60(6):1189-1194, (2001).

Timbrell et al., J. Pharmacol. Exp. Ther., 213: 364-369 (1980).
Timbrell et al., J. Toxicol. Environ. Health, 10: 955-968 (1982).
Timbrell, Arch. Toxicol. Suppl., 2: 1-8 (1979).
Tournier et al., Lab. Invest., 59: 657-665 (1988).
Trauner et al., N. Engl. J. Med., 339: 1217-1227 (1998).
Tu, Y., et al., Proc. Nat'l Acad. Sci. USA, 99(22):14031-14036, (2002).
Tucker et al., Fundam. Appl. Toxicol., 3: 579-586 (1983).
Tucker, Am. J. Med., 73: 27-30 (1982).
Tygstrup et al., J. Hepatol., 25: 183-190 (1996).
Tygstrup et al., J. Hepatol., 27: 156-162 (1997).
Tygstrup, et al., Biochem. And Biophys. Res. Commun., 290(1):518-525, (2002).
Uhl et al., Mutat. Res., 468: 213-225 (2000) Abstract only.
van Gijssel et al., Carcinogenesis, 18: 1027-1033 (1997).
Vance et al., Epilepsia, 35: 1016-1022 (1994).
Verstrepen, et al., Kidney Int'l, 43:1267-1279, (1993).
Venturelli et al., Overexpression of DR-nm23, 92: 7435-7439 (1995).
Visen et al., J. Pharmacol. Toxicol. Methods, 40: 173-179 (1998).
Wan et al., Infect. Immun., 63:2435-2442 (1995).
Wang & Dickinson, Drug Metab. Dispos., 26: 98-104 (1998).
Waring & Ulrich, Annu. Rev. Pharmacol. Toxicol., 40: 335-352 (2000).
Waring et al., Toxicol. Appl. Pharmacol., 175: 28-42 (2001).
Waring et al., Toxicol. Lett., 120: 359-368 (2001).
Waring, et al., Environ. Health Perspect., 111:863-870, (2003).
Waterfield et al., Biochem. Pharmacol., 46: 589-595 (1993).
Weber et al., Fundam. Appl. Toxicol., 21: 523-534 (1993).
Weber et al., Toxicology, 66: 133-144 (1991).
Weisenberg-Boettcher et al., A Novelty Highly Potent, 11/12: 501-509 (1989).
Wessely, S., et al., Human & Experimental Toxicology, 18:740-764, (1999).
White et al., Biochem. Pharmacol., 45: 21-30 (1993).
White et al., Carcinogenesis, 13: 2197-2203 (1992).
Wilson, et al. PNAS 96:12833-12838 (1999).
Woodcroft & Novak, Drug Metab. Dispos., 26: 372-378 (1998) Abstract only.
Woodward & Timbrell, Toxicology., 30: 65-74 (1984).
Woolf et al., Drug Metab. Dispos., 21: 874-882 (1993).
Xiong et al., "Feature (Gene) Selection in Gene Expression-Based Tumor Classification," Mol. Genet. Metab. 73:239-247 (2001).
Xiong et al., Life Sci., 65: 421-430 (1999).
Xu, et al., World J. Gastreonterol, 10(2):250-254, (2004).
Yamada et al., Life Sci., 61: 171-179 (1997) Abstract only.
Yamaki et al., "Cellular mechanism of lithiumk-induced nephrogenic diabetes insipidus in rats," Am. J. Physiol. Renal Physiol. 261:F505-F511, (1991).
Yang et al., Am J Physiology 277(1):F10-F16 (1999).
Yata et al., J. Hepatol., 30: 419-424 (1999).
Zarif et al., The Effect of A Selective 5-Lipoxygenase, vol. 20, 217-227 (1996).
Zeeberg, et al., Genome biology, 4:R28:1-8, (2003).
Zhao Y. et al, Activation of Pro-death Bcl-2 Family, vol. 276: 27432-27440 (2001).
Zhou G., et al, Role of AMP-activated protein kinase in mechanism, 108: 1167-1174, 2001.

METHODS FOR DETERMINING HEPATOTOXINS

RELATED APPLICATIONS

This is application is a divisional application of U.S. application Ser. No. 10/060,087 filed Jan. 31, 2002, now abandoned, which claims the benefit of U.S. Provisional Application No. 60/331,273 filed Nov. 13, 2001 and is a continuation-in-part of U.S. application Ser. No. 09/917,800, filed Jul. 31, 2001, now abandoned, which claims the benefit of U.S. Provisional Applications 60/303,459, filed Jul. 9, 2001; 60/298,884, filed Jun. 19, 2001; 60/297,457, filed Jun. 13, 2001; 60/295,798, filed Jun. 6, 2001; 60/292,336, filed May 22, 2001; 60/290,645, filed May 15, 2001; 60/290,029, filed May 11, 2001; 60/244,880, filed Nov. 2, 2000; and 60/222,040, filed Jul. 31, 2000, all of which are herein incorporated by reference in their entirety.

SEQUENCE LISTING SUBMISSION ON COMPACT DISC

The Sequence Listing submitted concurrently herewith on compact disc under 37 C.F.R. §§1.821(c) and 1.821(e) is herein incorporated by reference in its entirety. Three copies of the Sequence Listing, one on each of three compact discs are provided. Copy 1 and Copy 2 are identical. Copies 1 and 2 are also identical to the CRF. Each electronic copy of the Sequence Listing was created on Jan. 30, 2002 with a file size of 3083 KB. The file names are as follows: Copy 1—GL5038U1.txt; Copy 2—GL5038U1.txt; CRF—GL5038U1.txt.

BACKGROUND OF THE INVENTION

The need for methods of assessing the toxic impact of a compound, pharmaceutical agent or environmental pollutant on a cell or living organism has led to the development of procedures which utilize living organisms as biological monitors. The simplest and most convenient of these systems utilize unicellular microorganisms such as yeast and bacteria, since they are most easily maintained and manipulated. Unicellular screening systems also often use easily detectable changes in phenotype to monitor the effect of test compounds on the cell. Unicellular organisms, however, are inadequate models for estimating the potential effects of many compounds on complex multicellular animals, as they do not have the ability to carry out biotransformations to the extent or at levels found in higher organisms.

The biotransformation of chemical compounds by multicellular organisms is a significant factor in determining the overall toxicity of agents to which they are exposed. Accordingly, multicellular screening systems may be preferred or required to detect the toxic effects of compounds. The use of multicellular organisms as toxicology screening tools has been significantly hampered, however, by the lack of convenient screening mechanisms or endpoints, such as those available in yeast or bacterial systems. In addition, previous attempts to produce toxicology prediction systems have failed to provide the necessary modeling data and statistical information to accurately predict toxic responses (e.g., WO 00/12760, WO 00/47761, WO 00/63435, WO 01/32928, WO 01/38579, and the Affymetrix® Rat Tox Chip.

SUMMARY OF THE INVENTION

The present invention is based on the elucidation of the global changes in gene expression in liver tissues or cells exposed to known toxins, in particular hepatotoxins, as compared to unexposed tissues or cells as well as the identification of individual genes that are differentially expressed in liver tissues or cells upon toxin exposure.

In various aspects, the invention includes methods of predicting at least one toxic effect of a compound, predicting the progression of a toxic effect of a compound, and predicting the hepatoxicity of a compound. The invention also includes methods of identifying agents that modulate the onset or progression of a toxic response. Also provided are methods of predicting the cellular pathways that a compound modulates in a cell. The invention includes methods of identifying agents that modulate protein activities.

In a further aspect, the invention provides probes comprising sequences that specifically hybridize to genes in Tables 1-3. Also provided are solid supports comprising at least two of the previously mentioned probes. The invention also includes a computer system that has a database containing information identifying the expression level in a tissue or cell sample exposed to a hepatotoxin of a set of genes comprising at least two genes in Tables 1-3.

DETAILED DESCRIPTION

Many biological functions are accomplished by altering the expression of various genes through transcriptional (e.g. through control of initiation, provision of RNA precursors, RNA processing, etc.) and/or translational control. For example, fundamental biological processes such as cell cycle, cell differentiation and cell death are often characterized by the variations in the expression levels of groups of genes.

Changes in gene expression are also associated with the effects of various chemicals, drugs, toxins, pharmaceutical agents and pollutants on an organism or cells. For example, the lack of sufficient expression of functional tumor suppressor genes and/or the over expression of oncogene/protooncogenes after exposure to an agent could lead to tumorgenesis or hyperplastic growth of cells (Marshall, Cell, 64: 313-326 (1991); Weinberg, Science, 254:1138-1146 (1991)). Thus, changes in the expression levels of particular genes (e.g. oncogenes or tumor suppressors) may serve as signposts for the presence and progression of toxicity or other cellular responses to exposure to a particular compound.

Monitoring changes in gene expression may also provide certain advantages during drug screening and development. Often drugs are screened for the ability to interact with a major target without regard to other effects the drugs have on cells. These cellular effects may cause toxicity in the whole animal, which prevents the development and clinical use of the potential drug.

The present inventors have examined tissue from animals exposed to the known hepatotoxins which induce detrimental liver effects, to identify global changes in gene expression induced by these compounds. These global changes in gene expression, which can be detected by the production of expression profiles, provide useful toxicity markers that can be used to monitor toxicity and/or toxicity progression by a test compound. Some of these markers may also be used to monitor or detect various disease or physiological states, disease progression, drug efficacy and drug metabolism.

Identification of Toxicity Markers

To evaluate and identify gene expression changes that are predictive of toxicity, studies using selected compounds with well characterized toxicity have been conducted by the present inventors to catalogue altered gene expression during exposure in vivo and in vitro. In the present study, acyclovir, amitryptiline, alpha-naphthylisothiocyante (ANIT), acetaminophen, AY-25329, bicalutamide, carbon tetrachloride, clofibrate, cyproterone acetate (CPA), diclofenac, diflunisal, dioxin, 17α-ethinylestradiol, hydrazine, indomethacin, lipopolysaccharide, phenobarbital, tacrine, valproate, WY-14643 and zileuton were selected as a known hepatotoxins.

The pathogenesis of acute $CCl_4$-induced hepatotoxicity follows a well-characterized course in humans and experimental animals resulting in centrilobular necrosis and steatosis, followed by hepatic regeneration and tissue repair. Severity of the hepatocellular injury is also dose-dependent and may be affected by species, age, gender and diet.

Differences in susceptibility to $CCl_4$ hepatotoxicity are primarily related to the ability of the animal model to metabolize $CCl_4$ to reactive intermediates. $CCl_4$-induced hepatotoxicity is dependent on $CCl_4$ bioactivation to trichloromethyl free radicals by cytochrome P450 enzymes (CYP2E1), localized primarily in centrizonal hepatocytes. Formation of the free radicals leads to membrane lipid peroxidation and protein denaturation resulting in hepatocellular damage or death.

The onset of hepatic injury is rapid following acute administration of $CCl_4$ to male rats. Morphologic studies have shown cytoplasmic accumulation of lipids in hepatocytes within 1 to 3 hours of dosing, and by 5 to 6 hours, focal necrosis and hydropic swelling of hepatocytes are evident. Centrilobular necrosis and inflammatory infiltration peak by 24 to 48 hours post dose. The onset of recovery is also evident within this time frame by increased DNA synthesis and the appearance of mitotic figures. Removal of necrotic debris begins by 48 hours and is usually completed by one week, with full restoration of the liver by 14 days.

Increases in serum transaminase levels also parallel $CCl_4$-induced hepatic histopathology. In male Sprague Dawley (SD) rats, alanine aminotrasferase (ALT) and aspartate aminotransferase (AST) levels increase within 3 hours of $CCl_4$ administration (0.1, 1, 2, 3, 4 mL/kg, ip; 2.5 mL/kg, po) and reach peak levels (approximately 5-10 fold increases) within 48 hours post dose. Significant increases in serum α-glutathione s-transferase (α-GST) levels have also been detected as early as 2 hours after $CCl_4$ administration (25 µL/kg, po) to male SD rats.

At the molecular level, induction of the growth-related proto-oncogenes, c-fos and c-jun, is reportedly the earliest event detected in an acute model of $CCl_4$-induced hepatotoxicity (Schiaffonato et al., *Liver* 17:183-191 (1997)). Expression of these early-immediate response genes has been detected within 30 minutes of a single dose of $CCl_4$ to mice (0.05-1.5 mL/kg, ip) and by 1 to 2 hours post dose in rats (2 mL/kg, po; 5 mL/kg, po) (Schiaffonato et al., supra, and Hong et al., *Yonsei Medical J* 38:167-177 (1997)). Similarly, hepatic c-myc gene expression is increased by 1 hour following an acute dose of $CCl_4$ to male SD rats (5 mL/kg, po) (Hong et al., supra). Expression of these genes following exposure to $CCl_4$ is rapid and transient. Peak hepatic mRNA levels for c-fos, c-jun, and c-myc, after acute administration of $CCl_4$ have been reported at 1 to 2 hours, 3 hours, and 1 hour post dose, respectively.

The expression of tumor necrosis factor-α (TNF-α) is also increased in the livers of rodents exposed to $CCl_4$, and TNF-α has been implicated in initiation of the hepatic repair process. Pre-treatment with anti-TNF-α antibodies has been shown to prevent $CCl_4$-mediated increases in c-jun and c-fos gene expression, whereas administration of TNF-α induced rapid expression of these genes (Bruccoleri et al., *Hepatol* 25:133-141 (1997)). Up-regulation of transforming growth factor-β (TGF-β) and transforming growth factor receptors (TBRI-III) later in the repair process (24 and 48 hours after $CCl_4$ administration) suggests that TGF-β may play a role in limiting the regenerative response by induction of apoptosis (Grasl-Kraupp et al., *Hepatol* 28:717-7126 (1998)).

Acetaminophen is a widely used analgesic that at supratherapeutic doses can be metabolized to N-acetyl-p-benzoquinone imine (NAPQI) which causes hepatic and renal failure. At the molecular level, until the present invention little was known about the effects of acetominophen.

Amitriptyline is a commonly used antidepressant, although it is recognized to have toxic effects on the liver (*Physicians Desk Reference*, 47$^{th}$ ed., Medical Economics Co., Inc., 1993; Balkin, U.S. Pat. No. 5,656,284). Nevertheless, amitriptyline's beneficial effects on depression, as well as on sleep and dyspepsia (Mertz et al., *Am J Gastroenterol* 93(2):160-165 (1998)), migraines (Beubler, *Wien Med Wochenschr* 144(5-6):100-101 (1994)), arterial hypertension (Bobkiewicz et al., *Arch Immunol Ther Exp (Warsz)* 23(4): 543-547 (1975)) and premature ejaculation (Smith et al., U.S. Pat. No. 5,923,341) mandate its continued use.

Differences in susceptibility to amitriptyline toxicity are considered related to differential metabolism. Amitriptyline-induced hepatotoxicity is primarily mediated by development of cholestasis, the condition caused by the failure of the liver to secrete bile, resulting in accumulation in blood plasma of substances normally secreted into bile-bilirubin and bile salts. Cholestasis is also characterized by liver cell necrosis and bile duct obstruction, which leads to increased pressure on the lumenal side of the canalicular membrane and release of enzymes (alkaline phosphatase, 5'-nucleotidase, gamma-glutamyl transpeptidase) normally localized on the canalicular membrane. These enzymes also begin to accumulate in the plasma. Typical symptoms of cholestasis are general malaise, weakness, nausea, anorexia and severe pruritis (Cecil Textbook of Medicine, 20$^{th}$ ed., part XII, pp. 772-773, 805-808, J. C. Bennett and F. Plum Eds., W. B. Saunders Co., Philadelphia, 1996).

The effects of amitriptyline or phenobarbital (PB) on phospholipid metabolism in rat liver have been studied. In one study, male Sprague-Dawley rats received amitriptyline orally in one dose of 600 mg/kg. PB was given intraperitonially (IP) at a dosage of 80 mg/kg. Animals were sacrificed by decapitation at 6, 12, 18, and 24 hr. The phospholipid level in liver was measured by enzymatic assay and by gas chromatography-mass spectrometry. Both agents caused an increase in the microsomal phosphatidylcholine content. Levels of glycerophosphate acyltransferase (GAT) and phosphatidate cytidylyltransferase (PCT) were slightly affected by amitriptyline but were significantly affected by PB. Levels of phosphatidate phosphohydrolase (PPH) and choline phosphotransferase (CPT) were significantly altered by amitriptyline and by PB (Hoshi et al., *Chem Pharm Bull* 38:3446-3448 (1990)).

In another experiment, amitriptyline was given orally to male Sprague-Dawley rats (4-5 weeks old) in a single dose of 600 mg/kg. The animals were sacrificed 12 or 24 hours later. This caused a marked increase in -aminolevulinic acid (-ALA) activity at both time points. Total heme and cytochrome b5 levels were increased but cytochrome P450 (CYP450) content remained the same. The authors concluded that hepatic heme synthesis is increased through prolonged induction of -ALA but this may be accounted for by the increases in cytochrome b5 and total heme and not by the CYP450 content (Hoshi et al., *Jpn J Pharmacol* 50:289-293 (1989)).

Amitriptyline can cause hypersensititivity syndrome, a specific severe idiosyncratic reaction characterized by skin, liver, joint and haematological abnormalities (Milionis et al., *Postgrad Med* 76(896):361-363 (2000)). Amitriptyline has also been shown to cause drug-induced hepatitis, resulting in liver peroxisomes with impaired catalase function (De Creaemer et al., *Hepatology* 14(5):811-817 (1991)). The peroxisomes are larger in number, but smaller in size and deformed in shape. Using cultured hepatocytes, the cytotoxicity of amitriptyline was examined and compared to other psychotropic drugs (Boelsterli et al., *Cell Biol Toxicol* 3(3):231-250 (1987)). The effects observed were release of lactate dehydrogenase from the cytosol, as well as impairment of biosynthesis and secretion of proteins, bile acids and glycolipids.

Aromatic and aliphatic isothiocyanates are commonly used soil fumigants and pesticides (Shaaya et al., *Pesticide Science* 44(3):249-253 (1995); Cairns et al., *J Assoc Official Analytical Chemists* 71(3):547-550 (1988)). These compounds are also environmental hazards, however, because they remain as toxic residues in plants, either in their original or in a metabolized form (Cerny et al., *J Agricultural and Food Chemistry* 44(12):3835-3839 (1996)) and because they are released from the soil into the surrounding air (Gan et al., *J Agricutural and Food Chemistry* 46(3):986-990 (1998)). Alpha-naphthylthiourea, an amino-substituted form of ANIT, is a known rodenticide whose principal toxic effects are pulmonary edema and pleural effusion, resulting from the action of this compound on pulmonary capillaries. Microsomes from lung and liver release atomic sulfur (Goodman and Gilman's The Pharmacological Basis of Therapeutics, $9^{th}$ ed., chapter 67, p. 1690, J. G. Hardman et al. eds., McGraw-Hill, New York, N.Y., 1996).

In one study in rats, ANIT (80 mg/kg) was dissolved in olive oil and given orally to male Wistar rats (180-320 g). All animals were fasted for 24 hours before ANIT treatment, and blood and bile excretion were analyzed 24 hours later. Levels of total bitimbin, alkaline phosphatase, serum glutamic oxaloacetic transaminase and serum glutamic pyruvic transaminase were found to be significantly increased, while ANIT reduced total bile flow, all of which are indications of severe biliary dysfunction. This model is used to induce cholestasis with jaundice because the injury is reproducible and dose-dependent. ANIT is metabolized by microsomal enzymes, and a metabolite plays a fundamental role in its toxicity (Tanaka et al., *Clinical and Experimental Pharmacology and Physiology* 20:543-547 (1993))(92).

ANIT fails to produce extensive necrosis, but has been found to produce inflammation and edema in the portal tract of the liver (Maziasa et al., *Toxicol Appl Pharmacol* 110:365-373 (1991)). Livers treated with ANIT are significantly heavier than control-treated counterparts and serum levels of alanine aminotransferase (ALT), gamma-glutamyl transpeptidase (-GTP), total bilirubin, lipid peroxide and total bile acids showed significant increases (Anonymous, *Toxicol Lett* 105:103-110 (2000)).

ANIT-induced hepatotoxicity may also be characterized by cholangiolitic hepatitis and bile duct damage. Acute hepatotoxicity caused by ANIT in rats is manifested as neutrophildependent necrosis of bile duct epithelial cells (BDECs) and hepatic parenchymal cells. These changes mirror the cholangiolitic hepatitis found in humans (Hill, *Toxicol Sci* 47:118-125 (1999)).

Exposure to ANIT also causes liver injury by the development of cholestasis, the condition caused by failure to secrete bile, resulting in accumulation in blood plasma of substances normally secreted into bile, such as bilirubin and bile salts. Cholestasis is also characterized by liver cell necrosis, including bile duct epithelial cell necrosis, and bile duct obstruction, which leads to increased pressure on the lumenal side of the canalicular membrane, decreased canalicular flow and release of enzymes normally localized on the canalicular membrane (alkaline phosphatase, 5'-nucleotidase, gamma-glutamyl transpeptidase). These enzymes also begin to accumulate in the plasma. Typical symptoms of cholestasis are general malaise, weakness, nausea, anorexia and severe pruritis (Cecil Textbook of Medicine, $20^{th}$ ed., part XII, pp. 772-773, 805-808, J. C. Bennett and F. Plum Eds., W. B. Saunders Co., Philadelphia (1996) and Kossor et al., *Toxicol Appl Pharmacol* 119:108-114 (1993)).

ANIT-induced cholestatis is also characterized by abnormal serum levels of alanine aminotransferase, aspartic acid aminotransferase and total bilirubin. In addition, hepatic lipid peroxidation is increased, and the membrane fluidity of microsomes is decreased. Histological changes include an infiltration of polymorphonuclear neutrophils and elevated number of apoptotic hepatocytes (Calvo et al., *J Cell Biochem* 80(4):461-470 (2001)). Other known hepatotoxic effects of exposure to ANIT include a damaged antioxidant defense system, decreased activities of superoxide dismutase and catalase (Ohta et al., *Toxicology* 139(3):265-275 (1999)), and the release of several proteases from the infiltrated neutrophils, alanine aminotransferase, cathepsin G, elastase, which mediate hepatocyte killing (Hill et al., *Toxicol Appl Pharmacol* 148(1): 169-175 (1998)).

Indomethacin is a non-steroidal antiinflammatory, antipyretic and analgesic drug commonly used to treat rheumatoid arthritis, osteoarthritis, ankylosing spondylitis, gout and a type of severe, chronic cluster headache characterized by many daily occurrences and jabbing pain. This drug acts as a potent inhibitor of prostaglandin synthesis; it inhibits the cyclooxygenase enzyme necessary for the conversion of arachidonic acid to prostaglandins (PDR $47^{th}$ ed., Medical Economics Co., Inc., Montvale, N.J., 1993; Goodman & Gilman's The Pharmalogical Basis of Therapeutics $9^{th}$ ed., J. G. Hardman et al. eds., McGraw Hill, New York, 1996, pp. 1074-1075, 1089-1095; Cecil Textbook of Medicine, $20^{th}$ ed., part XII, pp. 772-773, 805-808, J. C. Bennett and F. Plum Eds., W. B. Saunders Co., Philadelphia, 1996).

The most frequent adverse effects of indomethacin treatment are gastrointestinal disturbances, usually mild dyspepsia, although more severe conditions, such as bleeding, ulcers and perforations can occur. Hepatic involvement is uncommon, although some fatal cases of hepatitis and jaundice have been reported. Renal toxicity can also result, particularly after long-term administration. Renal papillary necrosis has been observed in rats, and interstitial nephritis with hematuria, proteinuria and nephrotic syndrome have been reported in humans. Patients suffering from renal dysfunction risk developing a reduction in renal blood flow, because renal prostaglandins play an important role in renal perfusion.

In rats, although indomethacin produces more adverse effects in the gastrointestinal tract than in the liver, it has been shown to induce changes in hepatocytic cytochrome P450. In one study, no widespread changes in the liver were observed, but a mild, focal, centrilobular response was noted. Serum levels of albumin and total protein were significantly reduced, while the serum level of urea was increased. No changes in creatinine or aspartate aminotransferase (AST) levels were observed (Falzon et al., *Br J exp Path* 66:527-534 (1985)). In another rat study, a single dose of indomethacin has been shown to reduce liver and renal microsomal enzymes, including CYP450, within 24 hours. Histopathological changes were not monitored, although there were lesions in the GI tract. The effects on the liver seemed to be waning by 48 hours (Fracasso et al., *Agents Actions* 31:313-316, (1990)).

A study of hepatocytes, in which the relative toxicity of five nonsteroidal antiinflammatory agents was compared, showed that indomethacin was more toxic than the others. Levels of lactate dehydrogenase release and urea, as well as viability and morphology, were examined. Cells exposed to high levels of indomethacin showed cellular necrosis, nuclear pleomorphism, swollen mitochondria, fewer microvilli, smooth endoplasmic reticulum proliferation and cytoplasmic vacuolation (Sorensen et al., *J Toxicol Environ Health* 16(3-4); 425-440 (1985)).

17α-ethinylestradiol, a synthetic estrogen, is a component of oral contraceptives, often combined with the progestational compound norethindrone. It is also used in post-menopausal estrogen replacement therapy (PDR 47$^{th}$ ed., pp. 2415-2420, Medical Economics Co., Inc., Montvale, N.J., 1993; Goodman & Gilman's The Pharmalogical Basis of Therapeutics 9$^{th}$ ed., pp. 1419-1422, J. G. Hardman et al. Eds., McGraw Hill, New York, 1996).

The most frequent adverse effects of 17α-ethinylestradiol usage are increased risks of cardiovascular disease: myocardial infarction, thromboembolism, vascular disease and high blood pressure, and of changes in carbohydrate metabolism, in particular, glucose intolerance and impaired insulin secretion. There is also an increased risk of developing benign hepatic neoplasia, although the incidence of this disease is very low. Because this drug decreases the rate of liver metabolism, it is cleared slowly from the liver, and carcinogenic effects, such as tumor growth, may result.

In a recent study, 17α-ethinylestradiol was shown to cause a reversible intrahepatic cholestasis in male rats, mainly by reducing the bile-salt-independent fraction of bile flow (BSIF) (Koopen et al., *Hepatology* 27:537-545 (1998)). Plasma levels of bilirubin, bile salts, aspartate aminotransferase (AST) and alanine aminotransferase (ALT) in this study were not changed. This study also showed that 17-ethinylestradiol produced a decrease in plasma cholesterol and plasma triglyceride levels, but an increase in the weight of the liver after 3 days of drug administration, along with a decrease in bile flow. Further results from this study are as follows. The activities of the liver enzymes leucine aminopeptidase and alkaline phosphatase initially showed significant increases, but enzyme levels decreased after 3 days. Bilirubin output increased, although glutathione (GSH) output decreased. The increased secretion of bilirubin into the bile without affecting the plasma level suggests that the increased bilirubin production must be related to an increased degradation of heme from heme-containing proteins. Similar results were obtained in another experiment (Bouchard et al., *Liver* 13:193-202 (1993)) in which the livers were also examined by light and electron microscopy. Despite the effects of the drug, visible changes in liver tissue were not observed.

In another study of male rats, cholestasis was induced by daily subcutaneous injections of 17α-ethinylestradiol for five days. Cholestasis was assessed by measuring the bile flow rate. Rats allowed to recover for five days after the end of drug treatment showed normal bile flow rates (Hamada et al., *Hepatology* 21:1455-1464 (1995)).

An experiment with male and female rats (Mayol, *Carcinogenesis* 13:2381-2388 (1992)) found that 17α-ethinylestradiol induced acute liver hyperplasia (increase in mitotic index and BrdU staining) after two days of treatment, although growth regression occurred within the first few days of treatment. With long-term treatment, lasting hyperplasia was again observed after three to six months of administration of the drug. Apoptosis increased around day 3 and returned to normal by one week. Additional experiments in this same study showed that proliferating hepatocytes were predominantly located around a periportal zone of vacuolated hepatocytes, which were also induced by the treatment. Chronic induced activation was characterized by flow cytometry on hepatocytes isolated from male rats, and ploidy analysis of hepatocyte cell suspensions showed a considerably increased proportion of diploid hepatocytes. These diploid cells were the most susceptible to drug-induced proliferation. The results from this study support the theory that cell target populations exist that respond to the effects of tumor promoters. The susceptibility of the diploid hepatocytes to proliferation during treatment may explain, at least in part, the behavior of 17-ethinylestradiol as a tumor promoter in the liver.

Wy-14643, a tumor-inducing compound that acts in the liver, has been used to study the genetic profile of cells during the various stages of carcinogenic development, with a view toward developing strategies for detecting, diagnosing and treating cancers (Rockett et al., *Toxicology* 144(1-3):13-29, (2000)). In contrast to other carcinogens, Wy-14643 does not mutate DNA directly. Instead, it acts on the peroxisome proliferator activated receptor-alpha (PPARalpha), as well as on other signaling pathways that regulate growth (Johnson et al., *J Steroid Biochem Mol Biol* 77(1):59-71 (2001)). The effect is elevated and sustained cell replication, accompanied by a decrease in apoptosis (Rusyn et al., *Carcinogenesis* 21(12): 2141-2145 (2000)). These authors (Rusyn et al.) noted an increase in the expression of enzymes that repair DNA by base excision, but no increased expression of enzymes that do not repair oxidative damage to DNA. In a study on rodents, Johnson et al. noted that Wy-14643 inhibited liver-X-receptor-mediated transcription in a dose-dependent manner, as well as de novo sterol synthesis.

In experiments with mouse liver cells (Peters et al., *Carcinogenesis* 19(11):1989-1994 (1998), exposure to Wy-14643 produced increased levels of acyl CoA oxidase and proteins involved in cell proliferation: CDK-1, 2 and 4, PCNA and c-myc. Elevated levels may be caused by accelerated transcription that is mediated directly or indirectly by PPARalpha. It is likely that the carcinogenic properties of peroxisome proliferators are due to the PPARalpha-dependent changes in levels of cell cycle regulatory proteins.

Another study on rodents (Keller et al., *Biochim Biophys Acta* 1102(2):237-244 (1992)) showed that Wy-14643 was capable of uncoupling oxidative phosphorylation in rat liver mitochondria. Rates of urea synthesis from ammonia and bile flow, two energy-dependent processes, were reduced, indicating that the energy supply for these processes was disrupted as a result of cellular exposure to the toxin.

Wy-14643 has also been shown to activate nuclear factor kappaB, NADPH oxidase and superoxide production in Kupffer cells (Rusyn et al., *Cancer Res* 60(17):4798-4803 (2000)). NADPH oxidase is known to induce mitogens, which cause proliferation of liver cells.

CPA is a potent androgen antagonist and has been used to treat acne, male pattern baldness, precocious puberty, and prostatic hyperplasia and carcinoma (Goodman & Gilman's The Pharmacological Basis of Therapeutics 9$^{th}$ ed., p. 1453, J. G. Hardman et al., Eds., McGraw Hill, New York, 1996). Additionally, CPA has been used clinically in hormone replacement therapy (HRT). CPA is useful in HRT as it protects the endometrium, decreases menopausal symptoms, and lessens osteoporotic fracture risk (Schneider, "The role of antiandrogens in hormone replacement therapy," *Climacteric* 3 (Suppl. 2): 21-27 (2000)).

Although CPA has numerous clinical applications, it is tumorigenic, mitogenic, and mutagenic. CPA has been used to treat patients with adenocarcinoma of the prostate, however in two documented cases (Macdonald et al., *Clin Oncol*

13: 135-137 (2001)), patients developed femoral head avascular necrosis following CPA treatment. In one study (Krebs et al., *Carcinogenesis* 19(2): 241-245 (1998)), Big Blue transgenic F344 rats were giving varying doses of CPA. As the dose of CPA increased, so did the mutation frequency, but a threshold dose was not determined. Another study (Werner et al., *Mutat Res* 395(2-3): 179-187 (1997)), showed that CPA caused the formation of DNA adducts in primary cultures of human hepatocytes. The authors suggest that the genotoxicity associated with CPA may be due to the double bond in position 6-7 of the steroid.

In additional experiments with rats (Kasper et al., *Carcinogenesis* 17(10): 2271-2274 (1996)), CPA was shown to induce unscheduled DNA synthesis in vitro. After a single oral dose of 100 mg CPA/kg body weight, continuous DNA repair activity was observed after 16 hours. Furthermore, CPA increased the occurrence of S phase cells, which corroborated the mitogenic potential of CPA in rat liver.

CPA has also been shown to produce cirrhosis (Garty et al., *Eur J Pediatr* 158(5): 367-370 (1999)). A child, who had been treated with CPA for over 4 years for hypothalamic syndrome and precocious puberty, developed cirrhosis. Even though the medication was discontinued, the child eventually succumbed to sepsis and multiorgan failure four years later.

In one study on rat liver treated with CPA (Bursch et al., *Arch Toxicol* 69(4): 253-258 (1995)), the expression of clusterin, a marker for apoptosis, was examined and measured by Northern and slot blot analysis. Bursch et al. showed that post-CPA administration, the clusterin mRNA concentration level increased. Moreover, in situ hybridization demonstrated that clusterin was expressed in all hepatocytes, therefore it is not limited to cells in the process of death by apoptosis.

Diclofenac, a non-steroidal anti-inflammatory drug, has been frequently administered to patients suffering from rheumatoid arthritis, osteoarthritis, and ankylosing spondylitis. Following oral administration, diclofenac is rapidly absorbed and then metabolized in the liver by cytochrome P450 isozyme of the CYC2C subfamily (Goodman & Gilman's The Pharmacological Basis of Therapeutics 9$^{th}$ ed., p. 637, J. G. Hardman et al., eds., McGraw Hill, New York, 1996). In addition, diclofenac has been applied topically to treat pain due to corneal damage (Jayamanne et al., *Eye* 11(Pt. 1): 79-83 (1997); Dornic et al., "Topical diclofenac sodium in the management of anesthetic abuse keratopathy," *Am J Ophthalmol* 125(5): 719-721 (1998)).

Although diclofenac has numerous clinical applications, adverse side-effects have been associated with the drug. In one study, out of 16 patients suffering from corneal complications associated with diclofenac use, 6 experienced corneal or scleral melts, three experienced ulceration, and two experienced severe keratopathy (Guidera et al., *Ophthalmology* 108(5): 936-944 (2001)). Another report described a term newborn who had premature closure of the ductus arteriosus as a result of maternal treatment with diclofenac (Zenker et al., *J Perinat Med* 26(3): 231-234 (1998)). Although it was only two weeks prior to delivery, the newborn had severe pulmonary hypertension and required treatment for 22 days of high doses of inhaled nitric oxide.

Another study investigated 180 cases of patients who had reported adverse reactions to diclofenac to the Food and Drug Administration (Banks et al., *Hepatology* 22(3): 820-827 (1995)). Of the 180 reported cases, the most common symptom was jaundice (75% of the symptomatic patients). Liver sections were taken and analyzed, and hepatic injury was apparent one month after drug treatment. An additional report showed that a patient developed severe hepatitis five weeks after beginning diclofenac treatment for osteoarthritis (Bhogaraju et al., *South Med J* 92(7): 711-713 (1999)). Within a few months following the cessation of diclofenac treatment there was complete restoration of liver functions.

In one study on diclofenac-treated Wistar rats (Ebong et al., *Afr J Med Sci* 27(3-4): 243-246 (1998)), diclofenac treatment induced an increase in serum chemistry levels of alanine aminotransferase, aspartate aminotransferase, methaemoglobin, and total and conjugated bilirubin. Additionally, diclofenac enhanced the activity of alkaline phosphatase and 5'nucleotidase. Another study showed that humans given diclofenac had elevated levels of hepatic transaminases and serum creatine when compared to the control group (McKenna et al., *Scand J Rheumatol* 30(1): 11-18 (2001)).

The anti-hypertensive drug AY-25329 (Wyeth-Ayerst) exhibits nephrotoxicity in the proximal, and possibly distal, tubules of the kidney. Although no data on its effects in humans is publicly available, the inventors of the present invention have observed minor changes associated with liver necrosis in rats. Specifically, increased mitosis rates and decreased glycogen levels were seen in all rats examined, indicating some measure of toxic response.

Bicalutamide is a non-steroidal anti-androgen that is a mixed-oxidase inducer. This drug causes liver enlargement. Its effects on the liver have been described in studies on rats and dogs, but have not been demonstrated in humans (Iswaran et al., *J Toxicol Sci* 22(2):75-88 (1997). Studies by the instant inventors have shown an increase in mitosis rates and a minor degree of hepatocellular hypertrophy in the rat.

Clofibrate is a peroxisome proliferator that has also been reported to cause non-genotoxic carcinogenicity in rodent livers (Qu et al., *Free Radic Biol Med* 31 (5):659-969 (2001); Mochizuki et al., Carcinogenesis 3(9):1027 (1982)). This compound is also known to cause liver enlargement (IARC Geneva: World Health Organization, International Agency for Research on Cancer, 1972-Present, p.V24 45 (1980); Fort et al., *Toxicology* 28(4):305 (1983)). Studies by the present inventors show early increases in AST and ALT levels followed by dose-dependent hepatocellular alterations and increased mitotic activity.

Diflunisal is a non-steroidal anti-inflammatory drug that is thought to exhibit toxicity in humans, but not in rodent animal models. Its effects in rat hepatocytes, however, have been documented (Masubuchi et al., *J Pharmacol Exp Ther* 287 (1):208-213 (1998)). In addition, as a class of compounds, NSAIDS are infamous for their toxic effects (Johnson et al., *Drugs Aging* 1(2):130-143 (1991)).

Dioxin (2,3,7,8-tetrachlorodibenzo-p-dioxin) is known to cause hepatocellular carcinogenicity in rodent animal models (NTP; Bioassay of 2,3,7,8-Tetrachlorodibenzo-p-dioxin, p.v, DHHS Publication No (NIH) 80-1765 (1980)), although this effect is known to be specific to certain sensitive strains (Viluksela et al., *Cancer Res* 60(24):6911-6920 (2000). This chemical also causes liver cancers in humans (IARC Geneva: World Health Organization, International Agency for Research on Cancer, 1972-Present, p. 69 342 (1997)).

Hydrazine (Isoniazid) is a known liver carcinogen in the rodent and is also thought to cause steatosis (Waterfield et al., *Arch Toxicol* 67(4):244-254 (1993); American Conference of Governmental Industrial Hygienists, Inc., 6th ed., vols. I-III, p. 761, ACGIH, Cincinnati, Ohio, 1991). It may be carcinogenic in humans as well, but the data in humans is not yet sufficient to be conclusive. Hydarzine's toxicity has also been documented in rat primary cultured hepatocytes (Ghatineh et al., *Toxicology in Vitro* 8(3):393-399 (1994)).

Lipopolysaccharides are known endotoxins that induce inflammation (hepatitis) in the rat liver (Nolan, *Hepatology* 1(5):458-65 (1981)). They have also been shown to induce cytotoxicity in primary cultured rat hepatocytes and in Kupffer cells (Hartung et al., *Biochem Pharmacol* 42(5): 1129-1135 (1991)).

Phenobarbital is a barbiturate that is a known Cytochrome P450 inducer. Chronic dosing of this compound is known to induce non-genotoxic tumorigenesis (Whysner et al., *Pharmacol Ther* 71(1-2):153-191 (1996)).

Tacrine, a strong acetylcholinesterase (AChE) inhibitor, is used in the treatment of mild to moderate cases Alzheimer's dimentias. The effect seen in patients is a reversal of the cognitive and functional decline, but the drug does not appear to change the neurodegenerative process (*Goodman & Gilman's The Pharmacological Basis of Therapeutics*, 9$^{th}$ ed., p. 174, Hardman et al., eds., McGraw Hill, New York, 1996).

Hepatotoxicty caused by tacrine is typically reversible, although cases of severe hepatotoxicity have been seen. In one case study, a 75-year-old woman suffering from . Alzheimer's disease had been administered tacrine for a period of 14 months (Blackard et al. *J Clin Gastroenterol* 26:57-59 (1998)). The woman developed progressive jaundice, followed by hepatic failure and death.

Preclinical studies failed to detect adverse hepatic events (Viau et al., *Drug Chem Toxicol* 16: 227-239 (1993)). While hepatotoxicity has been found in humans, in vivo rat studies have not shown a correlation between tacrine and hepatotoxicity, and the mechanism of action is not completely understood. In one in vitro study, tacrine displayed cytotoxicity to human hepatoma cell lines and primary rat hepatocytes (Viau et al., supra). Another in vitro study compared the reaction of human and rat liver microsomal preparations to tacrine (Woolf et al., *Drug Metab Dispos* 21:874-882 (1993)). The study showed that the two species reacted differently to the drug, suggesting that the rat may not be the best model for monitoring tacrine-induced elevations in liver marker enzymes.

While tacrine does not reveal classic signs of hepatotoxicity in rats, gene expression changes due to tacrine administration can be used to predict that the drug will be a liver toxin in humans. This suggests that toxicogenomics might be able to detect drugs that prove to be toxic in the clinic, even when classical but more crude measures in preclinical screening fail to detect toxicity.

Valproate (valproic acid) is an anti-convulsant that causes fatty liver and necrosis in both humans and rodents (Eadie, *Med Toxicol Adverse Drug Exp* 3(2):85-106 (1988); Lewis, *Hepatology* 2(6):870-873, (1982)). This compound is also known to cause severe developmental defects (Briggs et al., *A Reference Guide to Fetal and Neonatal Risk. Drugs in Pregnancy and Lactation*, 4th ed., p. 869, Williams & Wilkins, Baltimore, Md. 1994).

Zileuton is thought to cause general inflammation (hepatitis) in the liver of humans. Its effects in rodents are minimal, with some observed cytochrome P450 induction and weak peroxisome proliferation (Rodrigues et al., *Toxicol Appl Pharmacol* 137(2): 193-201 (1996)).

Acyclovir (9-[(2-hydroxyethyl)methyl]guanine, Zovirax®), an anti-viral guanosine analogue, is used to treat herpes simplex virus (HSV), varicella zoster virus (VZV) and Epstein-Barr virus (EBV) infections. It is phosphorylated by virally encoded thymidine kinase (TK) and converted to its activated di- and triphosphate forms by other kinases. Viral polymerases preferentially incorporate acyclovir, over natural bases, into viral DNA, but, because acyclovir is incorporated as a monophosphate, chain elongation is terminated. Acyclovir is not effective against viruses or viral mutants that lack TK (Fields Virology 3d ed., Fields et al., eds., pp. 436-440, Lippincott-Raven Publishers, Philadelphia, 1996; Cecil Textbook of Medicine, 20$^{th}$ ed., part XII, p. 1742, J. C. Bennett and F. Plum Eds., W. B. Saunders Co., Philadelphia, 1996).

The pharmacokinetics of acyclovir show that it has a half-life of about three hours and that most of it is excreted in the urine largely unchanged (Brigden et al., "The clinical pharmacology of acyclovir and its prodrugs," *Scand J Infect Dis Suppl* 47:33-39, 1985). The most frequent adverse effect of acyclovir treatment is damage to various parts of the kidney, particularly the renal tubules, where the precipitation of crystals of acyclovir can occur (Fogazzi, "Crystalluria: a neglected aspect of urinary sediment analysis," *Nephrol Dial Transplant* 11(2):379-387, 1996). Although acyclovir is primarily a renal toxin, it has been shown to induce liver inflammation (hepatitis) (*Physicians' Desk Reference*, 56$^{th}$ ed., p. 1707, Medical Economics Co. Inc., Montvale, N.J., 2002). Findings of hepatotoxicity in animals have not yet been published.

Toxicity Prediction and Modeling

The genes and gene expression information, as well as the portfolios and subsets of the genes provided in Tables 1-3, may be used to predict at least one toxic effect, including the hepatotoxicity of a test or unknown compound. As used, herein, at least one toxic effect includes, but is not limited to, a detrimental change in the physiological status of a cell or organism. The response may be, but is not required to be, associated with a particular pathology, such as tissue necrosis. Accordingly, the toxic effect includes effects at the molecular and cellular level. Hepatotoxicity is an effect as used herein and includes but is not limited to the pathologies of liver necrosis, hepatitis, fatty liver and protein adduct formation. As used herein, a gene expression profile comprises any quantitative representation of the expression of at least one mRNA species in a cell sample or population and includes profiles made by various methods such as differential display, PCR, hybridization analysis, etc.

In general, assays to predict the toxicity or hepatotoxicity of a test agent (or compound or multi-component composition) comprise the steps of exposing a cell population to the test compound, assaying or measuring the level of relative or absolute gene expression of one or more of the genes in Tables 1-3 and comparing the identified expression level(s) to the expression levels disclosed in the Tables and database(s) disclosed herein. Assays may include the measurement of the expression levels of about 2, 3, 4, 5, 6, 7, 8, 9, 10, 15, 20, 25, 30, 50, 75, 100 or more genes from Tables 1-3.

In the methods of the invention, the gene expression level for a gene or genes induced by the test agent, compound or compositions may be comparable to the levels found in the Tables or databases disclosed herein if the expression level varies within a factor of about 2, about 1.5 or about 1.0 fold. In some cases, the expression levels are comparable if the agent induces a change in the expression of a gene in the same direction (e.g., up or down) as a reference toxin.

The cell population that is exposed to the test agent, compound or composition may be exposed in vitro or in vivo. For instance, cultured or freshly isolated hepatocytes, in particular rat hepatocytes, may be exposed to the agent under standard laboratory and cell culture conditions. In another assay format, in vivo exposure may be accomplished by administration of the agent to a living animal, for instance a laboratory rat.

Procedures for designing and conducting toxicity tests in in vitro and in vivo systems are well known, and are described in many texts on the subject, such as Loomis et al., *Loomis's Esstentials of Toxicology*, 4th Ed., Academic Press, New York, 1996; Echobichon, *The Basics of Toxicity Testing*, CRC Press, Boca Raton, 1992; Frazier, editor, *In Vitro Toxicity Testing*, Marcel Dekker, New York, 1992; and the like.

In in vitro toxicity testing, two groups of test organisms are usually employed: One group serves as a control and the other group receives the test compound in a single dose (for acute toxicity tests) or a regimen of doses (for prolonged or chronic toxicity tests). Because, in some cases, the extraction of tissue as called for in the methods of the invention requires sacrificing the test animal, both the control group and the group receiving compound must be large enough to permit removal of animals for sampling tissues, if it is desired to observe the dynamics of gene expression through the duration of an experiment.

In setting up a toxicity study, extensive guidance is provided in the literature for selecting the appropriate test organism for the compound being tested, route of administration. dose ranges, and the like. Water or physiological saline (0.9% NaCl in water) is the solute of choice for the test compound since these solvents permit administration by a variety of routes. When this is not possible because of solubility limitations, vegetable oils such as corn oil or organic solvents such as propylene glycol may be used.

Regardless of the route of administration, the volume required to administer a given dose is limited by the size of the animal that is used. It is desirable to keep the volume of each dose uniform within and between groups of animals. When rats or mice are used, the volume administered by the oral route generally should not exceed about 0.005 ml per gram of animal. Even when aqueous or physiological saline solutions are used for parenteral injection the volumes that are tolerated are limited, although such solutions are ordinarily thought of as being innocuous. The intravenous $LD_{50}$ of distilled water in the mouse is approximately 0.044 ml per gram and that of isotonic saline is 0.068 ml per gram of mouse. In some instances, the route of administration to the test animal should be the same as, or as similar as possible to, the route of administration of the compound to man for therapeutic purposes.

When a compound is to be administered by inhalation, special techniques for generating test atmospheres are necessary. The methods usually involve aerosolization or nebulization of fluids containing the compound. If the agent to be tested is a fluid that has an appreciable vapor pressure, it may be administered by passing air through the solution under controlled temperature conditions. Under these conditions, dose is estimated from the volume of air inhaled per unit time, the temperature of the solution, and the vapor pressure of the agent involved. Gases are metered from reservoirs. When particles of a solution are to be administered, unless the particle size is less than about 2 μm the particles will not reach the terminal alveolar sacs in the lungs. A variety of apparatuses and chambers are available to perform studies for detecting effects of irritant or other toxic endpoints when they are administered by inhalation. The preferred method of administering an agent to animals is via the oral route, either by intubation or by incorporating the agent in the feed.

When the agent is exposed to cells in vitro or in cell culture, the cell population to be exposed to the agent may be divided into two or more subpopulations, for instance, by dividing the population into two or more identical aliquots. In some preferred embodiments of the methods of the invention, the cells to be exposed to the agent are derived from liver tissue. For instance, cultured or freshly isolated rat hepatocytes may be used.

The methods of the invention may be used generally to predict at least one toxic response, and, as described in the Examples, may be used to predict the likelihood that a compound or test agent will induce various specific liver pathologies, such as liver necrosis, fatty liver disease, protein adduct formation, hepatitis, or other pathologies associated with at least one of the toxins herein described. The methods of the invention may also be used to determine the similarity of a toxic response to one or more individual compounds. In addition, the methods of the invention may be used to predict or elucidate the potential cellular pathways influenced, induced or modulated by the compound or test agent due to the similarity of the expression profile compared to the profile induced by a known toxin (see Tables 3A-3DD).

Diagnostic Uses for the Toxicity Markers

As described above, the genes and gene expression information or portfolios of the genes with their expression information as provided in Tables 1-3 may be used as diagnostic markers for the prediction or identification of the physiological state of tissue or cell sample that has been exposed to a compound or to identify or predict the toxic effects of a compound or agent. For instance, a tissue sample such as a sample of peripheral blood cells or some other easily obtainable tissue sample may be assayed by any of the methods described above, and the expression levels from a gene or genes from Tables 1-3 may be compared to the expression levels found in tissues or cells exposed to the toxins described herein. These methods may result in the diagnosis of a physiological state in the cell or may be used to identify the potential toxicity of a compound, for instance a new or unknown compound or agent. The comparison of expression data, as well as available sequence or other information may be done by researcher or diagnostician or may be done with the aid of a computer and databases as described below.

In another format, the levels of a gene(s) of Tables 1-3, its encoded protein(s), or any metabolite produced by the encoded protein may be monitored or detected in a sample, such as a bodily tissue or fluid sample to identify or diagnose a physiological state of an organism. Such samples may include any tissue or fluid sample, including urine, blood and easily obtainable cells such as peripheral lymphocytes.

Use of the Markers for Monitoring Toxicity Progression

As described above, the genes and gene expression information provided in Tables 1-3 may also be used as markers for the monitoring of toxicity progression, such as that found after initial exposure to a drug, drug candidate, toxin, pollutant, etc. For instance, a tissue or cell sample may be assayed by any of the methods described above, and the expression levels from a gene or genes from Tables 1-3 may be compared to the expression levels found in tissue or cells exposed to the hepatotoxins described herein. The comparison of the expression data, as well as available sequence or other information may be done by researcher or diagnostician or may be done with the aid of a computer and databases.

Use of the Toxicity Markers for Drug Screening

According to the present invention, the genes identified in Tables 1-3 may be used as markers or drug targets to evaluate the effects of a candidate drug, chemical compound or other agent on a cell or tissue sample. The genes may also be used as drug targets to screen for agents that modulate their expression and/or activity. In various formats, a candidate drug or agent can be screened for the ability to simulate the transcription or expression of a given marker or markers or to downregulate or counteract the transcription or expression of a marker or markers. According to the present invention, one can also compare the specificity of a drug's effects by looking at the number of markers which the drug induces and comparing them. More specific drugs will have less transcriptional targets. Similar sets of markers identified for two drugs may indicate a similarity of effects.

Assays to monitor the expression of a marker or markers as defined in Tables 1-3 may utilize any available means of monitoring for changes in the expression level of the nucleic acids of the invention. As used herein, an agent is said to modulate the expression of a nucleic acid of the invention if it is capable of up- or down-regulating expression of the nucleic acid in a cell.

In one assay format, gene chips containing probes to one, two or more genes from Tables 1-3 may be used to directly monitor or detect changes in gene expression in the treated or exposed cell. Cell lines, tissues or other samples are first exposed to a test agent and in some instances, a known toxin, and the detected expression levels of one or more, or preferably 2 or more of the genes of Tables 1-3 are compared to the expression levels of those same genes exposed to a known toxin alone. Compounds that modulate the expression patterns of the known toxin(s) would be expected to modulate potential toxic physiological effects in vivo. The genes in Tables 1-3 are particularly appropriate marks in these assays as they are differentially expressed in cells upon exposure to a known hepatotoxin.

In another format, cell lines that contain reporter gene fusions between the open reading frame and/or the transcriptional regulatory regions of a gene in Tables 1-3 and any assayable fusion partner may be prepared. Numerous assayable fusion partners are known and readily available including the firefly luciferase gene and the gene encoding chloramphenicol acetyltransferase (Alam et al., *Anal Biochem* 188: 245-254 (1990)). Cell lines containing the reporter gene fusions are then exposed to the agent to be tested under appropriate conditions and time. Differential expression of the reporter gene between samples exposed to the agent and control samples identifies agents which modulate the expression of the nucleic acid.

Additional assay formats may be used to monitor the ability of the agent to modulate the expression of a gene identified in Tables 1-3. For instance, as described above, mRNA expression may be monitored directly by hybridization of probes to the nucleic acids of the invention. Cell lines are exposed to the agent to be tested under appropriate conditions and time and total RNA or mRNA is isolated by standard procedures such those disclosed in Sambrook et al. (*Molecular Cloning: A Laboratory Manual, 2nd Ed.*, Cold Spring Harbor Laboratory Press, Cold Spring Harbor, N.Y., 1989).

In another assay format, cells or cell lines are first identified which express the gene products of the invention physiologically. Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines may be transduced or transfected with an expression vehicle (e.g., a plasmid or viral vector) construct comprising an operable non-translated 5'-promoter containing end of the structural gene encoding the gene products of Tables 1-3 fused to one or more antigenic fragments or other detectable markers, which are peculiar to the instant gene products, wherein said fragments are under the transcriptional control of said promoter and are expressed as polypeptides whose molecular weight can be distinguished from the naturally occurring polypeptides or may further comprise an immunologically distinct or other detectable tag. Such a process is well known in the art (see Sambrook et al., supra).

Cells or cell lines transduced or transfected as outlined above are then contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37 C. Said conditions may be modulated as deemed necessary by one of skill in the art. Subsequent to contacting the cells with the agent, said cells are disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the agent-contacted sample is then compared with the control samples (no exposure and exposure to a known toxin) where only the excipient is contacted with the cells and an increase or decrease in the immunologically generated signal from the agent-contacted sample compared to the control is used to distinguish the effectiveness and/or toxic effects of the agent.

Another embodiment of the present invention provides methods for identifying agents that modulate at least one activity of a protein(s) encoded by the genes in Tables 1-3. Such methods or assays may utilize any means of monitoring or detecting the desired activity.

In one format, the relative amounts of a protein (Tables 1-3) between a cell population that has been exposed to the agent to be tested compared to an un-exposed control cell population and a cell population exposed to a known toxin may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe, such as a specific antibody.

Agents that are assayed in the above methods can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent s action. Agents can be rationally selected or rationally designed by utilizing the peptide sequences that make up these sites. For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see G. A. Grant in: *Molecular Biology and*

*Biotechnology*, Meyers, ed., pp. 659-664, VCH Publishers, New York, 1995). A skilled artisan can readily recognize that there is no limit as to the structural nature of the agents of the present invention.

Nucleic Acid Assay Formats

The genes identified as being differentially expressed upon exposure to a known hepatotoxin (Tables 1-3) may be used in a variety of nucleic acid detection assays to detect or quantititate the expression level of a gene or multiple genes in a given sample. The genes described in Tables 1-3 may also be used in combination with one or more additional genes whose differential expression is associate with toxicity in a cell or tissue. In preferred embodiments, the genes in Tables 1-3 may be combined with one or more of the genes described in prior and related applications 60/222,040, 60/244,880, 60/290,029, 60/290,645, 60/292,336, 60/295,798, 60/297,457, 60/298,884, 60/303,459 and 09/917,800, all of which are incorporated by reference on page 1 of this application.

Any assay format to detect gene expression may be used. For example, traditional Northern blotting, dot or slot blot, nuclease protection, primer directed amplification, RT-PCR, semi- or quantitative PCR, branched-chain DNA and differential display methods may be used for detecting gene expression levels. Those methods are useful for some embodiments of the invention. In cases where smaller numbers of genes are detected, amplification based assays may be most efficient. Methods and assays of the invention, however, may be most efficiently designed with hybridization-based methods for detecting the expression of a large number of genes.

Any hybridization assay format may be used, including solution-based and solid support-based assay formats. Solid supports containing oligonucleotide probes for differentially expressed genes of the invention can be filters, polyvinyl chloride dishes, particles, beads, microparticles or silicon or glass based chips, etc. Such chips, wafers and hybridization methods are widely available, for example, those disclosed by Beattie (WO 95/11755).

Any solid surface to which oligonucleotides can be bound, either directly or indirectly, either covalently or non-covalently, can be used. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, from 2, 10, 100, 1000 to 10,000, 100,000 or 400,000 or more of such features on a single solid support. The solid support, or the area within which the probes are attached may be on the order of about a square centimeter. Probes corresponding to the genes of Tables 1-3 or from the related applications described above may be attached to single or multiple solid support structures, e.g., the probes may be attached to a single chip or to multiple chips to comprise a chip set.

Oligonucleotide probe arrays for expression monitoring can be made and used according to any techniques known in the art (see for example, Lockhart et al., *Nat Biotechnol* 14:1675-1680 (1996); McGall et al., *Proc Nat Acad Sci USA* 93:13555-13460 (1996)). Such probe arrays may contain at least two or more oligonucleotides that are complementary to or hybridize to two or more of the genes described in Tables 1-3. For instance, such arrays may contain oligonucleotides that are complementary or hybridize to at least 2, 3, 4, 5, 6, 7, 8, 9, 10, 20, 30, 50, 70, 100 or more the genes described herein. Preferred arrays contain all or nearly all of the genes listed in Tables 1-3, or individually, the gene sets of Tables 3A-3DD. In a preferred embodiment, arrays are constructed that contain oligonucleotides to detect all or nearly all of the genes in any one of or all of Tables 1-3 on a single solid support substrate, such as a chip.

The sequences of the expression marker genes of Tables 1-3 are in the public databases. Table 1 provides the GenBank Accession Number for each of the sequences. The sequences of the genes in GenBank are expressly herein incorporated by reference in their entirety as of the filing date of this application, as are related sequences, for instance, sequences from the same gene of different lengths, variant sequences, polymorphic sequences, genomic sequences of the genes and related sequences from different species, including the human counterparts, where appropriate. These sequences may be used in the methods of the invention or may be used to produce the probes and arrays of the invention. In some embodiments, the genes in Tables 1-3 that correspond to the genes or fragments previously associated with a toxic response may be excluded from the Tables.

As described above, in addition to the sequences of the GenBank Accessions Numbers disclosed in the Tables 1-3, sequences such as naturally occurring variant or polymorphic sequences may be used in the methods and compositions of the invention. For instance, expression levels of various allelic or homologous forms of a gene disclosed in the Tables 1-3 may be assayed. Any and all nucleotide variations that do not alter the functional activity of a gene listed in the Tables 1-3, including all naturally occurring allelic variants of the genes herein disclosed, may be used in the methods and to make the compositions (e.g., arrays) of the invention.

Probes based on the sequences of the genes described above may be prepared by any commonly available method. Oligonucleotide probes for screening or assaying a tissue or cell sample are preferably of sufficient length to specifically hybridize only to appropriate, complementary genes or transcripts. Typically the oligonucleotide probes will be at least about 10, 12, 14, 16, 18, 20 or 25 nucleotides in length. In some cases, longer probes of at least 30, 40, or 50 nucleotides will be desirable.

As used herein, oligonucleotide sequences that are complementary to one or more of the genes described in Tables 1-3 refer to oligonucleotides that are capable of hybridizing under stringent conditions to at least part of the nucleotide sequences of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

Assays and methods of the invention may utilize available formats to simultaneously screen at least about 100, preferably about 1000, more preferably about 10,000 and most preferably about 1,000,000 different nucleic acid hybridizations.

As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e., A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

The terms "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases.

While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Typically, stringent conditions will be those in which the salt concentration is at least about 0.01 to 1.0 M $Na^+$ ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical submit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Probe Design

One of skill in the art will appreciate that an enormous number of array designs are suitable for the practice of this invention. The high density array will typically include a number of test probes that specifically hybridize to the sequences of interest. Probes may be produced from any region of the genes identified in the Tables and the attached representative sequence listing. In instances where the gene reference in the Tables is an EST, probes may be designed from that sequence or from other regions of the corresponding full-length transcript that may be available in any of the sequence databases, such as those herein described. See WO 99/32660 for methods of producing probes for a given gene or genes. In addition, any available software may be used to produce specific probe sequences, including, for instance, software available from Molecular Biology Insights, Olympus Optical Co. and Biosoft International. In a preferred embodiment, the array will also include one or more control probes.

High density array chips of the invention include "test probes." Test probes may be oligonucleotides that range from about 5 to about 500, or about 7 to about 50 nucleotides, more preferably from about 10 to about 40 nucleotides and most preferably from about 15 to about 35 nucleotides in length. In other particularly preferred embodiments, the probes are 20 or 25 nucleotides in length. In another preferred embodiment, test probes are double or single strand DNA sequences. DNA sequences are isolated or cloned from natural sources or amplified from natural sources using native nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes may fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample to be screened. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to, the actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent) Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross hybridization to a nucleic acid in the sample other than the target to which the probe is directed. For example, if the target is present the perfect match probes should be consistently brighter than the mismatch probes. In addition, if all central mismatches are present, the mismatch probes can be used to detect a mutation, for instance, a mutation of a gene in the accompanying Tables 1-3. The difference in intensity between the perfect match and the mismatch probe provides a good measure of the concentration of the hybridized material.

Nucleic Acid Samples

Cell or tissue samples may be exposed to the test agent in vitro or in vivo. When cultured cells or tissues are used, appropriate mammalian liver extracts may also be added with the test agent to evaluate agents that may require biotransformation to exhibit toxicity. In a preferred format, primary isolates of animal or human hepatocytes which already express the appropriate complement of drug-metabolizing enzymes may be exposed to the test agent without the addition of mammalian liver extracts.

The genes which are assayed according to the present invention are typically in the form of mRNA or reverse transcribed mRNA. The genes may be cloned or not. The genes may be amplified or not. The cloning and/or amplification do not appear to bias the representation of genes within a population. In some assays, it may be preferable, however, to use polyA+ RNA as a source, as it can be used with less processing steps.

As is apparent to one of ordinary skill in the art, nucleic acid samples used in the methods and assays of the invention may be prepared by any available method or process. Methods of isolating total mRNA are well known to those of skill in the art. For example, methods of isolation and purification of nucleic acids are described in detail in Chapter 3 of *Laboratory Techniques in Biochemistry and Molecular Biology, Vol. 24*, Hybridization With Nucleic Acid Probes: Theory and Nucleic Acid Probes, P. Tijssen, Ed., Elsevier Press, New York, 1993. Such samples include RNA samples, but also include cDNA synthesized from a mRNA sample isolated from a cell or tissue of interest. Such samples also include DNA amplified from the cDNA, and RNA transcribed from the amplified DNA. One of skill in the art would appreciate that it is desirable to inhibit or destroy RNase present in homogenates before homogenates are used.

Biological samples may be of any biological tissue or fluid or cells from any organism as well as cells raised in vitro, such as cell lines and tissue culture cells. Frequently the sample will be a tissue or cell sample that has been exposed to a compound, agent, drug, pharmaceutical composition, potential environmental pollutant or other composition. In some formats, the sample will be a "clinical sample" which is a sample derived from a patient. Typical clinical samples include, but are not limited to, sputum, blood, blood-cells (e.g., white cells), tissue or fine needle biopsy samples, urine, peritoneal fluid, and pleural fluid, or cells therefrom.

Biological samples may also include sections of tissues, such as frozen sections or formalin fixed sections taken for histological purposes.

Forming High Density Arrays

Methods of forming high density arrays of oligonucleotides with a minimal number of synthetic steps are known. The oligonucleotide analogue array can be synthesized on a single or on multiple solid substrates by a variety of methods, including, but not limited to, light-directed chemical coupling, and mechanically directed coupling (see Pirrung, U.S. Pat. No. 5,143,854).

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5' photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In addition to the foregoing, additional methods which can be used to generate an array of oligonucleotides on a single substrate are described in PCT Publication Nos. WO 93/09668 and WO 01/23614. High density nucleic acid arrays can also be fabricated by depositing pre-made or natural nucleic acids in predetermined positions. Synthesized or natural nucleic acids are deposited on specific locations of a substrate by light directed targeting and oligonucleotide directed targeting. Another embodiment uses a dispenser that moves from region to region to deposit nucleic acids in specific spots.

Hybridization

Nucleic acid hybridization simply involves contacting a probe and target nucleic acid under conditions where the probe and its complementary target can form stable hybrid duplexes through complementary base pairing. See WO 99/32660. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization tolerates fewer mismatches. One of skill in the art will appreciate that hybridization conditions may be selected to provide any degree of stringency.

In a preferred embodiment, hybridization is performed at low stringency, in this case in 6× SSPET at 37° C. (0.005% Triton X-100), to ensure hybridization and then subsequent washes are performed at higher stringency (e.g., 1× SSPET at 37° C.) to eliminate mismatched hybrid duplexes. Successive washes may be performed at increasingly higher stringency (e.g., down to as low as 0.25× SSPET at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

Signal Detection

The hybridized nucleic acids are typically detected by detecting one or more labels attached to the sample nucleic acids. The labels may be incorporated by any of a number of means well known to those of skill in the art. See WO 99/32660.

Databases

The present invention includes relational databases containing sequence information, for instance, for the genes of Tables 1-3, as well as gene expression information from tissue or cells exposed to various standard toxins, such as those herein described (see Tables 3A-3DD). Databases may also contain information associated with a given sequence or tissue sample such as descriptive information about the gene associated with the sequence information (see Table 1), or descriptive information concerning the clinical status of the tissue sample, or the animal from which the sample was derived. The database may be designed to include different parts, for instance a sequence database and a gene expression database. Methods for the configuration and construction of such databases and computer-readable media to which such databases are saved are widely available, for instance, see U.S. Pat. No. 5,953,727, which is herein incorporated by reference in its entirety.

The databases of the invention may be linked to an outside or external database such as GenBank; KEGG; SPAD; HUGO; Swiss-Prot; Prosite; OMIM; GDB; and GeneCard. In a preferred embodiment, as described in Tables 1-3, the external database is GenBank and the associated databases maintained by the National Center for Biotechnology Information (NCBI).

Any appropriate computer platform, user interface, etc. may be used to perform the necessary comparisons between sequence information, gene expression information and any other information in the database or information provided as an input. For example, a large number of computer workstations are available from a variety of manufacturers, such has those available from Silicon Graphics. Client/server environments, database servers and networks are also widely available and appropriate platforms for the databases of the invention.

The databases of the invention may be used to produce, among other things, electronic Northerns that allow the user to determine the cell type or tissue in which a given gene is expressed and to allow determination of the abundance or expression level of a given gene in a particular tissue or cell.

The databases of the invention may also be used to present information identifying the expression level in a tissue or cell of a set of genes comprising one or more of the genes in Tables 1-3, comprising the step of comparing the expression level of at least one gene in Tables 1-3 in a cell or tissue exposed to a test agent to the level of expression of the gene in the database. Such methods may be used to predict the toxic potential of a given compound by comparing the level of expression of a gene or genes in Tables 1-3 from a tissue or cell sample exposed to the test agent to the expression levels found in a control tissue or cell samples exposed to a standard toxin or hepatotoxin such as those herein described. Such methods may also be used in the drug or agent screening assays as described herein.

Kits

The invention further includes kits combining, in different combinations, high-density oligonucleotide arrays, reagents for use with the arrays, protein reagents encoded by the genes of the Tables, signal detection and array-processing instruments, gene expression databases and analysis and database management software described above. The kits may be used, for example, to predict or model the toxic response of a test compound, to monitor the progression of hepatic disease states, to identify genes that show promise as new drug targets and to screen known and newly designed drugs as discussed above.

The databases packaged with the kits are a compilation of expression patterns from human or laboratory animal genes and gene fragments (corresponding to the genes of Tables 1-3). In particular, the database software and packaged information that may contain the databases saved to a computer-readable medium include the expression results of Tables 1-3 that can be used to predict toxicity of a test agent by comparing the expression levels of the genes of Tables 1-3 induced by the test agent to the expression levels presented in Tables 3A-3DD. In another format, database and software information may be provided in a remote electronic format, such as a website, the address of which may be packaged in the kit.

The kits may used in the pharmaceutical industry, where the need for early drug testing is strong due to the high costs associated with drug development, but where bioinformatics, in particular gene expression informatics, is still lacking. These kits will reduce the costs, time and risks associated with traditional new drug screening using cell cultures and laboratory animals. The results of large-scale drug screening of pre-grouped patient populations, pharmacogenomics testing, can also be applied to select drugs with greater efficacy and fewer side-effects. The kits may also be used by smaller biotechnology companies and research institutes who do not have the facilities for performing such large-scale testing themselves.

Databases and software designed for use with use with microarrays is discussed in Balaban et al., U.S. Pat. No. 6,229,911, a computer-implemented method for managing information, stored as indexed Tables 1-3, collected from small or large numbers of microarrays, and U.S. Pat. No. 6,185,561, a computer-based method with data mining capability for collecting gene expression level data, adding additional attributes and reformatting the data to produce answers to various queries. Chee et al., U.S. Pat. No. 5,974,164, discloses a software-based method for identifying mutations in a nucleic acid sequence based on differences in probe fluorescence intensities between wild type and mutant sequences that hybridize to reference sequences.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Example 1

Identification of Toxicity Markers

The hepatotoxins acyclovir, amitryptiline, alpha-naphthyl-isothiocyante (ANIT), acetaminophen, AY-25329, bicalutamide, carbon tetrachloride, clofibrate, cyproterone acetate (CPA), diclofenac, diflunisal, dioxin, 17α-ethinylestradiol, hydrazine, indomethacin, lipopolysaccharide, phenobarbital, tacrine, valproate, WY-14643, zileuton and control compositions were administered to male Sprague-Dawley rats at various time points using administration diluents, protocols and dosing regimes as previously described in the art and previously described in the priority applications discussed above.

After adminstration, the dosed animals were observed and tissues were collected as described below:

Observation of Animals

1. Clinical Observations—Twice daily: mortality and moribundity check.

Cage Side Observations—skin and fur, eyes and mucous membrane, respiratory system, circulatory system, autonomic and central nervous system, somatomotor pattern, and behavior pattern.

Potential signs of toxicity, including tremors, convulsions, salivation, diarrhea, lethargy, coma or other atypical behavior or appearance, were recorded as they occurred and included a time of onset, degree, and duration.

2. Physical Examinations—Prior to randomization, prior to initial treatment, and prior to sacrifice.

3. Body Weights—Prior to randomization, prior to initial treatment, and prior to sacrifice.

| CLINCAL PATHOLOGY | |
|---|---|
| 1. Frequency | Prior to necropsy. |
| 2. Number of animals | All surviving animals. |
| 3. Bleeding Procedure | Blood was obtained by puncture of the orbital sinus while under 70% $CO_2$/30% $O_2$ anesthesia. |

4. Collection of Blood Samples Approximately 0.5 mL of blood was collected into EDTA tubes for evaluation of hematology parameters. Approximately 1 mL of blood was collected into serum separator tubes for clinical chemistry analysis. Approximately 200 uL of plasma was obtained and frozen at ~−80° C. for test compound/metabolite estimation. An additional ~2 mL of blood was collected into a 15 mL conical polypropylene vial to which ~3 mL of Trizol was immediately added. The contents were immediately mixed with a vortex and by repeated inversion. The tubes were frozen in liquid nitrogen and stored at 80° C.

Termination Procedures

Terminal Sacrifice

Approximately 1 and 3 and 6 and 24 and 48 hours and 5-7 days after the initial dose, rats were weighed, physically examined, sacrificed by decapitation, and exsanguinated. The animals were necropsied within approximately five minutes of sacrifice. Separate sterile, disposable instruments were used for each animal, with the exception of bone cutters, which were used to open the skull cap. The bone cutters were dipped in disinfectant solution between animals.

Necropsies were conducted on each animal following procedures approved by board-certified pathologists.

Animals not surviving until terminal sacrifice were discarded without necropsy (following euthanasia by carbon dioxide asphyxiation, if moribund). The approximate time of death for moribund or found dead animals was recorded.

Postmortem Procedures

Fresh and sterile disposable instruments were used to collect tissues. Gloves were worn at all times when handling tissues or vials. All tissues were collected and frozen within approximately 5 minutes of the animal's death. The liver sections and kidneys were frozen within approximately 3-5 minutes of the animal's death. The time of euthanasia, an interim time point at freezing of liver sections and kidneys, and time at completion of necropsy were recorded. Tissues were stored at approximately −80° C. or preserved in 10% neutral buffered formalin.

Tissue Collection and Processing

Liver

1. Right medial lobe—snap frozen in liquid nitrogen and stored at ~−80° C.
2. Left medial lobe—Preserved in 10% neutral-buffered formalin (NBF) and evaluated for gross and microscopic pathology.
3. Left lateral lobe—snap frozen in liquid nitrogen and stored at ~−80° C.

Heart

A sagittal cross-section containing portions of the two atria and of the two ventricles was preserved in 10% NBF. The remaining heart was frozen in liquid nitrogen and stored at ~−80° C.

Kidneys (Both)

1. Left—Hiemi-dissected; half was preserved in 10% NBF and the remaining half was frozen in liquid nitrogen and stored at ~−80° C.
2. Right—Hemi-dissected; half was preserved in 10% NBF and the remaining half was frozen in liquid nitrogen and stored at ~−80° C.

Testes (Both)

A sagittal cross-section of each testis was preserved in 10% NBF. The remaining testes were frozen together in liquid nitrogen and stored at ~−80° C.

Brain (Whole)

A cross-section of the cerebral hemispheres and of the diencephalon was preserved in 10% NBF, and the rest of the brain was frozen in liquid nitrogen and stored at ~−80° C.

Microarray sample preparation was conducted with minor modifications, following the protocols set forth in the Affymetrix GeneChip Expression Analysis Manual. Frozen tissue was ground to a powder using a Spex Certiprep 6800 Freezer Mill. Total RNA was extracted with Trizol (Gibco-BRL) utilizing the manufacturer's protocol. The total RNA yield for each sample was 200-500 µg per 300 mg tissue weight. mRNA was isolated using the Oligotex mRNA Midi kit (Qiagen) followed by ethanol precipitation. Double stranded cDNA was generated from mRNA using the SuperScript Choice system (GibcoBRL). First strand cDNA synthesis was primed with a T7-(dT24) oligonucleotide. The cDNA was phenol-chloroform extracted and ethanol precipitated to a final concentration of 1 µg/ml. From 2 µg of cDNA, cRNA was synthesized using Ambion's T7 MegaScript in vitro Transcription Kit.

To biotin label the cRNA, nucleotides Bio-11-CTP and Bio-16-UTP (Enzo Diagnostics) were added to the reaction. Following a 37° C. incubation for six hours, impurities were removed from the labeled cRNA following the RNeasy Mini kit protocol (Qiagen). cRNA was fragmented (fragmentation buffer consisting of 200 mM Tris-acetate, pH 8.1, 500 mM KOAc, 150 mM MgOAc) for thirty-five minutes at 94° C. Following the Affymetrix protocol, 55 µg of fragmented cRNA was hybridized on the Affymetrix rat array set for twenty-four hours at 60 rpm in a 45° C. hybridization oven. The chips were washed and stained with Streptavidin Phycoerythrin (SAPE) (Molecular Probes) in Affymetrix fluidics stations. To amplify staining, SAPE solution was added twice with an anti-streptavidin biotinylated antibody (Vector Laboratories) staining step in between. Hybridization to the probe arrays was detected by fluorometric scanning (Hewlett Packard Gene Array Scanner). Data was analyzed using Affymetrix GeneChip® version 2.0 and Expression Data Mining (EDMT) software (version 1.0), GeneExpress2000, and S-Plus.

Table 1 discloses those genes that are differentially expressed in liver upon exposure to the named toxins and their corresponding GenBank Accession and Sequence Identification numbers, the identities of the metabolic pathways in which the genes function, the gene names if known, and the unigene cluster titles. The comparison code represents the various toxicity or liver pathology state that each gene is able to discriminate as well as the individual toxin type associated with each gene. The codes are defined in Table 2. The GLGC ID is the internal Gene Logic identification number.

Table 2 defines the comparison codes used in Table 1.

Tables 3A-3DD disclose the summary statistics for each of the comparisons performed. Each of these tables contains a set of predictive genes and creates a model for predicting the hepatotoxicity of an unknown, i.e., untested compound. Each gene is identified by its Gene Logic identification number and can be cross-referenced to a gene name and representative SEQ ID NO. in Table 1. For each comparison of gene expression levels between samples in the toxicity group (samples affected by exposure to a specific toxin) and samples in the non-toxicity group (samples not affected by exposure to that same specific toxin), the group mean (for toxicity group samples) is the mean signal intensity, as normalized for the various chip parameters that are being assayed. The non-group mean represents the mean signal intensity, as normalized for the various chip parameters that are being assayed, in samples from animals other than those treated with the high dose of the specific toxin. These animals were treated with a low dose of the specific toxin, or with vehicle alone, or with a different toxin. Samples in the toxicity groups were obtained from animals sacrificed at the timepoint(s) indicated in the tables, while samples in the non-toxicity groups were obtained from animals sacrificed at all time points in the experiments. For individual genes, an increase in the group mean compared to the non-group mean indicates up-regulation upon exposure to a toxin. Conversely, a decrease in the group mean compared to the non-group mean indicates down-regulation.

The mean values are derived from Average Difference (AveDiff) values for a particular gene, averaged across the corresponding samples. Each individual Average Difference value is calculated by integrating the intensity information from multiple probe pairs that are tiled for a particular fragment. The normalization algorithm used to calculate the AveDiff is based on the observation that the expression intensity values from a single chip experiment have different distributions, depending on whether small or large expression values are considered. Small values, which are assumed to be mostly noise, are approximately normally distributed with mean zero, while larger values roughly obey a log-normal distribution; that is, their logarithms are normally distributed with some nonzero mean.

The normalization process computes separate scale factors for "non-expressors" (small values) and "expressors" (large ones). The inputs to the algorithm are pre-normalized Average Difference values, which are already scaled to set the trimmed mean equal to 100. The algorithm computes the standard deviation SD noise of the negative values, which are assumed to come from non-expressors. It then multiplies all negative values, as well as all positive values less than 2.0* SD noise, by a scale factor proportional to 1/SD noise.

Values greater than 2.0* SD noise are assumed to come from expressors. For these values, the standard deviation SD log (signal) of the logarithms is calculated. The logarithms are then multiplied by a scale factor proportional to 1/SD log (signal) and exponentiated. The resulting values are then multiplied by another scale factor, chosen so there will be no discontinuity in the normalized values from unscaled values on either side of 2.0* SD noise. Some AveDiff values may be negative due to the general noise involved in nucleic acid hybridization experiments. Although many conclusions can be made corresponding to a negative value on the GeneChip platform, it is difficult to assess the meaning behind the negative value for individual fragments. Our observations show that, although negative values are observed at times within the predictive gene set, these values reflect a real biological phenomenon that is highly reproducible across all the samples from which the measurement was taken. For this reason, those genes that exhibit a negative value are included in the predictive set. It should be noted that other platforms of gene expression measurement may be able to resolve the negative numbers for the corresponding genes. The predictive ability of each of those genes should extend across platforms, however. Each mean value is accompanied by the standard deviation for the mean. The linear discriminant analysis score (discriminant score), as disclosed in the tables, measures the ability of each gene to predict whether or not a sample is toxic. The discriminant score is calculated by the following steps:

Calculation of a Discriminant Score

Let $X_i$ represent the AveDiff values for a given gene across the Group 1 samples, $i=1\ldots n$.

Let $Y_i$ represent the AveDiff values for a given gene across the Group 2 samples, $i=1\ldots t$.

The calculations proceed as follows:

Calculate mean and standard deviation for $X_i$'s and $Y_i$'s, and denote these by $m_X$, $m_Y$, $s_X$, $s_Y$.

For all $X_i$'s and $Y_i$'s, evaluate the function $f(z)=((1/s_Y)*\exp(-0.5*((z-m_Y)/s_Y)^2))/(((1/s_Y)*\exp(-0.5*((z-m_Y)/s_Y)^2))+((1/s_X)*\exp(-0.5*((z-m_X)/s_X)^2)))$.

The number of correct predictions, say P, is then the number of $Y_i$'s such that $f(Y_i)>0.5$ plus the number of $X_i$'s such that $f(X_i)<0.5$.

The discriminant score is then $P/(n+t)$.

Linear discriminant analysis uses both the individual measurements of each gene and the calculated measurements of all combinations of genes to classify samples. For each gene a weight is derived from the mean and standard deviation of the tox and nontox groups. Every gene is multiplied by a weight and the sum of these values results in a collective discriminate score. This discriminant score is then compared against collective centroids of the tox and nontox groups. These centroids are the average of all tox and nontox samples respectively. Therefore, each gene contributes to the overall prediction. This contribution is dependent on weights that are large positive or negative numbers if the relative distances between the tox and nontox samples for that gene are large and small numbers if the relative distances are small. The discriminant score for each unknown sample and centroid values can be used to calculate a probability between zero and one as to the group in which the unknown sample belongs.

Example 2

General Toxicity Modeling

Samples were selected for grouping into tox-responding and non-tox-responding groups by examining each study individually with Principal Components Analysis (PCA) to determine which treatments had an observable response. Only groups where confidence of their tox-responding and non-tox-responding status was established were included in building a general tox model.

Linear discriminant models were generated to describe toxic and non-toxic samples. The top discriminant genes and/or EST's were used to determine toxicity by calculating each gene's contribution with homo and heteroscedastic treatment of variance and inclusion or exclusion of mutual information between genes. Prediction of samples within the database exceeded 80% true positives with a false positive rate of less than 5%. It was determined that combinations of genes and/or EST's generally provided a better predictive ability than individual genes and that the more genes and/or EST used the better predictive ability. Although the preferred embodiment includes fifty or more genes, many pairings or greater combinations of genes and/or EST can work better than individual genes. All combinations of two or more genes from the selected list could be used to predict toxicity. These combinations could be selected by pairing in an agglomerate, divisive, or random approach. Further, as yet undetermined genes and/or EST's could be combined with individual or combination of genes and/or EST's described here to increase predictive ability. However, the genes and/or EST's described here would contribute most of the predictive ability of any such undetermined combinations.

Other variations on the above method can provide adequate predictive ability. These include selective inclusion of components via agglomerate, divisive, or random approaches or extraction of loading and combining them in agglomerate, divisive, or random approaches. Also the use of composite variables in logistic regression to determine classification of samples can also be accomplished with linear discriminate analysis, neural or Bayesian networks, or other forms of regression and classification based on categorical or continual dependent and independent variables.

Example 3

Modeling Methods

The above modeling methods provide broad approaches of combining the expression of genes to predict sample toxicity. One could also provide no weight in a simple voting method or determine weights in a supervised or unsupervised method using agglomerate, divisive, or random approaches. All or selected combinations of genes may be combined in ordered, agglomerate, or divisive, supervised or unsupervised clustering algorithms with unknown samples for classification. Any form of correlation matrix may also be used to classify unknown samples. The spread of the group distribution and discriminate score alone provide enough information to enable a skilled person to generate all of the above types of models with accuracy that can exceed discriminate ability of individual genes. Some examples of methods that could be used individually or in combination after transformation of data types include but are not limited to: Discriminant Analysis, Multiple Discriminant Analysis, logistic regression, multiple regression analysis, linear regression analysis, conjoint analysis, canonical correlation, hierarchical cluster analysis, k-means cluster analysis, self-organizing maps, multidimensional scaling, structural equation modeling, support vector machine determined boundaries, factor analysis, neural networks, bayesian classifications, and resampling methods.

Example 4

Grouping of Individual compound and Pathology Classes

Samples were grouped into individual pathology classes based on known toxicological responses and observed clinical chemical and pathology measurements or into early and late phases of observable toxicity within a compound (Tables 3A-3DD). The top 10, 25, 50, 100 genes based on individual discriminate scores were used in a model to ensure that combination of genes provided a better prediction than individual genes. As described above, all combinations of two or more genes from this list could potentially provide better prediction than individual genes when selected in any order or by ordered, agglomerate, divisive, or random approaches. In addition, combining these genes with other genes could provide better predictive ability, but most of this predictive ability would come from the genes listed herein.

Samples may be considered toxic if they score positive in any pathological or individual compound class represented here or in any modeling method mentioned under general toxicology models based on combination of individual time and dose grouping of individual toxic compounds obtainable from the data. The pathological groupings and early and late phase models are preferred examples of all obtainable combinations of sample time and dose points. Most logical groupings with one or more genes and one or more sample dose and time points should produce better predictions of general toxicity, pathological specific toxicity, or similarity to known toxicant than individual genes.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

Document Number 1740956

TABLE 1

| GLGC ID | SeqID | GenBank Acc | Model Code | Pathway Name | Known Gene Name | Unigene Cluster Title |
|---|---|---|---|---|---|---|
| 16419 | 274 | AA875102 | General | | | ESTs, Highly similar to RUXE_HUMAN SMALL NUCLEAR RIBONUCLEO-PROTEIN E [*M.musculus*] |
| 22514 | 2418 | X13983 | y | | Alpha-2-macroglobulin | Alpha-2-macroglobulin |
| 23360 | 605 | AA955104 | General | | | ESTs |
| 22705 | 588 | AA946032 | e | | | ESTs |
| 22979 | 199 | AA851372 | x | | | ESTs, Highly similar to R26445 1 [*H.sapiens*] |
| 24458 | 761 | AB003515 | d | | ganglioside expression factor 2 | ganglioside expression factor 2 |
| 5492 | 1969 | D38061 | f,q | Androgen and estrogen metabolism, Pentose and glucuronate interconversions, Porphyrin and chlorophyll metabolism, Starch and sucrose metabolism | UDP-glucuronosyltransferase 1 family, member 1 | ESTs, UDP-glucuronosyltransferase 1 family, member 1 |
| 2264 | 1333 | AI44741 | q | | | ESTs |
| 5026 | 459 | AA924783 | General | | | EST |
| 24665 | 874 | AI009098 | o | | | ESTs |
| 7414 | 1323 | AI137586 | i | | | ESTs, Highly similar to IMB3_HUMAN IMPORTIN BETA-3 SUBUNIT [*H.sapiens*] |
| 6735 | 1464 | AI172497 | f | | | *Rattus norvegicus* mRNA for peptide histidine transporter 1 homolog rPHT2, complete cds |
| 17709 | 2319 | U24489 | n | | Tenascin X | Tenascin X |
| 22490 | 394 | AA899289 | g,q | | | ESTs, Moderately similar to KIAA1049 protein [*H.sapiens*] |
| 23417 | 784 | AB022209 | General,dd | | ribonucleoprotein F | ribonucleoprotein F |
| 20899 | 2478 | X65948 | aa | | general transcription factor IIB | general transcription factor IIB |
| 1069 | 2423 | X15096 | a,w | | acidic ribosomal protein P0 | acidic ribosomal protein P0 |
| 1977 | 2072 | J05470 | k,o,bb | Fatty acid metabolism, Glycerolipid metabolism | Carnitine palmitoyltransferase 2 | Carnitine palmitoyltransferase 2 ferase 2 |
| 15543 | 1729 | AI231800 | d,General | Oxidative phosphorylation, Type III protein secretion system | HMm:ATPase, H+ transporting, lysosomal (vacuolar proton | *Rattus norvegicus* brain Na++/Ca++ exchanger-associated protein mRNA, complete cds |
| 7864 | 1931 | D10874 | t | | | *Rattus norvegicus* mRNA for K(+)- transporting ATPase, complete cds pump) 16kD |
| 164592 | 1139 | AI070315 | j,General | | | ESTs, Weakly similar to NFAT1-A [*M.musculus*] |
| 4434 | 3 | AA685221 | h | | | ESTs |
| 6226 | 92 | AA818521 | v | | | ESTs |
| 4271 | 488 | AA925603 | k,o,z | | | ESTs, Moderately similar to AF153605 1 androgen induced protein [*H.sapiens*] |
| 23435 | 1664 | AI229502 | j | | | ESTs, Highly similar to KIAA0601 protein [*H.sapiens*] |
| 15465 | 1860 | AI236280 | d,General | | protein S | protein S |
| 1869 | 2061 | J03959 | p,t | Purine metabolism | HMm:urate oxidase | Rat urate oxidase 2 mRNA, complete cds |
| 9254 | 333 | AA892470 | d,General | | | ESTs, Highly similar to HISTONE H2A.Z [*R.norvegicus*] |
| 15089 | 899 | AI009752 | General | | | ESTs |
| 11152 | 2234 | M91652 | General,x,cc | Glutamate metabolism, Nitrogen metabolism | Glutamine synthetase (glutamate-ammonia | Glutamine synthetase (glutamate-ammonia ligase) |
| 22713 | 582 | AA945904 | p | | | ESTs |
| 19438 | 127 | AA819450 | General,u,w | | | EST |
| 24366 | 627 | AA956246 | m,n,General | | | ESTs, Moderately similar to T46373 hypothetical protein DKFZp434B2119.1 [*H.sapiens*] |
| 3665 | 881 | AI009376 | c,General,bb | | | ESTs, Moderately similar to A34168 nucleolar phosphoprotein B23.2 - rat [*R.norvegicus*] |
| 19269 | 202 | AA851785 | General | | | ESTs, Highly similar to NIP1-like protein [*M.musculus*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 6824 | 133 | AA819709 | d | | transaldolase 1 | *Rattus norvegicus* mRNA for beta-carotene 15,15'-dioxygenase, complete cds |
| 16039 | 11 | AA799452 | e | | | transaldolase 1 |
| 24284 | 2236 | M94287 | y | | nucleolar phosphoprotein p130 p130 | nucleolar phosphoprotein p130 p130 |
| 17448 | 1666 | AI229637 | General | | MYB binding protein (P160) 1a | MYB binding protein (P160) 1a (P160) 1a |
| 5622 | 2403 | X05834 | b,x | | Fibronectin 1 | Fibronectin 1 |
| 21164 | 1319 | AI137488 | General | | | ESTs |
| 14495 | 377 | AA893658 | p,w | | | ESTs |
| 17963 | 775 | AB012231 | General | | nuclear factor I/B | nuclear factor I/B |
| 6613 | 150 | AA848758 | k | Butanoate metabolism, Fatty acid biosynthesis (path 2), Fatty acid metabolism, Lysine degradation, Tryptophan metabolism, Valine, leucine and isoleucine degradation | HMm:hydroxyacyl-Coenzyme A dehydrogenase nuclear gene for mitochondrial product | *Rattus norvegicus* L-3-hydroxyacyl-CoA dehydrogenase precursor (HAD) mRNA, complete cds; |
| 1496 | 2350 | U56839 | General | | purinergic receptor P2Y, G-protein coupled 2 | purinergic receptor P2Y, G-protein coupled 2 |
| 21957 | 831 | AF087437 | f | | | ESTs |
| 24161 | 211 | AA858588 | e | | | ESTs |
| 16164 | 2280 | S83025 | cc | | Y box protein 1 | Y box protein 1 |
| 20984 | 2002 | D90109 | g,h | Fatty acid metabolism | Acyl CoA synthetase, long chain | Acyl CoA synthetase, long chain long chain |
| 24798 | 2406 | X06357 | o,t | Alanine and aspartate metabolism, Glycine, serine and threonine metabolism | Alanine-glyoxylate aminotransferase (Serine-pyruvate aminotransferase) | Alanine-glyoxylate aminotransferase (Serine-pyruvate aminotransferase) |
| 8983 | 2095 | L10652 | a | | initiation factor 2 associated 67 kDa | initiation factor 2 associated 67 kDa protein protein |
| 21065 | 47 | AA800179 | dd | | | ESTs, Highly similar to hypothetical protein COX4AL [*M.musculus*] |
| 1427 | 2122 | L38644 | v | | Importin beta | Importin beta |
| 15301 | 2207 | M60921 | c | | B-cell translocation gene 2, anti-proliferative | B-cell translocation gene 2, anti-proliferative |
| 22993 | 846 | AI007872 | g | | | ESTs, Moderately similar to S12207 hypothetical protein [*M.musculus*] |
| 1690 | 68 | AA81729 | m | | | ESTs |
| 15002 | 1365 | AI169327 | u,w | | | *Rattus norvegicus* tissue inhibitor of metalloproteinase-1 (TIMP1), mRNA, complete cds |
| 3393 | 740 | AA998209 | a | | | ESTs |
| 3266 | 1440 | AI171948 | General | | | ESTs, Highly similar to T08675 hypothetical protein DKFZp564F0522.1 [*H.sapiens*] |
| 23440 | 462 | AA924881 | General | | | ESTs, Weakly similar to KIAA0365 [*H.sapiens*] |
| 25567 | 2282 | S85184 | t,y | | Histidine decarboxylase | Histidine decarboxylase |
| 18029 | 2191 | M38759 | k | Histidine metabolism | | |
| 23157 | 1463 | AI172489 | j | | | ESTs, Moderately similar to STRI RAT STRIATIN [*R.norvegicus*] |
| 4479 | 1285 | AI111599 | General | | | ESTs |
| 15188 | 1947 | D16302 | p,General | Glycoprotein biosynthesis | N-acetylglucos-aminyltransferase I | N-acetylglucosaminyltransferase I |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 21839 | 1165 | AI071644 | General | | | ESTs, Moderately similar to LMG1 MOUSE LAMININ GAMMA-1 CHAIN PRECURSOR [*M.musculus*] |
| 1973 | 2205 | M60103 | e,General | | protein tyrosine phosphatase, receptor-type, F | protein tyrosine phosphatase, receptor-type, F |
| 14324 | 176 | AA850402 | b | | | ESTs, Moderately similar to S21348 probable pol polyprotein-related protein 4 - rat [*R.norvegicus*] |
| 23347 | 257 | AA860015 | aa | | | ESTs, Weakly similar to T50607 hypothetical protein DKFZp434I1016.1 [*H.sapiens*] |
| 11404 | 1881 | AI237002 | d,r | | spermidine synthase | spermidine synthase |
| 21643 | 1271 | AI104544 | w | | ribosomal protein S17 | ribosomal protein S17 |
| 17211 | 2185 | M34331 | t | | | ESTs, Weakly similar to KRAB-zinc finger protein KZF-1 [*R.norvegicus*] |
| 26335 | 1864 | AI236460 | n | | | *Rattus norvegicus* retinol dehydrogenase type II mRNA, complete cds |
| 72 | 2193 | M57263 | u | | transglutaminase 1, K polypeptide | transglutaminase 1, K polypeptide |
| 16043 | 266 | AA874830 | r | | | ESTs, Weakly similar to PRTS RAT VITAMIN K-DEPENDENT PROTEIN S PRECURSOR [*R.norvegicus*] |
| 11465 | 1851 | AI236084 | u | | | ESTs, Moderately similar to 41BB MOUSE 4-1BB LIGAND RECEPTOR PRECURSOR [*M.musculus*] |
| 9192 | 1316 | AI137345 | q,z | | | ESTs |
| 15987 | 262 | AA866435 | l,cc | | | EST |
| 10829 | 1057 | AI044467 | v | | | EST |
| 21382 | 575 | AA945708 | i,General | | | ESTs |
| 21864 | 2018 | H31144 | General | | | ESTs, Moderately similar to 1914275A non-receptor Tyr kinase [*H.sapiens*] |
| 21173 | 155 | AA848990 | General | | | ESTs |
| 2789 | 1824 | AI234949 | t,aa | | | *Rattus norvegicus* mRNA for protein protein |
| 19412 | 158 | AA849222 | General,y | | | ESTs, Moderately similar to AC006978 1 supported by human and rodent ESTs [*H.sapiens*] |
| 1684 | 2452 | X56325 | n | | Hemoglobin, alpha 1 | Hemoglobin, alpha 1 |
| 8899 | 1259 | AI03957 | d,e | | CD81 antigen (target of antiproliferative antibody 1) | CD81 antigen (target of antiproliferative antibody 1) |
| 11827 | 240 | AA859468 | v | | | ESTs |
| 9423 | 2255 | S61868 | a,g | | Ryudocan/syndecan 4 | Ryudocan/syndecan 4 |
| 3310 | 732 | AA997945 | n | | | ESTs |
| 23272 | 617 | AA955819 | l | | | ESTs |
| 911 | 2344 | U49729 | aa | | Bcl2-associated X protein | Bcl2-associated X protein |
| 12613 | 2021 | H31620 | General | | | ESTs, Highly similar to hypothetical protein [*H.sapiens*] |
| 12093 | 148 | AA848628 | o | | | ESTs, Highly similar to N-acetylglucosamine-phosphate mutase [*H.sapiens*] |
| 588 | 2480 | X69834 | d,p | | | *R.norvegicus* mRNA for serine protease inhibitor 2.4 |
| 25563 | 2277 | S81497 | h | | | |
| 5602 | 1760 | AI232611 | o | ESTs, Weakly similar to mitochondrial | | ESTs, Weakly similar to mitochondrial very-long-chain acyl-CoA thioesterase [*R.norvegicus*] |
| 5711 | 1074 | AI045151 | r,General | | | ESTs, Moderately similar to AF118838 1 citrin [*H.sapiens*] |

Document Number 1740956

TABLE 1-continued

| GLGC ID | SeqID | GenBank Acc | Model Code | Pathway Name | Known Gene Name | Unigene Cluster Title |
|---|---|---|---|---|---|---|
| 19252 | 316 | AA892041 | d | Methane metabolism, Phenylalanine metabolism | HMn:peroxiredoxin 5 | *Rattus norvegicus* mRNA for thiol-specific antioxidant protein (1-Cys peroxiredoxin) |
| 16321 | 1726 | AI231506 | General | | | ESTs |
| 23491 | 538 | AA944422 | General | | acidic calponin | acidic calponin |
| 4954 | 449 | AA924444 | j | | | ESTs |
| 4444 | 1199 | AI100882 | c,m,General | | | ESTs, Moderately similar to homology to a plant EST:RICS2753A [*H.sapiens*] |
| 24013 | 1659 | AI229260 | r | | | ESTs |
| 2897 | 76 | AA818039 | j | | | ESTs |
| 6101 | 1401 | AI170752 | r | | | ESTs |
| 293 | 2074 | J05499 | p,General | Bile acid biosyntheses, Fatty acid biosynthesis (path 2), Fatty acid metabolism, Phenylalanine metabolism, Valine, leucine and isoleucine degradation | | *Rattus norvegicus* L-glutamine amidohydrolase mRNA complete cds |
| 23699 | 2044 | J02749 | k,o,p,cc | | Acetyl-CoA acyltransferase, 3-oxo acyl-CoA thiolase A, peroxisomal | Acetyl-CoA acyltransferase, 3-oxo acyl-CoA thiolase A, peroxisomal |
| 11762 | 1583 | AI178631 | m | | | ESTs |
| 25693 | 2444 | X53949 | bb | | | *R.norvegicus* beta-hO-r gene for beta-globin chain |
| 20308 | 2453 | X56327 | h | | | ESTs, Weakly similar to S70642 ubiquitin ligase Nedd4 - rat [*R.norvegicus*] |
| 10573 | 1200 | AI101003 | y | Porphyrin and chlorophyll metabolism | Ceruloplasmin (ferroxidase) | Ceruloplasmin (ferroxidase) |
| 16521 | 918 | AI010470 | o | | | |
| 4751 | 415 | AA900481 | x | | | ESTs |
| 12361 | 693 | AA965031 | General | | | ESTs |
| 11326 | 1010 | AI029015 | General | | | ESTs |
| 23578 | 603 | AA955042 | a | | | ESTs, Weakly similar to folate binding protein 6 |
| 21696 | 533 | AA944324 | i | | ADP-ribosylation factor 6 | ADP-ribosylation factor 6 |
| 18705 | 2173 | M30691 | a | | Ly6-C antigen gene | Ly6-C antigen gene |
| 25078 | 2333 | U33540 | a,General | ESTs | | ESTs |
| 26330 | 1844 | AI235911 | a | | | |
| 22686 | 1791 | AI233753 | aa | | histidine ammonia lyase | histidine ammonia lyase |
| 70 | 2198 | M58308 | p,General | Histidine metabolism, Nitrogen metabolism | | |
| 6554 | 840 | AF097723 | c,d | | plasma glutamate carboxypeptidase | plasma glutamate carboxypeptidase |
| 15148 | 237 | AA859325 | z | | | ESTs, Weakly similar to T26289 hypothetical protein W08E3.1 - *Caenorhabditis elegans* [*C.elegans*] |
| 24012 | 649 | AA957335 | b | | | ESTs |
| 21952 | 295 | AA891537 | r | | | ESTs, Weakly similar to unknown [*H.sapiens*] |
| 5215 | 495 | AA925774 | bb | | | ESTs |
| 4245 | 100 | AA818692 | p | | | ESTs, Moderately similar to ribosomal protein L33-like protein [*H.sapiens*] |
| 819 | 2392 | X02284 | k,m,n | Carbon fixation, Fructose and mannose metabolism, Glycolysis/Gluconeogenesis, Inositol metabolism, Pentose phosphate cycle | Aldolase B, fructose-biphosphate | Aldolase B, fructose-biphosphate |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 11422 | 36 | AA799812 | c,u | | | ESTs, Moderately similar to PTN3_HUMAN PROTEIN TYROSINE PHOSPHATASE, NON-RECEPTOR TYPE 3 [H.sapiens] |
| 58 | 2301 | U09870 | i | | major vault protein | major vault protein |
| 17817 | 349 | AA892777 | q | | | ESTs, Moderately similar to ribonuclease HI large subunit [H.sapiens] |
| 20650 | 2131 | M12335 | n,x | Arginine and proline metabolism, Glutamate metabolism, Nitrogen metabolism, Urea cycle and metabolism of amino groups | Carboamyl-phosphate synthetase 1 | Carboamyl-phosphate synthetase 1 |
| 14737 | 861 | AI008416 | g,r | | | ESTs |
| 25055 | 2127 | M11251 | l,x,dd | ESTs, Highly similar to DDRT helix- | | |
| 15011 | 40 | AA799893 | General | | | ESTs, Highly similar to DDR helix-destabilizing protein - rat [R.norvegicus] |
| 4174 | 943 | AI011613 | bb | | | ESTs |
| 20802 | 1114 | AI059508 | o | Carbon fixation, Pentose phosphate cycle | transketolase | transketolase |
| 402 | 555 | AA945143 | b | Tryptophan metabolism | tryptophan-2,3-dioxygenase | tryptophan-2,3-dioxygenase |
| 15610 | 2114 | L27075 | k | Citrate cycle (TCA cycle) | ATP citrate lyase | ATP citrate lyase |
| 6143 | 1279 | AI105167 | f,p,q,u | | | ESTs, Moderately similar to selenium-binding protein [H.sapiens] |
| 21856 | 210 | AA858550 | p | | | ESTs |
| 725 | 2356 | U62316 | z | | solute carrier family 16 (monocarboxylic acid transporters), mem | solute carrier family 16 (monocarboxylic acid transporters), member 7 |
| 24112 | 864 | AI008773 | x | | | ESTs |
| 18908 | 161 | AA849426 | v | | | ESTs, Weakly similar to YLC4_CAEEL HYPOTHETICAL 81.0 KD PROTEIN C35D10.4 IN CHROMOSOME III [C.elegans] |
| 14231 | 1174 | AI072358 | p,q | | | Rattus norvegicus outer mitochondrial membrane receptor rTOM20 mRNA, complete cds |
| 10545 | 2316 | U21871 | r,y | | | ESTs |
| 6783 | 701 | AA996463 | General | Butanoate metabolism, Glycolysis/Gluconegenesis, Pyruvate metabolism, Valine, leucine and isoleucine biosynthesis | HHs:pyruvate dehydrogenase (lipomide) beta | ESTs |
| 19370 | 669 | AA963797 | General,y | | | ESTs |
| 11998 | 352 | AA892828 | z | | | ESTs, Highly similar to ODPB RAT PYRUVATE DEHYDROGENASE E1 COMPONENT BETA SUBUNIT, MITOCHONDRIAL PRECURSOR [R.norvegicus] |
| 20354 | 2137 | M14369 | m,u | | K-kininogen, differential splicing leads to HMW Kngk | K-kininogen, differential splicing leads to HMW Kngk |
| 16984 | 984 | AI013161 | c | | | ESTs, Highly similar to EF1G_HUMAN ELONGATION FACTOR 1-GAMMA [H.sapiens] |
| 6047 | 1195 | AI073230 | General | | | ESTs |
| 16312 | 268 | AA875032 | n | | | ESTs |
| 2888 | 463 | AA924902 | k,General | | | ESTs |
| 22870 | 508 | AA926360 | j,General | | | ESTs |
| 15615 | 532 | AA944316 | cc | | | Rattus norvegicus thioredoxin mRNA, complete cds |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15372 | 277 | AA875205 | General | | | ESTs, Highly similar to IF39_HUMAN EUKARYOTIC TRANSLATION INITIATION FACTOR 3 SUBUNIT 9 |
| 2424 | 684 | AA964617 | f,g | | | ESTs |
| 14504 | 35 | AA799804 | z | | | ESTs |
| 14384 | 1543 | AI77096 | General,w | Purine metabolism | HMm:adenine phosphoribosyl transferase | Rat adenine phosphoribosyltransferas (APRT) gene, complete cds |
| 23860 | 1888 | AI237684 | d | | | ESTs |
| 18400 | 43 | AA799991 | v | | | ESTs |
| 17531 | 1662 | AI229440 | cc | Aminosugars metabolism | HHs:diaphorase (NADH) (cytochrome b-5 reductase) | Rat NADH-cytochrome b-5 reductase mRNA, complete cds |
| 15281 | 1937 | D13623 | General | | | ESTs |
| 1127 | 760 | AB003400 | p | Arginine and proline metabolism, D-Arginine and D-ornithine metabolism, Glycine, serine and threonine metabolism | HMm:D-amino acid | Rattus norvegicus mRNA for D-amino-acid oxidase, complete cds |
| 3924 | 186 | AA851017 | cc | | | ESTs, Highly similar to molybdopterin-synthase large subunit [M.musculus] |
| 18728 | 1406 | AI170776 | h | | growth factor receptor bound protein 2 | growth factor receptor bound protein 2 |
| 13446 | 1696 | AI230625 | General | | | ESTs |
| 2539 | 1289 | AI111960 | General | | | ESTs, Weakly similar to FKB5 MOUSE 51 KDA FK506-BINDING PROTEIN [M.musculus] |
| 22250 | 522 | AA943541 | g,q | | | ESTs, Weakly similar to T19468 hypothetical protein C25G4.2 - Caenorhabditis elegans [C.elegans] |
| 16190 | 1269 | AI04482 | k | | | ESTs, Weakly similar to ECHM RAT ENOYL-COA HYDRATASE, MITO-CHONDRIAL PRECURSOR [R.norvegicus] |
| 111 | 2286 | U02506 | n | | | Rattus norvegicus clone 15 polymeric immunoglobulin receptor mRNA, 3'UTR microsatellite repeats |
| 9215 | 467 | AA925116 | w | | interferon gamma inducing factor binding protein | interferon gamma inducing factor binding protein |
| 9432 | 1190 | AI072914 | General,y | | | EST |
| 3917 | 1768 | AI232970 | General | | | ESTs |
| 17837 | 376 | AA893641 | c | | | ESTs, Weakly similar to 1901177A wnt-2 gene [R.norvegicus] |
| 5573 | 1101 | AI059063 | a | | | ESTs, Weakly similar to gamma-fibrinogen [R.norvegicus] |
| 15638 | 287 | AA875633 | z | | | ESTs |
| 24712 | 2012 | E01884 | m,u | interact6-1 | Interleukin 1 beta | Interleukin 1 beta |
| 4026 | 1802 | AI233835 | m,u | | | ESTs |
| 13796 | 1656 | AI229056 | j,m | | | ESTs |
| 12312 | 373 | AA893453 | d,cc | | | ESTs |
| 15401 | 282 | AA875257 | General | | | ESTs |
| 6188 | 106 | AA818774 | General | | | ESTs |
| 25470 | 2242 | M95791 | m | | | |
| 16576 | 22 | AA799570 | j | | | ESTs |
| 18036 | 2341 | U40004 | d,General | | | Rattus norvegicus cytochrome P450 pseudogene (CYP2J3P1) mRNA |
| 12158 | 2091 | L00320 | k,l,x,cc,dd | | | |
| 17091 | 2368 | U73174 | f,g,l,General | | | |
| 15920 | 1594 | AI78938 | i | | | Rattus norvegicus glutathione reductase mRNA, complete cds |
| 1221 | 1933 | D11445 | m,n,u | | gro | gro |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 4365 | 1137 | AI070200 | w | | | ESTs, Weakly similar to T24938 hypothetical protein T15H9.1 - *Caenorhabditis elegans* [*C.elegans*] |
| 17502 | 2130 | M12156 | i,r | | heterogeneous nuclear ribonucleoprotein A1 | heterogeneous nuclear ribonucleoprotein A1 |
| 1462 | 1841 | AI235585 | f | Fatty acid metabolism, Propanoate metabolism, Valine, leucine and isoleucine degradation, beta-Alanine metabolism | Acyl-Coenzyme A dehydrogenase, C-4 to C-12 straight-chain | Rat mRNA for preprocathepsin D (EC 3.4.23.5) Acyl-Coenzyme A dehydrogenase, C-4 to C-12 straight-chain |
| 21078 | 2046 | J02791 | d,k,l,General | | | |
| 22266 | 569 | AA945601 | j,General | | | ESTs |
| 3131 | 364 | AA893032 | d,e | | | ESTs |
| 17340 | 843 | AI007803 | b,m | | ERM-binding phosphoprotein | ERM-binding phosphoprotein |
| 22655 | 531 | AA944308 | General | | | ESTs, Highly similar to N214_HUMAN NUCLEAR PORE COMPLEX PROTEIN NUP214 [*H.sapiens*] |
| 5493 | 2251 | S56936 | f,q | Androgen and estrogen metabolism, Pentose and glucuronate interconversions, Porphyrin and chlorophyll metabolism, Starch and sucrose metabolism | UDP-glucuronosyltransferase 1 family, member 1 | ESTs,UDP-glucuronosyltransferase 1 family, member 1 |
| 18028 | 1970 | D38062 | p,q | | decorin | *Rattus norvegicus* UDP-glucuronosyltransferase UGT1A7 mRNA, complete cds decorin |
| 18354 | 2462 | X59859 | m,u | | Heat shock 10 kD protein 1 (chaperonin 10) | Heat shock 10 kD protein 1 (chaperonin 10) |
| 5034 | 1393 | AI170613 | t | | | |
| 16163 | 1936 | D13309 | t | | Y box protein 1 | Y box protein 1 |
| 4781 | 1806 | AI233925 | General | | 5-aminoimidazole-4-carboxamide ribonucleotide formyltransferase/ | 5-aminoimidazole-4-carboxamide ribonucleotide formyltransferase/IMP cyclohydrolase |
| 20775 | 1477 | AI75494 | General | | dimerization cofactor of hepatocyte nuclear factor-1-alpha | ESTs, Moderately similar to PTD004 [*H.sapiens*] |
| 5059 | 1879 | AI236947 | General | | ribosomal protein L23 | ESTs |
| 21882 | 2223 | M83740 | h | | | *Rattus norvegicus* DCoH gene |
| 5667 | 2456 | X58200 | h,w | | | ESTs, Weakly similar to nucleosome assembly protein [*R.norvegicus*] |
| 16538 | 10 | AA799449 | a,dd | | Solute carrier family 11 member 2 (natural resistance-associated macrophage protein 2) | Solute carrier family 11 member 2 (natural resistance-associated macrophage protein 2) |
| 2013 | 332 | AA892390 | c | | | |
| 764 | 2501 | X84210 | r | Androgen and estrogen metabolism | Nuclear Factor IA | Nuclear Factor IA |
| 18717 | 551 | AA945050 | h | | Rat senescence marker protein 2A gene, exons | Rat senescence marker protein 2A gene, exons 1 and 2 1 and 2 |
| 4007 | 501 | AA926066 | p | | | ESTs |
| 6409 | 228 | AA858910 | o | | | ESTs |
| 11966 | 304 | AA891800 | d | | | ESTs, Highly similar to KIAA0694 protein [*H.sapiens*], ESTs, Moderately similar to pyrophosphatase [*H.sapiens*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 20443 | 2309 | U14192 | dd | | transcytosis associated protein, vesicle docking protein, 115 kDa | transcytosis associated protein, vesicle docking protein, 115 kDa |
| 489 | 2006 | E00778 | g,p,q,dd | Fatty acid metabolism, Tryptophan metabolism | Cytochrome P450, subfamily I (aromatic compound-inducible), member A1 (C6, form c) | Cytochrome P450, subfamily I (aromatic compound-inducible), member A1 (C6, form c) |
| 19408 | 2395 | X02610 | e | Gluconeogenesis, Phenylalanine, tyrosine and tryptophan biosynthesis | Enolase 1, alpha | Enolase 1, alpha |
| 8549 | 1785 | AI233639 | n | | | ESTs |
| 10109 | 2458 | X58465 | h,w,cc | | Ribosomal protein S5 | Ribosomal protein S5 |
| 20795 | 536 | AA944397 | z,dd | | | ESTs, Moderately similar to HS9B RAT HEAT SHOCK PROTEIN HSP 90-BETA [*R.norvegicus*] |
| 6502 | 1578 | AI78283 | General | | | ESTs, Highly similar to AF123263 1 phenylalanyl tRNA synthetase beta subunit [*M.musculus*] |
| 9514 | 184 | AA850978 | g | | | ESTs |
| 25608 | 2348 | U53927 | h | | | |
| 1876 | 1024 | AI030175 | f,n,cc | Fructose and mannose metabolism | Sorbitol dehydrogenase | Sorbitol dehydrogenase |
| 1391 | 2479 | X66366 | z | | gephyrin | gephyrin |
| 16649 | 814 | AF051895 | r | | Annexin V | Annexin V |
| 18611 | 2456 | X58200 | w | | ribosomal protein L23 | ESTs, Highly similar to RL23_HUMAN 60S RIBOSOMAL PROTEIN L23 [*R.norvegicus*] |
| 18713 | 972 | AI012604 | t | | eukaryotic initiation factor 5 (eIF-5) | eukaryotic initiation factor 5 (eIF-5) |
| 7497 | 1364 | AI169302 | General | Sphingophospholipid biosynthesis | HHs:sphingomyelin phosphodiesterase 1, acid lysosomal (acid sphingom | ESTs, Moderately similar to sphingomyelin phosphodiesterase 1, acid lysosomal [*H.sapiens*] |
| 14697 | 1821 | AI234834 | aa | | | *Rattus norvegicus* protein associating with small stress protein PASS1 (Pass1) mRNA, complete cds |
| 6842 | 900 | AI009764 | l | | | ESTs |
| 3816 | 1788 | AI233729 | f | | | ESTs, Highly similar to PSD5_HUMAN 26S PROTEASOME SUBUNIT S5B [*H.sapiens*] |
| 21712 | 1361 | AI169249 | General | | | ESTs |
| 9621 | 1476 | AI175486 | General | | ribosomal protein S7 | ribosomal protein S7 |
| 14766 | 1842 | AI235886 | aa | | | ESTs |
| 25084 | 2408 | X06769 | w | | | |
| 16053 | 1646 | AI228596 | General | | | |
| 3381 | 363 | AA892993 | l | | | ESTs, Weakly similar to T16757 hypothetical protein R144.3 - *Caenorhabditis elegans* [*C.elegans*] |
| 5884 | 1914 | AJ223184 | i | | | ESTs |
| 12447 | 638 | AA956769 | f,cc | | | *Rattus norvegicus* mRNA for DORA protein |
| 25281 | 1967 | D30804 | f,l,General | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 1774 | 2057 | J03754 | z | | ATPase isoform 2, Na+K+ transporting, beta polypeptide 2 | ATPase isoform 2, Na+K+ transporting, beta polypeptide 2 |
| 169 | 1076 | AI045171 | b | | calsequestrin 2 | calsequestrin 2 |
| 18824 | 1741 | AI232255 | m | | | ESTs, Moderately similar to S12207 hypothetical protein [M.musculus] |
| 11455 | 2165 | M24604 | General | | Proliferating cell nuclear antigen | Proliferating cell nuclear antigen |
| 21993 | 519 | AA943149 | General | | | ESTs, Weakly similar to T00084 hypothetical protein KIAA0512 [H.sapiens] |
| 20386 | 2364 | U68562 | General | | heat shock protein 60 (liver) | heat shock protein 60 (liver) |
| 16726 | 2228 | M86235 | h | Fructose and mannose metabolism | Ketohexokinase | Ketohexokinase |
| 6408 | 226 | AA858902 | t,aa | | | ESTs, Weakly similar to S24169 mucin - rat [R.norvegicus] |
| 15292 | 793 | AF012714 | General,t | | multiple inositol polyphosphate histidine phosphatase 1 | multiple inositol polyphosphate histidine phosphatase 1 |
| 8989 | 1147 | AI070792 | n | | | ESTs |
| 11039 | 1840 | AI235465 | i,General | | steroid sensitive gene-1 protein | steroid sensitive gene-1 protein |
| 6263 | 893 | AI009666 | l,General,y | | aminopeptidase A | Rattus norvegicus aminopeptidase A short variant mRNA, partial cds |
| 3909 | 1377 | AI169903 | i | | | ESTs |
| 15875 | 2465 | X62145 | h | | ribosomal protein L8 | ESTs, Highly similar to RL8_HUMAN 60S RIBOSOMAL PROTEIN L [R.norvegicus] |
| 17921 | 1506 | AI176422 | h | | | ESTs, Highly similar to ETFD_HUMAN ELECTRON TRANSFER FLAVOPROTEIN-UBIQUINONE OXIDOREDUCTASE PRECURSOR [H.sapiens] |
| 16619 | 717 | AA997544 | x,dd | | | EST |
| 20944 | 2497 | X82396 | w | | cathepsin B | cathepsin B |
| 5780 | 1571 | AI177869 | i,j | | | ESTs, Weakly similar to DRAL [R.norvegicus] |
| 2681 | 429 | AA901043 | x | | | ESTs |
| 14987 | 216 | AA858640 | k,General | | heat shock protein 60 (liver) | Rattus norvegicus CDK110 mRNA, heat shock protein 60 (liver) |
| 5998 | 1907 | AI639501 | General | | | ESTs |
| 23868 | 798 | AF023087 | General | | Early growth response 1 | Early growth response 1 |
| 9952 | 294 | AA891422 | General | | | ESTs, Moderately similar to AF077034 1 HSPC010 [H.sapiens] |
| 8864 | 1140 | AI070319 | a,f | | | ESTs |
| 26258 | 1559 | AI177501 | k | | | |
| 10245 | 1118 | AI059701 | v,dd | | | ESTs |
| 563 | 2532 | Z50051 | a | | Complement component 4 binding protein, alpha | Complement component 4 binding protein, alpha |
| 4155 | 1100 | AI059014 | t | | | ESTs |
| 23862 | 310 | AA891933 | aa | | | ESTs, Moderately similar to A Chain A, Crystal Structure Of SmacDIABLO [H.sapiens] |
| 5339 | 1432 | AI171727 | General,t | | | ESTs, Weakly similar to phenylethanolamine N-methyltransferase [R.norvegicus] |
| 13563 | 1795 | AI233773 | p,q,General,w | | | ESTs, Weakly similar to T24413 hypothetical protein T04A11.2 - Caenorhabditis elegans [C.elegans] |
| 2615 | 1660 | AI229318 | f | | | ESTs |
| 15125 | 2071 | J05132 | f,g,h,x | Androgen and estrogen metabolism, Pentose and glucuronate inter- | UDP-glucuronosyltransferase 1 family, member 1 | Rattus norvegicus UDP-glucuronosyltransferase UGT1A7 mRNA, complete cds, UDP-glucuronosyltransferase 1 family, member 1 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 19129 | 527 | AA943990 | p | conversions, Porphyrin and chlorophyll metabolism, Starch and sucrose metabolism | | ESTs |
| 14600 | 61 | AA801076 | m,General,u | | | ESTs |
| 5593 | 1698 | AI230698 | g,General | | Wolfram syndrome 1 (wolframin) | Wolfram syndrome 1 (wolframin) |
| 9942 | 510 | AA942697 | General | | | ESTs |
| 23260 | 1371 | AI169617 | a,General | | | ESTs, Highly similar to Bop1 [*M.musculus*] |
| 19367 | 1095 | AI058745 | g | | | EST, Weakly similar to HEPC HUMAN ANTIMICROBIAL PEPTIDE HEPCIDIN PRECURSOR [*H.sapiens*] |
| 21013 | 2047 | J02810 | a,x,cc | Glutathione metabolism | Glutathione-S-transferase, mu type 2 (Yb2) | Glutathione-S-transferase, mu type 2 (Yb2) |
| 7650 | 1682 | AI230142 | e | | | ESTs, Weakly similar to KUPFFER CELL RECEPTOR [*R.norvegicus*] |
| 1126 | 1712 | AI231007 | r | | | *Rattus norvegicus* cca1 mRNA, complete cds |
| 22849 | 1927 | D10754 | c | | | ESTs, Highly similar to PROTEASOME DELTA CHAIN PRECURSOR [*R.norvegicus*] |
| 15283 | 209 | AA858548 | General | | | ESTs |
| 8728 | 97 | AA818615 | General | | | ESTs |
| 4050 | 854 | AI008094 | g | | | ESTs |
| 347 | 2284 | U01914 | c,dd | | | *Rattus norvegicus* AKAP95 mRNA, partial cds |
| 18890 | 408 | AA899964 | k,o,General | | | ESTs |
| 5897 | 1086 | AI045862 | General | | | ESTs, Moderately similar to S64732 scaffold attachment factor B [*H.sapiens*] |
| 12933 | 667 | AA963682 | c | | | *Rattus norvegicus* 190 kDa ankyrin isoform mRNA, complete cds |
| 20056 | 1908 | AI639504 | General | | | ESTs, Weakly similar to T13607 hypothetical protein EG:87B1.3 - fruit fly [*D.melanogaster*] |
| 13054 | 1609 | AI79560 | General | | | ESTs |
| 20701 | 272 | AA875097 | b,w | | Fibrinogen, gamma polypeptide | Rat alpha-fibrinogen mRNA, 3' end |
| 6478 | 2404 | X05861 | n | | | Fibrinogen, gamma polypeptide |
| 20810 | 2419 | X14181 | h,w,cc | | Inwardly rectifying potassium channel gene, subfamily J-8 (ATP sensitive) | ESTs, Highly similar to 60S RIBOSOMAL PROTEIN L18A [*R.norvegicus*] |
| 15517 | 1976 | D42145 | u | | | Inwardly rectifying potassium channel gene, subfamily J-8 (ATP sensitive) |
| 20711 | 445 | AA924267 | k,o,z,bb | Fatty acid metabolism, Tryptophan metabolism | Cytochrome P450, subfamily IVB, polypeptide 1 | Cytochrome P450, subfamily IVB-polypeptide 1 |
| 5616 | 2090 | L00191 | b | | Fibronectin 1 | Fibronectin 1 |
| 20926 | 2274 | S81353 | dd | | Prosaposin (sulfated glycoprotein, sphingolipid hydrolase activator), enoyl hydratase-like protein, peroxisomal | Prosaposin (sulfated glycoprotein, sphingolipid hydrolase activator), enoyl hydratase-like protein, peroxisomal |
| 3434 | 1735 | AI232014 | General | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15138 | 1735 | AI009801 | l | | macrophage migration inhibitory factor | macrophage migration inhibitory factor |
| 24508 | 2186 | M34643 | v | | neurotrophin-3 (HDNF/NT-3) | neurotrophin-3 (HDNF/NT-3) |
| 25702 | 2458 | X58465 | cc | | | |
| 18356 | 2246 | R47042 | a | | decorin | decorin |
| 11850 | 2245 | R46985 | r,General | | ribosomal protein L10a | ribosomal protein L10a |
| 15654 | 17 | AA799501 | General | Oxidative phosphorylation, Ubiquinone biosynthesis | NADH ubiquinone oxido-reductase subunit B13 | NADH ubiquinone oxidoreductase subunit B13 |
| 24797 | 1938 | D13667 | t | Alanine and aspartate metabolism, Glycine, serine and threonine metabolism | Alanine-glyoxylate amino-transferase (Serine-pyruvate aminotransferase) | Alanine-glyoxylate aminotransferase (Serine-pyruvate aminotransferase) |
| 18837 | 1426 | AI171583 | General | | | ESTs, Moderately similar to PITP MOUSE PHOSPHOLIPID TRANSFER PROTEIN PRECURSOR [*M.musculus*] |
| 11331 | 1340 | AI145556 | aa | | | ESTs |
| 17693 | 297 | AA891737 | General | | | ESTs |
| 229 | 2314 | U20194 | d | | | *Rattus norvegicus* complement C8 beta (C8b) mRNA, partial cds |
| 1397 | 67 | AA817787 | j | | | ESTs, Highly similar to hypothetical protein [*M.musculus*] |
| 16346 | 38 | AA799824 | i | Oxidative phosphorylation, Type III protein secretion system | HHs:ATPase, H+ transporting, lysosomal (vacuolar proton pump) 42kD | ESTs, Highly similar to VATC_HUMAN VACUOLAR ATP SYNTHASE SUBUNIT C [*H.sapiens*] |
| 14311 | 2305 | U10699 | u | | G-protein coupled receptor 13 | G-protein coupled receptor 13 |
| 21703 | 2377 | U82591 | r | | | *Rattus norvegicus* RCL (Rcl) mRNA, complete cds |
| 18755 | 1867 | AI236599 | General | | | ESTs, Highly similar to T50630 hypothetical protein DKFZp762NO610.1 [*H.sapiens*] |
| 1995 | 807 | AF038870 | t,u,cc | Glycine, serine and threonine metabolism, Methionine metabolism | betaine-homocysteine methyltransferase | betaine-homocysteine methyltransferase |
| 358 | 2346 | U52948 | h | | | *Rattus norvegicus* complement component C9 precursor mRNA, partial cds |
| 8310 | 1593 | AI178868 | dd | | | ESTs |
| 24722 | 2172 | M30282 | bb | | Plasma kallikrein | Plasma kallikrein |
| 2250 | 964 | AI012354 | j,y | | | ESTs, Highly similar to 0506206A histone H2B [*R.norvegicus*] |
| 12184 | 1394 | AI170621 | General | | | ESTs, Weakly similar to YN57_YEAST HYPOTHETICAL 53.1 KD TRP-ASP REPEATS CONTAINING PROTEIN IN HXT14-PHA2 INTERGENIC REGION [*S.cerevisiae*] |
| 21380 | 56 | AA800739 | General | | | ESTs, Weakly similar to KT12_YEAST KTI12 PROTEIN [*S.cerevisiae*] |
| 14521 | 1749 | AI232350 | General | | | ESTs, Weakly similar to coding sequence of pol [*R.norvegicus*] |
| 15476 | 539 | AA944426 | aa | | | *Rattus norvegicus* calmodulin III (Calm3) mRNA, 3' untranslated region |
| 18597 | 778 | AB013732 | q,cc | Nucleotide sugars metabolism, Pentose and glucuronate interconversions, Starch and sucrose metabolism | UDP-glucose dehydrogeanse | UDP-glucose dehydrogenase |
| 4066 | 999 | AI013782 | b | | | ESTs |
| 11166 | 63 | AA801346 | y | | | ESTs, Weakly similar to JC4975 plexin 2 precursor - mouse [*M.musculus*] |
| 1991 | 2221 | M83196 | y | | Microtubule-associated protein 1a | Microtubule-associated protein 1a |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 10667 | 1862 | AI236366 | General | | siah binding protein 1; FBP interacting repressor; pyrimidine tr eukaryotic translation elongation factor 2, mitogen activated protein kinase 2 | siah binding protein 1; FBP interacting repressor; Ro ribonucleoprotein-binding protein 1 |
| 17560 | 666 | AA963674 | g | | | mitogen activated protein kinase kinase 2 |
| 13330 | 724 | AA997716 | f | | | *Rattus norvegicus* cytosolic inhibitor of Nrf2 (INrf2) mRNA, complete cds |
| 11488 | 1509 | AI176477 | bb | | | ESTs, Highly similar to transmembrane protein [*H.sapiens*] |
| 23033 | 255 | AA859938 | g | | | ESTs, Highly similar to NIPL MOUSE BCL2/ADENOVIRUS E1B 19-KDA PROTEIN-INTERACTING PROTEIN 3 LIKE [*M.musculus*] |
| 22854 | 1292 | AI112101 | General | | | ESTs, Highly similar to RXRA RAT RETINOIC ACID RECEPTOR RXR-ALPHA [*R.norvegicus*] |
| 22603 | 811 | AF044574 | k,o,bb | | putative peroxisomal 2,4-dienoyl-CoA reductase | putative peroxisomal 2,4-dienoyl-CoA reductase |
| 17305 | 2460 | X59051 | f | | Ribosomal protein S29 | Ribosomal protein S29 |
| 24501 | 1734 | AI232006 | General | | | *Rattus norvegicus* translation elongation factor 1-delta subunit mRNA, partial cds |
| 19371 | 1197 | AI100841 | dd | | | ESTs |
| 20430 | 2069 | J05035 | p | Androgen and estrogen metabolism, Bile acid biosynthesis | Steroid-5-alpha-reductase, alpha polypeptide 1 (3-oxo-5 alpha-steroid delta 4-dehydrogenase alpha 1) | Steroid-5-alpha-reductase, alpha polypeptide 1 (3-oxo-5 alpha-steroid delta 4-dehydrogenase alpha 1) |
| 24170 | 1342 | AI45601 | e,General | | | ESTs |
| 22416 | 535 | AA944380 | k,o | | | ESTs, Weakly similar to T26648 hypothetical protein Y38A8.1 - *Caenorhabditis elegans* [*C.elegans*] |
| 1175 | 2492 | X79081 | u,cc,dd | Fatty acid metabolism, Tryptophan metabolism | Cytochrome P450, subfamily IIC (mephenytoin 4-hydroxylase) | Cytochrome P450, subfamily IIC (mephenytoin 4-hydroxylase) |
| 1169 | 1548 | AI177161 | q,r | | NF-E2-related factor 2 | NF-E2-related factor 2 |
| 13187 | 2318 | U23056 | p | | carcinoembryonic antigen-related cell adhesion molecule | carcinoembryonic antigen-related cell adhesion molecule |
| 17847 | 1577 | AI78214 | o | | | ESTs |
| 18562 | 1479 | AI175515 | General | | | ESTs, Highly similar to PRITP MOUSE LYSOSOMAL PROTECTIVE PROTEIN PRECURSOR [*M.musculus*] |
| 20839 | 296 | AA891729 | w | | ribosomal protein S27a | ribosomal protein S27a |
| 16205 | 2407 | X06423 | c | | ribosomal protein S8 | ribosomal protein S8 |
| 4452 | 933 | AI011196 | General | Valine, leucine and isoleucine degradation | Isovaleryl Coenzyme A dehydrogenase | Isovaleryl Coenzyme A dehydrogenase |
| 17906 | 402 | AA899762 | n | | | *Rattus norvegicus* epidermal growth factor receptor related protein (Errp) mRNA, complete cds |
| 762 | 789 | AF007107 | x,cc | | cytochrome b5 | cytochrome b5 |
| 3845 | 941 | AI011481 | n | | | ESTs |
| 3191 | 981 | AI013075 | General | | | ESTs, Weakly similar to T03454 ALR protein [*H.sapiens*] |
| 19009 | 173 | AA850164 | q | | | ESTs |
| 12164 | 187 | AA851029 | aa | | | ESTs |

TABLE 1-continued

| GLGC ID | SeqID | GenBank Acc | Model Code | Pathway Name | Known Gene Name | Unigene Cluster Title |
|---|---|---|---|---|---|---|
| 19004 | 1489 | AI175875 | u | | | ESTs |
| 21115 | 829 | AF086624 | r | | serine threonine kinase pim3 | serine threonine kinase pim3 |
| 20555 | 2322 | U26033 | k,o | | carnitine octanoyltransferase | carnitine octanoyltransferase |
| 9223 | 2189 | M36151 | u | | | Rat mRNA for MHC class II antigen RT1.B 1 beta-chain, *Rattus norvegicus* MHC class II antigen RT1.B beta chain mRNA, partial cds |
| 6781 | 149 | AA848753 | q | Fatty acid metabolism | Acyl Coenzyme A dehydrogenase, long chain | Acyl Coenzyme A dehydrogenase, long chain |
| 3664 | 1418 | AI171289 | p | | | ESTs, Highly similar to JC2472 brain and reproductive organ-expressed protein [*H.sapiens*] |
| 15075 | 283 | AA875269 | i | | stearoyl-CoA desaturase 2 | stearoyl-CoA desaturase 2 |
| 16345 | 986 | AI013250 | f,p | | | *Rattus norvegicus* zinc finger protein Y1 (RLZF-Y) mRNA, complete cds |
| 14256 | 1529 | AI176845 | aa | | | ESTs, Weakly similar to cornichon [*M.musculus*] |
| 8490 | 1123 | AI059962 | c,General | | | ESTs |
| 4235 | 1270 | AI104524 | General | | heterogeneous nuclear ribonucleoprotein A/B | heterogeneous nuclear ribonucleoprotein A/B |
| 1858 | 2523 | Y09333 | k,o | | acyl-CoA thioesterase 1, cytosolic | *R.norvegicus* mRNA for mitochondrial very-long-chain acyl-CoA thioesterase, acyl-CoA thioesterase 1, |
| 1877 | 2486 | X74593 | n,cc | Fructose and mannose metabolism | Sorbitol dehydrogenase | Sorbitol dehydrogenase |
| 7268 | 991 | AI013541 | j | | | ESTs, Moderately similar to ribonuclease 6 precursor [*H.sapiens*] |
| 5907 | 1264 | AI104261 | h | | | ESTs |
| 11632 | 1215 | AI102427 | General | | | ESTs, Weakly similar to KIAA0324 [*H.sapiens*] |
| 4198 | 2220 | M83143 | b | | | Rat beta-galactoside-alpha 2,6-sialyltransferase mRNA |
| 23106 | 1337 | AI145081 | General | | | ESTs, Highly similar to cell division control protein CDC21 [*H.sapiens*] |
| 18672 | 1576 | AI178189 | General | | | ESTs, Weakly similar to Kruppel-like transcription factor [*R.norvegicus*], ESTs, Weakly similar to OZF RAT ZINC FINGER PROTEIN OZF [*R.norvegicus*] |
| 6791 | 571 | AA945613 | General,bb,dd | | DNA-damage inducible transcript 3 | ESTs |
| 1599 | 6 | AA686470 | j,w | | | DNA-damage inducible transcript 3 |
| 24049 | 1552 | AI177341 | General | | | ESTs, Highly similar to CGI-10 protein [*H.sapiens*] |
| 19038 | 204 | AA851818 | n | | | ESTs |
| 22183 | 520 | AA943217 | d | | | EST |
| 15907 | 698 | AA996422 | General,z | | | ESTs |
| 6439 | 1092 | AI058436 | k | | | ESTs, Moderately similar to P2CG MOUSE PROTEIN PHOSPHATASE 2C GAMMA ISOFORM [*M.musculus*] |
| 8212 | 1730 | AI231807 | h,q,cc | | ferritin light chain 1 | ferritin light chain 1 |
| 20169 | 2398 | X03347 | c | | | ESTs, Weakly similar to ankyrin [*R.norvegicus*] |
| 16656 | 1612 | AI179634 | General | | | ESTs, Moderately similar to AC006978 1 supported by human and rodent ESTs [*H.sapiens*] |
| 19411 | 378 | AA893667 | b,v | | | |
| 18910 | 1755 | AI232419 | y | | | ESTs, Weakly similar to YLC4_CAEEL HYPOTHETICAL 81.0 KD PROTEIN C35D10.4 IN CHROMOSOME III [*C.elegans*] |
| 23500 | 256 | AA860010 | m,r | | | *Rattus norvegicus* protein tyrosine phosphatase mRNA, complete cds |
| 15995 | 2267 | S74351 | e | | | ESTs |
| 3918 | 62 | AA801333 | a | | | |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 17753 | 1242 | AI103246 | General | | | ESTs, Highly similar to S65568 CCAAT-binding factor CBF2 - mouse [*M.musculus*] |
| 6044 | 935 | AI011285 | t | | | ESTs |
| 3091 | 1848 | AI236027 | aa | | | ESTs |
| 5723 | 1077 | AI045191 | General | | | ESTs, Weakly similar to FSPO RAT F-SPONDIN PRECURSOR [*R.norvegicus*] |
| 15312 | 275 | AA875126 | General | | | ESTs |
| 19322 | 205 | AA851960 | p | | melanoma antigen, family D, 1 | melanoma antigen, family D, 1 |
| 573 | 1737 | AI232087 | c | Glyoxylate and dicarboxylate metabolism | hydroxyacid oxidase 3 (medium-chain) | hydroxyacid oxidase 3 (medium-chain) |
| 25687 | 2435 | X51706 | w,cc | | ribosomal protein L9 | |
| 24237 | 66 | AA817726 | u | | | ESTs |
| 18522 | 1347 | AI145870 | n | | | ESTs |
| 16982 | 2202 | M58634 | e | | Insulin-like growth factor binding protein 1 | Insulin-like growth factor binding protein 1 |
| 21274 | 1871 | AI236726 | aa | | | ESTs |
| 6778 | 688 | AA964763 | General | | | ESTs, Highly similar to DRIM protein [*H.sapiens*] |
| 4588 | 771 | AB009636 | General | | | *Rattus norvegicus* mRNA for phosphoinositide 3-kinase, complete cds |
| 4441 | 2466 | X62146 | h,cc | | | ESTs, Highly similar to 60S RIBOSOMAL PROTEIN L11 [*R.norvegicus*] |
| 3073 | 1782 | AI233494 | m | | | ESTs, Weakly similar to I38079 OXA1 homolog [*H.sapiens*] |
| 20848 | 2446 | X54617 | c | | | Rat mRNA for myosin regulatory light chain (RLC) |
| 670 | 2445 | X54096 | dd | | Lecithin-cholesterol acyltransferase | Lecithin-cholesterol acyltransferase |
| 17809 | 5 | AA686461 | z | | ribosomal protein L30 | ribosomal protein L30 |
| 18957 | 1917 | D00512 | k,o | Butanoate metabolism, Fatty acid biosynthesis (path 2), Fatty acid metabolism, Lysine degradation, Propanoate metabolism, Pyruvate metabolism, Synthesis and degradation of ketone bodies, Tryptophan metabolism | Acetyl-Co A acetyltransferase 1, mitochondrial | Acetyl-Co A acetyltransferase 1, mitochondrial |
| 12248 | 513 | AA942829 | aa | | | ESTs, Weakly similar to T27118 hypothetical protein Y53C10A.5 - *Caenorhabditis elegans* [*C.elegans*] |
| 669 | 2085 | K03039 | i | | | ESTs, Rat mRNA for leucocyte-common antigen (L-CA) |
| 24590 | 2188 | M35299 | p | | Serine protease inhibitor, kanzai type 1/ Trypsin inhibitor-like protein, pancreatic | Serine protease inhibitor, kanzai type 1/Trypsin inhibitor-like protein, pancreatic |
| 5952 | 661 | AA963102 | e,General | | | *Rattus norvegicus* amino acid transporter system A (ATA2) mRNA, complete cds |
| 18425 | 1686 | AI230208 | General | | | ESTs, Weakly similar to p58 [*R.norvegicus*] |
| 9214 | 467 | AA925116 | a,w | | interferon gamma inducing factor binding protein | interferon gamma inducing factor binding protein |
| 4314 | 792 | AF010597 | g,x | | ATP-binding cassette, sub-family B (MDR/TAP), member 11 | ATP-binding cassette, sub-family B (MOR/TAP), member 11 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 18618 | 2163 | M24026 | w | | RT1 class Ib gene | RT1 class Ib gene |
| 19105 | 236 | AA859230 | General | | | ESTs, Highly similar to HG14 MOUSE NONHISTONE CHROMOSOMAL PROTEIN HMG-14 [*M.musculus*] |
| 9016 | 1152 | AI070903 | c | | | EST |
| 23005 | 512 | AA942770 | w | | | ESTs |
| 22379 | 1725 | AI231448 | z | | | ESTs, Highly similar to G6PI MOUSE GLUCOSE-6-PHOSPHATE ISOMERASE [*M.musculus*] |
| 9322 | 1551 | AI177333 | aa | | | ESTs |
| 18507 | 1482 | AI175551 | d,General,y | | | ESTs, Moderately similar to AF145O50 1 translation elongation factor 1-delta subunit [*R.norvegicus*] |
| 14258 | 1676 | AI229902 | e,i,General | | | ESTs |
| 21504 | 1327 | AI137941 | r | | | ESTs |
| 1801 | 215 | AA858636 | General | | | ESTs, Weakly similar to MCM6 RAT DNA REPLICATION LICENSING FACTOR MCM6 [*R.norvegicus*] |
| 22635 | 675 | AA964289 | e | | | ESTs |
| 17159 | 2036 | J00797 | General | | alpha-tubulin | alpha-tubulin |
| 6512 | 1843 | AI235898 | bb | | | ESTs |
| 15032 | 2382 | U89905 | l | | Methylacyl-CoA racemase alpha | Methylacyl-CoA racemase alpha |
| 15007 | 411 | AA900236 | General | | | ESTs |
| 5608 | 113 | AA819041 | General | | | ESTs |
| 9719 | 1166 | AI071722 | General | | | ESTs, Moderately similar to AF151892 1 CGI-134 protein [*H.sapiens*] |
| 12094 | 400 | AA899681 | k,bb,cc | | | ESTs, Weakly similar to 16.7Kd protein [*H.sapiens*] |
| 7926 | 1050 | AI043913 | f,x | | | ESTs |
| 21094 | 1925 | D10354 | p,z | Alanine and aspartate metabolism, Carbon fixation, Glutamate metabolism | glutamic-pyruvate trans-aminase (alanine amino-transferase) | glutamic-pyruvate transaminase (alanine aminotransferase) |
| 5141 | 481 | AA925393 | e | | | Rat mRNA for acetyl-coenzyme A carboxylase (EC 6.4.1.2.) 3' untranslated region |
| 16579 | 645 | AA957143 | j,v | | | ESTs, Weakly similar to T28060 hypothetical protein ZK863.6 - *Caenorhabditis elegans* [*C.elegans*] |
| 14509 | 618 | AA955871 | d | Glyoxylate and dicarboxylate metabolism | calpactin I heavy chain, hydroxyacid oxidase 3 (medium-chain), | ESTs |
| 6373 | 221 | AA858726 | n | | | ESTs |
| 574 | 2097 | L13039 | r,w | | unknown Glu-Pro dipeptide repeat protein | *Rattus norvegicus* clone BB.1.4.1 unknown Glu-Pro dipeptide repeat protein mRNA, complete cds, calpactin I heavy chain, hydroxyacid oxidase 3 (medium-chain) |
| 17577 | 21 | AA799566 | h | | | ESTs, Weakly similar to MT18_YEAST DNA REPAIR/TRANSCRIPTION PROTEIN MET18/MMS19 [*S.cerevisiae*] |
| 699 | 2349 | U55765 | p | | | *Rattus norvegicus* RASP1 mRNA, complete cds |
| 4730 | 412 | AA900326 | d | | | ESTs |
| 19288 | 1721 | AI231305 | q | pdgf | Platelet-derived growth factor receptor alpha | Platelet-derived growth factor receptor alpha |
| 8522 | 1127 | AI060071 | b | | | ESTs |
| 1884 | 1981 | D50695 | i,General | | | *Rattus norvegicus* mRNA for proteasomal ATPase (Tat-binding protein7), complete cds |
| 21471 | 198 | AA851343 | c | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 14393 | 937 | AI011367 | y | | immunoglobulin (CD79A) binding protein 1 | ESTs, Highly similar to coded for by human cDNAs W37389 [H.sapiens] immunoglobulin (CD79A) binding protein 1 |
| 21772 | 931 | AI011179 | h,r | | | ESTs |
| 11893 | 1709 | AI230951 | i | | | ESTs |
| 13332 | 366 | AA893080 | b,General | | | ESTs |
| 7782 | 1814 | AI234515 | a | | | ESTs |
| 4381 | 2026 | H33003 | p | | | ESTs, Highly similar to I49523 Mouse primary response gene B94 mRNA, 3' end mouse [M.musculus] |
| 20422 | 1288 | AI111858 | General | | | |
| 18958 | 1940 | D13921 | k,o | Butanoate metabolism, Fatty acid biosynthesis (path 2), Fatty acid metabolism, Lysine degradation, Propanoate metabolism, Pyruvate metabolism, Synthesis and degradation of ketone bodies, Tryptophan metabolism | Acetyl-Co A acetyltransferase 1, mitochondrial | Acetyl-Co A acetyltransferase 1, mitochondrial |
| 1598 | 2327 | U30186 | w | | DNA-damage inducible transcript 3 | DNA-damage inducible transcript 3 |
| 17301 | 2213 | M69246 | General | | serine proteinase inhibitor, clade H (heat shock protein 47), member 1 | collagen binding protein 1 |
| 11798 | 1108 | AI059337 | cc | | | ESTs |
| 11382 | 1311 | AI136692 | General | | | ESTs |
| 6825 | 1088 | AI045972 | n | | | ESTs |
| 12314 | 568 | AA945596 | p,q,General | | | ESTs, Moderately similar to LECT2 precursor [H.sapiens] |
| 4486 | 325 | AA892298 | c | | | ESTs, Weakly similar to matrin cyclophilin [R.norvegicus] |
| 18952 | 438 | AA924006 | h | | Tissue inhibitor of metalloproteinase 3 | Tissue inhibitor of metalloproteinase 3 |
| 8834 | 1348 | AI145899 | j | | | ESTs, Moderately similar to FLI-LRR associated protein-1 [M.musculus] |
| 4040 | 1622 | AI179993 | General | | | ESTs, Highly similar to Pax transcription activation domain interacting protein PTIP [M.musculus] |
| 3934 | 942 | AI011510 | e | | | ESTs |
| 18141 | 1555 | AI177413 | General | Oxidative phosphorylation, Type III protein | ATP synthase subunit d | ATP synthase subunit d, ESTs, Moderately similar to T46317 hypothetical protein DKFZp434A0612.1 [H.sapiens] |
| 24290 | 1067 | AI045040 | General | | | ESTs, Weakly similar to T15251 hypothetical protein K07B1.4 - Caenorhabditis elegans [C.elegans] |
| 3254 | 1929 | D10756 | c | Proteasome | proteasome (prosome, macropain) subunit, alpha type 5 | proteasome (prosome, macropain) subunit, alpha type 5 |
| 23469 | 1243 | AI03282 | aa | | | ESTs |
| 17962 | 774 | AB012230 | General | | nuclear factor I/B | nuclear factor I/B |
| 13138 | 1783 | AI233552 | u | | | ESTs |
| 10596 | 629 | AA956405 | bb | | | ESTs |
| 23320 | 607 | AA955164 | General,bb | | | ESTs |
| 15579 | 2181 | M33648 | o | | | Rat mitochondrial 3-hydroxy-3-methylglutaryl-CoA synthase mRNA, complete cds |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 6236 | 99 | AA818627 | f,g,y | | | EST, Moderately similar to ISI1 RAT INSULIN-INDUCED PROTEIN 1 [*R.norvegicus*] |
| 6633 | 1654 | AI228931 | x | | | ESTs |
| 26190 | 1183 | AI072578 | y | | | ESTs, Weakly similar to T46906 hypothetical protein DKFZp761D0223.1 [*H.sapiens*] |
| 7667 | 1766 | AI233687 | n | | | ESTs |
| 13932 | 1711 | AI230988 | b,m,General,y | Arginine and proline metabolism | Protein disulfide isomerase (Prolyl 4-hydroxylase, beta polypeptide) | Protein disulfide isomerase (Prolyl 4-hydroxylase, beta polypeptide) |
| 19392 | 2397 | X02918 | a,t | | | |
| 10695 | 132 | AA819679 | e | | | ESTs |
| 20704 | 2169 | M26127 | f,g,h,q,cc,dd | Fatty acid metabolism, Tryptophan metabolism | Cytochrome P450, subfamily I (aromatic compound-inducible), member A2 (Q42, form d) | Cytochrome P450, subfamily I (aromatic compound-inducible), member A2 (Q42, form d) |
| 1475 | 2103 | L16764 | c | | Heat shock protein 70-1 | ESTs, Highly similar to S10A RAT S-100 PROTEIN, ALPHA CHAIN [*R.norvegicus*], Heat shock protein 70-1 |
| 22725 | 416 | AA900506 | n | | Epoxide hydrolase 1 (microsomal xenobiotic hydrolase) | ESTs, Highly similar to TS24 MOUSE PROTEIN TSG24 [*M.musculus*] |
| 17541 | 2168 | M26125 | h,x,cc | | | Epoxide hydrolase 1 (microsomal xenobiotic hydrolase) |
| 21586 | 2516 | X97772 | General | Glycine, serine and threonine metabolism | 3-phosphoglycerate dehydrogenase | 3-phosphoglycerate dehydrogenase |
| 12551 | 1680 | AI230056 | c,m,General,u | | | ESTs |
| 17529 | 1423 | AI171460 | z | | | ESTs, Weakly similar to amyloid beta-peptide binding protein [*R.norvegicus*] |
| 21848 | 656 | AA957896 | k | | mitogen activated protein kinase kinase 2 | mitogen activated protein kinase kinase 2 |
| 4511 | 534 | AA944348 | p,General | | | ESTs |
| 14083 | 1549 | AI177181 | d | | | ESTs, Weakly similar to T18290 FYVE finger-containing phosphoinositide kinase mouse [*M.musculus*] |
| 3723 | 971 | AI012599 | dd | | | ESTs |
| 11546 | 1481 | AI175535 | General | | | ESTs, Moderately similar to putative oncogene protein [*H.sapiens*] |
| 19319 | 311 | AA891937 | i | | | ESTs, Highly similar to S66254 dolichyl-diphosphooligosaccharide-protein glycotransferase [*H.sapiens*] |
| 20088 | 343 | AA892666 | b,g | | | ESTs |
| 5241 | 499 | AA925986 | l | | | ESTs |
| 16124 | 1537 | AI176963 | | | | *Rattus norvegicus* transcription factor MRG1 mRNA, complete cds |
| 15599 | 2487 | X75253 | e,p,t | | phosphatidylethanolamine binding protein | phosphatidylethanolamine binding protein |
| 382 | 826 | AF080507 | General | | Mannose binding protein A, serum | Mannose binding protein A, serum |
| 2367 | 838 | AF095741 | n | | | *Rattus norvegicus* MG87 mRNA, complete cds |
| 17532 | 2059 | J03867 | General | Aminosugars metabolism | HHs:diaphorase (NADH) (cytochrome b-5 reductase) | Rat NADH-cytochrome b-5 reductase mRNA, complete cds |
| 12437 | 2030 | H33686 | j | | | ESTs, Moderately similar to SYC_HUMAN CYSTEINYL-TRNA SYNTHETASE [*H.sapiens*] |
| 16310 | 2098 | L13600 | x,dd | | | *Rattus norvegicus* glycine transporter mRNA, complete cds |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 12191 | 1959 | D26073 | v | | phosphoribosylpyro-phosphate synthetase-associated protein (39 kD) | phosphoribosylpyrophosphate synthetase-associated protein (39 kDa) |
| 5264 | 504 | AA926107 | r | | | ESTs, Highly similar to RGS3 RAT REGULATOR OF G-PROTEIN SIGNALING 3 [*R.norvegicus*] |
| 4428 | 1420 | AI171362 | bb | Oxidative phosphorylation, Ubiquinone biosynthesis | HHs:NADH dehydrogenase (ubiquinone) Fe-S protein 1 (75kD) (NADH-coenzyme Q reductase) | ESTs, Moderately similar to NUAM_HUMAN NADH-UBIQUINONE OXIDOREDUCTASE 75 KD SUBUNIT PRECURSOR [*H.sapiens*] |
| 7893 | 1047 | AI043761 | i | | | EST |
| 9498 | 1194 | AI073164 | c,v | | secretory carrier membrane protein 1 | secretory carrier membrane protein 1 |
| 15860 | 1234 | AI102868 | m | | Asialoglycoprotein receptor 1 (hepatic lectin) | ESTs, Weakly similar to phosphoserine aminotransferase [*H.sapiens*] |
| 20153 | 2084 | K02817 | f | | | Asialoglycoprotein receptor 1 (hepatic lectin) |
| 15398 | 1865 | AI236566 | General | | | ESTs, Moderately similar to T12473 hypothetical protein DKFZp564G1762.1 [*H.sapiens*] |
| 7776 | 1009 | AI028963 | General | | | ESTs |
| 17897 | 381 | AA893905 | d,e | | | ESTs |
| 570 | 2498 | X82445 | r | | nuclear distribution gene C homolog (Aspergillus) | nuclear distribution gene C homolog (Aspergillus) |
| 8856 | 1179 | AI072402 | o | | | ESTs, Moderately similar to KRAB-zinc finger protein KZF-2 [*R.norvegicus*] |
| 20448 | 2431 | X17053 | i | | Small inducible gene JE | Small inducible gene JE |
| 12365 | 1623 | AI180013 | d | | | Rat MHC class I IgG Fc region receptor large subunit p51 (FcRn) mRNA, complete cds |
| 9800 | 1169 | AI072014 | General | | | ESTs, Weakly similar to AF165892 1 RNA binding protein SiahBP [*R.norvegicus*] |
| 13899 | 1691 | AI230424 | General | | | ESTs |
| 1386 | 2094 | L08505 | i | | dynein, cytoplasmic, heavy chain 1 | dynein, cytoplasmic, heavy chain 1 |
| 4650 | 1206 | AI101582 | General | | | ESTs, Weakly similar to T26236 hypothetical protein W06D4.4 - *Caenorhabditis elegans* [*C.elegans*] |
| 5541 | 1286 | AI111707 | i | | | ESTs |
| 6985 | 927 | AI010862 | h | | | EST |
| 5874 | 1345 | AI45801 | General | | | ESTs |
| 22023 | 1799 | AI233822 | i, | | | ESTs |
| 9166 | 1317 | AI37406 | m | | | ESTs |
| 11937 | 1314 | AI37218 | General | | | ESTs |
| 1888 | 2017 | E13573 | l | | | Rat brain mRNA for neuronal death protein, complete cds |
| 10544 | 1982 | D63411 | c,r | | | *Rattus norvegicus* outer mitochondrial membrane receptor rTOM20 mRNA, complete cds |
| 2557 | 1525 | AI176820 | v | | | ESTs |
| 22667 | 552 | AA945069 | c | | | ESTs |
| 20859 | 2235 | M92074 | bb | | troponin I, cardiac | troponin I, cardiac |
| 4107 | 391 | AA899109 | General,y | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 6891 | 2347 | U53922 | n | | DnaJ-like protein | DnaJ-like protein |
| 25400 | 2140 | M14776 | h,n,x | | diacylglycerol acyltransferase | diacylglycerol acyltransferase |
| 14621 | 242 | AA859529 | bb | | | |
| 5497 | 825 | AF080468 | g,bb,dd | | glucose-6-phosphatase, transport protein 1 | glucose-6-phosphatase, transport protein 1 |
| 1764 | 2499 | X83399 | dd | | | R.norvegicus mRNA eIF-4E |
| 25170 | 800 | AF030087 | cc | | | |
| 23171 | 1685 | AI230190 | i | | damage-specific DNA binding protein 1 | damage-specific DNA binding protein 1 |
| 23711 | 1505 | AI176376 | t | | ATPase Na+/K+ transporting beta 1 polypeptide | ATPase Na+/K+ transporting beta 1 polypeptide |
| 13762 | 1688 | AI230326 | m | | | ESTs |
| 20808 | 195 | AA851281 | dd | | | ESTs, Weakly similar to JC4230 ribosomal protein L7 - rat [*R.norvegicus*] |
| 17591 | 1419 | AI721354 | c | | | ESTs |
| 19271 | 1727 | AI231566 | x,aa | | | ESTs, Highly similar to MAX RAT MAX PROTEIN [*R.norvegicus*] |
| 16898 | 1382 | AI170249 | General | | | ESTs, Highly similar to similar to nitrogen permease regulator [*H.sapiens*] |
| 15471 | 251 | AA859869 | h | | 26S proteasome, subunit p112 | 26S proteasome, subunit p112 |
| 4439 | 2 | AA685175 | u | | | ESTs, Weakly similar to ES/130-related protein [*H.sapiens*] |
| 8058 | 91 | AA818475 | r | | | ESTs |
| 13874 | 1674 | AI229832 | General | | | ESTs, Weakly similar to KIAA0859 protein [*H.sapiens*] |
| 4017 | 87 | AA818287 | a | | | ESTs |
| 2744 | 1994 | D87991 | w | | | ESTs, Highly similar to JC5026 UDP-galactose transporter related protein 1 - rat [*R.norvegicus*] |
| 4491 | 108 | AA818798 | i | | | *Rattus norvegicus* mRNA for cathepsin Y, partial cds |
| 11904 | 1989 | D85183 | b,w | | Protein tyrosine phosphatase, non-receptor type substrate 1 (SHP substrate 1) | Protein tyrosine phosphatase, non-receptor type substrate 1 (SHP substrate 1) |
| 6107 | 1935 | D13122 | d,i | | ATPase inhibitor (rat mitochondrial IF1 protein) | ATPase inhibitor (rat mitochondrial IF1 protein) |
| 1572 | 1592 | AI178828 | u | | | *Rattus norvegicus* Sprague/Dawley PHAS I mRNA, complete cds |
| 11191 | 979 | AI013042 | General | | | ESTs, Moderately similar to SRE1_HUMAN STEROL REGULATORY ELEMENT BINDING PROTEIN-1 [*H.sapiens*] |
| 12734 | 934 | AI011208 | b | | | ESTs |
| 1291 | 758 | AB000491 | c | | for proteasomal ATPase (SUG1) | for proteasomal ATPase (SUG1) |
| 1843 | 2182 | M33962 | y,aa | | Protein-tyrosine phosphatase | Protein-tyrosine phosphatase |
| 14390 | 1753 | AI232385 | n | | | ESTs |
| 7872 | 2231 | M86912 | d,e | | | EST |
| 21748 | 181 | AA850777 | General | | | ESTs |
| 15743 | 699 | AA996434 | q | | phosphatidylinositol 3-kinase | phosphatidylinositol 3-kinase |
| 23445 | 2227 | M84719 | x | | Flavin-containing monooxygenase 1 | Flavin-containing monooxygenase 1 |
| 14651 | 1846 | AI235919 | dd | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 17289 | 302 | AA891785 | z | Citrate cycle (TCA cycle), Glutathione metabolism, Reductive carboxylate cycle (CO2 fixation) | HMn:isocitrate dehydrogenase 2 (NADP+), mitochondrial | ESTs, Weakly similar to IDHC RAT ISOCITRATE DEHYDROGENASE [*R.norvegicus*] |
| 21011 | 2024 | H32189 | x,dd | Glutathione metabolism | Glutathione-S-transferase, mu type 2 (Yb2) | Glutathione-S-transferase, mu type 2 (Yb2) |
| 17734 | 747 | AA998683 | j | | Heat shock 27 kDa protein | ESTs, Heat shock 27 kDa protein |
| 1682 | 523 | AA943555 | h | | linker of T-cell receptor pathways | linker of T-cell receptor pathways |
| 21657 | 2463 | X61381 | a,e,w | | | *Rattus norvegicus* interferon-inducible protein variant 10 mRNA, complete cds |
| 17573 | 983 | AI013132 | v | | | *Rattus norvegicus* membrane- and microfilament-associated protein p58 mRNA, complete cds |
| 4001 | 1213 | AI02070 | General | | | ESTs |
| 24321 | 1748 | AI232340 | e,n | | Stromal cell-derived factor 1 | Stromal cell-derived factor 1 |
| 5384 | 288 | AA891041 | n,v | | jun B proto-oncogene | jun B proto-oncogene |
| 6013 | 83 | AA818144 | t | | C-reactive protein | C-reactive protein |
| 9754 | 1294 | AI112194 | c,z | | | ESTs |
| 17676 | 2391 | V01235 | n,x | | Fatty acid binding protein 1, liver | Fatty acid binding protein 1, liver |
| 17524 | 921 | AI010568 | c | | Growth hormone receptor | Growth hormone receptor |
| 11960 | 300 | AA891740 | l | | | ESTs, Weakly similar to EPOR RAT ERYTHROPOIETIN RECEPTOR PRECURSOR [*R.norvegicus*] |
| 3645 | 1835 | AI235362 | f | | | ESTs, Highly similar to NOF1 [*H.sapiens*] |
| 12964 | 1857 | AI236227 | z | | | ESTs |
| 18750 | 1978 | D45250 | w | | protease (prosome, macropain) 28 subunit, beta | protease (prosome, macropain) 28 subunit, beta |
| 21053 | 2143 | M15481 | f,t | | | Rat insulin-like growth factor-I mRNA, 3' end |
| 14910 | 1564 | AI177631 | General | | | ESTs, Moderately similar to myosin-binding C-protein [*R.norvegicus*] |
| 3963 | 435 | AA923955 | j | | | ESTs |
| 8898 | 1259 | AI103957 | d,e | | CD81 antigen (target of antiproliferative antibody 1) | CD81 antigen (target of antiproliferative antibody 1) |
| 2799 | 998 | AI013778 | c,u | | Lectin, galactose binding, soluble 9 (Galectin-9) | Lectin, galactose binding, soluble 9 (Galectin-9) |
| 957 | 2367 | U72741 | t | | | |
| 862 | 2357 | U62940 | k | | stress-inducible chaperone mt-GrpE#1 | stress-inducible chaperone mt-GrpE#1 |
| 19067 | 248 | AA859663 | General | | | ESTs |
| 12482 | 1336 | AI144965 | q | | | ESTs, Weakly similar to T34021 protein kinase SK2 - rat [*R.norvegicus*] |
| 356 | 2260 | S66024 | g,General | | CAMP responsive element modulator, transcriptional repressor CREM | CAMP responsive element modulator |
| 606 | 2484 | X71898 | j | | urinary plasminogen activator receptor 2 | urinary plasminogen activator receptor 2 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 5360 | 950 | AI011763 | General | | alpha actinin 4 | alpha actinin 4 |
| 5995 | 1759 | AI232565 | General | | | ESTs |
| 23512 | 608 | AA955282 | n,General | | | ESTs |
| 18421 | 572 | AA945617 | General | | | ESTs, Highly similar to nitrilase homolog 1 [*M.musculus*] |
| 2536 | 1518 | AI176616 | e,m,q | | | ESTs |
| 22213 | 1822 | AI234858 | General | | | ESTs, Highly similar to KIAA0017 protein [*H.sapiens*] |
| 17832 | 960 | AI012182 | General | | | Rat major beta-globin mRNA, complete cds |
| 1321 | 2120 | L37333 | g | Galactose metabolism, Glycolysis/Gluconeogenesis, Starch and sucrose metabolism | Glucose-6-phosphatase | Glucose-6-phosphatase |
| 10503 | 1957 | D21215 | d,h | | coagulation factor X | coagulation factor X |
| 19040 | 2055 | J03627 | x | | S-100 related protein, clone 42C | S-100 related protein, clone 42C |
| 14545 | 53 | AA800456 | r | | | ESTs |
| 4250 | 101 | AA818700 | v | | | ESTs |
| 7084 | 1689 | AI230362 | q | | | ESTs, Moderately similar to T46458 hypothetical protein DKFZp434M102.1 [*H.sapiens*] |
| 11424 | 928 | AI010936 | b | | | ESTs, Moderately similar to PTN3_HUMAN PROTEIN TYROSINE PHOSPHATASE, NON-RECEPTOR TYPE 3 [*H.sapiens*] |
| 1641 | 2014 | E03428 | m,v,w | | Peptidylglycine alpha-amidating monooxygenase | Peptidylglycine alpha-amidating monooxygenase |
| 10153 | 1102 | AI059110 | dd | | | EST |
| 22311 | 1492 | AI176007 | t,aa | | | ESTs, Highly similar to PM5P_HUMAN PROTEIN PM5 PRECURSOR [*H.sapiens*] |
| 12358 | 1395 | AI170661 | r | | RAS p21 protein activator 3 | RAS p21 protein activator 3 |
| 23312 | 309 | AA891920 | i | | | ESTs, Weakly similar to A Chain A, Nuclear Transport Factor 2 [*R.norvegicus*] |
| 18085 | 212 | AA858603 | r | | | EST, Weakly similar to T16084 hypothetical F16H11.1 - *Caenorhabditis elegans* mRNA for thiol-specific |
| 19254 | 794 | AF014009 | d | Methane metabolism, Phenylalanine metabolism | HMm:peroxiredoxin 5 | *Rattus norvegicus* mRNA for thiol-specific antioxidant protein (1-Cys peroxiredoxin) |
| 19069 | 525 | AA943737 | e,j | | endothelial differentiation sphingolipid G-protein-coupled recep | endothelial differentiation sphingolipid G-protein-coupled receptor 1 |
| 3467 | 1894 | AI237835 | n,General,aa | | | ESTs, Moderately similar to MXI1 RAT MAX INTERACTING PROTEIN 1 [*R.norvegicus*] |
| 8215 | 1431 | AI171692 | m,General | | ferritin light chain 1 | *Rattus norvegicus* kynurenine aminotransferase/glutamine transaminase K (Kat) gene, complete cds, ferritin light chain 1 |
| 3882 | 910 | AI010191 | a | | Solute carrier family 2 A2 (glucose transporter, type 2) | ESTs, Highly similar to serine/threonine kinase [*R.norvegicus*] |
| 15872 | 2117 | L28135 | t,u,w | | | Solute carrier family 2 A2 (glucose transporter, type 2) |
| 21604 | 1004 | AI013913 | General | | | ESTs |
| 19575 | 182 | AA850814 | y | | | ESTs, Moderately similar to AF151807 1 CGI-49 protein [*H.sapiens*] |
| 23612 | 1400 | AI170751 | g | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 23884 | 2214 | M73714 | k | Arginine and proline metabolism, Ascorbate and aldarate metabolism, Bile acid biosynthesis, Butanoate metabolism, Fatty acid metabolism, Glycerolipid metabolism, Histidine metabolism, Lysine degradation, Propanoate metabolism, Pyruvate metabolism, Tryptophan metabolism, Valine, leucine and isoleucine degradation, beta-Alanine metabolism | alcohol dehydrogenase famile 3, subfamily A2 | alcohol dehydrogenase family 3, subfamily A2 |
| 3256 | 1370 | AI69479 | d,General | Proteasome | proteasome (prosome, macropain) subunit, alpha type 5 | proteasome (prosome, macropain) subunit, alpha type 5 |
| 2691 | 694 | AA965075 | General | | | ESTs |
| 15914 | 723 | AA997711 | General | | | ESTs |
| 16427 | 2156 | M21354 | d | | procollagen, type III, alpha 1 | procollagen, type III, alpha 1 |
| 13782 | 1570 | AI177848 | General | | | ESTs |
| 4312 | 773 | AB010635 | l,General,x,z | | | Rattus norvegicus mRNA for carboxylesterase precursor, complete cds |
| 16150 | 15 | AA799489 | k,o | Fatty acid metabolism | acyl-coA oxidase | acyl-coA oxidase |
| 21660 | 1375 | AI169751 | General,w | | | Rattus norvegicus interferon-inducible protein variant 10 mRNA, complete cds |
| 17903 | 1713 | AI231083 | n,aa | | | ESTs, Moderately similar to AF155103 1 NY-REN-25 antigen [H.sapiens] |
| 1583 | 2296 | U07201 | m,y | | Asparagine synthetase | Asparagine synthetase |
| 18417 | 1683 | AI230166 | a | | | ESTs |
| 6743 | 1719 | AI231219 | d,General | | | ESTs |
| 21916 | 992 | AI013627 | e | | | Rattus norvegicus DAD-1 gene |
| 48 | 1950 | D17310 | bb | | | Rat 3-alpha-hydroxysteroid dehydrogenase (3-alpha-HSD) mRNA, complete cds |
| 21975 | 1453 | AI172247 | b | Purine metabolism | xanthine dehydrogenase | xanthine dehydrogenase |
| 15980 | 261 | AA866426 | z | | | ESTs |
| 18302 | 2332 | U33500 | n | | | Rattus norvegicus retinol dehydrogenase type II mRNA, complete cds |
| 2103 | 189 | AA851135 | z | | | Rattus norvegicus ribosomal protein S271 (S27-1) mRNA, complete cds |
| 3145 | 712 | AA997237 | y | | | ESTs |
| 17549 | 348 | AA892776 | k,General | | | Rat mitochondrial proton/phosphate symporter mRNA, complete cds |
| 798 | 2338 | U38253 | y | | | Rattus norvegicus initiation factor eIF-2B gamma subunit (eIF-2B gamma) mRNA, complete cds |
| 15997 | 2287 | U02553 | e | | | Rattus norvegicus protein tyrosine phosphatase mRNA, complete cds |
| 18000 | 2313 | U19485 | t | | | Rattus norvegicus spp-24 precursor mRNA, partial cds |
| 18002 | 1041 | AI043655 | i,j,v,z,aa | | | Rattus norvegicus spp-24 precursor mRNA, partial cds |
| 5967 | 1218 | AI102520 | w | | | ESTs, Moderately similar to AF161588 1 GABA-A receptor-associated protein [R.norvegicus] |
| 18393 | 1697 | AI230632 | c | | | ESTs |
| 3993 | 484 | AA925540 | l | | | ESTs |

TABLE 1-continued

| GLGC ID | SeqID | GenBank Acc | Model Code | Pathway Name | Known Gene Name | Unigene Cluster Title |
|---|---|---|---|---|---|---|
| 17849 | 414 | AA900460 | d,General | | | ESTs, Weakly similar to TCPA RAT T-COMPLEX PROTEIN 1, ALPHA SUBUNIT [R.norvegicus] |
| 4272 | 1722 | AI231309 | k,o | | | ESTs, Moderately similar to AF153605 1 androgen induced protein [H.sapiens] |
| 24091 | 653 | AA957612 | a | | | EST |
| 23031 | 665 | AA963661 | e | | | ESTs |
| 7420 | 1016 | AI029291 | k | | | ESTs, Highly similar to ClpX-like protein [H.sapiens] |
| 22619 | 904 | AI009825 | m | | | ESTs |
| 26123 | 860 | AI008396 | General | | | Rattus norvegicus aiar mRNA for androgen-inducible aldehyde reductase, complete cds |
| 23322 | 351 | AA892821 | g,x | | | |
| 20716 | 2237 | M94548 | a,h,t | Fatty acid metabolism, Tryptophan metabolism | cytochrome P450 4F1 | cytochrome P450 4F1 |
| 12999 | 1502 | AI167276 | j | | | ESTs, Highly similar to UAP1_HUMAN UDP-N-ACETYLHEXOSAMINE PYROPHOSPHORYLASE [H.sapiens] |
| 1159 | 313 | AA891949 | General | | | ESTs |
| 24019 | 2489 | X77235 | j | | ADP-ribosylation-like 4 | ADP-ribosylation-like 4 |
| 7427 | 2070 | J05122 | u | | Benzodiazepin receptor (peripheral) | Benzodiazepin receptor (peripheral) |
| 6121 | 146 | AA848573 | p | | | ESTs, Highly similar to H4_HUMAN HISTONE H4 [R.norvegicus] |
| 18473 | 1353 | AI168975 | x | | sulfate anion transporter | sulfate anion transporter |
| 43 | 2110 | L23413 | General | | | |
| 6919 | 917 | AI010461 | o,General,y | | | ESTs |
| 11431 | 1853 | AI236120 | j,aa | | | ESTs |
| 16173 | 642 | AA957003 | w | | | Rattus norvegicus intercellular calcium-binding protein (MRP8) mRNA, complete cds |
| 17489 | 970 | AI012566 | bb | | unconventional myosin Myr2 I heavy chain | unconventional myosin Myr2 I heavy chain |
| 18704 | 1425 | AI171562 | dd | | nuclear protein E3-3 orf1 | nuclear protein E3-3 orf1 |
| 23321 | 351 | AA892821 | f,m,u | | | Rattus norvegicus aiar mRNA for androgen-inducible aldehyde reductase complete cds |
| 906 | 2378 | U83112 | l | | forkhead box M1 | forkhead box M1 |
| 22958 | 1422 | AI171374 | j | | | ESTs, Moderately similar to meningioma-expressed antigen 11 [H.sapiens] |
| 2330 | 676 | AA964292 | General | Androgen and estrogen metabolism, Pentose and glucuronate interconversions, Porphyrin and chlorophyll metabolism, Starch and sucrose metabolism | UDP-glucuronosyltransferase 1 family, member 1 | EST |
| 1354 | 1971 | D38065 | f,l,x | | | Rattus norvegicus cytoplasmic dynein intermediate chain 2C mRNA, complete cds, UDP-glucuronosyltransferase 1 family, member 1 |
| 5824 | 1082 | AI045555 | f,l | | | ESTs |
| 19783 | 1605 | AI179388 | g | | | ESTs, Weakly similar to T24789 hypothetical protein T10C6.5 - Caenorhabditis elegans [C.elegans] |
| 268 | 2362 | U67908 | General,bb | | Chymase 1, mast cell | Chymase 1, mast cell |
| 20988 | 418 | AA900562 | j | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 20123 | 1173 | AI072214 | c,d,General,u | | | ESTs, Weakly similar to T26686 hypothetical protein Y38F1A.6 - Caenorhabditis elegans [C.elegans] |
| 23192 | 289 | AA891107 | p,r,General | | | Rattus norvegicus diphosphoinositol polyphosphate phosphohydolase type II (Nudt4) mRNA, complete cds |
| 5197 | 1246 | AI103376 | m | | | ESTs, Weakly similar to T31650 hypothetical protein Y57A10A.cc - Caenorhabditis elegans [C.elegans] |
| 21462 | 194 | AA851261 | General | | | ESTs, Weakly similar to A61382 phosphorylation regulatory protein HP-10 [H.sapiens] |
| 11504 | 1429 | AI171652 | b | | | ESTs |
| 15081 | 234 | AA859218 | General | | | ESTs |
| 6826 | 888 | AI009493 | d,General | | | ESTs |
| 11403 | 1412 | AI171088 | d | | spermidine synthase | spermidine synthase |
| 15551 | 1704 | AI230759 | n | | | ESTs, Moderately similar to ornithine decarboxylase antizyme 2 [M.musculus] |
| 14033 | 978 | AI012979 | aa | | | ESTs |
| 15191 | 1508 | AI176456 | b,g | | | Rat metallothionein-2 and metallothionein-1 genes, complete cds |
| 24234 | 2359 | U63923 | d,General | Pyrimidine metabolism | thioredoxin reductase 1 | thioredoxin reductase 1 |
| 5873 | 1084 | AI045767 | General | | | ESTs |
| 18168 | 516 | AA942995 | z | | | ESTs, Highly similar to T50630 hypothetical protein DKFZp762N0610.1 [H.sapiens] |
| 21904 | 2164 | M24239 | h,q,x,cc,dd | Prostaglandin and | prostaglandin D2 | prostaglandin D2 synthase 2, hematopoietic |
| 1125 | 1984 | D82071 | g,General | leukotriene metabolism | synthase 2, hematopoietic | |
| 1266 | 2273 | S80631 | m | | | Rat ig epsilon heavy chain, complete coding region and 3' ut, mma |
| 17353 | 852 | AI008020 | bb | | | Rat cytosolic malic enzyme mRNA, 3' flank |
| 3404 | 1966 | D30740 | c | | 14 - 3 - 3 - zeta isoform, Tyrosine 3-monooxygenase/tryptophan 5-monooxygenase activation protein, zeta polypeptide | Tyrosine 3-monooxygenase/tryptophan 5-monooxygenase activation protein, zeta polypeptide |
| 5953 | 1416 | AI171231 | General | | | Rattus norvegicus amino acid transporter system A (ATA2) mRNA, complete cds |
| 9079 | 1157 | AI071251 | g | | | ESTs |
| 22081 | 543 | AA944818 | General,aa | | | ESTs |
| 16267 | 1261 | AI103977 | i,j | | | ESTs, Highly similar to I39358 heterogeneous nuclear ribonucleoprotein H [H.sapiens] |
| 23547 | 1521 | AI176734 | General | | | ESTs, Weakly similar to T22286 hypothetical protein F46B6.3 - Caenorhabditis elegans [C.elegans] |
| 16518 | 1511 | AI176546 | o | | | ESTs, Moderately similar to HS9B RAT HEAT SHOCK PROTEIN HSP 90-BETA [R.norvegicus] |
| 16696 | 24 | AA799607 | cc | | | ESTs |
| 10093 | 1096 | AI058746 | cc | | | ESTs |
| 6291 | 1335 | AI144797 | General | | | ESTs |
| 25070 | 2281 | S83279 | k,o | Androgen and estrogen metabolism | peroxisomal multifunctional enzyme type II | peroxisomal multifunctional enzyme type II |
| 10985 | 112 | AA818998 | General | | | ESTs, Weakly similar to HP33 [R.norvegicus] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 4317 | 1161 | AI071531 | i | | | *Rattus norvegicus* mRNA for endothelial receptor for oxidized low-density lipoprotein, complete cds |
| 3265 | 728 | AA997784 | c,m | | | EST |
| 3242 | 719 | AA997596 | General | | | ESTs |
| 16781 | 1815 | AI234527 | p,General | Glutathione metabolism | HMm:glutathione S-transferase, alpha 4 | ESTs, Highly similar to XURT8C glutathione transferase (EC 2.5.1.18)8, cytosolic - rat [*R.norvegicus*] |
| 23874 | 1250 | AI103556 | g,General | | | ESTs, Highly similar to CKS1_HUMAN CYCLIN-DEPENDENT KINASES REGULATORY SUBUNIT 1 [*M.musculus*] |
| 1394 | 2336 | U37099 | l | | | *Rattus norvegicus* GTP-binding protein (rab 3C) mRNA, complete cds |
| 1597 | 795 | AF014503 | t | | | *Rattus norvegicus* p8 mRNA, complete cds |
| 22747 | 1437 | AI171832 | General | | | ESTs, Moderately similar to AF151848 1 CGI-90 protein [*H.sapiens*] |
| 19590 | 1992 | D87336 | r | | | ESTs, Highly similar to BLMH RAT BLEOMYCIN HYDROLASE [*R.norvegicus*] |
| 24368 | 1630 | AI180392 | d | | | ESTs, Highly similar to AF114169 1 nucleotide-binding protein short form [*M.musculus*] |
| 11416 | 1452 | AI172185 | c,General,w | Sterol biosynthesis | HMm:sterol-C5-desaturase (fungal ERG3, delta-5-desaturase) homolog [*S.cerevisae*] | ESTs, Highly similar to NOF 1 [*H.sapiens*] |
| 7916 | 1049 | AI043855 | General | | | *Rattus norvegicus* C5D mRNA for sterol C5-desaturase, complete cds |
| 18606 | 2443 | X53504 | w,cc | | | ESTs, Highly similar to 60S RIBOSOMAL PROTEIN L12 [*R.norvegicus*] |
| 19584 | 2417 | X13905 | v | | | ESTs, Moderately similar to RB1A RAT RAS-RELATED PROTEIN RAB-1A [*R.norvegicus*] |
| 12606 | 2204 | M59861 | General,u,cc | One carbon pool by folate | 10-formyltetrahydrofolate dehydrogenase | 10-formyltetrahydrofolate dehydrogenase |
| 3362 | 736 | AA998092 | z | | | EST |
| 2123 | 1673 | AA229746 | dd | | | ESTs, Weakly similar to CD53 RAT LEUKOCYTE SURFACE ANTIGEN CD53 [*R.norvegicus*] |
| 20601 | 2438 | X52625 | d,r | Butanoate metabolism, Synthesis and degradation of ketone bodies, Valine, leucine and isoleucine degradation | 3-hydroxy-3-methyl-glutaryl-Coenzyme A synthase 1 | 3-hydroxy-3-methylglutaryl-Coenzyme A synthase 1 |
| 25091 | 2476 | X65190 | a | | | ESTs |
| 14353 | 244 | AA859585 | c | | | ESTs, Highly similar to MAN2 RAT ALPHA-MANNOSIDASE II [*R.norvegicus*] |
| 6628 | 1591 | AI178793 | p | | | |
| 515 | 2474 | X63854 | i,v | | Transporter 2, ABC (ATP binding cassette) | Transporter 2, ABC (ATP binding cassette) |
| 22187 | 521 | AA943229 | a | | | EST |
| 14996 | 2426 | X16038 | m,r,y | Folate biosynthesis, Glycerolipid metabolism | Tissue-nonspecific ALP alkaline phosphatase | Tissue-nonspecific ALP alkaline phosphatase |
| 1114 | 1019 | AI029917 | b | | | Rat brain neuron-specific enolase mRNA, complete cds |
| 6033 | 1769 | AI233081 | m | | | ESTs |
| 16650 | 1975 | D42137 | r | | Annexin V | Annexin V |
| 24211 | 1287 | AI111853 | b | | | ESTs, Highly similar to H33_HUMAN HISTONE H3.3 [*R.norvegicus*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 6816 | 1249 | AI103458 | General | | | ESTs, Weakly similar to T22612 hypothetical protein F54B3.3 - Caenorhabditis elegans [C.elegans] |
| 17333 | 312 | AA891940 | dd | | | ESTs, Highly similar to RHOC MOUSE TRANSFORMING PROTEIN RHOC [M.musculus] |
| 16216 | 611 | AA955392 | General | | | ESTs |
| 8860 | 583 | AA945915 | General | | | ESTs |
| 17359 | 850 | AI007981 | p | | | ESTs, Moderately similar to AC004882 5 similar to cytochrome Bc1 J chain [H.sapiens] |
| 4207 | 567 | AA945591 | o,u | | | ESTs, Weakly similar to JC5105 stromal cell-derived factor 2 - mouse [M.musculus] |
| 5979 | 75 | AA817990 | General | Arginine and proline metabolism, D-Glutamine and D-glutamate metabolism, Glutamate metabolism, Nitrogen metabolism, Urea cycle and metabolism of amino groups | Glutamate dehydrogenase | ESTs |
| 4573 | 1611 | AI179613 | x | | | Glutamate dehydrogenase |
| 16449 | 2241 | M95591 | General | Sterol biosynthesis, Terpenoid biosynthesis | farnesyl diphosphate transferase 1 | farnesyl diphosphate farnesyl transferase 1 |
| 2532 | 1513 | AI76590 | b | | | ESTs, Weakly similar to S68418 protein phosphatase 1 M chain M110 isoform - [R.norvegicus] |
| 5046 | 1895 | AI237855 | c,dd | | | ESTs |
| 3095 | 709 | AA997077 | b | | | ESTs, Moderately similar to 3'-5' exonuclease TREX1 [M.musculus] |
| 19993 | 1407 | AI170777 | General | | mitochondrial aconitase (nuclear aco2 gene) | mitochondrial aconitase (nuclear aco2 gene) |
| 3916 | 1378 | AI169947 | d,u | | | ESTs |
| 21812 | 718 | AA997588 | bb | | | ESTs, Weakly similar to T23657 hypothetical protein M0F1.6 - Caenorhabditis elegans [C.elegans] |
| 4917 | 443 | AA924140 | General | | | ESTs, Weakly similar to Y193_HUMAN HYPOTHETICAL PROTEIN KIAA0193 [H.sapiens] |
| 4134 | 192 | AA851240 | p,General | | | ESTs |
| 12766 | 968 | AI012505 | General | | | ESTs, Weakly similar to AC004876 5 similar to predicted proteins AAB54240 [H.sapiens] |
| 6547 | 959 | AI012181 | r | | | ESTs, Highly similar to S65755 tetrahydrofolylpolyglutamate synthase [M.musculus] |
| 18867 | 1995 | D88250 | e,q | Glutathione metabolism | glutathione S-transferase, mu type 3 (Yb3) | Rattus norvegicus mRNA for serine protease, complete cds |
| 20862 | 2009 | E01415 | General,w | | | glutathione S-transferase, mu type 3 (Yb3) |
| 1549 | 2075 | J05519 | t | Folate biosynthesis, Glyoxylate and dicarboxylate metabolism, One carbon pool by folate | C1-tetrahydrofolate synthase | C1-tetrahydrofolate synthase |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 20431 | 2275 | S81448 | General | Androgen and estrogen metabolism, Bile biosynthesis | Steroid-5-alpha-reductase, alpha polypeptide 1 (3-oxo-5 alpha-steroid delta 4-dehydrogenase alpha 1) | Steroid-5-alpha-reductase, alpha polypeptide 1 (3-oxo-5 alpha-steroid delta 4-dehydrogenase alpha 1) |
| 3149 | 384 | AA894030 | o | | | ESTs |
| 7381 | 1013 | AI029132 | z | | | ESTs, Moderately similar to Similar to S.cerevisiae hypothetical protein L311 [H.sapiens] |
| 21400 | 2190 | M36410 | General | Folate biosynthesis | sepiapterin reductase | sepiapterin reductase |
| 25137 | 763 | AB005540 | c | | | ESTs |
| 11228 | 1235 | AI102871 | k | | | ESTs, Moderately similar to purine nucleoside phosphorylase [M.musculus] |
| 15218 | 1216 | AI102495 | General | | | ESTs, Moderately similar to G01251 Rar protein [H.sapiens] |
| 23163 | 480 | AA925328 | General | | | Rat mRNA for mitochondrial long-chain enoyl-CoA hydratase/3-hydroxyacyl-CoA dehydrogenase alpha-subunit of mitochondrial trifunctional protein, complete cds |
| 16768 | 1948 | D16478 | k,o | | | ESTs |
| 3516 | 1472 | AI175064 | General,aa | | | ESTs, Weakly similar to 100K RAT 100 KD PROTEIN [R.norvegicus] |
| 15685 | 1803 | AI233870 | r,General | | | EST |
| 23847 | 637 | AA956723 | General | | | ESTs, Moderately similar to AF132950 1 CGI-16 protein [H.sapiens] |
| 25566 | 612 | AA955482 | bb | | | Rattus norvegicus liver-specific transport protein mRNA, complete cds |
| 32 | 2115 | L27651 | d | | solute carrier family 22 (organic anion transporter), member 7 | |
| 23802 | 635 | AA956535 | j | | | ESTs, Highly similar to similar to human Sua1 [M.musculus] |
| 21354 | 401 | AA899721 | k,o | | | ESTs |
| 8977 | 33 | AA799741 | z | | | ESTs, Moderately similar to putative ATP-dependent mitochondrial RNA helicase [H.sapiens] |
| 18891 | 452 | AA924598 | k,o | | | ESTs, Highly similar to Sid393p [M.musculus] |
| 21672 | 303 | AA891789 | General | | telomerase protein component 1 | telomerase protein component 1 |
| 20781 | 2381 | U89282 | r | | | ESTs |
| 16465 | 428 | AA901042 | n,General | | | Rattus norvegicus ischemia responsive 94 kDa protein (irp94) mRNA, complete cds |
| 15711 | 823 | AF077354 | a | | | Rat mRNA for protein tyrosine phosphatase, complete cds |
| 959 | 1973 | D38072 | v | | | ESTs, Moderately similar to erythroblast macrophage protein EMP [H.sapiens] |
| 11080 | 197 | AA851330 | n | | | ESTs |
| 19501 | 179 | AA850601 | f | | | ESTs |
| 14492 | 1023 | AI030091 | c | | | protein.phosphatase 1, regulatory (inhibitor) subunit 5 |
| 14332 | 1909 | AJ001044 | z | | protein phosphatase 1, regulatory (inhibitor) subunit 5 | |
| 13286 | 1035 | AI030790 | j | | | ESTs |
| 21785 | 1550 | AI177312 | z | | | ESTs |
| 6135 | 115 | AA819065 | e | | | ESTs, Weakly similar to PON1 RAT SERUM PARAOXONASE/ARYLESTERASE 1 [R.norvegicus] |
| 1335 | 1355 | AI169105 | General | | | |

Document Number 1740956

TABLE 1-continued

| GLGC ID | SeqID | GenBank Acc | Model Code | Pathway Name | Known Gene Name | Unigene Cluster Title |
|---|---|---|---|---|---|---|
| 11324 | 691 | AA964832 | l,General | | | ESTs |
| 4115 | 868 | AI008890 | General | | | ESTs |
| 15175 | 565 | AA945583 | k,General | Butanoate metabolism, Fatty acid biosynthesis (path 2), Fatty acid metabolism, Lysine degradation, Tryptophan metabolism, Valine, leucine and isoleucine degradation | hydroxyacyl-Coenzyme A dehydrogenase, type II | hydroxyacyl-Coenzyme A dehydrogenase, type II |
| 16700 | 866 | AI008838 | c | | | ESTs, Weakly similar to LONN_HUMAN MITOCHONDRIAL LON PROTEASE HOMOLOG PRECURSOR [*H.sapiens*] |
| 713 | 2507 | X91234 | w | Androgen and estrogen metabolism | 17-beta hydroxysteroid dehydrogenase type 2 | 17-beta hydroxysteroid dehydrogenase type 2 |
| 11830 | 1598 | AI179093 | r,General | | | *Rattus norvegicus* diphosphoinositol polyphosphate phosphohydrolase type II (Nudt4) mRNA, complete cds |
| 13697 | 1520 | AI176718 | General | | | ESTs |
| 8457 | 1121 | AI059835 | q | | | ESTs |
| 488 | 2005 | E00717 | g,q,cc,dd | Fatty acid metabolism, Tryptophan metabolism | Cytochrome P450, subfamily I (aromatic compound-inducible), member A1 (C6, form c) | Cytochrome P450, subfamily I (aromatic compound-inducible), member A1 (C6, form c) |
| 1853 | 2414 | X12367 | f | Glutathione metabolism | Glutathione peroxidase 1 | ESTs, Glutathione peroxidase 1 |
| 22511 | 2158 | M22670 | m,u | | Alpha-2-macroglobulin | Alpha-2-macroglobulin |
| 10016 | 827 | AF083269 | u | | Actin-related protein complex 1b | Actin-related protein complex 1b |
| 19775 | 420 | AA900590 | dd | | | ESTs |
| 10071 | 1900 | AI639058 | u | | | ESTs, Moderately similar to dJ71817.1 [*H.sapiens*] |
| 9889 | 1060 | AI044621 | k,p,aa | | | ESTs, Weakly similar to I59337 mammary transforming protein - mouse [*M.musculus*] |
| 23137 | 1141 | AI070408 | j | | | ESTs |
| 1373 | 2112 | L24907 | r | | | ESTs, Weakly similar to T14171 ataxin-2 - mouse [*M.musculus*] |
| 17064 | 2514 | X95986 | bb | Prostaglandin and leukotriene metabolism | carbonyl reductase | *Rattus norvegicus* CaM-like protein kinase mRNA, complete cds carbonyl reductase |
| 4868 | 1403 | AI170763 | n | | | ESTs |
| 12556 | 1629 | AI180376 | x | | | ESTs, Weakly similar to Y310_HUMAN HYPOTHETICAL PROTEIN KIAA0310 [*H.sapiens*] |
| 6536 | 305 | AA891834 | r | | | ESTs |
| 3910 | 389 | AA894345 | i | | | ESTs, Weakly similar to I59337 mammary transforming protein - mouse [*M.musculus*] |
| 20911 | 406 | AA899901 | n | | | ESTs, Weakly similar to T14171 ataxin-2 - mouse [*M.musculus*] |
| 13959 | 1869 | AI236696 | t | | | ESTs |
| 2179 | 138 | AA848270 | z | | | hypothetical protein EG:52C10.5 - fruit fly [*D.melanogaster*] |
| 9422 | 1189 | AI072888 | a | Androgen and estrogen metabolism, Pentose and glucuronate interconver- | UDP-glucuronosyltrans-ferase 1 family, member 1 | ESTs |
| 25675 | 2419 | X14181 | h,w | | | |
| 15126 | 1986 | D83796 | f,g,h,k,cc | | | *Rattus norvegicus* UDP-glucuronosyltransferase UGT1A7 mRNA, complete cds, UDP-glucuronosyltransferase 1 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 8132 | 1124 | AI060050 | General | sions, Porphyrin and chlorophyll metabolism, Starch and sucrose metabolism | family, member 1 | ESTs, Highly similar to NGP_HUMAN AUTOANTIGEN NGP-1 [H.sapiens] |
| 18686 | 1920 | D00729 | k,o | Fatty acid metabolism | dodecenoyl-Coenzyme A delta isomerase (3,2 trans-enoyl-Coenzyme A | Rat mRNA for delta3, delta2-enoyl-CoA isomerase, dodecenoyl-Coenzyme A delta isomerase (3,2 trans-enoyl-Coenyme A isomerase) |
| 13283 | 2128 | M11266 | u | Arginine and proline metabolism, Urea cycle and metabolism of amino groups | Ornithine carbamoyltransferase | Ornithine carbamoyltransferase |
| 7219 | 1767 | AI232900 | General | | peroxiredoxin 4 | peroxiredoxin 4 |
| 21229 | 859 | AI008371 | aa | | | ESTs |
| 23872 | 2151 | M18416 | General | | Early growth response 1 | Early growth response 1 |
| 7362 | 1011 | AI029026 | n,General | | | ESTs |
| 11162 | 856 | AI008183 | z | | | ESTs, Weakly similar to ENT1_RAT EQUILIBRATIVE NUCLEOSIDE TRANSPORTER 1 (EQUILIBRATIVE NITROBENZYLMERCAPTOPURINE RIBOSIDE-SENSITIVE NUCLEOSIDE TRANSPORTER) (EQUILIBRATIVE NBMPR-SENSITIVE NUCLEOSIDE TRANSPORTER) (NUCLEOSIDE TRANSPORTER, ES-TYPE) [R.norvegicus] |
| 5110 | 476 | AA925274 | b,General | | | ESTs, Highly similar to CAMP-DEPENDENT PROTEIN KINASE TYPE II-ALPHA REGULATORY CHAIN [R.norvegicus] |
| 23836 | 1276 | AI105088 | General | | | ESTs |
| 24256 | 1641 | AI228256 | aa | | | ESTs |
| 12698 | 1397 | AI170665 | z | | | ESTs |
| 16204 | 2407 | X06423 | h,w | | ribosomal protein S8 | ribosomal protein S8 |
| 17382 | 213 | AA858607 | cc | | | ESTs |
| 22545 | 898 | AI009747 | t | | | ESTs |
| 956 | 2107 | L21711 | g,t | | Lectin, galactose binding, soluble 5 (Galectin-5), Lectin, galactose binding, soluble 9 (Galectin-9) | Lectin, galactose binding, soluble 9 (Galectin-9) |
| 25204 | 826 | AF080507 | d,e | | | ESTs, Highly similar to Y069_HUMAN HYPOTHETICAL PROTEIN KIAA0069 [H.sapiens] |
| 16879 | 1363 | AI169284 | m | | | ESTs |
| 20523 | 306 | AA891842 | h,i | | | ESTs, Weakly similar to SE34_YEAST TRNA-SPLICING ENDONUCLEASE SUBUNIT SEN34 (TRNA-INTRON ENDONUCLEASE) [S.cerevisiae] |
| 5488 | 1670 | AI229684 | General | | | |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 17618 | 1875 | AI236786 | General | | | ESTs, Weakly similar to FKB1 RAT FK506 BINDING PROTEIN [R.norvegicus] |
| 17634 | 1915 | AJ223355 | v | | | Rattus norvegicus mRNA for mitochondrial dicarboxylate carrier |
| 24251 | 619 | AA955887 | t | | | ESTs |
| 11256 | 581 | AA945898 | aa | | | ESTs |
| 18990 | 2265 | S72506 | General | Glutathione metabolism | Glutathione-S-transferase, alpha type (Yc?) | Glutathione-S-transferase, alpha-type (Yc?) |
| 2587 | 1738 | AI232103 | r,General | | | ESTs |
| 25852 | 1896 | AI638998 | n | | | |
| 17805 | 2294 | U06274 | x,bb | | UDP-glucuronosyltransferase | UDP-glucuronosyltransferase |
| 6615 | 514 | AA942889 | u | | | ESTs, Weakly similar to T26686 hypothetical protein Y38F1A.6 - Caenorhabditis elegans [C.elegans] |
| 6957 | 924 | AI010707 | b | | | EST, Moderately similar to S12207 hypothetical protein [M.musculus] |
| 12797 | 58 | AA800790 | u | | | ESTs |
| 22515 | 419 | AA900582 | u,w | | Alpha-2-macroglobulin initiation factor 2 associated 67 kDa protein | Alpha-2-macroglobulin initiation factor 2 associated 67 kDa protein |
| 8984 | 2095 | L10652 | c,r | | | |
| 5712 | 1075 | AI045154 | z | | | ESTs, Moderately similar to origin recognition complex subunit 5 homolog [H.sapiens] |
| 4318 | 766 | AB005900 | u | | | Rattus norvegicus mRNA for endothelial receptor for oxidized low-density lipoprotein, complete cds |
| 20741 | 828 | AF084186 | r | | noerythroid alpha-spectrin 2 | noerythroid alpha-spectrin 2 |
| 8274 | 1105 | AI059270 | v | | | ESTs, Weakly similar to hypothetical protein [H.sapiens] |
| 11301 | 1312 | AI136709 | q | | | ESTs |
| 2296 | 1303 | AI112979 | General | | | ESTs, Highly similar to SAP3 MOUSE GANGLIOSIDE GM2 ACTIVATOR PRECURSOR [M.musculus] |
| 5930 | 64 | AA817688 | General | | | ESTs |
| 18327 | 19 | AA799537 | v | | | ESTs |
| 17119 | 2321 | U25746 | i | | | Rattus norvegicus RNA helicase with arginine-serine-rich domain mRNA, complete cds |
| 9591 | 1587 | AI178769 | a | | | Rattus norvegicus mRNA for proliferation related acidic leucine rich protein PAL31, complete cds |
| 23515 | 1608 | AI179498 | g,General | | | ESTs, Highly similar to S23B_HUMAN PROTEIN TRANSPORT PROTEIN SEC23 HOMOLOG ISOFORM B [H.sapiens] |
| 22952 | 353 | AA892831 | g | | | ESTs, Highly similar to 26S proteasome subunit p44.5 [H.sapiens] |
| 16085 | 267 | AA874889 | n | | | ESTs |
| 17517 | 2096 | L12383 | General | | ADP-ribosylation factor 4 | ADP-ribosylation factor 4 |
| 24779 | 2058 | J03863 | r | | | Rat serine dehydratase (SDH2) mRNA, complete cds |
| 5684 | 1069 | AI045056 | g | | | ESTs |
| 23651 | 2138 | M14656 | w | | Sialoprotein (osteopontin) | Sialoprotein (osteopontin) |
| 17933 | 308 | AA891916 | k | | membrane interacting protein of RGS16 | membrane interacting protein of RGS16 |
| 16019 | 862 | AI008498 | x | | brain expressed X-linked 3 | brain expressed X-linked 3 |
| 7697 | 1534 | AI176942 | c | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 899 | 2334 | U35245 | m | | vacuolar protein sorting homolog r-vps33b | vacuolar protein sorting homolog r-vps33b |
| 7047 | 1414 | AI171172 | b | | | ESTs, Highly similar to I48724 zinc finger protein PZF - mouse [*M.musculus*] |
| 24596 | 2427 | X16044 | v | | Protein phosphatase 2 (formerly 2A), catalytic subunit, beta isoform | Protein phosphatase 2 (formerly 2A), catalytic subunit, beta isoform |
| 9136 | 292 | AA891226 | General | | | ESTs, Highly similar to PRCE RAT PROTEASOME EPSILON CHAIN PRECURSOR [*R.norvegicus*] |
| 3062 | 749 | AA998857 | d,j,p | | | *Rattus norvegicus* mRNA for pre-procarboxypeptidase R, complete cds |
| 20744 | 2063 | J04171 | t,y | Alanine and aspartate metabolism, Arginine and proline metabolism, Carbon fixation, Cysteine metabolism, Glutamate metabolism, Phenylalanine metabolism, Phenylalanine, tyrosine and trytophan biosynthesis, Tyrosine metabolism | Glutamic-oxaloacetic transaminase 1, soluble (aspartate aminotransferase, cytosolic) see also D1Mgh12 | Glutamic-oxaloacetic transaminase 1, soluble (aspartate aminotransferase, cytosolic) see also D1Mgh12 |
| 15601 | 1372 | AI169631 | k | | Prohibitin | Prohibitin |
| 24860 | 2135 | M13506 | f,l,w,x,cc | | | Rat liver UDP-glucuronosyltransferase, phenobarbital-inducible form mRNA, complete cds |
| 10555 | 410 | AA900198 | General,y | | | ESTs, Highly similar to POLIOVIRUS RECEPTOR HOMOLOG PRECURSOR [*M.musculus*] |
| 11215 | 73 | AA817921 | y | | | ESTs, Moderately similar to T25763 hypothetical protein F46F11.4 - *Caenorhabditis elegans* [*C.elegans*] |
| 3847 | 315 | AA892036 | v | | | ESTs, Highly similar to histone deacetylase mHDA2 [*M.musculus*] |
| 3823 | 1770 | AI233147 | r | | | ESTs, Weakly similar to nuclear RNA helicase [*R.norvegicus*] |
| 15098 | 2176 | M31837 | p,General,w | | Insulin-like growth factor-binding protein (IGF-BP3) | Insulin-like growth factor-binding protein (IGF-PB3) |
| 17506 | 1134 | AI070068 | g | | | ESTs, Weakly similar to 2104282A Gadd45 gene [*R.norvegicus*] |
| 7344 | 1007 | AI028942 | General | | | ESTs |
| 2133 | 386 | AA894193 | General | | | ESTs |
| 18627 | 1744 | AI232284 | h | | RT1 class Ib gene | RT1 class Ib gene |
| 11203 | 339 | AA892554 | v | | | ESTs, Highly similar to ras-GTPase-activating protein SH3-domain binding protein [*M.musculus*] |
| 25198 | 821 | AF069782 | General | | Nopp140 associated protein | Nopp140 associated protein |
| 28 | 1968 | D31662 | d,e | | Regucalcin | Regucalcin |
| 6614 | 142 | AA848389 | d,General,u,w | | | ESTs, Weakly similar to T26686 hypothetical protein Y38F1A.6 - *Caenorhabditis elegans* [*C.elegans*] |
| 22804 | 932 | AI011194 | dd | | | ESTs, Moderately similar to mBLVR [*M.musculus*] |
| 2096 | 1796 | AI233801 | dd | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 16684 | 1953 | D17445 | General,v | | Tyrosine 3-monooxy-genase/tryptophan 5-monooxygenase activation protein, eta polypeptide | Tyrosine 3-monooxygenase/tryptophan 5-monooxygenase activation protein, eta polypeptide |
| 1588 | 2254 | S61865 | General,t | | Syndecan 1 | Syndecan 1 |
| 14346 | 2174 | M31109 | f,l,General,cc | | | Rat UDP-glucuronosyltransferase mRNA, complete cds |
| 20864 | 812 | AF045464 | | | aflatoxin B1 aldehyde reductase | aflatoxin B1 aldehyde reductase |
| 15906 | 1780 | AI233425 | dd | Citrate cycle (TCA cycle), Glutathione metabolism, Reductive carboxylate cycle CO2 fixation | | ESTs |
| 17427 | 328 | AA892314 | h | | Isocitrate dehydrogenase 1, soluble | Isocitrate dehydrogenase 1, soluble |
| 19275 | 886 | AI009460 | i | | | ESTs, Highly similar to filamin [*H.sapiens*] |
| 12965 | 1302 | AI112926 | General | | | ESTs |
| 4879 | 434 | AA923852 | e,General,y | | | ESTs |
| 13694 | 1693 | AI230538 | j | | | ESTs, Weakly similar to PHP DROME POLYHOMEOTIC- PROXIMAL CHROMATIN PROTEIN [*D.melanogaster*] |
| 3510 | 1507 | AI176423 | l | | | ESTs, Highly similar to ZO1 MOUSE TIGHT JUNCTION PROTEIN ZO-1 [*M.musculus*] |
| 8303 | 1110 | AI059352 | General | | | ESTs |
| 22042 | 598 | AA946476 | w,dd | | | ESTs |
| 13768 | 136 | AA819792 | v | | | ESTs, Highly similar to R33683_3 [*H.sapiens*] |
| 9866 | 1911 | AJ005424 | c,v | | | *Rattus norvegicus* mRNA for BMK1/ERK5 protein, partial |
| 18637 | 217 | AA858651 | z | RT1 class Ib gene | | RT1 class Ib gene |
| 22077 | 1544 | AI177099 | z | | | ESTs, Highly similar to serine protease [*H.sapiens*] |
| 11559 | 1029 | AI030472 | General | | | ESTs |
| 9841 | 2385 | U94856 | p,t,x | | paraoxonase 1 | paraoxonase 1 |
| 21524 | 954 | AI012014 | v | | | ESTs, Highly similar to hypothetical protein [*H.sapiens*] |
| 25317 | 2035 | J00735 | b | | | ESTs, Highly similar to NHPX RAT NHP2/RS6 FAMILY PROTEIN YEL026W HOMOLOG [*R.norvegicus*] |
| 3417 | 963 | AI012337 | General | | | ESTs, Moderately similar to KIAA0264 [*H.sapiens*] |
| 16397 | 172 | AA850155 | General | | | EST |
| 14677 | 1818 | AI234620 | aa | Glycolysis/Gluconeogenesis, Phenyl-alanine, tyrosine and tryptophan biosynthesis | Enolase 1, alpha | Enolase 1, alpha |
| 19407 | 2395 | X02610 | t | | | |
| 6382 | 880 | AI009362 | General | | | ESTs |
| 7665 | 1033 | AI030668 | o,General,bb | | | *Rattus norvegicus* nucleosome assembly protein mRNA, complete cds |
| 9433 | 1191 | AI072917 | General | Carbon fixation, Pentose phosphate cycle | transketolase | ESTs |
| 20803 | 2298 | U09256 | l,m,cc | | | transketolase |
| 9712 | 1527 | AI176836 | v | | | ESTs, Weakly similar to T21364 hypothetical protein F25H5.6 - *Caenorhabditis elegans* [*C.elegans*] |
| 353 | 2119 | L32591 | v | | DNA-damage-inducible transcript 1 | DNA-damage-inducible transcript 1 |
| 1903 | 1553 | AI177377 | c | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 2480 | 375 | AA893471 | cc | | | ESTs |
| 25754 | 2505 | X89696 | h | | | ESTs |
| 9128 | 1427 | AI171611 | g,General | | | ESTs, Highly similar to RS18_HUMAN 40S RIBOSOMAL PROTEIN S18 [*R.norvegicus*] |
| 15106 | 2454 | X57529 | h,t | | | EST |
| 20350 | 1758 | AI232552 | General | | | ESTs, Weakly similar to AF114170 1 nucleotide-binding protein long form [*M.musculus*] |
| 3848 | 327 | AA892306 | z | | | EST, Weakly similar to T19326 |
| 24225 | 482 | AA925490 | j,General | | | hypothetical protein C16C10.5 - *Caenorhabditis elegans* [*C.elegans*] |
| 10055 | 1089 | AI058291 | t | | | ESTs |
| 6715 | 1642 | AI228284 | General | | | ESTs |
| 15500 | 1661 | AI229337 | i,l | | | ESTs |
| 14021 | 153 | AA848834 | General,bb | | | Cytochrome P450, subfamily IVB, poylpeptide 1 |
| 20713 | 2196 | M57718 | k,o | Fatty acid metabolism, Tryptophan metabolism | Cytochrome P450, subfamily IVB, polypeptide 1 | |
| 22929 | 1162 | AI071578 | c,d,m | Oxidative phosphorylation | HHs:succinate dehy-drogenase complex, subunit A, flavoprotein (Fp) | ESTs, Moderately similar to NEURONAL PROTEIN 3.1 [*M.musculus*] |
| 17514 | 486 | AA925554 | j,General | | | ESTs, Highly similar to DHSA_HUMAN SUCCINATE DEHYDROGENASE [*H.sapiens*] |
| 11791 | 1569 | AI177843 | p | | | ESTs, Highly similar to SAS_HUMAN sarcoma amplified sequenc [*H.sapiens*] |
| 19456 | 729 | AA997841 | i | | | *Rattus norvegicus* osteoactivin mRNA, complete cds |
| 4374 | 380 | AA893869 | m | | | ESTs, Weakly similar to T16084 hypothetical protein F16H11.1 - *Caenorhabditis elegans* [*C.elegans*] |
| 16546 | 46 | AA800120 | k,o | | | *R.norvegicus* mRNA for carnitine/acylcarnitine carrier protein |
| 17764 | 1816 | AI234604 | o | | Heat shock cognate protein 70 | Heat shock cognate protein 70 |
| 14102 | 1739 | AI232131 | General | | | ESTs, Highly similar to beta-hexosaminidase alpha-subunit [*M.musculus*] |
| 4091 | 1367 | AI169417 | General,cc | Glycolsis/Gluconeogenesis | HHs:phosphoglycerate mutase 1 (brain) | *R.norvegicus phosphoglycerate mutase B* isozyme (PGAM) mRNA, complete cds |
| 11563 | 1219 | AI102560 | q | | | ESTs |
| 9383 | 1120 | AI059824 | q | | | ESTs |
| 22235 | 444 | AA924152 | dd | | | ESTs, Moderately similar to AF135422 1 GDP-mannose pyrophosphorylase A [*H.sapiens*] |
| 17908 | 1006 | AI014163 | t,v | | interferon-related developmental regulator 1 | interferon-related developmental regulator 1 |
| 21204 | 839 | AF095927 | a | | protein phosphatase 2C | protein phosphatase 2C |
| 23709 | 1293 | AI112173 | a,t | | ATPase Na+/K+ transporting beta 1 polypeptide | ATPase Na+/K+ transporting beta 1 polypeptide |
| 21039 | 2051 | J03190 | f,x | Glycine, serine and threonine metabolism | aminolevulinic acid synthase 1 | aminolevulinic acid synthase 1 |
| 2629 | 2518 | Y00396 | r,General | | Avian myelocytomatosis viral (v-myc) oncogene homolog | Avian myelocytomatosis viral (v-myc) oncogene homolog |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 7548 | 1045 | AI043724 | General | | | ESTs |
| 23781 | 1898 | AI639012 | i | | | ESTs, Moderately similar to unnamed protein product [H.sapiens] |
| 25719 | 2466 | X62146 | w | | | ESTs |
| 6032 | 86 | AA818258 | General | | MYB binding protein (P160) 1a | MYB binding protein (P160) 1a |
| 17449 | 1884 | AI237258 | y | | | EST |
| 10348 | 1133 | AI069934 | dd | | Cathepsin L | ESTs |
| 23449 | 1526 | AI176828 | g,q | | Diaphorase (NADH/NADPH) | Cathepsin L |
| 3430 | 2282 | S85184 | t | Sterol biosynthesis | | Diaphorase (NADH/NADPH) |
| 1698 | 2042 | J02679 | p,q,General | Proteasome | proteasome (prosome, macropain) subunit, beta type 3 | proteasome (prosome, macropain) subunit, beta type 3 |
| 12524 | 1958 | D21800 | General | | | |
| 14933 | 2020 | H31588 | General | | ATP synthase subunit d | ESTs, Moderately similar to KIAA0351 [H.sapiens] |
| 22727 | 496 | AA925814 | p | Oxidative phosphoryl-ation, Type III protein secretion system | | ATP synthase subunit d |
| 20789 | 2413 | X12355 | g | | ER-60 protease, glucose regulated protein, 58 kDa | ER-60 protease, glucose regulated protein, 58 kDa |
| 20384 | 1951 | D17349 | x,cc,dd | | | ESTs, Highly similar to PTD001 [H.sapiens] |
| 6508 | 1002 | AI013900 | General | | | Rattus norvegicus mRNA for proteasomal ATPase (MSS1), complete cds |
| 2578 | 1980 | D50694 | General | | | ESTs |
| 6943 | 923 | AI010637 | bb | | | ESTs, Highly similar to PRC6 RAT PROTEASOME SUBUNIT RC6-1 [R.norvegicus] |
| 9032 | 1619 | AI179950 | c,d,General | | | ESTs, Weakly similar to CLP3 RAT CALPONIN, ACIDIC ISOFORM [R.norvegicus] |
| 20055 | 1705 | AI230762 | q | | HMm:inosine 5'-phosphate dehydrogenase 2 | ESTs, Weakly similar to guanosine monophosphate reductase [R.norvegicus] |
| 22820 | 140 | AA848315 | General | Purine metabolism | | ESTs |
| 4791 | 1600 | AI179106 | q | | | ESTs |
| 22927 | 253 | AA859920 | c,h | | | ESTs |
| 9053 | 358 | AA892861 | dd | | Gap junction membrane channel, protein alpha 4 (connexin 37) | Gap junction membrane channel, protein alpha 4 (connexin 37) |
| 12736 | 1807 | AI233972 | u | | P-glycoprotein/multidrug resistance 1 | P-glycoprotein/multidrug resistance 1 |
| 5733 | 2219 | M81855 | i | | | |
| 12845 | 1387 | AI170497 | b | | | ESTs |
| 18588 | 399 | AA899635 | p,x,cc,dd | | | ESTs, Moderately similar to 2020285A BRG1 protein [M.musculus] |
| 17155 | 1449 | AI172090 | d,General | | | Rat clathrin light chain (LCB2) mRNA, complete cds, Rat clathrin light chain (LCB3) mRNA, complete cds |
| 6640 | 1204 | AI101500 | n | | | ESTs |
| 5200 | 1584 | AI178699 | j | | DNA-damage inducible transcript 3 | ESTs |
| 1600 | 6 | AA686470 | j,w | | | DNA-damage inducible transcript 3 |
| 21510 | 201 | AA851620 | General | | | ESTs |
| 14550 | 1263 | AI104146 | General | | | ESTs, Moderately similar to AC008015_2 unknown [H.sapiens] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 20708 | 767 | AB006461 | j | | neurochondrin | *Rattus norvegicus* mRNA for NORBIN, complete cds |
| 13551 | 1563 | AI177602 | m | | | ESTs |
| 6352 | 721 | AA997600 | b,n,y | | PCTAIRE-1 protein kinase, alternatively spliced | PCTAIRE-1 protein kinase, alternatively spliced |
| 8283 | 1107 | AI059290 | d,f,General | | | ESTs |
| 3690 | 750 | AA999006 | i,q | | | ESTs |
| 25508 | 2261 | S67620 | n,v | | | |
| 26320 | 1823 | AI234927 | u | | | |
| 18250 | 2435 | X51706 | w | | ribosomal protein L9 | ESTs, Highly similar to RL9 RAT 60S RIBOSOMAL PROTEIN L9 [*R.norvegicus*] |
| 16458 | 549 | AA944956 | a | | | ESTs |
| 11483 | 796 | AF020618 | General | | | ESTs, Moderately similar to MY16 MOUSE MYELOID DIFFERENTIATION PRIMARY RESPONSE PROTEIN MYD116 [*M.musculus*], *Rattus norvegicus* progression elevated gene 3 protein mRNA, complete cds |
| 4950 | 1910 | AJ005046 | bb | | | EST, Highly similar to fructose-1,6-bisphosphatase [*R.norvegicus*] |
| 18299 | 9 | AA799369 | h | | | ESTs, Weakly similar to RS9 RAT 40S RIBOSOMAL PROTEIN S9 [*R.norvegicus*] |
| 14881 | 2155 | M20629 | bb | | Esterase 2 | Esterase 2 |
| 21656 | 49 | AA800202 | z | | | ESTs |
| 2736 | 388 | AA894330 | i | | Ca++/calmodulin-dependent protein kinase II, delta subunit | Ca++/calmodulin-dependent protein kinase II, delta subunit |
| 20888 | 1343 | AI145680 | bb | | Solute carrier 16 (monocarboxylic acid transporter), member 1 | Solute carrier 16 (monocarboxylic acid transporter), member 1 |
| 21708 | 641 | AA956930 | v,y | | | Rat mRNA for endothelin-converting enzyme, complete cds |
| 635 | 2490 | X78848 | h,w,cc | Gluthione metabolism | Glutathione-S-transferase, alpha type (Ya) | Glutathione-S-transferase, alpha type (Ya) |
| 26030 | 2185 | M34331 | cc | Glycine, serine and threonine metabolism | aminolevulinic acid synthase 1 | aminolevulinic acid synthase 1 |
| 21040 | 948 | AI011734 | f,g | | olfactory receptor 41 | olfactory receptor 41 |
| 20236 | 835 | AF091570 | a | | | ESTs |
| 14594 | 1856 | AI236152 | General | | ferritin light chain 1 | ferritin light chain 1 |
| 8211 | 1730 | AI231807 | n | | | ESTs |
| 6171 | 129 | AA819633 | b | | | ESTs, Highly similar to SPS2 MOUSE SELENIDE, WATER DIKINASE 2 [*M.musculus*] |
| 2040 | 32 | AA799700 | t | Selenoamino acid metabolism | HMn:selenophosphate synthetase 2 | |
| 15577 | 450 | AA924557 | o | | | ESTs, Highly similar to hepatitis delta antigen interacting protein A [*H.sapiens*] |
| 4196 | 395 | AA899304 | o,bb | | | ESTs |
| 21074 | 1001 | AI013890 | w | | | ESTs |
| 8130 | 869 | AI008894 | q | | | ESTs |
| 3674 | 566 | AA945587 | j | | | ESTs, Highly similar to T00358 hypothetical protein KIAA0684 [*H.sapiens*] |
| 26109 | 707 | AA997009 | k,o,z | | | EST |
| 5921 | 1580 | AI178556 | aa | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 4636 | 396 | AA899491 | u | Aminoacyl-tRNA biosynthesis, Tryptophan metabolism | HMm:tryptophanyl-tRNA synthetase | ESTs, Highly similar to SYW MOUSE TRYPTOPHANYL-TRNA SYNTHETASE [M.musculus] |
| 155 | 2331 | U32681 | v | | crp-ductin | crp-ductin |
| 11727 | 163 | AA849518 | e | | | ESTs |
| 9595 | 1310 | AI136630 | General | | | ESTs |
| 20925 | 2297 | U08976 | k,o | | enoyl hydratase-like protein, peroxisomal | enoyl hydratase-like protein, peroxisomal |
| 2515 | 1954 | D17512 | b | | cysteine-rich protein 2 | cysteine-rich protein 2 |
| 17626 | 2271 | S78556 | k | | | ESTs, Highly similar to I56581 dnaK-type molecular chaperone grp75 precursor - rat [R.norvegicus] |
| 22548 | 550 | AA945031 | General | | Transducin-like enhancer of split 4, homolog of Drosophila E(spl) | ESTs |
| 20652 | 2101 | L14463 | v | | | Transducin-like enhancer of split 4, homolog of Drosophila E(spl) |
| 15296 | 1652 | AI228738 | q | | FK506-binding protein 1 (12kD) | FK506-binding protein 1 (12kD) |
| 20846 | 1715 | AI231140 | z | | | ESTs, Highly similar to RL2B_HUMAN 60S RIBOSOMAL PROTEIN L23A [R.norvegicus] |
| 22204 | 1409 | AI170820 | t | | | ESTs |
| 3693 | 938 | AI011448 | p | | | ESTs, Highly similar to A49128 cell-fate determining gene Notch2 protein - rat [R.norvegicus] |
| 17887 | 1461 | AI172414 | General | | | Rattus norvegicus apoptosis-regulating basic protein mRNA, complete cds |
| 13294 | 1789 | AI233731 | d,r,General | | | ESTs, Weakly similar to TCPA RAT T-COMPLEX PROTEIN 1, ALPHA SUBUNIT [R.norvegicus] |
| 18319 | 492 | AA925752 | bb | | CD36 antigen (collagen type I receptor, thrombospondin receptor) | CD36 antigen (collagen type I receptor, thrombospondin receptor) |
| 20897 | 1487 | AI175812 | dd | | complement component 1, q subcomponent binding protein | ESTs, Highly similar to Copa protein [M.musculus] |
| 15259 | 1575 | AI178135 | r,General | | | complement component 1, q subcomponent binding protein |
| 22039 | 2307 | U13176 | j | | | Rattus norvegicus clone ubc2e ubiquitin conjugating enzyme (E217kB) mRNA, complete cds |
| 16859 | 1872 | AI236753 | m | | | ESTs |
| 5937 | 1430 | AI171684 | aa | | | ESTs |
| 8025 | 1090 | AI058365 | i | | | ESTs |
| 5989 | 640 | AA956907 | t | | | ESTs, Highly similar to p162 protein [M.musculus] |
| 4360 | 2023 | H31813 | e,z | | | ESTs, Moderately similar to T14781 hypothetical protein DKFZp586B 1621.1 [H.sapiens] |
| 24763 | 1510 | AI176488 | General | | nuclear factor I/B | nuclear factor I/B |
| 10886 | 2250 | S49003 | c,d | | Growth hormone receptor | Growth hormone receptor |
| 21601 | 528 | AA943997 | g,General | | | ESTs, Moderately similar to p27 [H.sapiens] |
| 15932 | 2306 | U12402 | n | | ADP-ribosylation factor-like 1 | ADP-ribosylation factor-like 1 |
| 23665 | 208 | AA852055 | h | | Bruton agammaglobulinemia tyrosine kinase | Bruton agammaglobulinemia tyrosine kinase |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 16780 | 2468 | X62660 | General,z | Glutathione metabolism | HMn:glutathione S-transferase, alpha 4 cytosolic - rat [*R.norvegicus*] | ESTs, Highly similar to XURT8C glutathione transferase (EC 2.5.1.18), |
| 23524 | 2067 | J04792 | General | Arginine and proline metabolism, Urea cycle and metabolism of amino groups | Ornitine decarboxylase | Ornitine decarboxylase |
| 15879 | 1644 | AI228313 | f,g,h,General,x | | | ESTs |
| 10020 | 1083 | AI045632 | General | | | ESTs |
| 15041 | 780 | AB016532 | z | | period homolog 2 (*Drosophila*) | period homolog 2 (*Drosophila*) |
| 20299 | 1944 | D14564 | c | Ascorbate and aldarate metabolism | L-gulono-gamma-lactone oxidase | L-gulono-gamma-lactone oxidase |
| 1822 | 70 | AA817843 | p,v | | CCAAT binding transcription factor of CBF-B/NFY-B | CCAAT binding transcription factor of CBF B/NFY-B |
| 21588 | 392 | AA899160 | dd | | | ESTs |
| 13458 | 1475 | AI175338 | aa | | | ESTs |
| 13166 | 1585 | AI178736 | v | | | ESTs |
| 21679 | 31 | AA799691 | General | | | ESTs, Moderately similar to T31432 K-CI cotransport protein 2, furosemide-sensitive - rat [*R.norvegicus*] |
| 17431 | 1144 | AI070521 | r | | | Rat unr mRNA for unr protein with unknown function |
| 9339 | 1201 | AI101160 | General | | | ESTs, Weakly similar to S46930 teg292 protein - mouse [*M.musculus*] |
| 2855 | 1870 | AI236707 | i | | Cystatin beta | Cystatin beta |
| 15469 | 1912 | AJ006340 | c | | 26S proteasome, subunit p112 | 26S proteasome, subunit p112 |
| 10534 | 1148 | AI070832 | n | Oxidative phosphorylation, Type III secretion system | HHs:ATP synthase, H+ transporting, mitochondrial F0 complex, subunit c (subunit 9) isoform 3 | ESTs |
| 10909 | 1631 | AI180425 | k | | | *Rattus norvegicus* ATP synthase lipid-binding protein P3 precursor (Atp5g3) mRNA, complete cds; nuclear gene for mitochondrial product |
| 2901 | 1046 | AI043752 | e | | | ESTs |
| 11057 | 1160 | AI071509 | General | | | ESTs, Weakly similar to FIBA RAT FIBRINOGEN ALPHA/ALPHA-E CHAIN PRECURSOR [*R.norvegicus*] |
| 14763 | 541 | AA944481 | o | | | |
| 15955 | 1745 | AI232294 | i,x,cc | | | ESTs |
| 9583 | 1156 | AI071185 | c,m,u | | | ESTs |
| 12704 | 876 | AI009194 | y | | | ESTs |
| 16821 | 751 | AA999042 | n | | | ESTs |
| 3718 | 1667 | AI229643 | aa | | | ESTs |
| 22396 | 250 | AA859806 | y,aa | | | Rat mitochondrial 3-hydroxy-3-methylglutaryl-CoA synthase mRNA, complete cds |
| 15580 | 2181 | M33648 | o | | | |
| 135 | 1993 | D87839 | e | | 4-aminobutyrate aminotransferase | 4-aminobutyrate aminotransferase |
| 1431 | 1059 | AI044610 | General | Histidine metabolism, Phenylalanine metabolism, | Dopa decarboxylase (aromatic L-amino acid decarboxylase) | Dopa decarboxylase (aromatic L-amino acid decarboxylase) |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 193 | 1530 | AI176856 | p | Tryptophan metabolism, Tyrosine metabolism | decarboxylase) | |
| 17564 | 666 | AA963674 | n | Fatty acid metabolism, Tryptophan metabolism | Cytochrome P450 1b1 | Cytochrome P450 1b1 |
| 22592 | 996 | AI013740 | General | | mitogen activated protein kinase kinase 2 | mitogen activated protein kinase kinase 2 |
| 2519 | 951 | AI011770 | aa | | ESTs, Highly similar to proteo-lipid protein 2 [*M.musculus*] | ESTs |
| 2242 | 973 | AI012635 | g,i,n,General,y | | flavin-containing mono-oxygenase 3 | flavin-containing monooxygenase 3 |
| 7451 | 1017 | AI029450 | General | Aminoacyl-tRNA bio-synthesis, Arginine and proline metabolism, Glutamate metabolism, Porphyrin and chlorophyll | HHs:glutamyl-prolyl-tRNA synthetase AMINOACYL-TRNA SYN-THETASE [*H.sapiens*] | ESTs, Moderately similar to SYEP_HUMAN MULTIFUNCTIONAL AMINOACYL-TRNA SYNTHETASE [*H.sapiens*] |
| 25743 | 2493 | X80130 | c | | | ESTs, Weakly similar to DHQU RAT NAD(P)H DEHYDROGENASE [*R.norvegicus*] |
| 22612 | 573 | AA945624 | j,General | | | ESTs, Highly similar to TCPZ MOUSE T-COMPLEX PROTEIN 1, ZETA SUBUNIT [*M.musculus*] |
| 16319 | 270 | AA875047 | l | | | ESTs |
| 4232 | 977 | AI012958 | l,General,y | | | ESTs, Moderately similar to unnamed protein product [*H.sapiens*] |
| 19363 | 1500 | AI76247 | l,m | | | ESTs, Weakly similar to T19468 hypothetical protein C25G4.2 - *Caenorhabditis elegans* [*C.elegans*] |
| 22251 | 644 | AA957037 | General | | | ESTs |
| 12694 | 657 | AA957906 | i | | | ESTs, Highly similar to CB45 MOUSE 45 KDA CALCIUM-BINDING PROTEIN PRECURSOR [*M.musculus*] |
| 3458 | 730 | AA997861 | r | | | ESTs, Moderately similar to T50621 hypothetical protein DKFZp762O076.1 [*H.sapiens*] |
| 17913 | 2022 | H31707 | m | | | ESTs, Highly similar to chaperonin containing TCP-1 theta subunit [*M.musculus*] |
| 3589 | 745 | AA998590 | b | | | EST |
| 18682 | 1113 | AI059499 | General | | | lipopolysaccharide binding protein |
| 6151 | 119 | AA819199 | General | | lipopolysaccharide binding protein | |
| 20529 | 2118 | L32132 | General,w | | | |
| 778 | 2379 | U84410 | r | | Caspase 3, apoptosis related cysteine protease (ICE-like cysteine protease) | Caspase 3, apoptosis related cysteine protease (ICE-like cysteine protease) |
| 16721 | 1965 | D30647 | k,z,bb | | Acyl-Coa dehydrogenase, Very long chain | Acyl-Coa dehydrogenase, Very long chain |
| 22715 | 591 | AA946120 | l | | | ESTs |
| 2997 | 1032 | AI030545 | General,w,bb | | | ESTs |
| 22884 | 925 | AI010755 | f,x | | | ESTs |

Document Number 1740956

TABLE 1-continued

| GLGC ID | SeqID | GenBank Acc | Model Code | Pathway Name | Known Gene Name | Unigene Cluster Title |
|---|---|---|---|---|---|---|
| 18266 | 1812 | AI234256 | General | | mitochondrial aconitase (nuclear aco2 gene) | ESTs, Highly similar to 2208369A signal peptidase:SUBUNIT |
| 19991 | 1258 | AI103956 | General | | | mitochondrial aconitase (nuclear aco2 gene) |
| 4998 | 455 | AA924683 | b | | | EST |
| 23644 | 655 | AA957808 | General | | | ESTs, Weakly similar to AF121859 1 sorting nexin 9 [H.sapiens] |
| 2354 | 726 | AA997763 | g,p,q | | | ESTs, Highly similar to hypothetical protein [H.sapiens] |
| 7806 | 89 | AA818421 | aa | | | ESTs |
| 19011 | 1226 | AI102618 | b | | | ESTs |
| 7003 | 1026 | AI030259 | n | | | ESTs, Weakly similar to REG2 DROME RHYTHMICALLY EXPRESSED GENE 2 PROTEIN [D.melanogaster] |
| 24048 | 1390 | AI170570 | General | | | ESTs, Highly similar to CGI-10 protein [H.sapiens] |
| 17324 | 815 | AF056031 | p,w | | kynurenine 3-hydroxylase | kynurenine 3-hydroxylase |
| 19249 | 713 | AA997342 | m,General | | | ESTs |
| 14171 | 1573 | AI178073 | c | | | ESTs, Weakly similar to T26935 hypothetical protein Y45F10D.8 - Caenorhabditis elegans [C.elegans] |
| 19938 | 623 | AA955980 | g | | | ESTs, Moderately similar to pescadillo [H.sapiens] |
| 10161 | 1104 | AI059168 | dd | | | EST |
| 1529 | 2218 | M81687 | e,q | | Ryudocan/syndecan 2 | Ryudocan/syndecan 2 |
| 2554 | 1922 | D00913 | v | | Intercellular adhesion molecule 1 | Intercellular adhesion molecule 1 |
| 21285 | 169 | AA849898 | w,z | | | EST |
| 1857 | 772 | AB010428 | k,o,bb | | acyl-CoA thioesterase 1, cytosolic | acyl-CoA thioesterase 1, cytosolic |
| 9644 | 1159 | AI071410 | z | | | ESTs |
| 21917 | 291 | AA891220 | b | | | ESTs |
| 17281 | 2304 | U10697 | cc | | carboxylesterase 1 | carboxylesterase 1 |
| 23865 | 1229 | AI102760 | General | | | ESTs, Moderately similar to KIAA0710 protein [H.sapiens] |
| 1813 | 2152 | M19651 | j | | Fos-like antigen 1 | Fos-like antigen 1 |
| 4242 | 372 | AA893325 | c,d,General | Arginine and proline metabolism, Urea cycle and metabolism of amino groups | ornithine aminotransferase | ornithine aminotransferase |
| 355 | 2260 | S66024 | o,General | | transcriptional repressor CREM | |
| 18580 | 206 | AA851963 | w | | | ESTs |
| 4833 | 875 | AI009178 | b | | | ESTs, Highly similar to glycogen phosphorylase [R.norvegicus] |
| 8759 | 1887 | AI237646 | j | | | ESTs |
| 3023 | 1408 | AI170795 | General | | | ESTs |
| 25183 | 813 | AF050159 | l | | insulin receptor substrate 2 | |
| 1173 | 2150 | M18363 | m | Fatty acid metabolism, Tryptophan metabolism | Cytochrome P450, subfamily IIC (mephenytoin 4-hydroxylase) | Cytochrome P450, subfamily IIC (mephenytoin 4-hydroxylase) |
| 21488 | 2330 | U32575 | p,v | | | ESTs, Highly similar to similar to yeast Sec6p, Swiss-Prot Accession Number P32844 [R.norvegicus] |
| 23886 | 660 | AA963008 | z | | | ESTs, Highly similar to U123_HUMAN HYPOTHETICAL 12.4 KDA PROTEIN BK223H9.2 [H.sapiens] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 818 | 2393 | X02291 | n | Carbon fixation, Fructose and mannose metabolism, Glycolysis/Gluconeogenesis, Inositol metabolism, Pentose phosphate cycle | Aldolase B, fructose-biphosphate | Aldolase B, fructose-biphosphate |
| 23344 | 45 | AA800034 | General | Androgen and estrogen metabolism | | ESTs |
| 9931 | 2281 | S83279 | f,k,o | | peroxisomal multifunctional enzyme type II | peroxisomal multifunctional enzyme type II |
| 17736 | 2229 | M86389 | bb | | Heat shock 27 kDa protein | ESTs, Heat shock 27 kDa protein |
| 18352 | 2527 | Z12298 | u | | decorin | decorin |
| 11876 | 879 | AI009321 | General,dd | | | ESTs, Highly similar to similar to human DNA-binding protein 5 [*H.sapiens*] |
| 22540 | 454 | AA924630 | General | Glyoxylate and dicarboxylate metabolism, Pyruvate metabolism | HHs:glyoxylate reductase/hydroxy-pyruvate reductase | ESTs, Weakly similar to SERA RAT D-3-PHOSPHOGLYCERATE DEHYDROGENASE [*R.norvegicus*] |
| 23068 | 500 | AA926036 | e,General | | | ESTs |
| 20816 | 2199 | M58404 | u | | thymosin beta-10 | thymosin beta-10 |
| 10087 | 1435 | AI171803 | General | | | ESTs |
| 6166 | 1309 | AI136516 | General | | | ESTs |
| 12563 | 683 | AA964533 | General | | | ESTs, Moderately similar to density-regulated protein [*H.sapiens*] |
| 24479 | 368 | AA893091 | j | | | ESTs, Moderately similar to KRAB-zinc finger protein KZF-2 [*R.norvegicus*] |
| 8182 | 570 | AA945608 | t,bb | | serum amyloid P-component | serum amyloid P-component |
| 12071 | 885 | AI009456 | d,l,General | | | ESTs, Moderately similar to KIAA0822 protein [*H.sapiens*] |
| 19256 | 2144 | M15562 | l | | | Rat (diabetic BB) MHC class II alpha chain RT1.D alpha (u) |
| 12320 | 592 | AA946149 | w | | | ESTs |
| 6085 | 1443 | AI171990 | v | | | ESTs, Moderately similar to axonemal dynein heavy chain [*H.sapiens*] |
| 21288 | 1637 | AI227935 | p,q | | | ESTs |
| 12523 | 1958 | D21800 | General | Proteasome | proteasome (prosome, macropain) subunit, beta type, 3 | proteasome (prosome, macropain) subunit, beta type, 3 |
| 4395 | 2027 | H33149 | i | | | ESTs, Weakly similar to T29897 hypothetical protein F38A5.1 - *Caenorhabditis elegans* [*C.elegans*] |
| 16026 | 264 | AA874802 | aa | | Histone H1-0 | Histone H1-0 |
| 16809 | 2459 | X58828 | m,General,u | | | Rat PTP-S mRNA for protein-tyrosine phosphatase |
| 1447 | 2451 | X55986 | General | Proteasome | proteasome (prosome, macropain) subunit, alpha type 4 | proteasome (prosome, macropain) subunit, alpha type 4 |
| 5451 | 1053 | AI044322 | bb | | | ESTs, Highly similar to 26S proteasome subunit p55 [*H.sapiens*] |
| 6532 | 1810 | AI234105 | a,m,u | | | ESTs |
| 7171 | 974 | AI012761 | General | | | ESTs |
| 3019 | 1718 | AI231218 | n | | | ESTs |
| 23099 | 1297 | AI112365 | General,aa | | | ESTs, Highly similar to mm-Mago [*M.musculus*] |
| 18989 | 2077 | K00136 | f,q,x | Glutathione metabolism | Glutathione-S-transferase, alpha type (Yc?) | Glutathione-S-transferase, alpha type (Yc?) |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 13911 | 1859 | AI236262 | j,aa | | | *Rattus norvegicus* epidermal Langerhans cell protein LCP1 mRNA, complete cds |
| 23855 | 1874 | AI236773 | v | | | ESTs |
| 15718 | 2371 | U75689 | | | | *Rattus norvegicus* DNAseY mRNA, complete cds |
| 12118 | 347 | AA892775 | u | | Lysozyme | Lysozyme |
| 12092 | 147 | AA848618 | a | | | ESTs |
| 24219 | 2116 | L27843 | g,m,n,t,u,v | | protein tyrosine phosphatase 4a1 | protein tyrosine phosphatase 4a1 |
| 16706 | 1624 | AI180032 | General | | | ESTs |
| 5176 | 748 | AA998722 | u | | pyruvate kinase 3 | Rat mRNA for pituitary pyruvate kinase |
| 10018 | 453 | AA924622 | General | | | ESTs |
| 17685 | 1305 | AI113055 | l | | | EST |
| 23080 | 651 | AA957423 | General | | | ESTs, Moderately similar to Rat NBP60 [*R.norvegicus*] |
| 8850 | 1828 | AI235059 | j,aa | | | ESTs |
| 5186 | 489 | AA925674 | aa | | | ESTs |
| 15286 | 1366 | AI169361 | General | | | ESTs, Highly similar to U1 snRNP-specific protein C [*M.musculus*] |
| 4183 | 1231 | AI102789 | y | | | ESTs, Weakly similar to PTB RAT POLYPYRIMIDINE TRACT-BINDING PROTEIN [*R.norvegicus*] |
| 8527 | 700 | AA996461 | f,o | | | ESTs |
| 6438 | 122 | AA819269 | n,General | | | ESTs |
| 16272 | 2488 | X76456 | f,cc | | | *R.norvegicus* (Sprague Dawley) alpha albumin gene |
| 6108 | 307 | AA891873 | d,General | | ATPase inhibitor (rat mitochondrial IF1 protein) | ATPase inhibitor (rat mitochondrial IF1 protein) |
| 11660 | 1595 | AI178944 | General,aa | | | ESTs, Highly similar to AF167573 1 protein methyltransferase [*M.musculus*] |
| 15185 | 2471 | X62952 | u | | vimentin | vimentin |
| 10019 | 1586 | AI178756 | General | | | ESTs |
| 23587 | 1517 | AI176598 | v | | | ESTs |
| 650 | 2450 | X55286 | c | Sterol biosynthesis | 3-hydroxy-3-methylglutaryl-Coenzyme A reductase | 3-hydroxy-3-methylglutaryl-Coenzyme A reductase |
| 1794 | 2475 | X64401 | f,g,h,cc,dd | | Cytochrome P450, subfamily IIIA, polypeptide 3 | Cytochrome P450, subfamily IIIA, polypeptide 3 |
| 23679 | 830 | AF087037 | aa | | B-cell translocation gene 3 | B-cell translocation gene 3 |
| 15365 | 1562 | AI177598 | General | | cofilin, non-muscle | cofilin, non-muscle |
| 15080 | 1210 | AI102045 | t | | | ESTs, Highly similar to OS-4 protein [*H.sapiens*] |
| 21066 | 1926 | D10587 | c,General,u | | | Rat lysosomal membrane protein (LIMPII) mRNA, complete cds |
| 10533 | 1091 | AI058430 | j,General | | | ESTs, Highly similar to HG17 RAT NONHISTONE CHROMOSOMAL PROTEIN HMG-17 [*R.norvegicus*] |
| 21341 | 174 | AA850195 | k,o,y | | | *Rattus norvegicus* cytokeratin-18 mRNA, partial cds |
| 1501 | 1185 | AI072634 | w | | | ESTs |
| 17953 | 385 | AA894090 | v | | | ESTs |
| 19732 | 1850 | AI236066 | dd | | | ESTs |
| 22846 | 436 | AA923982 | General | | | ESTs, Highly similar to ATP-specific succinyl-CoA synthetase beta subunit [*M.musculus*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 21522 | 540 | AA944449 | w | | | ESTs, Highly similar to SR68_HUMAN SIGNAL RECOGNITION PARTICLE 68 KDA PROTEIN (SRP68)[H.sapiens] |
| 17214 | 1897 | AI639008 | v | | | ESTs |
| 8387 | 1504 | AI176365 | e | | | ESTs |
| 10229 | 1117 | AI059618 | General | | | ESTs, Highly similar to UDP1_HUMAN UTP-GLUCOSE-1-PHOSPHATE URIDYLYLTRANSFERASE 1 [H.sapiens] |
| 18316 | 822 | AF072411 | bb | | CD36 antigen (collagen type I receptor, thrombospondin receptor) | CD36 antigen (collagen type I receptor, thrombospondin receptor) |
| 23494 | 1410 | AI170967 | General | | | Rattus norvegicus zygin-related protein type II (Zrp2) mRNA, partial cds |
| 20146 | 2159 | M22926 | e | | muscarinic acetylcholine receptor M5 | muscarinic acetylcholine receptor M5 |
| 16922 | 2248 | S45663 | h | | | ESTs, Weakly similar to S5A2 RAT 3-OXO-5-ALPHA-STEROID 4-DEHYDROGENASE 2 [R.norvegicus] |
| 22352 | 1491 | AI175959 | e | | | ESTs |
| 17995 | 2136 | M13646 | x | | | Rattus norvegicus Sprague Dawley testosterone 6-beta-hydroxylase, cytochrome P450/6-beta-A, (CYP3A2) mRNA, complete cds |
| 870 | 2361 | U66478 | v | | MAD (mothers against decapentaplegic, Drosophila) homolog 1 | MAD (mothers against decapentaplegic, Drosophila) homolog 1 |
| 5421 | 1202 | AI101270 | i | | | ESTs, Highly similar to GDIS MOUSE RHO GDP-DISSOCIATION INHIBITOR 2 [M.musculus] |
| 14664 | 1736 | AI232081 | j | | | ESTs |
| 21228 | 1056 | AI044404 | l | | | ESTs |
| 173 | 2424 | X15580 | r | Fructose and mannose metabolism | 6-Phosphofructo-2-kinase/fructose-2,6-bisphosphatase 1 (liver and muscle) | 6-Phosphofructo-2-kinase/fructose-2,6-bisphosphatase 1 (liver and muscle) |
| 19259 | 421 | AA900613 | r,bb | | | ESTs |
| 14267 | 949 | AI011738 | o,dd | | | ESTs, Highly similar to P044 RAT 0-44 PROTEIN [R.norvegicus] |
| 18386 | 2093 | L03294 | i | Glycerolipid metabolism | Lipoprotein lipase | ESTs, Highly similar to LIPL RAT LIPOPROTEIN LIPASE PRECURSOR [R.norvegicus], Lipoprotein lipase |
| 26051 | 387 | AA894316 | General | | RNA binding protein p45AUF1 | RNA binding protein p45AUF1 |
| 23390 | 1460 | AI172328 | General | | | |
| 23331 | 1781 | AI233457 | aa | | | ESTs, Weakly similar to HUD RAT ENCEPHALOMYELITIS ANTIGEN HUD PARANEOPLASTIC HOMOLOG [R.norvegicus] |
| 22953 | 600 | AA946509 | f | | | ESTs, Highly similar to 26S proteasome subunit p44.5 [H.sapiens] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 23930 | 711 | AA997182 | x | | | ESTs, Highly similar to RPB8_HUMAN DNA-DIRECTED RNA POLYMERASES I, II, AND III 17.1 KD POLYPEPTIDE [H.sapiens] |
| 5990 | 640 | AA956907 | g,t | | ornithine decarboxylase antizyme inhibitor | ESTs, Highly similar to p162 protein [M.musculus] ornithine decarboxylase antizyme inhibitor |
| 21062 | 1039 | AI043631 | y | | | |
| 3292 | 1921 | D00753 | b | | Serine protease inhibitor | Serine protease inhibitor |
| 666 | 2126 | M10072 | u | | | Rat nRNA for leucocyte-common antigen (L-CA) |
| 7684 | 1025 | AI030242 | a | | | ESTs |
| 19884 | 1388 | AI170501 | v | | | ESTs, Moderately similar to 0806162H protein URF3 [M.musculus] |
| 17997 | 54 | AA800671 | General | | | ESTs, Moderately similar to A54854 Ras GTPase activating protein-related protein [H.sapiens] |
| 9821 | 1626 | AI180114 | v | Fatty acid metabolism, Lysine degradation, Tryptophan metabolism | HMm:glutaryl-Coenzyme A dehydrogenase | ESTs, Highly similar to NIP2I [M.musculus] |
| 23596 | 1282 | AI105435 | General | | | ESTs, Highly similar to GCDH MOUSE GLUTARYL-COA DEHYDROGENASE PRECURSOR [M.musculus] |
| 12233 | 990 | AI013474 | z | | | ESTs, Weakly similar to AF189764 1 alpha/beta hydrolase-1 [M.musculus] |
| 6016 | 84 | AA818163 | d,m,p,v | | Inhibitor of DNA binding 1, helix-loop-helix protein (splice variation) | EST |
| 10248 | 2109 | L23148 | n,r | | | Inhibitor of DNA binding 1, helix-loop-helix protein (splice variation) |
| 18293 | 2401 | X05341 | f,k,o | Bile acid biosynthesis, Fatty acid biosynthesis (path 2), Fatty acid metabolism, Phenylalanine metabolism, Valine, leucine and icoleucine degradation | HHs:acetyl-Coenzyme A acyltransferase 2 (mitochondrial 3-oxoacyl-Coenzyme A thiolase) | Rat mRNA for 3-oxoacyl-CoA thiolase |
| 6844 | 901 | AI009770 | General | | | ESTs |
| 17368 | 417 | AA900548 | General | | | ESTs, Weakly similar to T30021 hypothetical protein K08F11.4 - Caenorhabditis elegans [C.elegans] |
| 11419 | 1421 | AI171365 | General | | | ESTs, Weakly similar to DDX4 RAT DEAD BOX PROTEIN 4 [R.norvegicus] |
| 2047 | 663 | AA963366 | a | | | ESTs, Highly similar to TPMB RABIT TROPOMYOSIN BETA CHAIN, SKELETAL MUSCLE [R.norvegicus] |
| 671 | 2289 | U04808 | a,General | | | Rattus norvegicus Sprague-Dawley putative G-protein coupled receptor (GCR) mRNA, complete cds |
| 3705 | 752 | AA999054 | aa | | | ESTs |
| 26133 | 905 | AI009950 | b,General | | | ESTs |
| 7067 | 1669 | AI229655 | General | | | ESTs |
| 6945 | 1663 | AI229467 | d,General | | | ESTs |
| 19624 | 743 | AA998422 | m | | | EST |
| 18244 | 151 | AA848776 | w | | | ESTs |
| 21029 | 42 | AA799981 | x | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15849 | 853 | AI008074 | z | | | ESTs, ESTs, Highly similar to HS9B RAT HEAT SHOCK PROTEIN HSP 90-BETA [R.norvegicus] |
| 18369 | 27 | AA799645 | General | | FXYD domain-containing ion transport regulator 1 | FXYD domain-containing ion transport regulator 1 |
| 22130 | 517 | AA943020 | aa | | | ESTs |
| 15180 | 915 | AI010354 | n | | | ESTs |
| 15621 | 2065 | J04473 | t | Citrate cycle (TCA cycle), Reductive carboxylate cycle (CO2 fixation) | Fumarate hydratase | Fumarate hydratase |
| 17284 | 2048 | J02827 | w | Valine, leucine and isoleucine degradation | Branched chain alpha-ketoacid dehydrogenase subunit | Branched chain alpha-ketoacid dehydrogenase subunit E1 alpha E1 alpha |
| 9162 | 1178 | AI072392 | a | | | ESTs, Highly similar to complement component C2 [M.musculus] |
| 3944 | 422 | AA900688 | r | | | ESTs, Highly similar to phosphoprotein [M.musculus] |
| 24521 | 574 | AA945636 | cc | | | ESTs, Highly similar to 60S ACIDIC RIBOSOMAL PROTEIN P1 [R.norvegicus] |
| 5027 | 460 | AA924793 | bb | | | ESTs |
| 15252 | 1582 | AI178605 | p,q,dd | | | ESTs, Highly similar to CSK RAT TYROSINE-PROTEIN KINASE CSK [R.norvegicus] |
| 16993 | 20 | AA799560 | d,g,u | | | ESTs |
| 16411 | 1094 | AI058647 | bb | | | ESTs |
| 20783 | 1442 | AI171966 | u | | | R.norvegicus mRNA for RT1.Mb |
| 17154 | 2145 | M15883 | f | | | Rat clathrin light chain (LCB2) mRNA, complete cds, Rat clathrin light chain (LCB3) mRNA, complete cds |
| 17588 | 356 | AA892849 | v | | | ESTs, Weakly similar to MXI1 RAT MAX INTERACTING PROTEIN 1 [H.sapiens] |
| 22978 | 254 | AA859931 | a | | | ESTs, Moderately similar to R26445 1 [H.sapiens] |
| 24146 | 1373 | AI169668 | j | | | ESTs, Weakly similar to hypothetical protein [H.sapiens] |
| 9929 | 1000 | AI013834 | k,o | Androgen and estrogen metabolism | peroxisomal multifunc-tional enzyme type II | peroxisomal multifunctional enzyme type II |
| 25090 | 2473 | X63594 | General | | DNA-damage-inducible transcript 1 | DNA-damage-inducible transcript 1 |
| 354 | 2119 | L32591 | o | | | ESTs |
| 7246 | 988 | AI013331 | f | | | R.norvegicus mRNA for histone H3.3 |
| 15644 | 911 | AI010256 | g | | | Rattus norvegicus gcd-10S mRNA, complete cds |
| 14199 | 1811 | AI234133 | i | | | ESTs, Moderately similar to ZNF127-Xp [H.sapiens] |
| 7317 | 1307 | AI136123 | | | | ESTs, Weakly similar to PE2R RAT 20-ALPHA-HYDROXYSTEROID DEHYDROGENASE [R.norvegicus] |
| 9191 | 1170 | AI072107 | c,u | | | |
| 15850 | 1876 | AI236795 | f,o | | | ESTs, ESTs, Highly similar to HS9B RAT HEAT SHOCK PROTEIN HSP 90-BETA [R.norvegicus] |
| 17394 | 2062 | J03969 | General,t | | Nucleoplasmin-related protein (Nuclear protein B23 | Nucleoplasmin-related protein (Nuclear protein B23 |
| 14004 | 1776 | AI233261 | j | Glutamate metabolism, Glutathione metabolism | Glutamate-cysteine ligase (gamma-glutamyl-cysteine synthetase), regulatory | Glutamate-cysteine ligase (gamma-glutamylcysteine synthetase), regulatory |
| 9150 | 877 | AI009198 | g,General | | | ESTs, Highly similar to serine-threonine kinase receptor-associated protein [M.musculus] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 13785 | 1655 | AI228970 | General | | | ESTs |
| 23078 | 1668 | AI229647 | General | | | ESTs |
| 17339 | 162 | AA849497 | j | | | ESTs |
| 17787 | 1376 | AI169758 | n | | Apolipoprotein C-III | Apolipoprotein C-III |
| 3279 | 1241 | AI103224 | z | | | ESTs, Weakly similar to putative short-chain dehydrogenase/reductase [*R.norvegicus*] |
| 145 | 820 | AF064541 | h | | arginine vasopressin receptor 1B | arginine vasopressin receptor 1B |
| 22876 | 1445 | AI172041 | General | | | ESTs, Moderately similar to CGI-137 protein [*H.sapiens*] |
| 2911 | 1036 | AI030835 | e | Sterol biosynthesis, Terpenoid biosynthesis | | ESTs |
| 15069 | 2232 | M89945 | e | | testis-specific farnesyl pyrophosphate synthetase | testis-specific farnesyl pyrophosphate synthetase |
| 13434 | 1466 | AI172552 | General | | | EST |
| 23305 | 652 | AA957451 | bb | | | *Rattus norvegicus* mRNA for NAD+-specific isocitrate dehydrogenase a-subunit, complete cds |
| 1246 | 2195 | M57507 | c | Purine metabolism | Guanylate cyclase, soluble, beta 2 (GTP pyrophosphate - lyase) | Guanylate cyclase, soluble, beta 2 (GTP pyrophosphate - lyase) |
| 6537 | 1798 | AI233817 | v | | kidney-derived aspartic protease-like protein | kidney-derived aspartic protease-like protein |
| 19728 | 1385 | AI170394 | General | | | ESTs |
| 9267 | 1177 | AI072384 | General,u | | | *Rattus norvegicus* formininotransferase-cyclodeaminase mRNA, complete cds |
| 9524 | 1196 | AI073249 | aa | | | ESTs, Highly similar to U4/U6-associated RNA splicing factor [*H.sapiens*] |
| 3880 | 371 | AA893247 | r | | | ESTs, Highly similar to serine/threonine kinase [*R.norvegicus*] |
| 24598 | 2167 | AI013690 | i | | phosphatidylinositol transfer protein | phosphatidylinositol transfer protein |
| 1479 | 2329 | U32314 | l | Alanine and aspartate metabolism, Citrate cycle (TCA cycle), Pyruvate metabolism | Pyruvate carboxylase | Pyruvate carboxylase |
| 20449 | 2431 | X17053 | m | | Small inducible gene JE | Small inducible gene JE |
| 23055 | 515 | AA942929 | General | | | ESTs |
| 15018 | 685 | AA964688 | General | | | ESTs |
| 12306 | 547 | AA944898 | i,p | | | ESTs |
| 9674 | 1588 | AI178784 | General | | | ESTs |
| 7069 | 912 | AI010301 | e | | | ESTs |
| 17167 | 994 | AI013690 | i | | | ESTs |
| 21625 | 1597 | AI179012 | t | | cytoplasmic beta-actin | cytoplasmic beta-actin |
| 23869 | 2369 | U75397 | General | | Early growth response 1 | Early growth response 1 |
| 16320 | 252 | AA859899 | f,General | | | EST |
| 21977 | 2249 | S46785 | m | | | *Rattus norvegicus* onsulin-like growth factor binding complex acid-labile subunit gene, complete cds |
| 1301 | 2037 | J02585 | z | | | Rat liver stearyl-CoA desaturase mRNA, complete cds |
| 15374 | 2033 | H34186 | d,General | | | ESTs, Highly similar to IF39_HUMAN EUKARYOTIC TRANSLATION INITIATION FACTOR 3 SUBUNIT 9 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 2005 | 1964 | D29646 | u,v | Nicotinate and nicotinamide metabolism | CD38 antigen (ADP-riosyl cyclase/cyclic ADP-ribose hydrolase) | CD38 antigen (ADP-ribosyl cyclase/cyclic ADP-ribose hydrolase) |
| 2619 | 1720 | AI231290 | General | | | ESTs, Moderately similar to ARDH_HUMAN N-TERMINAL ACETYLTRANSFERASE COMPLEX ARD1 SUBUNIT HOMOLOG [H.sapiens] |
| 13317 | 1252 | AI103637 | General | | | ESTs, Weakly similar to D52 [M.musculus] |
| 8344 | 1115 | AI059511 | c,e | | | EST |
| 3114 | 1493 | AI176018 | dd | | | ESTs, Highly similar to apyrase [H.sapiens] |
| 7804 | 1794 | AI233771 | r,t | | | ESTs |
| 18927 | 152 | AA848813 | General | | | ESTs, Highly similar to DP1 MOUSE POLYPOSIS LOCUS PROTEIN 1 HOMOLOG [M.musculus] |
| 5916 | 1448 | AI172078 | aa | | | ESTs |
| 12119 | 159 | AA849354 | t | | | ESTs, Moderately similar to KIAA0948 protein [H.sapiens] |
| 8036 | 1708 | AI230884 | l | | | ESTs |
| 2373 | 682 | AA964455 | General,z | Nitrogen metabolism | | ESTs |
| 6017 | 806 | AF037072 | c | | carbonic anhydrase 3 | carbonic anhydrase 3 |
| 494 | 2529 | Z24721 | General | | Superoxide dimutase 3 | Superoxide dimutase 3 |
| 11520 | 708 | AA997068 | bb | | | ESTs, Weakly similar to CAG6 RAT CMP-N-ACETYLNEURAMINATE-BETA-1,4-GALACTOSIDE ALPHA-2,3-SIALYLTRANSFERASE [R.norvegicus] |
| 1748 | 2225 | M84488 | u | | Vascular cell adhesion molecule 1 | Vascular cell adhesion molecule 1 |
| 24582 | 2430 | X16554 | c | Pentose phosphate cycle, Purine metabolism | phosphoribosyl pyrophosphate synthetase 1 | phosphoribosyl pyrophosphate synthetase 1 |
| 15623 | 168 | AA849769 | f | | follistatin-related protein precursor | follistatin-related protein precursor |
| 5597 | 1207 | AI101622 | e | Glutathione metabolism | | ESTs |
| 634 | 2082 | K01932 | h,t,w,x,cc | | Glutathione-S-transferase, alpha type (Ya) | Glutathione-S-transferase, alpha type (Ya) |
| 10176 | 128 | AA819530 | y | | E-septin | E-septin |
| 6322 | 109 | AA818801 | u | | | ESTs |
| 19463 | 1256 | AI103915 | aa | | | ESTs, Weakly similar to T25460 hypothetical protein B0432.3 - Caenorhabditis elegans [C.elegans] |
| 15786 | 1005 | AI013924 | n,y | | | ESTs |
| 15606 | 537 | AA944401 | General | | | ESTs, Moderately similar to B Chain B, Vhs Domain Of Tom1 Protein From H. Sapien [H.sapiens] |
| 26045 | 379 | AA893803 | General | | | ESTs |
| 17334 | 219 | AA858704 | aa | | | ESTs, Weakly similar to Reg receptor [R.norvegicus] |
| 22069 | 594 | AA946349 | v | | | ESTs |
| 17377 | 2416 | X13058 | v | | Tumor protein p53 (Li-Fraumeni syndrome) | Tumor protein p53 (Li-Fraumeni syndrome) |
| 5934 | 65 | AA817695 | e,m | | | ESTs, Highly similar to 2008147C protein RAKd [R.norvegicus] |
| 25287 | 1972 | D38069 | i | | | |

TABLE 1-continued

| GLGC ID | SeqID | GenBank Acc | Model Code | Pathway Name | Known Gene Name | Unigene Cluster Title | Document Number 1740956 |
|---|---|---|---|---|---|---|---|
| 1430 | 2226 | M84648 | e,General | Histidine metabolism, Phenylalanine metabolism, Tryptophan metabolism, Tyrosine metabolism | Dopa decarboxylase (aromatic L-amino acid decarboxylase) | Dopa decarboxylase (aromatic L-amino acid decarboxylase) | |
| 15663 | 1484 | AI175566 | General | | t-complex testis expressed 1 | t-complex testis expressed 1 | |
| 13757 | 1650 | AI228676 | n | | | ESTs, Weakly similar to T15736 hypothetical protein C32D5.6 - *Caenorhabditis elegans* [*C.elegans*] | |
| 20983 | 1065 | AI044900 | d,r | Fatty acid metabolism | | Acyl CoA synthetase, long chain | |
| 4674 | 404 | AA899847 | General | | | ESTs, Weakly similar to S26689 hypothetical protein hc1 - mouse [*M.musculus*] | |
| 9029 | 1967 | D30804 | General | | | ESTs, Highly similar to PRC6 RAT PROTEASOME SUBUNIT RC6-1 [*R.norvegicus*] | |
| 16561 | 1325 | AI137862 | b,General | | p38 mitogen activated protein kinase | P38 mitogen activated protein kinase | |
| 22917 | 1640 | AI228120 | l | | | *Rattus norvegicus* GCIP-interacting protein p29 mRNA, complete cds | |
| 14506 | 2025 | H32584 | z | | | ESTs | |
| 11066 | 1163 | AI071602 | a | | | ESTs | |
| 16327 | 271 | AA875050 | a | | | ESTs | |
| 17879 | 1702 | AI230741 | General | | | ESTs | |
| 4703 | 1728 | AI231606 | General | | | ESTs, Weakly similar to YII3_YEAST HYPOTHETICAL 41.9 KD PROTEIN IN SDS3-THS1 INTERGENIC REGION [*S.cerevisiae*] | |
| 21799 | 1222 | AI102576 | y | | | ESTs | |
| 11067 | 966 | AI012397 | General | | | ESTs | |
| 9410 | 1188 | AI072842 | aa | | | ESTs | |
| 11542 | 1396 | AI170664 | aa | | | ESTs | |
| 20842 | 166 | AA849722 | f | Proteasome | HMm:proteasome (prosome, macropain) subunit, beta type 1 | Rat mRNA for proteasome subunit RC5 | |
| 10152 | 1102 | AI059110 | f,x,dd | | | EST | |
| 2822 | 1793 | AI233763 | General | | | ESTs | |
| 17721 | 578 | AA945762 | j,General | | | ESTs, Weakly similar to PTNL RAT PROTEIN TYROSINE PHOSPHATASE, NON-RECEPTOR TYPE 21 [*R.norvegicus*] | |
| 15703 | 770 | AB009372 | b,p,General | epo, ifn_gamma, il3, il6, interact6-1, | Janus kinase 2 (a protein tyrosine kinase) | *Rattus norvegicus* mRNA for Lysophospholipase, complete cds | |
| 25581 | 2308 | U13396 | i | | | Janus kinase 2 (a protein tyrosine kinase) | |
| 5193 | 491 | AA925693 | aa | | | EST | |
| 8592 | 2029 | H33491 | General | | | *Rattus norvegicus* sterol delta 8-isomerase (RSI) mRNA, complete cds | |
| 15124 | 2039 | J02612 | f,g,h,k,q,x,cc | Androgen and estrogen metabolism, Pentose and | UDP-glucuronosyltransferase 1 family, | *Rattus norvegicus* UDP-glucuronosyltransferase UGT1A7 mRNA, | |

Document Number 1740956

TABLE 1-continued

| GLGC ID | SeqID | GenBank Acc | Model Code | Pathway Name | Known Gene Name | Unigene Cluster Title |
|---|---|---|---|---|---|---|
| 24693 | 2042 | J02720 | h | glucuronate inter-conversions, Porphyrin and chlorophyll metabolism, Starch and sucrose metabolism | member 1 glucuronosyltransferase 1 family, member 1 | complete cds, UDP- |
| 5082 | 1943 | D14015 | r,General | Arginine and proline metabolism, Urea cycle and metabolism of amino groups | arginase 1, liver | arginase 1, liver |
| 22966 | 1687 | AI230320 | aa | | Cyclin e | ESTs, Highly similar to CGE1 RAT G1/S-SPECIFIC CYCLIN E1 [R.norvegicus] |
| 4462 | 258 | AA866264 | General | | | ESTs |
| 20853 | 819 | AF063302 | bb | Fatty acid metabolism, Glycerolipid metabolism | Carnitine palmitoyl-transferase 1 beta, muscle isoform | ESTs, Weakly similar to PE2R RAT 20-ALPHA-HYDROXYSTEROID DEHYDROGENASE [R.norvegicus] Carnitine palmitoyltransferase 1 beta, muscle isoform |
| 20868 | 2177 | M32062 | u | | | Rat Fc-gamma receptor mRNA, complete cds |
| 926 | 759 | AB003042 | i | | | R.norvegicus mRNA for C5a receptor |
| 5969 | 1218 | AI102520 | w | | | ESTs, Moderately similar to AF161588 1 GABA-A receptor-associated protein [R.norvegicus] |
| 17956 | 681 | AA964379 | r | | | R.norvegicus beta-chain clathrin associated protein complex.AP-2 mRNA, complete cds |
| 20819 | 2217 | M81225 | v | | Farnesyltransferase, subunit alpha | Farnesyltransferase, subunit alpha |
| 15088 | 1761 | AI232613 | General | | | ESTs, Highly similar to AF151886 1 CGI-128 protein [H.sapiens] |
| 5936 | 674 | AA964214 | c | | K-kininogen, differential splicing leads to HMW Kngk, T-kininogen | ESTs |
| 1854 | 2083 | K02814 | a,b | | | K-kininogen, differential splicing leads to HMW Kngk, T-kininogen |
| 25691 | 2443 | X53504 | cc | | | ESTs, Moderately similar to YCD1_HUMAN HYPOTHETICAL PROTEIN CGI-131 [H.sapiens] |
| 13167 | 1346 | AI145832 | General,aa | | | |
| 7063 | 2133 | M12919 | v,y | Carbon fixation, Fructose and mannose metabolism, Glycolysis/Gluconeogenesis, Inositol metabolism, Pentose phosphate cycle | Aldolase A, fructose-bisphosphate | Aldolase A, fructose-bisphosphate |
| 4199 | 2220 | M83143 | b,c,bb | | | Rat beta-galactoside-alpha 2,6-sialyltransferase mRNA |
| 11708 | 1436 | AI171807 | g | | | ESTs |
| 1923 | 1402 | AI170754 | j | | | ESTs, Highly similar to AF151885 1 CGI-127 protein [H.sapiens] |
| 21895 | 872 | AI008971 | bb | | | ESTs |
| 21014 | 2060 | J03914 | x | Glutathione metabolism | Glutathione-S-transferase, mu type 2 (Yb2) | Glutathione-S-transferase, mu type 2 (Yb2) |
| 2713 | 659 | AA962943 | q | | | ESTs, Moderately similar to Notch4 [M.musculus] |

TABLE 1-continued

| GLGC ID | SeqID | GenBank Acc | Model Code | Pathway Name | Known Gene Name | Unigene Cluster Title |
|---|---|---|---|---|---|---|
| 9180 | 1044 | AI043694 | bb | | | ESTs, Weakly similar to T27134 hypothetical protein Y53C12B.2 - Caenorhabditis elegans [C.elegans] |
| 17104 | 2171 | M29358 | General,cc | | ribosomal protein S6 | ribosomal protein S6 |
| 3365 | 870 | AI008919 | v | | | ESTs |
| 5962 | 72 | AA817875 | m | | | ESTs |
| 3082 | 754 | AA999172 | General | Glutamate metabolism, Purine metabolism | HHs:guanine monophosphate synthetase | ESTs, Highly similar to GUAA_HUMAN GMP SYNTHASE [H.sapiens] |
| 10110 | 1098 | AI058863 | j | | | EST |
| 23536 | 1483 | AI175558 | General | | | ESTs |
| 23285 | 622 | AA955976 | bb | | | ESTs |
| 12829 | 218 | AA858695 | z,bb | | | ESTs, Highly similar to ganglioside-induced differentiation associated protein 3 [M.musculus] |
| 534 | 2197 | M58041 | h | | 14 - 3 - 3 - zeta isoform, Tyrosine 3-monooxygenase/ tryptophan 5-monooxygenase activation protein, zeta polypeptide | Rat p450Md mRNA for cytochrome P-450 |
| 25279 | 1966 | D30740 | i | | | Tyrosine 3-monooxygenase/tryptophan 5-monooxygenase activation protein, zeta polypeptide |
| 16618 | 1352 | AI168967 | j,aa | | | ESTs, Moderately similar to methyl-CpG binding protein MBD1 [M.musculus] |
| 17958 | 2184 | M34176 | h | | | R.norvegicus beta-chain clathrin associated protein complex AP-2 mRNA, complete cds |
| 15787 | 837 | AF095576 | i | | 5'-AMP-activated protein kinase, beta subunit | Rattus norvegicus APS protein mRNA, complete cds |
| 17601 | 2513 | X95577 | k | | | 5'-AMP-activated protein kinase, beta subunit |
| 13646 | 2467 | X62166 | General | | | ESTs, Highly similar to RL3 RAT 60S RIBOSOMAL PROTEIN L3 [R.norvegicus] |
| 7784 | 2066 | J04591 | z | | Dipeptidyl peptidase 4 | Dipeptidyl peptidase 4 |
| 3860 | 1764 | AI232703 | bb | | malonyl-CoA decarboxylase | malonyl-CoA decarboxylase |
| 1478 | 2329 | U32314 | d,l | Alanine and aspartate metabolism, Citrate cycle (TCA cycle), Pyruvate metabolism | Pyruvate carboxylase | Pyruvate carboxylase |
| 3655 | 85 | AA818183 | General,aa | | | ESTs, Highly similar to RPA5 MOUSE DNA-DIRECTED RNA POLYMERASE I 40 KDA POLYPEPTIDE [M.musculus] |
| 19443 | 354 | AA892832 | p,q | | | ESTs |
| 9288 | 1180 | AI072458 | aa | | | ESTs |
| 19018 | 2230 | M86870 | w | | | Rat calcium-binding protein mRNA, complete cds |
| 18978 | 1902 | AI639208 | e | | | ESTs, Highly similar to AF186115 1 putative secreted protein ZSIG9 [M.musculus] |
| 9633 | 842 | AI007768 | e | | SH-PTP2 protein tyrosine phosphatase, non-receptor type 11 | Rattus norvegicus CPI17 (Cpi17) mRNA, complete cds |
| 18095 | 1558 | AI177482 | d | | | SH-PTP2 protein tyrosine phosphatase, non-receptor type 11 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 21042 | 37 | AA799814 | t | | | ESTs, Weakly similar to KCCD RAT CALCIUM/CALMODULIN-DEPENDENT PROTEIN KINASE TYPE II DELTA CHAIN [R.norvegicus] |
| 16278 | 1974 | D38381 | dd | Carbon fixation, Glycolysis/Gluconeogenesis, Purine metabolism, Pyruvate metabolism | | R.norvegicus CYP3 mRNA |
| 20513 | 2402 | X05684 | e | | Pyruvate kinase, liver and RBC | Pyruvate kinase, liver and RBC |
| 17999 | 2313 | U19485 | f,bb | | | Rattus norvegicus spp-24 precursor mRNA, partial cds |
| 2899 | 702 | AA996698 | y | | | EST |
| 16217 | 2373 | U75928 | d | | Secreted acidic cystein-rich glycoprotein (osteonectin) | Secreted acidic cystein-rich glycoprotein (osteonectin) |
| 20429 | 2069 | J05035 | p | Androgen and estrogen metabolism, Bile acid biosynthesis | Steroid-5-alpha-reductase, alpha polypeptide 1 (3-oxo-5 alpha-steroid delta 4 dehydrogenase alpha 1) | Steroid-5-alpha-reductase, alpha polypeptide 1 (3-oxo-5 alpha-steroid delta 4-dehydrogenase alpha 1) |
| 1792 | 788 | AF004218 | f | | opioid receptor, sigma 1 | opioid receptor, sigma 1 |
| 9134 | 1977 | D45247 | f | Proteasome | proteasome beta type subunit 5 | |
| 7031 | 936 | AI011291 | bb | Arginine and proline metabolism, Ascorbate and aldarate metabolism, Bile acid biosynthesis, Butanoate metabolism, Fatty acid metabolism, Glycerolipid metabolism, Histidine metabolism, Lysine degradation, Propanoate metabolism, Pyruvate metabolism, Tryptophan metabolism, Valine, leucine and isoleucine degradation, beta-Alanine metabolism | | ESTs |
| 17107 | 1581 | AI178582 | General,z | | ribosomal protein S6 | ribosomal protein S6 |
| 12299 | 1444 | AI172017 | h | | aldehyde dehydrogenase 2, mitochondrial | aldehyde dehydrogenase 2, mitochondrial |
| 25406 | 2149 | M18330 | dd | | | |
| 23448 | 471 | AA925167 | g,q,General | | | ESTs |
| 5999 | 116 | General | | | | ESTs |
| 24649 | 1825 | AI234950 | p,q | Riboflavin metabolism | Acid phosphatase 2, lysozymal | Acid phosphatase 2, lysozymal |
| 11576 | 1350 | AI146177 | n | | | ESTs |
| 25574 | 2295 | U06752 | h | | protein phosphatase 1, regulatory (inhibitor) subunit 5 | protein phosphatase 1, regulatory (inhibitor) subunit 5 |
| 15379 | 1901 | AI639162 | p | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 6598 | 2201 | M58887 | n | il6, interact6-1 | Interleukin 6 receptor | Interleukin 6 receptor |
| 373 | 1991 | D86086 | General,x,y,bb | | Canalicular multispecific organic anion transporter | Canalicular multispecific organic anion transporter |
| 24825 | 2396 | X02741 | a,t | Phenylalanine metabolism, Phenylalanine, tyrosine and tryptophan biosynthesis, Tyrosine metabolism | Tyrosine aminotransferase | Tyrosine aminotransferase |
| 25725 | 2468 | X62660 | General,x,z | | | |
| 19185 | 1284 | AI111361 | q | | | ESTs |
| 25679 | 2421 | X15013 | a,w,cc | | | |
| 4899 | 439 | AA924017 | n | | | EST |
| 21923 | 293 | AA891260 | y | | | ESTs |
| 23698 | 2044 | J02749 | k,o,z,cc | Bile acid biosynthesis, Fatty acid biosynthesis (path 2), Fatty acid metabolism, Phenylalanine metabolism, Valine, leucine and isoleucine degradation | Acetyl-CoA acyltransferase, 3-oxo acyl-CoA thiolase A, peroxisomal | Acetyl-CoA acyltransferase, 3-oxo acyl-CoA thiolase A, peroxisomal |
| 5791 | 1081 | AI045423 | m | | | ESTs |
| 5074 | 1209 | AI101695 | l,aa | | | ESTs |
| 25718 | 2465 | X62145 | General | | ribosomal protein L8 | |
| 21746 | 2092 | L02896 | cc | | glypican 1 | glypican 1 |
| 12946 | 1643 | AI228291 | e | | | ESTs |
| 6387 | 1819 | AI234664 | e,m | | | ESTs |
| 8795 | 1469 | AI172618 | j | | | ESTs *Caenorhabditis elegans* [*C.elegans*] |
| 20880 | 2123 | L46791 | General | | carboxylesterase 1 | carboxylesterase 1 |
| 13645 | 1763 | AI232694 | c | | | ESTs, Weakly similar to Y079_HUMAN HYPOTHETICAL PROTEIN KIAA0079 [*H.sapiens*] |
| 2468 | 690 | AA964807 | g,General | | | hypothetical protein K05C4.2 - *Caenorhabditis elegans* [*C.elegans*] |
| 154 | 2331 | U32681 | w | | crp-ductin | crp-ductin |
| 11726 | 163 | AA849518 | e | | | ESTs |
| 23584 | 604 | AA955071 | p-q | | retinoid X receptor gamma ( | retinoid X receptor gamma ( |
| 24577 | 2449 | X55153 | c,w | | | ESTs, Highly similar to 60S ACIDIC RIBOSOMAL PROTEIN P2 [*R.norvegicus*] |
| 6472 | 1490 | AI175880 | General,dd | | | ESTs |
| 14254 | 1262 | AI103988 | General | | | ESTs, Highly similar to I67805 purine synthesis multifunctional protein - mouse [*M.musculus*] |
| 15003 | 1365 | AI169327 | m,u | | | *Rattus norvegicus* tissue inhibitor of metalloproteinase-1 (TIMP1), mRNA, complete cds |
| 25480 | 2249 | S46785 | c,m | | | Rat mitochondrial succinyl-CoA synthetase alpha subunit (cytoplasmic precursor) mRNA, complete cds |
| 18175 | 2054 | J03621 | k | | | |
| 20162 | 2432 | X17163 | m | egf, epo, igf-1, il2, il6, insulin, ngf, pdgf, tpo | Avian sarcoma virus 17 (v-jun) oncogene homolog | Avian sarcoma virus 17 (v-jun) oncogene homolog |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 20735 | 2503 | X89225 | d,g | | antigen identified by monoclonal antibodies 4F2 | antigen identified by monoclonal antibodies 4F2 |
| 6479 | 1374 | AI169690 | l,General | | Fibrinogen, gamma polypeptide | Fibrinogen, gamma polypeptide |
| 23606 | 2293 | U05784 | q,General,y | | microtubule-associated proteins 1A/1B light chain 3 | microtubule-associated proteins 1A/1B light chain 3 |
| 23608 | 1773 | AI233190 | n,q,General | | microtubule-associated proteins 1A/1B light chain 3 | microtubule-associated proteins 1A/1B light chain 3 |
| 11720 | 1743 | AI232273 | m,General | | | ESTs, Highly similar to RNA cyclase homolog [H.sapiens] |
| 15127 | 2252 | S56937 | f,g,l,q,General,x | Androgen and estrogen metabolism, Pentose and glucuronate interconversions, Porphyrin and chlorophyll metabolism, Starch and sucrose metabolism | UDP-glucuronosyltransferase 1 family, member 1 | Rattus norvegicus UDP-glucuronosyltransferase UGT1A7 mRNA, complete cds, UDP-glucuronosyltransferase 1 family, member 1 |
| 4205 | 953 | AI011982 | General | | | ESTs |
| 22534 | 465 | AA925045 | g | | | ESTs |
| 1571 | 2291 | U05014 | General | | | Rattus norvegicus Sprague/Dawley PHASI mRNA, complete cds |
| 20646 | 1886 | AI237641 | General | | | ESTs, Weakly similar to JC4230 ribosomal protein L7 - rat [R.norvegicus] |
| 21995 | 871 | AI008955 | bb | | | ESTs |
| 6431 | 232 | AA859085 | l,m | | | ESTs |
| 20 | 2113 | L26268 | y | | B-cell translocation gene 1, anti-proliferative | B-cell translocation gene 1, anti-proliferative |
| 4226 | 1567 | AI177752 | i | | | ESTs |
| 1061 | 791 | AF009329 | i | | | Rattus norvegicus enhancer-of-split and hairy-related protein 1 (SHARP-1) mRNA, complete cds |
| 20385 | 2448 | X54793 | h,k,x | | heat shock protein 60 (liver) | heat shock protein 60 (liver) |
| 21818 | 804 | AF036537 | General | | | Rattus norvegicus homocysteine respondent protein HCYP2 mRNA, complete cds |
| 15408 | 1918 | D00569 | k,o | | | Rattus norvegicus mRNA for 2,4-dienoyl-CoA reductase precursor, complete cds |
| 1409 | 975 | AI012802 | c | Pyruvate metabolism | HHs:hydroxyacyl glutathione hydrolase | Rattus norvegicus round spermatid protein RSP29 gene, complete cds |
| 15056 | 2354 | U60578 | r | Nitrogen metabolism | carbonic anhydrase 2 | carbonic anhydrase 2 |
| 1920 | 2125 | M10068 | g,General | | P450 (cytochrome) oxidoreductase | P450 (cytochrome) oxidoreductase |
| 9620 | 2440 | X53377 | h | | ribosomal protein S7 | ribosomal protein S7 |
| 18385 | 2093 | L03294 | i | Glycerolipid metabolism | Lipoprotein lipase | Lipoprotein lipase |
| 1749 | 2148 | M17526 | l | | GTP-binding protein | GTP-binding protein |
| 18719 | 2472 | X63410 | h,bb | Androgen and estrogen metabolism | Rat senescence marker protein 2A gene, exons 1 and 2 | Rat senescence marker protein 2A gene, exons 1 and 2 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 405 | 2481 | X70223 | d | | peroxisomal membrane protein 2, 22 kDa | peroxisomal membrane protein 2, 22 kDa |
| 11525 | 1457 | AI172286 | bb | | | ESTs, Weakly similar to L130_HUMAN 130 KD LEUCINE-RICH PROTEIN [*H.sapiens*] |
| 21196 | 1063 | AI044873 | General | | | ESTs |
| 23766 | 631 | AA956456 | cc | | | ESTs |
| 15558 | 286 | AA875537 | General,t | | | ESTs, Weakly similar to A46241 interferon response element-binding factor IREBF-2 mouse [*M.musculus*] |
| 17703 | 1757 | AI232498 | General | | | ESTs |
| 22957 | 1275 | AI104897 | j | | | ESTs, Moderately similar to meningioma-expressed antigen 11 [*H.sapiens*] |
| 21491 | 809 | AF040954 | v | | putative protein phosphatase 1 nuclear targeting subunit | putative protein phosphatase 1 nuclear targeting subunit |
| 19942 | 790 | AF008554 | v | | | *Rattus norvegicus* implantation-associated protein (LAG2) mRNA, partial cds |
| 191 | 2299 | U09540 | p | Fatty acid metabolism, Tryptophan metabolism | Cytochrome P450 1b1 | Cytochrome P450 1b1 |
| 9157 | 1618 | AI179947 | q | | Tyrosine 3-monooxygen-ase/tryptophan 5-mono-oxygenase activation protein, theta polypep-tide | ESTs |
| 14421 | 511 | AA942751 | i,r | | | Tyrosine 3-monooxygenase/tryptophan 5-monooxygenase activation protein, theta polypeptide |
| 12616 | 720 | AA997599 | General | | Dipeptidyl peptidase 4 | ESTs |
| 7783 | 317 | AA892069 | z | | | Dipeptidyl peptidase 4 |
| 22851 | 472 | AA925204 | o | | | ESTs, Highly similar to T08747 hypothetical protein DKFZp586B0519.1 [*H.sapiens*] |
| 17419 | 1031 | AI030524 | General | Glycoprotein biosynthesis | Ribophorin I | ESTs |
| 19335 | 2400 | X05300 | e | | | Ribophorin I |
| 7384 | 1014 | AI029143 | d | | | ESTs |
| 11561 | 1772 | AI233182 | General | | | ESTs |
| 14959 | 2288 | U03390 | General | | | *Rattus norvegicus* Sprague Dawley protein kinase C receptor mRNA, complete cds |
| 21111 | 1633 | AI227832 | v | | | ESTs |
| 15085 | 1801 | AI233839 | k,o | | | ESTs, Weakly similar to PTD011 [*H.sapiens*] |
| 22840 | 895 | AI009676 | General | | | ESTs |
| 25598 | 2330 | U32575 | p | Butanoate metabolism, Glycolysis/Gluconeogenesis, Pyruvate metabolism, Valine, leucine and isoleucine biosynthesis | HHs:pyruvate dehydrogenase (lipoamide) beta | ESTs, Highly similar to ODPB RAT PYRUVATE DEHYDROGENASE E1 COMPONENT BETA SUBUNIT, MITOCHONDRIAL PRECURSOR [*R.norvegicus*] |
| 12000 | 648 | AA957319 | g | | | |
| 14003 | 2259 | S65555 | General | Glutamate metabolism, Glutathione metabolism | Glutamate-cysteine ligase (gamma-glutamyl-cysteine synthetase), regulatory | Glutamate-cysteine ligase (gamma-glutamylcysteine synthetase), regulatory |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 16873 | 851 | AI008015 | p | | Thymopoietin (lamina associated polypeptide 2) | Thymopoietin (lamina associated polypeptide 2) |
| 25468 | 2238 | M94918 | q | | | |
| 20879 | 2477 | X65296 | u | | carboxylesterase 1 | carboxylesterase 1 |
| 1957 | 1451 | AI172143 | l | | Hras-revertant gene 107 | Hras-revertant gene 107 |
| 2811 | 1413 | AI171090 | o,bb | Butanoate metabolism, Synthesis and degradation of ketone bodies, Valine, leucine and isoleucine degradation | 3-hydroxy-3-methylglutaryl CoA lyase | 3-hydroxy-3-methylglutaryl CoA lyase |
| 10988 | 130 | AA819640 | b | | | ESTs |
| 3406 | 1070 | AI045083 | h | | | ESTs, Weakly similar to Y256_HUMAN HYPOTHETICAl PROTEIN KIAA0256 [*H.sapiens*] |
| 15376 | 278 | AA875206 | j | | | *Rattus norvegicus* mRNA for DA41, complete cds |
| 12371 | 456 | AA924752 | dd | | Zipper (leucine) protein kinase | Zipper (leucine) protein kinase |
| 1551 | 2405 | X06150 | l | Glycine, serine and threonine metabolism | Glycine methyltransferase | Glycine methyltransferase |
| 10249 | 1119 | AI059711 | m | | | EST |
| 16484 | 1356 | AI169116 | General | | | ESTs |
| 13670 | 1632 | AI227734 | e,General | | | ESTs |
| 6604 | 1657 | AI229192 | n | | | ESTs, Weakly similar to EXRT coagulation factor Xa [*R.norvegicus*] |
| 22690 | 586 | AA945970 | u | | | ESTs, Weakly similar to KIAA0062 [*H.sapiens*] |
| 14937 | 1883 | AI237159 | z | | | ESTs, Highly similar to lipoic acid synthetase [*H.sapiens*] |
| 14094 | 1836 | AI235377 | n | | | ESTs, Moderately similar to T12520 hypothetical protein DKFZp434G173.1 [*H.sapiens*] |
| 2153 | 2370 | U75404 | aa | | | ESTs |
| 25928 | 1903 | AI639236 | f | | | |
| 10187 | 1522 | AI176781 | General | | | ESTs |
| 23029 | 548 | AA944935 | e,General | | | ESTs |
| 17105 | 2171 | M29358 | h | Purine metabolism | ribosomal protein S6 | ribosomal protein S6 |
| 17050 | 14 | AA799466 | y | | Adenylate kinase 2 | Adenylate kinase 2 |
| 3264 | 727 | AA997779 | bb | | | ESTs, Moderately similar to A53184 myc far upstream element-binding protein [*H.sapiens*] |
| 21531 | 2233 | M91595 | z | | Insulin-like growth factor binding protein 2 | Insulin-like growth factor binding protein 2 |
| 16947 | 2412 | X08056 | h | Arginine and proline metabolism, Glycine, serine and threonine metabolism, Urea cycle and metabolism of amino groups | Guanidinoacetate methyltransferase | Guanidinoacetate methyltransferase |
| 9527 | 1962 | D28560 | q | | | *Rattus norvegicus* mRNA for phosphodiesterase I |
| 22512 | 2158 | M22670 | y | | Alpha-2-macroglobulin | Alpha-2-macroglobulin |
| 16364 | 323 | AA892251 | d,p | | | *R.norvegicus* mRNA for V1a arginine vasopressin receptor |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 18770 | 1778 | AI233362 | a | | Lysosomal associated membrane protein 1 (120 kDa) | Lysosomal associated membrane protein 1 (120 kDa) |
| 23471 | 606 | AA955162 | t | | | ESTs |
| 11376 | 1301 | AI112863 | i | | | ESTs |
| 19560 | 1037 | AI030921 | a | | | EST |
| 21043 | 1892 | AI237813 | t | | | ESTs, Weakly similar to KCCD RAT CALCIUM/CALMODULIN-DEPENDENT PROTEIN KINASE TYPE II DELTA CHAIN [*R.norvegicus*] |
| 21742 | 1497 | AI176172 | e | | | ESTs |
| 2230 | 654 | AA957643 | r | | | ESTs |
| 20986 | 370 | AA893242 | General | Fatty acid metabolism | Acyl CoA synthetase, long chain | Acyl CoA synthetase, long chain |
| 17237 | 2428 | X16145 | z | Glycoprotein degradation | Fucosidase, alpha-L-1, tissue | Fucosidase, alpha-L-1, tissue |
| 6366 | 220 | AA858716 | u | | | *Rattus norvegicus* mRNA for signal peptidase 21kDa subunit, complete cds |
| 3905 | 1247 | AI103403 | r,General | | polypyrimidine tract binding protein | polypyrimidine tract binding protein |
| 23245 | 1610 | AI179570 | General | | | ESTs |
| 2010 | 2292 | U05675 | b,n | | | *Rattus norvegicus* Sprague-Dawley fibrinogen B beta chain mRNA, complete cds |
| 18349 | 34 | AA799744 | General | | | ESTs |
| 2310 | 1020 | AI029969 | b | | | ESTs |
| 3167 | 1038 | AI031012 | bb | | | ESTs, Highly similar to CLPP MOUSE PUTATIVE ATP-DEPENDENT CLP PROTEASE PROTEOLYTIC SUBUNIT, MITOCHONDRIAL PRECURSOR [*M.musculus*] |
| 4940 | 1590 | AI178788 | k | Fatty acid metabolism, Tryptophan metabolism | rap7a | rap7a |
| 20715 | 2410 | X07259 | k,o,z | Sterol biosynthesis, | Cytochrome P450, subfamily IVB, polypeptide 1 | Cytochrome P450, subfamily IVB, polypeptide 1 |
| 25460 | 2232 | M89945 | e | Terpenoid biosynthesis | testis-specific farnesyl pyrophosphate synthetase | testis-specific farnesyl pyrophosphate synthetase |
| 18128 | 304 | AA891800 | General | | | ESTs, Moderately similar to pyrophosphatase [*H.sapiens*] |
| 2446 | 697 | AA965241 | x | | | ESTs, Highly similar to S32604 collagen alpha 2(VI) chain - mouse [*M.musculus*] |
| 14929 | 1384 | AI170353 | i,w | | | *Rattus norvegicus* ribosomal protein L21 mRNA, complete cds |
| 15181 | 1831 | AI235234 | l,General | | | ESTs |
| 22387 | 1703 | AI230753 | c | | | ESTs, Highly similar to I3 protein [*H.sapiens*] |
| 14997 | 2052 | J03572 | t,y | Folate biosynthesis, Glycerolipid metabolism | Tissue-nonspecific ALP alkaline phosphatase | Tissue-nonspecific ALP alkaline phosphatase |
| 17614 | 139 | AA848306 | q | | | ESTs |

TABLE 1-continued

| GLGC ID | SeqID | GenBank Acc | Model Code | Pathway Name | Known Gene Name | Unigene Cluster Title |
|---|---|---|---|---|---|---|
| 16769 | 2517 | X98225 | bb | | | Rat mRNA for mitochondrial long-chain enoyl-CoA hydratase/3-hydroxyacyl-CoA dehydrogenase alpha-subunit of mitochondrial trifunctional protein, complete cds |
| 15642 | 1560 | AI177503 | t | | | R.norvegicus mRNA for histone H3.3 |
| 22370 | 530 | AA944158 | d,k,General | | | ESTs |
| 24138 | 1359 | AI169160 | General | | | ESTs |
| 945 | 1996 | D88666 | m | | | Rattus norvegicus mRNA for PS-PLA1, complete cds |
| 17896 | 381 | AA893905 | General | | | ESTs |
| 15193 | 1665 | AI229508 | General,cc | | | ESTs |
| 22689 | 585 | AA945962 | aa | | | GTP-binding protein (G-alpha-i2) |
| 15888 | 279 | AA875225 | aa | | GTP-binding protein (G-alpha-i2) | GTP-binding protein (G-alpha-i2) |
| 16025 | 1751 | AI232374 | aa | | Histone H1-0 | Histone H1-0 |
| 15832 | 2262 | S68589 | i | | | ESTs, Moderately similar to NADH-ubiquinone oxidoreductase B14.5B subunit [H.sapiens] |
| 11097 | 1167 | AI071749 | a | | | EST |
| 11021 | 134 | AA819767 | e | | | ESTs |
| 10310 | 1536 | AI176961 | d,General | | ribosomal protein, mitochondrial, L12 | ribosomal protein, mitochondrial, L12 |
| 5926 | 1565 | AI177638 | j,General | | | ESTs, Moderately similar to M phase phosphoprotein 10 [H.sapiens] |
| 16701 | 866 | AI008838 | i,k,y,cc | | | ESTs, Weakly similar to LONN_HUMAN MITOCHONDRIAL LON PROTEASE HOMOLOG PRECURSOR [H.sapiens] |
| 15538 | 1298 | AI112633 | General | Proteasome | proteasome (prosome, macropain) subunit, alpha type 6 | proteasome (prosome, macropain) subunit, alpha type 6 |
| 23544 | 280 | AA875233 | t | | Prosaposin (sulfated glycoprotein, sphingolipid hydrolase activator) | Prosaposin (sulfated glycoprotein, sphingolipid hydrolase activator) |
| 4896 | 437 | AA924000 | General | | | ESTs |
| 15759 | 832 | AF089825 | General | | activin beta E | activin beta E |
| 6911 | 1987 | D85035 | d,General,w | | dihydropyrimidine dehydrogenase | dihydropyrimidine dehydrogenase |
| 590 | 2442 | X53428 | p | | glycogen synthase kinase 3 beta | glycogen synthase kinase 3 beta |
| 1921 | 2010 | E01524 | g,General | | P450 (cytochrome) oxidoreductase | P450 (cytochrome) oxidoreductase |
| 2670 | 969 | AI012552 | General | | | ESTs |
| 13393 | 1809 | AI234100 | General | | cysteine rich protein | cysteine rich protein |
| 2352 | 1267 | AI104325 | General | | | ESTs |
| 20788 | 1849 | AI236053 | i | | acyl-coenzyme A: cholesterol acyltransferase | acyl-coenzyme A:cholesterol acyltransferase |

Document Number 1740956

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15965 | 260 | AA866404 | a | | | ESTs, Weakly similar to amyloid beta-peptide binding protein [R.norvegicus] |
| 6895 | 1381 | AI170067 | aa | | | ESTs |
| 16426 | 2482 | X70369 | d | | procollagen, type III, alpha 1 | procollagen, type III, alpha 1 |
| 9067 | 1135 | AI070087 | General | Riboflavin metabolism | | ESTs, Weakly similar to NUCL RAT NUCLEOLIN [R.norvegicus] |
| 18709 | 2179 | M32397 | u | | prostatic acid phosphatase (rPAP) | prostatic acid phosphatase (rPAP) |
| 24437 | 2157 | M22357 | a | | Myelin-associated glycoprotein | Myelin-associated glycoprotein |
| 13229 | 222 | AA858760 | General | | | ESTs |
| 11528 | 1404 | AI170766 | aa | | | ESTs |
| 23933 | 1863 | AI236376 | a | | | ESTs |
| 7918 | 1615 | AI179750 | c | | | ESTs |
| 25479 | 2248 | S45663 | h,dd | | | |
| 21153 | 922 | AI010632 | t | | | Rattus norvegicus cis-Golgi p28 (p28) mRNA, complete cds |
| 5579 | 1531 | AI176863 | b | | | ESTs |
| 20914 | 2162 | M23995 | g,x | | aldehyde dehydrogenase family 1, subfamily A4 | aldehyde dehydrogenase family 1, subfamily A4 |
| 15135 | 2263 | S71021 | w,cc | | | R.norvegicus mRNA for ribosomal protein L6 |
| 24249 | 878 | AI009273 | e | Fatty acid biosynthesis (path 1) | fatty acid synthase | fatty acid synthase |
| 18387 | 1891 | AI237731 | i,u | Glycerolipid metabolism | Lipoprotein lipase | Lipoprotein lipase |
| 26368 | 2032 | H34047 | b | | T-complex 1 | T-complex 1 |
| 18434 | 448 | AA924413 | General | | | ESTs, Weakly similar to dJ465N24.2.1 [H.sapiens] |
| 22375 | 1679 | AI230046 | General | | | ESTs |
| 812 | 1983 | D63704 | d | Pantothenate and CoA biosynthesis, Pyrimidine metabolism, beta-Alanine metabolism | dihydropyrimidinase | dihydropyrimidinase |
| 7937 | 1837 | AI235414 | aa | | | ESTs |
| 12581 | 1338 | AI145235 | i | epo, itn_gamma, iL3, il6, Interact6-1, pdgf, tpo | Janus kinase 2 (a protein tyrosine kinase) | Janus kinase 2 (a protein tyrosine kinase) |
| 17161 | 329 | AA892333 | General | | alpha-tubulin | alpha-tubulin |
| 12156 | 2079 | K00996 | f,l,o,x,cc,dd | Fatty acid metabolism, Tryptophan metabolism | cytochrome P450, 2b19 | cytochrome P450, 2b19 |
| 14502 | 1747 | AI232339 | General | | | ESTs |
| 23851 | 1313 | AI136862 | p,q | | | ESTs |
| 23368 | 55 | AA800678 | b | | | ESTs |
| 17664 | 1813 | AI234496 | c,m,n,General | | | ESTs, Weakly similar to T22521 hypothetical protein F52H3.5 - Caenorhabditis elegans [C.elegans] |
| 17256 | 299 | AA891739 | f | | | |
| 18712 | 110 | AA818894 | i | | proteoglycan peptide core protein | proteoglycan peptide core protein |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 22604 | 563 | AA945578 | k,o,r,General,z | | putative peroxisomal 2,4-dienoyl-CoA reductase | putative peroxisomal 2,4-dienoyl-CoA reductase |
| 13619 | 1607 | AI179464 | j,q | | | ESTs |
| 17590 | 357 | AA892851 | r,General,y | | | ESTs |
| 1559 | 2326 | U28504 | p | | Interleukin 1 receptor, type I | *Rattus norvegicus* Na+/Pi cotransporter-1 mRNA, complete cds |
| 24570 | 2240 | M95578 | v | | | Interleukin 1 receptor, type I |
| 21489 | 200 | AA851443 | p | | | ESTs, Highly similar to similar to yeast Sec6p, Swiss-Prot Accession Number P32844 [*R.norvegicus*] |
| 397 | 2522 | Y09332 | k | | acyl-CoA hydrolase | *Rattus norvegicus* brain cytosolic acyl coenzyme A thioester hydrolase mRNA, complete cds, acyl-CoA hydrolase |
| 8808 | 1136 | AI070132 | j,General,aa | | | ESTs |
| 24200 | 965 | AI012355 | b | | | ESTs |
| 1262 | 783 | AB017044 | q,dd | | | Hepatocyte nuclear factor 3 gamma |
| 21254 | 1380 | AI170059 | General | | Hepatocyte nuclear factor 3 gamma | ESTs |
| 24163 | 1368 | AI169430 | f,g | | | ESTs, Moderately similar to AF151904 1 CGI-146 protein [*H.sapiens*] |
| 18068 | 2272 | S79676 | v | | Interleukin 1beta converting enzyme | Interleukin 1beta converting enzyme |
| 891 | 2360 | U66322 | m,General | | | *Rattus norvegicus* dithiolethione-inducible gene-1 (DIG-1) mRNA, complete cds |
| 7858 | 1040 | AI043654 | w | | | EST |
| 23297 | 1008 | AI028953 | General | | | ESTs, Highly similar to S55054 Sm protein G [*H.sapiens*] |
| 11988 | 107 | AA819193 | x | | | ESTs |
| 1796 | 2111 | L24207 | f,g,i,x | | Cytochrome P450, sub-family IIIA, polypeptide 3 | Cytochrome P450, subfamily IIIA, polypeptide 3 |
| 18125 | 865 | AI008787 | o | | | ESTs, Highly similar to S16788 probable reverse transcriptase - rat [*R.norvegicus*] |
| 17613 | 18 | AA799511 | General | | | ESTs |
| 17407 | 958 | AI012145 | j | | | ESTs |
| 18829 | 107 | AA818796 | l,General | | | ESTs |
| 23387 | 584 | AA945952 | b | | RNA binding protein p45AUF1 | RNA binding protein p45AUF1 |
| 23203 | 41 | AA799971 | General,z | | | ESTs, Weakly similar to S52675 probable membrane protein YDR109c - yeast (*Saccharomyces cerevisiae*) [*S.cerevisiae*] |
| 13004 | 1861 | AI236284 | k | Fatty acid metabolism | HHs:fatty-acid-Coenzyme A ligase, long-chain 4 | *Rattus norvegicus* mRNA for Acyl-CoA synthetase, complete cds |
| 12155 | 2034 | J00728 | f,g,k,l,x,cc,dd | | Protein kinase, cAMP-dependent, catalytic, alpha | |
| 25701 | 2455 | X57986 | General | | | |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 20427 | 2441 | X53378 | h,t | | | *Rattus norvegicus* ribosomal protein S13 (RPS13) mRNA, 3' end |
| 3822 | 424 | AA900863 | d | | | ESTs, Weakly similar to nuclear RNA helicase [*R.norvegicus*] |
| 15419 | 919 | AI010476 | a | | | ESTs, Weakly similar to Chp [*R.norvegicus*] |
| 24728 | 2192 | M55532 | w | | | Rat Kupffer cell receptor mRNA, complete cds |
| 23355 | 144 | AA848530 | General | | | ESTs, Weakly similar to retinoblastoma binding protein [*R.norvegicus*] |
| 2677 | 664 | AA963443 | e,General | | | ESTs, Moderately similar to KIAA0822 protein [*H.sapiens*] |
| 20851 | 1997 | D88890 | bb | | acyl-CoA hydrolase | acyl-CoA hydrolase |
| 20895 | 1694 | AI230549 | e,General | | | ESTs |
| 21740 | 1524 | AI176810 | b | | | ESTs |
| 22083 | 178 | AA850587 | o | | | ESTs |
| 17386 | 1358 | AI169144 | General | | | ESTs, Weakly similar to T23206 hypothetical protein K01H12.1 - *Caenorhabditis elegans* [*C.elegans*] |
| 23595 | 1878 | AI236834 | j | | | ESTs |
| 16510 | 1322 | AI137583 | g | | Inhibitor of DNA binding 2, dominant negative helix-loop-helix protein | Inhibitor of DNA binding 2, dominant negative helix-loop-helix protein |
| 2486 | 692 | AA964871 | General,x,y | | | ESTs |
| 3106 | 710 | AA997109 | General | | | ESTs |
| 3831 | 2525 | Y12635 | i | | | *R.norvegicus* mRNA for vacuolar adenosine triphosphatase subunit B |
| 17092 | 369 | AA893189 | d,f,i,General,cc | | | *Rattus norvegicus* glutathione reductase mRNA, complete cds |
| 24162 | 1362 | AI169279 | r | | | ESTs |
| 14840 | 1889 | AI237698 | i,l,u | | | ESTs |
| 4892 | 1052 | AI044292 | b | | | ESTs |
| 21663 | 1979 | D50436 | h | | ferredoxin 1 | ferredoxin 1 |
| 22303 | 1616 | AI179779 | General | | | ESTs |
| 17127 | 961 | AI012213 | bb | | | ESTs, Highly similar to RL26 RAT 60S RIBOSOMAL PROTEIN L26 [*R.norvegicus*] |
| 18541 | 2420 | X14671 | w | | | ESTs |
| 6873 | 906 | AI010055 | a | | | ESTs, Weakly similar to T31425 C-terminal domain-binding protein rA4, splice form 2 - rat (fragment) [*R.norvegicus*] |
| 13966 | 1723 | AI231421 | General | | | ESTs |
| 13701 | 1684 | AI230180 | General | | | ESTs |
| 4005 | 1557 | AI174481 | General | Proteasome | Low molecular mass polypeptide 2 | Low molecular mass polypeptide 2 |
| 21321 | 1805 | AI233902 | General | | | ESTs |
| 25471 | 2243 | M96630 | u | | | ESTs, Weakly similar to T18653 hypothetical protein B0035.3 - *Caenorhabditis elegans* [*C.elegans*] |
| 12450 | 1257 | AI103955 | m | | | |
| 5256 | 503 | AA926088 | g | | | EST |
| 4043 | 1634 | AI227852 | v | | | ESTs |
| 16756 | 78 | AA818089 | d | | | ESTs, Highly similar to glycyl-tRNA synthetase [*H.sapiens*] |
| 22119 | 247 | AA859661 | bb | | | ESTs, Moderately similar to glutaminyl cyclase [*R.norvegicus*] |

Document Number 1740956

TABLE 1-continued

| GLGC ID | SeqID | GenBank Acc | Model Code | Pathway Name | Known Gene Name | Unigene Cluster Title |
|---|---|---|---|---|---|---|
| 11514 | 1438 | AI171855 | General,dd | | | ESTs, Moderately similar to unknown [*H.sapiens*] |
| 11844 | 241 | AA859473 | General | | | *Rattus norvegicus* VAMP5 mRNA, complete cds |
| 25670 | 2411 | X07648 | v | | | |
| 24799 | 2007 | E01050 | t | Alanine and aspartate metabolism, Glycine, serine and threonine metabolism | Alanine-glyoxylate aminotransferase (Serine-pyruvate aminotransferase) | Alanine-glyoxylate aminotransferase (Serine-pyruvate aminotransferase) |
| 17580 | 908 | AI010145 | j | | D-dopachrome tautomerase | ESTs, Highly similar to MCT-1 [*H.sapiens*] |
| 17227 | 2530 | Z36980 | t | | | D-dopachrome tautomerase |
| 11478 | 507 | AA926231 | e | | | ESTs |
| 24646 | 2160 | M23264 | h | | Androgen receptor (Testicular feminization) | Androgen receptor (Testicular feminization) |
| 1728 | 1949 | D16479 | k,o,z | Bile acid biosynthesis, Fatty acid biosynthesis (path 2), Fatty acid metabolism, Phenylalanine metabolism, Valine, leucine and isoleucine degradation | HHs;hydroxyacyl-Coenzyme A dehydrogenase/3-ketoacyl-Coenzyme A thiolase/enoyl-Coenzyme A hydratase (trifunctional protein), beta subunit | Rat mRNA for mitochondrial long-chain 3-ketoacyl-CoA thiolase beta-subunit of mitochondrial trifunctional protein, complete cds |
| 23768 | 947 | AI011709 | General | | | ESTs, Highly similar to S21977 Pm5 protein [*H.sapiens*] |
| 9697 | 1164 | AI071642 | x | | | ESTs |
| 7516 | 1172 | AI072183 | c | | | ESTs |
| 62 | 2015 | E06822 | c,General | | | Rat mRNA for 20-alpha-hydroxysteroid dehydrogenase (20-alpha-HSD), complete cds |
| 21729 | 602 | AA946532 | o | | ATP-binding cassette, sub-family D (ALD), member 3 | ATP-binding cassette, sub-family D (ALD), member 3 |
| 6619 | 103 | AA818743 | q | | | ESTs, Highly similar to KIAA0728 protein [*H.sapiens*] |
| 12958 | 1547 | AI177155 | r,General | | | ESTs, Highly similar to putative NAD(P)H steroid dehydrogenase [*M.musculus*] |
| 11997 | 352 | AA892828 | cc | Butanoate metabolism, Glycolysis/Gluconeogenesis, Pyruvate metabolism, Valine, leucine and isoleucine biosynthesis | HHs;pyruvate dehydrogenase (lipoamide) beta | ESTs, Highly similar to ODPB RAT PYRUVATE DEHYDROGENASE E1 COMPONENT BETA SUBUNIT, MITOCHONDRIAL PRECURSOR [*R.norvegicus*] |
| 1472 | 2323 | U26356 | u | | | ESTs, Highly similar to S10A RAT S-100 PROTEIN, ALPHA CHAIN [*R.norvegicus*] |
| 17844 | 621 | AA955927 | b | | | ESTs |
| 11608 | 245 | AA859633 | j | | | ESTs |
| 22513 | 2161 | M23566 | b,y | | Alpha-2-macroglobulin | Alpha-2-macroglobulin |
| 14479 | 231 | AA858969 | p | | | ESTs, Moderately similar to I56526 interleukin 1 receptor type I - rat [*R.norvegicus*] |
| 910 | 2270 | S76511 | i, | | Bcl2-associated X protein | Bcl2-associated X protein |
| 17831 | 955 | AI012017 | p | | | Rat major beta-globin mRNA, complete cds |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 3031 | 824 | AF079864 | General | | | *Rattus norvegicus* putative G-protein coupled receptor RA1c mRNA, complete cds |
| 1521 | 2210 | M63122 | General | | Tumor necrosis factor receptor | Tumor necrosis factor receptor |
| 2125 | 1217 | AI102519 | l | | | ESTs, Moderately similar to DAP12 [*M.musculus*] |
| 25469 | 2239 | M94919 | q | | | ESTs |
| 8232 | 1103 | AI059122 | a | | | ESTs, Moderately similar to KIAA0966 protein [*H.sapiens*] |
| 13481 | 1834 | AI235352 | n | | | ESTs |
| 21851 | 238 | AA859330 | General | | | ESTs, Highly similar to PSD8 _ HUMAN 26S PROTEASOME REGULATORY SUBUNIT S14 [*H.sapiens*] |
| 18900 | 1784 | AI233570 | General | | | ESTs, Weakly similar to T19073 hypothetical protein C08B11.9 - *Caenorhabditis elegans* [*C.elegans*] |
| 21973 | 545 | AA944840 | m | | | *Rattus norvegicus* glycine transporter mRNA, complete cds |
| 16311 | 524 | AA943735 | d | | Protein tyrosine phosphatase, receptor type, D | Protein tyrosine phosphatate, receptor type D |
| 14973 | 2105 | L19180 | r | | | |
| 18718 | 2180 | M33329 | General | Androgen and estrogen metabolism | Rat senescence marker protein 2A gene, exons 1 and 2 | Rat senescence marker protein 2A gene, exons 1 and 2 |
| 18027 | 808 | AF039212 | f,p,q | | | *Rattus norvegicus* UDP-glucuronosyltransferase UGT1A7 mRNA, complete cds |
| 17788 | 390 | AA899045 | l | | | ESTs, Highly similar to sid478p [*M.musculus*] |
| 14191 | 229 | AA858924 | e,General | | | ESTs |
| 4989 | 1473 | AI175087 | i | | | ESTs |
| 18107 | 2509 | X94242 | General | | ribosomal protein L14 | ribosomal protein L14 |
| 23299 | 1528 | AI176839 | r,General | | | ESTs, Highly similar to T46259 hypothetical protein DKFZp761E0323.1 [*H.sapiens*] |
| 20971 | 23 | AA799576 | a | | | ESTs, Highly similar to myosin X [*M.musculus*] |
| 10002 | 1328 | AI137988 | r | Butanoate metabolism, Synthesis and degradation of ketone bodies, Valine, leucine and isoleucine degradation | 3-hydroxy-3-methyl-glutaryl-Coenzyme A synthase 1 | 3-hydroxy-3-methylglutaryl-Coenzyme A synthase 1 |
| 20600 | 1540 | AI177004 | d,r | | | |
| 9424 | 2255 | S61868 | g | | Ryudocan/syndecan 4 | Ryudocan/syndecan 4 |
| 4477 | 2375 | U77829 | r | | | ESTs |
| 344 | 867 | AI008865 | y | | Signal transducer and activator of transcription 3 | Signal transducer and activator of transcription 3 |
| 633 | 1714 | AI231127 | r,y | | | ESTs |
| 21010 | 478 | AA925306 | a,k,o | | | ESTs, Weakly similar to CLAT RAT CHOLINE O-ACETYLTRANSFERASE [*R.norvegicus*] |
| 9528 | 1962 | D28560 | q | | | *Rattus norvegicus* mRNA for phosphodiesterase I |
| 4914 | 1291 | AI112086 | u,w,z | | | ESTs |
| 15996 | 2276 | S81478 | e | | | *Rattus norvegicus* protein tyrosine phosphatase mRNA, complete cds |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 23579 | 1434 | AI171802 | General,z | | | ESTs |
| 13171 | 1332 | AI144722 | aa | | | ESTs, Moderately similar to I37356 epithelial microtubule-associated protein, 115K [*H.sapiens*] |
| 1795 | 2111 | L24207 | f,g,h,l,x | | Cytochrome P450, subfamily IIIA, polypeptide 3 | Cytochrome P450, subfamily IIIA, polypeptide 3 |
| 5091 | 1193 | AI073092 | General | | | ESTs |
| 4731 | 1707 | AI230773 | General | | | ESTs |
| 21933 | 1012 | AI029057 | b,General | | | ESTs |
| 23275 | 2515 | X97443 | i | | integral membrane protein Tmp21-I (p23) | integral membrane protein Tmp21-I (p23) |
| 15029 | 1399 | AI170696 | c | | | ESTs, Weakly similar to development-related protein [*R.norvegicus*] |
| 17090 | 2368 | U73174 | l | | | *Rattus norvegicus* glutathione reductase mRNA, complete cds |
| 2297 | 1251 | AI103602 | General | | | ESTs, Highly similar to SAP3 MOUSE GANGLIOSIDE GM2 ACTIVATOR PRECURSOR [*M.musculus*] |
| 15427 | 1596 | AI78951 | j | | neutral solute channel aquaporin 9 | ESTs |
| 15755 | 777 | AB013112 | l,n | | | neutral solute channel aquaporin 9 |
| 22602 | 811 | AF044574 | k,o,bb | | putative peroxisomal 2,4-dienoyl-CoA reductase | putative peroxisomal 2,4-dienoyl-CoA reductase |
| 20651 | 2335 | U36992 | i | | Cytochrom P450 | Cytochrom P450 |
| 19086 | 342 | AA892598 | n | | | ESTs |
| 1841 | 1306 | AI113289 | General,v,aa | | Protein-tyrosine phosphatase | Protein-tyrosine phosphatase |
| 16148 | 2045 | J02752 | k,o | Fatty acid metabolism | acyl-coA oxidase | acyl-coA oxidase |
| 4849 | 431 | AA901155 | General | | | *Rattus norvegicus* CDK105 mRNA |
| 640 | 2278 | S82229 | b | Purine metabolism, Purine metabolism, receptor A/Guanylate cyclase A | Natriuretic peptide cyclase A | Natriuretic peptide receptor A/Guanylate |
| 12287 | 1228 | AI102751 | aa | DNA polymerase, Purine metabolism, Pyrimidine metabolism | HHs;polymerase (DNA directed), delta 2, regulatory subunit (50kD) | ESTs, Highly similar to DPD2_HUMAN DNA POLYMERASE DELTA SMALL SUBUNIT [*H.sapiens*] |
| 21816 | 1717 | AI231217 | g | | | ESTs, Highly similar to S61A RAT PROTEIN TRANSPORT PROTEIN SEC61 ALPHA SUBUNIT [*R.norvegicus*] |
| 3833 | 193 | AA851255 | j | | | ESTs, Highly similar to HSPC017 [*H.sapiens*] |
| 7053 | 939 | AI011467 | b,m | | | ESTs |
| 21623 | 2389 | V01217 | h | | cytoplasmic beta-actin | cytoplasmic beta-actin |
| 14676 | 1817 | AI234615 | b,General | | | *Rattus norvegicus* MLS2s mRNA for melastatin like 2, complete cds |
| 3997 | 494 | AA925771 | l | | | ESTs, Moderately similar to T12483 hypothetical protein DKFZp564B0769.1 [*H.sapiens*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 25139 | 765 | AB005743 | bb | | CD36 antigen (collagen type I receptor, thrombospondin receptor) | CD36 antigen (collagen type I receptor, thrombospondin receptor) |
| 24388 | 1873 | AI236772 | j | | | ESTs |
| 1844 | 2182 | M33962 | v,aa | | Protein-tyrosine phosphatase | ESTs, Protein-tyrosine phosphatase |
| 21260 | 1804 | AI233885 | x | | | ESTs, Weakly similar to AF151835 1 CGI-78 protein [*H.sapiens*] |
| 4527 | 346 | AA892774 | c,v | | | ESTs |
| 11635 | 246 | AA859645 | c | | attractin | attractin |
| 16704 | 4 | AA686132 | General | | | |
| 10184 | 2028 | H33426 | e,General | | | ESTs, Highly similar to AF151825 1 CGI-67 protein [*H.sapiens*] |
| 12792 | 1532 | AI176883 | j,m,n | | | ESTs |
| 14275 | 1566 | AI177748 | aa | Fatty acid metabolism | dodecenoyl-Coenzyme A delta isomerase (3,2 trans-enoyl-Coenyme A | dodecenoyl-Coenzyme A delta isomerase (3,2 trans-enoyl-Coenyme A isomerase) |
| 18685 | 725 | AA997746 | o | | | ESTs |
| 14501 | 1486 | AI175778 | v | | proteasome (prosome, macropain) subunit, beta type, 7 | *Rattus norvegicus* proteasome z subunit mRNA, complete cds |
| 18401 | 1266 | AA104300 | f,General | Proteasome | | |
| 8784 | 1237 | AI103007 | General,bb | | | ESTs, Moderately similar to unknown [*H.sapiens*] |
| 4003 | 1930 | D10757 | e | | Low molecular mass polypeptide 2 | Low molecular mass polypeptide 2 |
| 16953 | 2011 | E01534 | h | | ribosomal protein S15 | ribosomal protein S15 |
| 6912 | 1987 | D85035 | z | | dihydropyrimidine dehydrogenase | dihydropyrimidine dehydrogenase |
| 7274 | 995 | AI013715 | k | | | ESTs, Moderately similar to BMP6 RAT BONE MORPHOGENETIC PROTEIN 6 PRECURSOR [*R.norvegicus*] |
| 14462 | 1198 | AI100871 | General | | | ESTs, Weakly similar to T20358 hypothetical protein D2030.8 - *Caenorhabditis elegans* [*C.elegans*] |
| 13975 | 177 | AA850450 | y | | | *Rattus norvegicus* mRNA for class I beta-tubulin, complete cds |
| 20778 | 1990 | D85844 | g | | rabaptin 5 | rabaptin 5 |
| 14827 | 1885 | AI237404 | v | | | ESTs, Moderately similar to PKL2 RAT PROTEIN KINASE C-LIKE 2 [*R.norvegicus*] |
| 25325 | 2087 | K03045 | n | | | ESTs, Weakly similar to T15846 hypothetical protein C56C10.7 - *Caenorhabditis elegans* [*C.elegans*] |
| 4926 | 1471 | AI175034 | General | | | ESTs, Highly similar to NICA_MOUSE NICASTRIN PRECURSOR [*M.musculus*] |
| 4267 | 239 | AA859412 | m | | | |
| 16565 | 2383 | U91847 | n | | p38 mitogen activated protein kinase | p38 mitogen activated protein kinase |
| 21305 | 367 | AA893082 | General | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 22867 | 331 | AA892353 | General | | | ESTs, Weakly similar to T33520 hypothetical protein T10B11.6 - *Caenorhabditis elegans* [*C.elegans*] |
| 15090 | 235 | AA859224 | General,aa | | | *Rattus norvegicus* mRNA for NAD+-specific isocitrate dehydrogenase a-subunit, complete cds |
| 2342 | 679 | AA964336 | t | | | ESTs |
| 11553 | 1706 | AI230765 | m | | | ESTs, Weakly similar to P24 RAT COP-COATED VESICLE MEMBRANE PROTEIN P24 PRECURSOR [*R.norvegicus*] |
| 3044 | 722 | AA997701 | n | | | EST |
| 18777 | 1230 | AI102788 | j | | | ESTs |
| 23983 | 1672 | AI229708 | General | | | ESTs, Moderately similar to NADC_HUMAN NICOTINATE-NUCLEOTIDE PYROPHOSPHORYLASE [*H.sapiens*] |
| 7756 | 359 | AA892864 | z | | Organic cation transporter | ESTs |
| 1603 | 2491 | X78855 | General,x | | | Organic cation transporter |
| 9309 | 668 | AA963794 | General | | | ESTs |
| 23637 | 614 | AA955587 | a | | | ESTs, Highly similar to CST1_HUMAN CLEAVAGE STIMULATION FACTOR, 50 KD SUBUNIT [*H.sapiens*] |
| 1174 | 2041 | J02657 | p | Fatty acid metabolism, Tryptophan metabolism 4-hydroxylase) | Cytochrome P450, sub-family IIC (mephenytoin 4-hydroxylase) | Cytochrome P450, subfamily IIC (mephenytoin 4-hydroxylase) |
| 15829 | 801 | AF034577 | bb | | pyruvate dehydrogenase kinase, isoenzyme 4 | *Rattus norvegicus* pyruvate dehydrogenase kinase isoenzyme 4 (PDK4) mRNA, complete cds |
| 17554 | 1988 | D85100 | k | | solute carrier family 27 (fatty acid transporter), member 2 | solute carrier family 27 (fatty acid transporter), member 2 |
| 2970 | 2139 | M14775 | h | Fatty acid metabolism, Tryptophan metabolism | cytochrome P450, 2c39 | cytochrome P450, 2c39 |
| 10307 | 1254 | AI103695 | m | | ribosome associated membrane protein 4 | ribosome associated membrane protein 4 |
| 15391 | 907 | AI010083 | k,l | | | Rat mRNA for HBP23 (heme-binding protein 23 kDa), complete cds |
| 6057 | 1450 | AI172102 | b,General | | | ESTs, Weakly similar to T33238 hypothetical protein T10H9.3 - *Caenorhabditis elegans* [*C.elegans*] |
| 18687 | 1389 | AI170568 | k,o | Fatty acid metabolism | dodecenoyl-Coenzyme A isomerase (3,2 trans-enoyl-Coenyme A | Rat mRNA for delta3, delta2-enoyl-CoA isomerase, dodecenoyl-Coenoyl-Coenzyme A delta isomerase (3,2 trans-enoyl-Coenyme A isomerase) |
| 3537 | 1208 | AI101690 | e | | dishevelled 1 | dishevelled 1 |
| 22914 | 447 | AA924335 | l,General | | | ESTs |
| 6471 | 180 | AA850706 | General | | | ESTs |
| 4801 | 425 | AA900981 | General | | | EST |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 7022 | 1494 | AI176041 | General | Alanine and aspartate metabolism, Aminoacyl-tRNA biosynthesis | HHs:alanyl-tRNA synthetase | ESTs, Highly similar to pirin [*H.sapiens*] |
| 23424 | 1625 | AI180068 | b | | | ESTs, Highly similar to SYA_HUMAN ALANYL-TRNA SYNTHETASE [*H.sapiens*] |
| 17742 | 259 | AA866302 | q,t | Phenylalanine metabolism, Tyrosine metabolism | 4-hydroxyphenylpyruvic acid dioxygenase | 4-hydroxyphenylpyruvic acid dioxygenase |
| 21090 | 764 | AB005547 | General | aquaporin 8 | aquaporin 8 | aquaporin 8 |
| 14939 | 1645 | AI228557 | General,aa | | | ESTs |
| 19035 | 1866 | AI236576 | General | | | ESTs, Highly similar to RB1B RAT RAS-RELATED PROTEIN RAB-1B [*R.norvegicus*] |
| 23826 | 2337 | U38180 | a | | solute carrier family 19 (sodium/hydrogen exchanger), member 1 | solute carrier family 19 (sodium/hydrogen exchanger), member 1 |
| 16007 | 818 | AF062594 | i,General | | nucleosome assembly protein 1-like 1 | *Rattus norvegicus* nucleosome assembly protein mRNA, complete cds |
| 9349 | 957 | AI012143 | a,g | | | ESTs, Highly similar to KIAA0242 protein [*H.sapiens*] |
| 20464 | 2154 | M20406 | q,cc | | | Rat cytochrome P450IIB3 (P450IIB subfamily) mRNA, complete cds |
| 17044 | 909 | AI010173 | bb | | | ESTs |
| 1850 | 2083 | K02814 | a,b,q | | T-kininogen | T-kininogen |
| 24849 | 2253 | S60953 | x | | neurotrophic tyrosine kinase, receptor, type 3 | neurotrophic tyrosine kinase, receptor, type3 |
| 4592 | 2040 | J02646 | a,General,y | | eukaryotic translation initiation factor 2, subunit 1 (alpha) | eukaryotic translation tnitiation factor 2, subunit 1 (alpha) |
| 17533 | 1919 | D00636 | e,General | Aminosugars metabolism | HHs:diaphorase (NADH) (cytochrome b-5 reductase) | R at NADH-cytochrome b-5 reductase mRNA, complete cds |
| 19221 | 1245 | AI103374 | j | | | ESTs, Highly similar to homolog of the *Aspergillus nidulans* sudD gene product [*H.sapiens*] |
| 18674 | 165 | AA849603 | General | | | ESTs |
| 3866 | 365 | AA893074 | l | | | ESTs |
| 17684 | 330 | AA892345 | General,u | | | Rat mRNA for dimethylglycine dehydrogenase (EC number 1.5.99.2) |
| 10626 | 1945 | D14988 | h | | | Rat hydroxysteroid sulfotransferase mRNA, complete cds |
| 23452 | 477 | AA925289 | e | | | ESTs, Moderately similar to dJ167A19.4 [*H.sapiens*] |
| 23839 | 636 | AA956684 | m | | | ESTs |
| 20311 | 2345 | U52045 | p,q | | Homeobox gene Pem | Homeobox gene Pem |
| 20161 | 2447 | X54686 | n,v | | jun B proto-oncogene | jun B proto-oncogene |
| 12060 | 39 | AA799890 | g,x,cc | | | ESTs |
| 14619 | 1880 | AI236989 | aa | | | ESTs |
| 22006 | 2387 | U96490 | w | | | *Rattus norvegicus* liver mRNA, complete cds |
| 16304 | 768 | AB008424 | a | | | Rat cytochrome P-450 IID3 mRNA, complete cds |
| 21326 | 1678 | AI230013 | j | | | ESTs, Highly similar to HG17 RAT NONHISTONE CHROMOSOMAL PROTEIN HMG-17 [*R.norvegicus*] |
| 17349 | 1621 | AI179987 | General,bb | | | ESTs |
| 23243 | 203 | AA851803 | g,i,x,y,dd | | | ESTs |
| 8594 | 976 | AI012932 | p | | | ESTs |
| 17496 | 505 | AA926109 | m | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 22598 | 1320 | AI137506 | k,w | | | ESTs, Weakly similar to SPI-2 serine protease inhibitor [R.norvegicus] |
| 309 | 263 | AA866460 | e,w | | | ESTs |
| 17049 | 1462 | AI172417 | c,d,e | | | ESTs, Weakly similar to T20356 hypothetical protein D2030.5 - Caenorhabditis elegans [C.elegans] |
| 3895 | 383 | AA894029 | i,u | | | ESTs |
| 23159 | 479 | AA925318 | General | | I-kappa-B-beta | I-kappa-B-beta |
| 25525 | 2264 | S72505 | h,w,x | Glutathione metabolism | Glutathione-S-transferase, alpha type (Ya) | Glutathione-S-transferase, alpha type (Ya) |
| 12108 | 154 | AA848963 | General | | | ESTs, Moderately similar to DNA-REPAIR PROTEIN COMPLEMENTING XP-C CELLS HOMOLOG [M.musculus] |
| 18239 | 1617 | AI179942 | c | | | ESTs |
| 1426 | 2531 | Z48225 | y | | | R.norvegicus mRNA for protein synthesis initiation factor eIF-2B delta subunit |
| 19433 | 135 | AA819776 | z | | | ESTs, Weakly similar to HS9B RAT HEAT SHOCK PROTEIN HSP 90-BETA [R.norvegicus] |
| 11644 | 1832 | AI235282 | l,General | | cortactin isoform B | ESTs, Moderately similar to AM2 receptor [M.musculus] |
| 19057 | 1829 | AI235094 | b | | translocase of inner mitochondrial membrane 8 (yeast) homolog A | cortactin isoform B |
| 12223 | 1417 | AI171266 | General | | | translocase of inner mitochondrial membrane 8 (yeast) homolog A |
| 5175 | 111 | AA818951 | h,i,u,w | | pyruvate kinase 3 | Rat mRNA for pituitary pyruvate kinase |
| 3945 | 1766 | AI232719 | f | | | ESTs |
| 5789 | 1061 | AI044718 | General | | | ESTs, Weakly similar to A24264 proline-rich protein MP2 - mouse [M.musculus] |
| 9212 | 1154 | AI071098 | d | | | ESTs |
| 22142 | 518 | AA943066 | General | | | ESTs, Weakly similar to p68 RNA helicase [R.norvegicus] |
| 6365 | 393 | AA899163 | e,u | | | Rattus norvegicus mRNA for signal peptidase 21kDa subunit, complete cds |
| 1379 | 2222 | M83676 | r,v | | RAB12, member RAS oncogene family | RAB12, member RAS oncogene family |
| 16496 | 706 | AA996955 | g | | | ESTs |
| 15848 | 844 | AI007820 | f,o | | | ESTs, ESTs, Highly similar to HS9B RAT HEAT SHOCK PROTEIN HSP 90-BETA [R.norvegicus] |
| 20779 | 2142 | M15185 | q | Methionine metabolism, Selenoamino acid metabolism | 5-adenosylhomocysteine hydrolase | S-adenosylhomocysteine hydrolase |
| 16274 | 1924 | D10261 | n,x | | alpha 2 HS-glycoprotein alpha 2 (fetuin) | alpha 2 HS-glycoprotein alpha 2 (fetuin) |
| 21128 | 145 | AA848555 | i | | | ESTs |
| 14520 | 1589 | AI178785 | General | | | ESTs, Weakly similar to coding sequence of pol [R.norvegicus] |
| 20872 | 2436 | X51707 | f,w | | ribosomal protein S19 | ESTs, Highly similar to RS19 RAT 40S RIBOSOMAL PROTEIN S19 [R.norvegicus] |
| 25056 | 2134 | M13234 | f,x,cc,dd | | | |
| 25066 | 2268 | S75280 | dd | | | |

TABLE 1-continued

| GLGC ID | SeqID | GenBank Acc | Model Code | Pathway Name | Known Gene Name | Unigene Cluster Title |
|---|---|---|---|---|---|---|
| 18453 | 1952 | D17370 | u | Cysteine metabolism, Methionine metabolism, Nitrogen metabolism, Selenoamino acid metabolism | CTL target antigen | CTL target antigen |
| 1557 | 756 | AB000216 | General | | | Rattus norvegicus mRNA for CCA3, complete cds |
| 17758 | 2089 | K03249 | k,o,w,z | | | Rat peroxisomal enoyl-CoA: hydrotase-3-hydroxyacyl-CoA bifunctional enzyme mRNA, complete cds |
| 9469 | 1192 | AI073023 | a | | | ESTs |
| 12343 | 1724 | AI231433 | j | | | ESTs |
| 20705 | 2008 | E01184 | d,f,g,q,bb,cc,dd | Fatty acid metabolism, Tryptophan metabolism | Cytochrome P450, subfamily I (aromatic compound-inducible), member A2 (Q42, form d) | Cytochrome P450, subfamily I (aromatic compound-inducible), member A2 (Q42, form d) |
| 5675 | 1066 | AI045026 | b | | | ESTs |
| 23538 | 1227 | AI102727 | i,j | | solute carrier family 20 (phosphate transporter), member 1 | solute carrier family 20 (phosphate transporter), member 1 |
| 10260 | 2277 | S81497 | p | | | ESTs |
| 3134 | 1628 | AI180292 | w | | | ESTs, Moderately similar to YLHUA serum amyloid A2 protein precursor [H.sapiens] |
| 9325 | 1184 | AI072617 | General,aa | | | EST |
| 16125 | 833 | AF090134 | General,cc | | | Rattus norvegicus lin-7-Bb mRNA, complete cds |
| 14616 | 487 | AA925559 | aa | | lin-7-Ba | ESTs |
| 19150 | 13 | AA799461 | General | | | ESTs, Weakly similar to EP15 MOUSE EPIDERMAL GROWTH FACTOR RECEPTOR SUBSTRATE SUBSTRATE 15 [M.musculus] |
| 25747 | 2496 | X81448 | w | Glutamate metabolism, Nitrogen metabolism | Glutamine synthetase (glutamate-ammonia ligase) | Glutamine synthetase (glutamate-ammonia ligase) |
| 11153 | 2234 | M91652 | General,cc | | | |
| 22607 | 564 | AA945580 | General | | | ESTs, Weakly similar to ARG2 RAT ARGINASE II PRECURSOR [R.norvegicus] |
| 15141 | 2003 | D90265 | a | Proteasome | proteasome (prosome, macropain) subunit, alpha type 1 | proteasome (prosome, macropain) subunit, alpha type 1 |
| 19410 | 378 | AA893667 | y | | | ESTs, Moderately similar to AC006978 1 supported by human and rodent ESTs [H.sapiens] |
| 25802 | 2013 | E02315 | w | | Calmodulin 1 (phosphorylase kinase, delta) | Calmodulin 1 (phosphorylase kinase, delta) |
| 25644 | 2376 | U77931 | t,v | | glucose-6-phosphatase, transport protein 1 | glucose-6-phosphatase, transport protein 1 |
| 5496 | 825 | AF080468 | g,General,bb | | Insulin-like growth factor-binding protein (IGF-BP3) | Insulin-like growth factor-binding protein (IGF-BP3) |
| 15097 | 882 | AI009405 | General | | | |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 7252 | 1827 | AI235058 | General | | | ESTs, Highly similar to mitochondrial outer membrane protein [*M.musculus*] |
| 4689 | 405 | AA899899 | cc | | | ESTs |
| 25057 | 2200 | M58495 | l,q,General | | | |
| 7199 | 980 | AI013044 | r,General | | | ESTs |
| 2150 | 2004 | D90404 | d | | Cathepsin C (dipeptidyl peptidase I) | Cathepsin C (dipeptidyl peptidase I) |
| 5696 | 1072 | AI045116 | General,y | | | ESTs |
| 4172 | 483 | AA925514 | i | | | ESTs |
| 23182 | 1710 | AI230981 | General | | | ESTs |
| 4723 | 836 | AF093773 | t | | | *Rattus norvegicus* cytosolic malate dehydrogenase (Mdh) mRNA, complete cds |
| 21683 | 2211 | M65149 | c,m,General,v | | CCAAT/enhancerbinding, protein (C/EBP) delta | CCAAT/enhancerbinding, protein (C/EBP) delta |
| 21750 | 892 | AI009663 | o | | | ESTs |
| 15173 | 1731 | AI231846 | q | | | ESTs |
| 3148 | 847 | AI007881 | General,aa | | | ESTs |
| 6295 | 131 | AI819672 | General | | | EST |
| 8715 | 1132 | AI069920 | i,j,General | | | ESTs |
| 7312 | 1561 | AI177543 | dd | | | ESTs, Weakly similar to T32252 hypothetical protein T15B7.2 - *Caenorhabditis elegans* [*C.elegans*] |
| 3535 | 753 | AA999135 | General | | | ESTs |
| 15107 | 1774 | AI233220 | p | | | ESTs, Highly similar to RS18_HUMAN 40S RIBOSOMAL PROTEIN S18 [*R.norvegicus*] |
| 13682 | 2121 | L38482 | General | Fatty acid metabolism | Acyl Coenzyme A dehydrogenase, long chain | *Rattus norvegicus* serine protease gene, complete cds |
| 6780 | 2068 | J05029 | k | | | Acyl Coenzyme A dehydrogenase, long chain |
| 575 | 2425 | X15734 | a,g | Methionine metabolism, Selenoamino acid metabolism | S - adenosylmethionine synthetase | S - adenosylmethionine synthetase |
| 20772 | 2355 | U60882 | y | | heterogeneous nuclear ribonucleoproteins methyltransferase-like | heterogeneous nuclear ribonucleoproteins methyltransferase-like 2 (*S. cerevisiae*) |
| 25799 | 2016 | E12625 | e | | carcinoembryonic antigen-related cell adhesion molecule | carcinoembryonic antigen-related cell adhesion molecule |
| 13185 | 2317 | U23055 | p | | | |
| 23878 | 30 | AA799686 | j | | vesicle associated protein | ESTs |
| 21103 | 802 | AF034582 | r | | | *Rattus norvegicus* vesicle associated protein (VAP1) mRNA, complete cds |
| 18389 | 16 | AA799498 | y | | Brain natriuretic factor | Brain natriuretic factor |
| 7197 | 1441 | AI171962 | v | | Annexin 1 (p35) (Lipocortin 1) | Annexin 1 (p35) (Lipocortin 1) |
| 20462 | 2153 | M20156 | w | Histidine metabolism, Phenylalanine metabolism, Tyrosine metabolism | ribosomal protein L18 | ribosomal protein L18 |
| 24644 | 2056 | J03637 | p | | Aldehyde dehydrogenase class 3 | aldehyde dehydrogenase family 3, subfamily A1 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 23149 | 1415 | AI171213 | General | | | ESTs, Highly similar to putative ATP/GTP-binding protein [H.sapiens] |
| 16034 | 863 | AI008701 | dd | | | ESTs |
| 22631 | 156 | AA849030 | j | | | ESTs |
| 21355 | 1277 | AI105094 | k,o,bb | | | ESTs |
| 22566 | 1545 | AI177122 | c,v | | | ESTs |
| 5007 | 1858 | AI236229 | p | | | ESTs |
| 174 | 2064 | J04197 | r | Fructose and mannose metabolism | 6-Phosphofructo-2-kinase/fructose-2,6-bisphos-phatase 1 (liver and muscle) | 6-Phosphofructo-2-kinase/fructose-2,6-bisphosphatase 1 (liver and muscle) |
| 18725 | 799 | AF029240 | General | | polypyrimidine tract binding protein | Rattus norvegicus MHC class Ib RT1.S3 (RT1.S3) mRNA, partial cds polypyrimidine tract binding protein |
| 3903 | 409 | AA899986 | k,bb | | | |
| 16762 | 816 | AF059530 | h | | protein arginine N-methyl-transferase 3(hnRNP methyltransferase S. cerevisiae)-like 3 | Rattus norvegicus protein arginine N-methyltransferase 3 (PRMT3) mRNA, complete cds |
| 1797 | 2464 | X62086 | f,x,cc,dd | | Cytochrome P450, sub-family IIIA, polypeptide 3 | Cytochrome P450, subfamily IIIA, polypeptide 3, Rattus norvegicus Sprague Dawley testosterone 6-beta-hydroxylase, cytochrome P450/6-beta-A, (CYP3A2) mRNA, complete cds |
| 8661 | 95 | AA818604 | f,q | Carbon fixation, Pentose phosphate cycle | Heat shock protein 70-1 transketolase | Heat shock protein 70-1 transketolase |
| 20804 | 946 | AI011684 | l | | | |
| 15684 | 1424 | AI171535 | r,General | | | ESTs, Weakly similar to 100K RAT 100 KD PROTEIN [R.norvegicus] |
| 19187 | 191 | AA851230 | General,aa | | | ESTs, Weakly similar to T28050 hypothetical protein ZK856.11 - Caenorhabditis elegans [C.elegans] |
| 6002 | 79 | AA818101 | General | | | EST |
| 6234 | 96 | AA818612 | aa | | | ESTs, Highly similar to S53583 splicing factor SF3a60 [H.sapiens] |
| 2079 | 2100 | L14462 | General | | related to Drosophila groucho gene | related to Drosophila groucho gene |
| 18906 | 341 | AA892561 | l | | | ESTs, Moderately similar to PTD012 [H.sapiens] |
| 9268 | 1176 | AI072375 | k | | | ESTs, Highly similar to HIV-Nef associated acyl CoA thioesterase [H.sapiens] |
| 4154 | 887 | AI009467 | t | | | ESTs, Highly similar to HIGH MOBILITY GROUP PROTEIN HMG-Y [M.musculus] |
| 16012 | 2469 | X62875 | i | | | |
| 19287 | 1752 | AI232379 | h | pdgf | Platelet-derived growth factor receptor alpha | Platelet-derived growth factor receptor alpha |
| 17894 | 2320 | U25264 | r | | Selenoprotein W muscle 1 | Selenoprotein W muscle 1 |
| 9143 | 744 | AA998450 | cc,dd | | | ESTs |
| 3498 | 1131 | AI069912 | t | | | ESTs |
| 4330 | 104 | AA818747 | c,d | | | ESTs |
| 6237 | 123 | AA819288 | d,General | | | ESTs |
| 16883 | 714 | AA997345 | c,d | | | ESTs, Weakly similar to nitrilase homolog 1 [M.musculus] |

US 7,590,493 B2

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15582 | 1746 | AI232320 | k | | | Rat mitochondrial 3-hydroxy-3-methylglutaryl-CoA synthase mRNA, complete cds |
| 6638 | 1321 | AI137579 | General | | | ESTs |
| 14738 | 1539 | AI176993 | g,General | | | ESTs |
| 16006 | 818 | AF062594 | i,r | | nucleosome assembly protein 1-like 1 | *Rattus norvegicus* nucleosome assembly protein mRNA, complete cds |
| 5094 | 470 | AA925165 | z | | | ESTs |
| 24427 | 2050 | J03170 | y | | Transcription factor 1, hepatic nuclear factor (HNF1) | Transcription factor 1, hepatic; LF-B1, hepatic; LF-B1, hepatic nuclear factor (HNF1): albumin proximal factor, also TCF1 |
| 21903 | 562 | AA945571 | q,x,cc,dd | Fatty acid metabolism, Tryptophan metabolism | cytochrome P450, 2c37 | cytochrome P450, 2c37 |
| 15357 | 926 | AI010803 | q | | | ESTs, Moderately similar to TESTOSTERONE-REGULATED RP2 PROTEIN [*M.musculus*] |
| 6544 | 1212 | AI102064 | b | | | ESTs, Weakly similar to AF147718 1 glycine decarboxylase [*R.norvegicus*] |
| 7403 | 1015 | AI029212 | c,General | | | EST |
| 6060 | 102 | AA818702 | y | | | ESTs |
| 6132 | 114 | AA819055 | d | | | ESTs, Weakly similar to G35070 apolipoprotein H-related protein 13G1 - mouse [*M.musculus*] |
| 18831 | 1268 | AI104357 | General | | | ESTs, Highly similar to AI TRTC actin beta - rat [*R.norvegicus*] |
| 6072 | 1647 | AI228630 | f,g,y | | | ESTs, Weakly similar to T20360 hypothetical protein D2030.9b - *Caenorhabditis elegans* [*C.elegans*] |
| 1962 | 755 | AB000199 | General | | CAMP responsive element modulator | *Rattus norvegicus* cca2 mRNA, complete cds |
| 357 | 2290 | U04835 | f | | | CAMP responsive element modulator |
| 20980 | 26 | AA799633 | z,bb | | | ESTs |
| 22847 | 436 | AA923982 | bb | | | ESTs, Highly similar to ATP-specific succinyl-CoA synthetase beta subunit [*M.musculus*] |
| 14234 | 230 | AA858928 | General | | | ESTs, Moderately similar to Unknown [*H.sapiens*] |
| 19085 | 342 | AA892598 | n,y | | | ESTs |
| 25746 | 2495 | X80778 | y | | | |
| 538 | 2510 | X94246 | h | | Pax-8 protein | Pax-8 protein |
| 18192 | 785 | AF000899 | j | | | *Rattus norvegicus* nucleoporin p58 mRNA, complete cds |
| 10937 | 1681 | AI230131 | aa | | | ESTs, Weakly similar to AF151834 1 CGI-76 protein [*H.sapiens*] |
| 20797 | 446 | AA924310 | General | | clathrin, heavy polypeptide (Hc) | ESTs, Highly similar to A49630 ubiquitin conjugating enzyme [*H.sapiens*] clathrin, heavy polypeptide (Hc) |
| 17507 | 2053 | J03583 | t | | | |
| 15679 | 929 | AI011058 | General | | | ESTs |
| 6697 | 1079 | AI045340 | t | | | ESTs |
| 11467 | 430 | AA901069 | a | | | |
| 21052 | 2143 | M15481 | d,General | | | Rat insulin-like growth factor-I mRNA, 3' end |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 24654 | 125 | AA819333 | a,General | | | Sprague-Dawley (clone LRB2) RAB16 mRNA, complete cds |
| 18524 | 587 | AA946017 | r,General | | | ESTs |
| 10710 | 1030 | AI030494 | p,General | | | ESTs |
| 4190 | 1541 | AI177016 | General | | | ESTs, Highly similar to similar to *Schizosaccharomyces pombe* splicing factor [*H.sapiens*] |
| 1371 | 2325 | U27319 | a | Aminosugars metabolism, Fructose and mannose metabolism, Galactose metabolism, Glycolysis/ Gluconeogenesis, Starch and sucrose metabolism | Hexokinase 1 | Hexokinase 1 |
| 2666 | 658 | AA962942 | dd | | | ESTs |
| 23228 | 1838 | AI235446 | z | | | ESTs |
| 19936 | 634 | AA956517 | General | | ceroid-lipofuscinosis, neuronal 2 | ceroid-lipofuscinosis, neuronal 2 |
| 21063 | 2000 | D89983 | y | | ornithine decarboxylase antizyme inhibitor | ornithine decarboxylase antizyme inhibitor |
| 5006 | 1677 | AI229908 | p | | putative potassium channel TWIK | ESTs |
| 19665 | 797 | AF022819 | h | | | putative potassium channel TWIK |
| 4186 | 556 | AA945169 | n,x | | Transthyretin (prealbumin, amyloidosis type I), solute carrier family 25 (mitochondrial carrier; citrate transpo | Transthyretin (prealbumin, amyloidosis type I), solute carrier family 25 (mitochondrial carrier; citrate transporter) member 1 |
| 17187 | 51 | AA800315 | z,bb | | | ESTs, Highly similar to PxF protein [*M.musculus*] |
| 18742 | 1278 | AI105131 | k,o | | | ESTs, Highly similar to AF189764 1 alpha/beta hydrolase-1 [*M.musculus*] |
| 4900 | 440 | AA924024 | j | | | ESTs |
| 15382 | 1459 | AI172302 | cc | | | ESTs, Weakly similar to S43056 hypothetical protein - mouse [*M.musculus*] |
| 2248 | 1383 | AI170332 | m | | | ESTs, Highly similar to T18295 Ap-3 adaptor complex beta3A chain - mouse [*M.musculus*] |
| 10532 | 891 | AI009602 | General | | cadherin 2, type 1, N-cadherin (neuronal) | ESTs |
| 6673 | 1054 | AI044325 | General | | | cadherin 2, type 1, N-cadherin (neuronal) |
| 22018 | 858 | AI008309 | b | | | ESTs, Moderately similar to PIM1 RAT PROTO-ONCOGENE SERINE/THREONINE-PROTEIN KINASE PIM-1 [*R.norvegicus*] |
| 5108 | 475 | AA925264 | General | | | ESTs |
| 14768 | 1845 | AI235912 | v | | | ESTs, Weakly similar to hypothetical protein [*H.sapiens*] |
| 7186 | 1187 | AI072833 | z | | | ESTs |
| 21092 | 52 | AA800380 | General,u | | | ESTs, Weakly similar to CORTICOSTEROID 11-BETA-DEHYDROGENASE, ISOZYME 1 [*R.norvegicus*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 22866 | 1792 | AI233754 | b,q,General,aa | | prolactin regulatory element binding | prolactin regulatory element binding |
| 18205 | 1062 | AI044836 | General,w | | | ESTs, Weakly similar to AF 165892 1 RNA binding protein SiahBP [R.norvegicus] |
| 11485 | 1833 | AI23548 | General | | | ESTs, Weakly similar to polycomb-group protein [R.norvegicus] |
| 14070 | 1762 | AI232649 | o | | | ESTs, Weakly similar to IS2328 ubiquitin/ribosomal protein S27a - rat [R.norvegicus] |
| 5944 | 1635 | AI227892 | aa | | | ESTs |
| 1312 | 2175 | M31788 | e | | | ESTs, Highly similar to PGK2 RAT PHOSPHOGLYCERATE KINASE, TESTIS SPECIFIC [R.norvegicus], Rat X-chromosome linked phosphoglycerate kinase mRNA, complete cds |
| 4590 | 350 | AA892778 | d,General | | | ESTs |
| 2939 | 705 | AA996885 | y,cc | | | ESTs, Moderately similar to EBI-1 ligand chemokine [M.musculus] |
| 12542 | 716 | AA997499 | c,j | | | ESTs, Highly similar to 0506206A histone H2B [R.norvegicus] |
| 2569 | 695 | AA965122 | f,r,y | | | ESTs, Weakly similar to T24832 hypothetical protein T11F9.11 - Caenorhabditis elegans [C.elegans] |
| 9963 | 1073 | AI045144 | j,General | | | EST, Moderately similar to CO6_HUMAN COMPLEMENT COMPONENT C6 PRECURSOR [H.sapiens] |
| 14882 | 1916 | D00362 | cc | | Esterase 2 | Esterase 2 |
| 4067 | 461 | AA924813 | o | | | ESTs |
| 13118 | 1315 | AI137292 | cc | | | ESTs |
| 23889 | 334 | AA892520 | i | | | ESTs |
| 17468 | 337 | AA892545 | e | | | ESTs, Highly similar to multi-membrane spanning polyspecific transporter [M.musculus] |
| 4093 | 1733 | AI232001 | General,cc | Glycolysis/Gluconeogenesis | HHs:phosphoglycerate mutase 1 (brain) | R.norvegicus phosphoglycerate mutase B isozyme (PGAM) mRNA, complete cds |
| 10108 | 845 | AI007857 | j | | Hrs | Hrs |
| 18669 | 630 | AA956453 | l | | | ESTs, Highly similar to AF139209 1 OB-receptor gene related protein [R.norvegicus] |
| 16126 | 833 | AF090134 | General | | lin-7-Ba | Rattus norvegicus lin-7-Bb mRNA, complete cds |
| 958 | 2367 | U72741 | t | | Lectin, galactose binding, soluble 9 (Galectin-9) | Lectin, galactose binding, soluble 9 (Galectin-9) |
| 23678 | 830 | AF087037 | i,j | | B-cell translocation gene 3 | B-cell translocation gene 3 |
| 341 | 2504 | X89383 | dd | | | R.norvegicus mRNA for SNF1-related kinase |
| 23348 | 265 | AA874813 | h | | hypertension-related protein | hypertension-related protein |
| 7870 | 1203 | AI101319 | General | | | ESTs |
| 22972 | 779 | AB015946 | r | | | Rattus norvegicus mRNA for tubulin, complete cds |
| 19031 | 1145 | AI070532 | j,u | | T-cell death associated gene | T-cell death associated gene |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15496 | 1750 | AI232370 | General | | | ESTs, Weakly similar to DPSD_CAEEL PUTATIVE PHOSPHATIDYLSERINE DECARBOXYLASE PROENZYME [C.elegans] |
| 13618 | 1700 | AI230724 | General | | | Rattus norvegicus phosphoinositide phosphatase SAC1 mRNA, complete cds |
| 1928 | 2303 | U10357 | General | | pyruvate dehydrogenase kinase 2 subunit p45 (PDK2) | pyruvate dehydrogenase kinase 2 subunit p45 (PDK2) |
| 21842 | 1458 | AI172293 | e | Fatty acid metabolism, Tryptophan metabolism | | Rattus norvegicus mRNA for RANP-1, complete cds |
| 190 | 2299 | U09540 | p | | Cytochrome P450 1b1 | Cytochrome P450 1b1 |
| 17210 | 1790 | AI233746 | General | | | ESTs, Weakly similar to SC14_HUMAN SEC14-LIKE PROTEIN [H.sapiens] |
| 18165 | 324 | AA892259 | v | | | ESTs, Moderately similar to ICSB MOUSE INTERFERON CONSENSUS SEQUENCE BINDING PROTEIN [M.musculus] |
| 15383 | 610 | AA955358 | l,o,General | | | ESTs |
| 5213 | 493 | AA925767 | o | | | ESTs |
| 20589 | 2409 | X06916 | w | | Protein 9 Ka homologous to calcium-binding protein | Protein 9 Ka homologous to calcium-binding protein |
| 8597 | 94 | AA818593 | h,u,dd | | phosphatidate phosphohydrolase type 2 | phosphatidate phosphohydrolase type 2 |
| 15004 | 1830 | AI235224 | w | | | Rattus norvegicus tissue inhibitor of metalloproteinase-1 (TIMP1), mRNA, complete cds |
| 16367 | 360 | AA892888 | p,q,cc | | | EST |
| 7351 | 1985 | D83036 | h | | homeo box, msh-like 1 | homeo box, msh-like 1 |
| 5102 | 473 | AA925211 | x | | activating transcription factor ATF-4 | activating transcription factor ATF-4 |
| 13633 | 962 | AI012335 | General | | | EST |
| 15213 | 59 | AA800908 | i | | | ESTs |
| 23224 | 1349 | AI146033 | General | | | Rattus norvegicus small zinc finger-like protein (TIM9a) mRNA, partial cds |
| 18301 | 2332 | U33500 | dd | | | Rattus norvegicus retinol dehydrogenase type II mRNA, complete cds |
| 2913 | 1742 | AI232272 | General | | | ESTs, Weakly similar to T25417 hypothetical protein T28D6.9 - Caenorhabditis elegans [C.elegans] |
| 3143 | 1754 | AI232408 | l,General,x | | | ESTs |
| 5899 | 1379 | AI170038 | m,u | | | ESTs |
| 19852 | 589 | AA946053 | o | | | ESTs |
| 12160 | 88 | AA818412 | l,x,dd | Fatty acid metabolism, Tryptophan metabolism | cytochrome P450, 2b19 | cytochrome P450, 2b19 |
| 26147 | 989 | AI013387 | aa | | Insulin-like growth factor 2 receptor | Insulin-like growth factor 2 receptor |
| 15174 | 2351 | U59809 | i | | | |
| 21980 | 374 | AA893454 | b,y | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 1818 | 2524 | Y11283 | a,b,k,n,dd | | inter-alpha-inhibitor H4 heavy chain | inter-alpha-inhibitor H4 heavy chain |
| 20913 | 2162 | M23995 | x | | aldehyde dehydrogenase family 1, subfamily A4 | aldehyde dehydrogenase family 1, subfamily A4 |
| 16724 | 185 | AA850987 | dd | | | ESTs |
| 18902 | 284 | AA875390 | c | | | ESTs, ESTs, Highly similar to thioredoxin-related protein [*M.musculus*] |
| 18726 | 799 | AF029240 | General,bb | | | *Rattus norvegicus* MHC class Ib RT1.S3 (RT1.S3) mRNA, partial cds |
| 24800 | 2187 | M35270 | t | Alanine and aspartate metabolism, Glycine, serine and threonine metabolism | Alanine-glyoxylate amino-transferase (Serine-pyruvate aminotransferase) | Alanine-glyoxylate aminotransferase (Serine-pyruvate aminotransferase) |
| 6440 | 233 | AA859130 | General | | | ESTs, Moderately similar to P2CG MOUSE PROTEIN PHOSPHATASE 2C GAMMA ISOFORM [*M.musculus*] |
| 15146 | 1538 | AI176969 | General | | | ESTs |
| 22051 | 397 | AA899498 | bb | | | ESTs, Weakly similar to T26581 hypothetical protein Y32B12A.3 - *Caenorhabditis elegans* [*C.elegans*] |
| 4375 | 380 | AA893869 | i | | | ESTs, Weakly similar to T16084 hypothetical protein F16H11.1 - *Caenorhabditis elegans* [*C.elegans*] |
| 23576 | 2485 | X72757 | q,t | Oxidative phosphory-lation | Cytochrome c oxidase subunit VIa (liver) | Cytochrome c oxidase subunit VIa (liver) |
| 18317 | 7 | AA799326 | bb | | CD36 antigen (collagen type I receptor, thrombospondin receptor) | CD36 antigen (collagen type I receptor, thrombospondin receptor) |
| 1045 | 757 | AB000280 | i | | | *Rattus norvegicus* mRNA for peptide/histidine transporter, complete cds |
| 2267 | 884 | AI009450 | bb | | | ESTs, Highly similar to HIRA-interacting protein [*M.musculus*] |
| 9195 | 1171 | AI072118 | dd | | | EST |
| 11549 | 1740 | AI232174 | j | | | ESTs |
| 14109 | 1775 | AI233227 | General | | | ESTs |
| 18529 | 1699 | AI230716 | General | | | ESTs |
| 16703 | 1603 | AI179300 | f,k,o,x,y | | | ESTs, Weakly similar to LONN_HUMAN MITOCHONDRIAL LON PROTEASE HOMOLOG PRECURSOR [*H.sapiens*] |
| 4561 | 1236 | AI102927 | p,q | | glutaredoxin | glutaredoxin |
| 10190 | 1109 | AI059342 | a | | | ESTs, Weakly similar to death inducer-obliterator-1 [*M.musculus*] |
| 6390 | 224 | AA85821 | General | | | ESTs |
| 1602 | 2374 | U76379 | General,x | | Organic cation transporter | Organic cation transporter |
| 12331 | 597 | AA946466 | e | | | *Rattus norvegicus* membrane-bound aminopeptidase P mRNA, complete cds |
| 13799 | 1488 | AI175871 | g | | | ESTs |
| 22139 | 1512 | AI176548 | bb | | | ESTs, Weakly similar to T32252 hypothetical protein T15B7.2 - *Caenorhabditis elegans* [*C.elegans*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 6381 | 223 | AA858768 | u | Citrate cycle (TCA cycle), Glutathione metabolism, Reductive carboxylate cycle CO2 fixation) | HMm:isocitrate dehydrogenase 2 (NADP+), mitochondrial | ESTs |
| 17290 | 302 | AA891785 | z | | | ESTs, Weakly similar to IDHC RAT ISOCITRATE DEHYDROGENASE [R.norvegicus] |
| 22052 | 397 | AA899498 | f | | | ESTs, Weakly similar to T26581 hypothetical protein Y32B12A.3 - Caenorhabditis elegans [C.elegans] |
| 17530 | 670 | AA963839 | General | Aminosugars metabolism | HHs:diaphorase (NADH) (cytochrome b-5 reductase) | Rat NADH-cytochrome b-5 reductase mRNA, complete cds |
| 18383 | 596 | AA946421 | t | | | ESTs, Highly similar to transcription factor TFEB [M.musculus] |
| 23520 | 609 | AA955305 | p | | | ESTs |
| 14303 | 1716 | AI231159 | v | | | ESTs, Highly similar to KIAA1049 protein [H.sapiens] |
| 7281 | 997 | AI013755 | g | | | ESTs, Highly similar to KIAA0066 [H.sapiens] |
| 14556 | 1893 | AI237820 | i | | | ESTs |
| 23468 | 502 | AA926067 | r | | | ESTs |
| 10073 | 1093 | AI058515 | z | | | EST |
| 40 | 2285 | U02096 | o | | fatty acid binding protein 7, brain | fatty acid binding protein 7, brain |
| 2457 | 686 | AA964752 | k,o | | | EST |
| 475 | 1800 | AI233828 | m,General,u | | | ESTs, Moderately similar to LYSOSOMAL ALPHA-MANNOSIDASE PRECURSOR [M.musculus] |
| 23863 | 615 | AA955628 | dd | | | ESTs, Moderately similar to KIAA0710 protein [H.sapiens] |
| 14081 | 1771 | AI233164 | m | | | ESTs |
| 24323 | 1274 | AI104798 | General,cc | | | ESTs, Moderately similar to GTM1 RAT GLUTATHIONE S-TRANSFERASE YB1 [R.norvegicus] |
| 13369 | 1956 | D21132 | General,y | | | Rat mRNA for phosphatidylinositol transfer protein (beta isoform), complete cds |
| 9795 | 1168 | AI071989 | a,b | | | ESTs, Weakly similar to NPA1 MOUSE NEURONAL PAS DOMAIN PROTEIN 1 [M.musculus] |
| 17117 | 1639 | AI228042 | f,l | | | ESTs, Weakly similar to AC007080 2 NG38 [M.musculus] |
| 10015 | 827 | AF083269 | c,u | | Actin-related protein complex 1b | Actin-related protein complex 1b |
| 5848 | 1354 | AI168994 | m | Glycine, serine and threonine metabolism Pantothenate and CoA biosynthesis, Pyrimidine metabolism, beta-Alanine metabolism | aminolevulinic acid synthase 1 | ESTs |
| 21038 | 2051 | J03190 | f,x | | | aminolevulinic acid synthase 1 |
| 811 | 1983 | D63704 | d,e,z | | dihydropyrimidinase | dihydropyrimidinase |
| 10999 | 1155 | AI071110 | General | Phenylalanine, tyrosine and tryptophan bosynthesis | cyclin H | EST |
| 12577 | 1283 | AI111344 | a,General | | Phenylalanine hydroxylase | cyclin H |
| 6055 | 2132 | M12337 | l,bb | | | Phenylalanine hydroxylase |
| 7161 | 1779 | AI233407 | i,j,General,aa | | | ESTs, Weakly similar to S44853 K12H4.3 protein - Caenorhabditis elegans [C.elegans] |
| 22755 | 593 | AA946323 | p,q | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 15371 | 277 | AA875205 | General,t | | | ESTs, Highly similar to IF39_HUMAN EUKARYOTIC TRANSLATION INITIATION FACTOR 3 SUBUNIT 9 |
| 18991 | 553 | AA945082 | General,cc | Glutathione metabolism | Glutathione-S-transferase, alpha type (Yc?) | Glutathione-S-transferase, alpha type (Yc?) |
| 7225 | 993 | AI013657 | e,General,dd | | | ESTs |
| 18396 | 8 | AA799330 | j | | | ESTs, Highly similar to AF132951 1 CGI-17 protein [*H.sapiens*] |
| 228 | 2314 | U20194 | a,d | | | *Rattus norvegicus* complement C8 beta (C8b) mRNA, partial cds |
| 14459 | 1326 | AI137930 | b,n | | | ESTs |
| 8339 | 1344 | AI145761 | General | | | ESTs, Weakly similar to T21659 hypothetical protein F32D8.4 - *Caenorhabditis elegans* [*C.elegans*] |
| 9292 | 1181 | AI072485 | General | | | ESTs |
| 8999 | 1149 | AI070839 | dd | | | ESTs |
| 14051 | 1756 | AI232489 | dd | | | ESTs, Weakly similar to PIR1 [*H.sapiens*] |
| 25064 | 2247 | S45392 | f,o | | | |
| 25370 | 2104 | L16995 | e,General | | | |
| 22802 | 1602 | AI179291 | dd | | | ESTs |
| 3568 | 403 | AA899821 | bb | | | ESTs |
| 11150 | 207 | AA852004 | General,x | Glutamate metabolism, Nitrogen metabolism | Glutamine synthetase (glutamate-ammonia ligase) | Glutamine synthetase (glutamate-ammonia ligase) |
| 2161 | 1514 | AI176592 | c,m,General | | | ESTs |
| 21068 | 1485 | AI175675 | z | | | ESTs, Highly similar to RAS-RELATED PROTEIN RAB-24 [*M.musculus*] |
| 2467 | 689 | AA964789 | p | | | ESTs |
| 20850 | 407 | AA899956 | n,y | | | ESTs, Moderately similar to imogen 44 [*M.musculus*] |
| 11314 | 28 | AA799656 | t | | | ESTs, Weakly similar to T13747 |
| 3282 | 81 | AA818113 | y | | | hypothetical protein EG:22E5.9 - fruit fly [*D.melanogaster*] |
| 22903 | 322 | AA892250 | i | Aminoacyl-tRNA biosynthesis, Lysine biosynthesis | HHs:lysyl-tRNA synthetase | ESTs, Highly similar to similar to lysyl tRNA synthetase [*H.sapiens*] |
| 22283 | 557 | AA945172 | j,General | | | ESTs, Highly similar to leucine aminopeptidase [*H.sapiens*] |
| 23229 | 1808 | AI234038 | General | | | ESTs |
| 17768 | 1281 | AI105196 | q,General | | | ESTs |
| 22211 | 1265 | AI102479 | General | | | ESTs, Highly similar to translation initiation factor eIF6 [*M.musculus*] |
| 5902 | 1087 | AI045871 | bb | | | ESTs, Moderately similar to inhibitor of MyoD family-a [*M.musculus*] |
| 3803 | 1405 | AI170773 | d | | | *Rattus norvegicus* 250 kDa estrous-specific protein mRNA, partial cds |
| 17236 | 227 | AA858903 | q | | Tissue inhibitor of metalloproteinase 3 | Tissue inhibitor of metalloproteinase 3 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 2350 | 680 | AA964368 | f,General | | | ESTs, Highly similar to TGT_HUMAN QUEUINE TRNA-RIBOSYLTRANSFERASE [H.sapiens] |
| 7913 | 1048 | AI043849 | General,t | | | ESTs, Weakly similar to ELL MOUSE RNA POLYMERASE II ELONGATION FACTOR ELL [M.musculus] |
| 22308 | 398 | AA899535 | z | | | ESTs |
| 2922 | 703 | AA996816 | p | | | ESTs |
| 17379 | 2208 | M62388 | v | | ubiquitin conjugating enzyme | ubiquitin conjugating enzyme |
| 17729 | 2437 | X52619 | cc | | ribosomal protein L28 | ribosomal protein L28 |
| 4234 | 781 | AB016536 | g,l,t | Alanine and aspartate metabolism, Arginine and proline metabolism, Urea cycle and metabolism of amino groups | argininosuccinate lyase, heterogeneous nuclear ribonucleoprotein A/B | heterogeneous nuclear ribonucleoprotein A/B |
| 1523 | 1960 | D26439 | General | | CD1D antigen | CD1D antigen |
| 22855 | 1855 | AI236150 | General | | | ESTs, Highly similar to JC7301 Down syndrome critical region protein 5 alpha [H.sapiens] |
| 1809 | 599 | AA946503 | b,General | | | Rat mRNA for alpha-2u globulin-related protein |
| 23656 | 1058 | AI044533 | General | | | calpain 8 |
| 5464 | 1055 | AI044345 | General | | calpain 10 | ESTs |
| 21822 | 1648 | AI228642 | a,General | | | ESTs, Highly similar to seven transmembrane domain protein [H.sapiens] |
| 1561 | 2533 | Z50052 | b,w | | Complement component 4 binding protein, beta | Complement component 4 binding protein, beta |
| 17589 | 357 | AA892851 | v | | Alanine-glyoxylate amino-transferase (Serine-pyruvate aminotransferase) | ESTs |
| 24801 | 2187 | M35270 | a,t | Alanine and aspartate metabolism, Glycine, serine and threonine metabolism | | Alanine-glyoxylate aminotransferase (Serine-pyruvate aminotransferase) |
| 21707 | 249 | AA859722 | m | | | ESTs |
| 16214 | 2194 | M57276 | i | | Leukocyte antigen (Ox-44) | Leukocyte antigen (Ox-44) |
| 14013 | 1732 | AI231992 | General | | | EST |
| 11842 | 214 | AA858617 | v | | | ESTs |
| 16943 | 1852 | AI236097 | r,General | | | ESTs, Highly similar to E25B protein [M.musculus] |
| 13162 | 1455 | AI172269 | General | | | ESTs |
| 16457 | 546 | AA944856 | i | | O-linked N-acetylglucosamine (GlcNAc) transferase | O-linked N-acetylglucosamine (GlcNAc) transferase |
| 22487 | 1223 | AI102578 | m | | | ESTs, Highly similar to I49523 Mouse primary response gene B94 mRNA, 3'end mouse [M.musculus] |
| 18368 | 27 | AA799645 | f | | FXYD domain-containing ion transport regulator 1 | FXYD domain-containing ion transport regulator 1 |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 14252 | 12 | AA799457 | h | | | ESTs, Weakly similar to T32564 hypothetical protein ZK185.2 - *Caenorhabditis elegans* [*C.elegans*] |
| 8438 | 362 | AA892986 | g,q,General | | | ESTs |
| 20915 | 787 | AF001898 | k,o,w,x | Arginine and proline metabolism, Ascorbate and aldarate metabolism, Bile acid biosynthesis, Butanoate metabolism, Fatty acid metabolism, Glycerolipid metabolism, Histidine metabolism, Lysine degradation, Propanoate metabolism, Pyruvate metabolism, Tryptophan metabolism, Valine, leucine and isoleucine degradation, beta-Alanine metabolism | aldehyde dehydrogenase family 1, subfamily A1 | aldehyde dehydrogenase family 1, subfamily A1 |
| 20421 | 2106 | L19699 | i | | | Rat GTP-binding protein (ral B) mRNA, complete cds |
| 15052 | 2183 | M34043 | bb,cc | | thymosin beta-4 | thymosin beta-4 |
| 2501 | 1296 | AI112343 | j | | | ESTs |
| 10636 | 945 | AI011634 | e,j,bb | | | ESTs, Weakly similar to I(3)S12 protein [*D.melanogaster*] |
| 3233 | 80 | AA818105 | General | | | ESTs, Moderately similar to Unknown gene product [*H.sapiens*] |
| 3431 | 1515 | AI176595 | a,o,q | | Cathepsin L | Cathepsin L |
| 16885 | 1280 | AI105188 | u | Arginine and proline metabolism, Ascorbate and aldarate metabolism, Bile acid biosynthesis, Butanoate metabolism, Fatty acid metabolism, Glycerolipid metabolism, Histidine metabolism, Lysine degradation, Propanoate metabolism, Pyruvate metabolism, Tryptophan metabolism, Valine, leucine and isoleucine degradation, beta-Alanine metabolism | aldehyde dehydrogenase family 9, subfamily A1 | aldehyde dehydrogenase family 9, subfamily A1 |
| 19230 | 1116 | AI059604 | General | | | ESTs |
| 15313 | 275 | AA875126 | General | | | ESTs |
| 8944 | 1146 | AI070597 | k | | | ESTs, Highly similar to CGI-97 protein [*H.sapiens*] |
| 16416 | 273 | AA875098 | o,r,General,u | | | ESTs, Highly similar to ARF3_HUMAN ADP-RIBOSYLATION FACTOR [*H.sapiens*] |
| 20707 | 2380 | U88036 | f,h,l,m,w,x | | | *Rattus norvegicus* brain digoxin carrier protein mRNA, complete cds |
| 25041 | 1942 | D14014 | q | | | |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 24771 | 2216 | M77479 | cc | | Solute carrier family 10 (sodium/bile acid cotransporter family), member 1 | Solute carrier family 10 (sodium/bile acid cotransporter family), member 1 |
| 13945 | 2300 | U09793 | aa | epo, il2, il3, il6, insulin, interact6-1, ngf, pdgf, tpo | Kirsten rat sarcoma viral oncogene homologue 2 (active) | Kirsten rat sarcoma viral oncogene homologue 2 (active) |
| 16366 | 360 | AA892888 | p,q | | | EST |
| 24648 | 2215 | M74054 | General | | Angiotensin II receptor, type 1 (AT1A) | Angiotensin II receptor, type 1 (AT1A) |
| 15961 | 956 | AI012130 | b | | | ESTs |
| 19191 | 164 | AA849525 | i | | Calmodulin 1 (phosphorylase kinase, delta) | Calmodulin 1 (phosphorylase kinase, delta) |
| 16420 | 48 | AA800191 | a | | | ESTs |
| 9842 | 2385 | U94856 | d,k,p,q | | paraoxonase 1 | paraoxonase 1 |
| 8520 | 1125 | AI060052 | General | | | ESTs |
| 22350 | 529 | AA944014 | r | | | ESTs |
| 17644 | 442 | AA924036 | l,General,bb | | | ESTs |
| 21502 | 920 | AI010483 | e | | | ESTs, Highly similar to nucleic acid binding protein [H.sapiens] |
| 13382 | 1205 | AI101527 | General | | | ESTs, Highly similar to SR19_HUMAN SIGNAL RECOGNITION PARTICLE 19 KD PROTEIN [H.sapiens] |
| 7859 | 1042 | AI043660 | General | | Glucokinase regulatory protein | Glucokinase regulatory protein |
| 22582 | 559 | AA945442 | c,h | | | ESTs |
| 1802 | 69 | AA817841 | cc | | tissue-type transglutaminase | tissue-type transglutaminase |
| 16 | 883 | AI009426 | General | | | |
| 2057 | 1224 | AI102579 | d,General | | cyclic AMP phosphoprotein, 19kD | cyclic AMP phosphoprotein, 19kD |
| 21209 | 1433 | AI171772 | m,y | | | ESTs |
| 23775 | 633 | AA956483 | a | | Myelin protein zero (Charcot-Marie-Tooth | Myelin protein zero (Charcot-Marie-Tooth neuropathy 1B) |
| 14970 | 298 | AA891738 | e | | sulfite oxidase | sulfite oxidase |
| 12516 | 1613 | AI179651 | y | | | ESTs, Moderately similar to SM32_HUMAN UBIQUITIN-LIKE PROTEIN SMT3B [H.sapiens] |
| 1170 | 1548 | AI177161 | q,r | | NF-E2-related factor 2 | NF-E2-related factor 2 |
| 3773 | 742 | AA998356 | b,m,n,v | | | ESTs, Weakly similar to BCL3_HUMAN B-CELL LYMPHOMA 3-ENCODED PROTEIN [H.sapiens] |
| 5020 | 458 | AA924768 | y | | | ESTs, Weakly similar to MRJ [M.musculus] |
| 8119 | 1620 | AI179974 | i | | | ESTs, Weakly similar to T12542 hypothetical protein DKFZp434L194.1 [H.sapiens] |
| 19186 | 190 | AA851226 | g | | | Rattus norvegicus brain-enriched WD-repeat protein (Bwd) mRNA, complete cds |
| 13467 | 1330 | AI138034 | aa | | UDP-glucose:ceramide glycosyltransferase | UDP-glucose:ceramide glycosyltransferase |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 8317 | 320 | AA892234 | u | Glutathione metabolism | HHs:microsomal glutathione S-transferase 3 | ESTs, Moderately similar to microsomal glutathione S-transferase 3 [*H.sapiens*] |
| 11516 | 1260 | AI103962 | aa | | | ESTs |
| 17662 | 1255 | AI103774 | bb | | | *Rattus norvegicus* dynein light chain-2 (Dlc2) mRNA, complete cds |
| 7416 | 1692 | AI230458 | t | | | ESTs, Highly similar to 1702360A KDEL receptor [*H.sapiens*] |
| 12628 | 737 | AA998123 | General | | | ESTs, Moderately similar to HYA22 [*H.sapiens*] |
| 714 | 2302 | U10279 | 1 | | | *Rattus norvegicus* Sprague-Dawley sodium-dependent nucleoside transporter (rCNT1) mRNA, complete cds |
| 11303 | 2415 | X12752 | General | | CAAT/enhancer-binding protein, DNA-binding protein | CAAT/enhancer-binding protein, DNA-binding protein |
| 13574 | 340 | AA892557 | General | | | ESTs |
| 410 | 873 | AI008974 | General,y | | | *R.norvegicus* mRNA encoding 45kDa protein which binds to heymann nephritis antigen gp330 |
| 3302 | 731 | AA997905 | g,t | Sterol biosynthesis, Terpenoid biosynthesis | farnesyl diphosphate farnesyl transferase 1 | ESTs |
| 19358 | 894 | AI009675 | z | | | EST |
| 16450 | 2241 | M95591 | e,General | | | farnesyl diphosphate farnesyl transferase 1 |
| 13952 | 225 | AA858886 | General | | | ESTs, Weakly similar to T33225 hypothetical protein W02G9.1 - *Caenorhabditis elegans* [*C.elegans*] |
| 25768 | 2511 | X94769 | h | | | ESTs, Moderately similar to COMPLEMENT C5 PRECURSOR [*M.musculus*] |
| 10378 | 1777 | AI233300 | General | | | |
| 11724 | 1232 | AI02812 | l,p | | | ESTs |
| 7266 | 1295 | AI112237 | h | | | ESTs, Moderately similar to NADH-ubiquinone oxidoreductase AGGG subunit [*H.sapiens*] |
| 22883 | 441 | AA924028 | f | | | ESTs |
| 1448 | 2422 | X15030 | k | | | Rat CoxVa mRNA for mitochondrial cytochrome c oxidase subunit Va |
| 20703 | 2088 | K03241 | f,g,p,q,dd | Fatty acid metabolism, Tryptophan metabolism | Cytochrome P450, subfamily I (aromatic compound-inducible), member A2 (Q42, form d) | Cytochrome P450, subfamily I (aromatic compound-inducible), member A2 (Q42, form d) |
| 12463 | 1765 | AI232706 | General | | translin-associated factor X | translin-associated factor X |
| 2337 | 677 | AA964307 | z | | peroxisomal biogenesis factor 3 | peroxisomal biogenesis factor 3 |
| 17516 | 1519 | AI176621 | k | Citrate cycle (TCA cycle), Glyoxylate and dicarboxylate metabolism, Reductive carboxylate cycle (CO2 fixation) | iron-responsive element-binding protein | iron-responsive element-binding protein |
| 6189 | 1572 | AI178027 | m,u | | | ESTs, Weakly similar to GLUTATHIONE S TRANSFERASE P [*R.norvegicus*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 23502 | 734 | AA998025 | General | | | ESTs, Weakly similar to A60716 somatotropin intron-related protein RDE.25 - rat [R.norvegicus] |
| 6941 | 1064 | AI044892 | cc | | | ESTs, Highly similar to TYROSINE-PROTEIN KINASE FLK [R.norvegicus] |
| 5460 | 1535 | AI176944 | d,General | | | ESTs |
| 1678 | 2244 | M96674 | General,w | | Glucagon receptor | Glucagon receptor |
| 2544 | 74 | AA817968 | General | | | ESTs, Weakly similar to alkaline phosphodiesterase [R.norvegicus] |
| 9313 | 29 | AA799681 | h | | | ESTs |
| 7436 | 141 | AA848354 | General | | | ESTs, Weakly similar to T29201 hypothetical protein T03F1.1 - Caenorhabditis elegans [C.elegans] |
| 20524 | 1078 | AI045201 | b | | | ESTs |
| 2388 | 952 | AI011806 | f,General | | | ESTs, Moderately similar to putative Rab5 interacting protein {clone L1-57 [H.sapiens] |
| 19555 | 506 | AA926120 | l | | | EST |
| 23968 | 1454 | AI172260 | bb | | | ESTs, Weakly similar to similar to yeast SSU72 [H.sapiens] |
| 20869 | 2177 | M32062 | u | | | Rat Fc-gamma receptor mRNA, complete cds |
| 17480 | 2328 | U31598 | u | | | R.norvegicus mRNA for RT1.Ma |
| 23577 | 613 | AA955513 | y | | | ESTs |
| 23035 | 576 | AA945712 | i,General | | | ESTs |
| 12082 | 782 | AB016800 | General | | 7-dehydrocholesterol reductase | 7-dehydrocholesterol reductase |
| 6252 | 126 | AA819381 | n | Fatty acid metabolism, Tryptophan metabolism | Cytochrom P450 Lanosterol 14 alpha-demethylase | Cytochrom P450 Lanosterol 14 alpha-demethylase |
| 20931 | 2311 | U17697 | e | | | |
| 8384 | 2178 | M32167 | g | | vascular endothelial growth factor | vascular endothelial growth factor |
| 8837 | 1233 | AI102849 | n,General | | | ESTs |
| 6000 | 77 | AA818088 | x | | | EST |
| 23825 | 2337 | U38180 | r | | solute carrier family 19 (sodium/hydrogen exchanger), member 1 | solute carrier family 19 (sodium/hydgogen exchanger), member 1 |
| 4090 | 2257 | S63233 | t | Glycolysis/Gluconeogenesis | HHs;phosphoglycerate mutase 1 (brain) | R.norvegicus phosphoglycerate mutase B isozyme (PGAM) mRNA, complete cds |
| 23183 | 1331 | AI144586 | o,General | | evectin-1 | evectin-1 |
| 17469 | 338 | AA892549 | d | | | ESTs |
| 20090 | 1904 | AI639353 | General,v,x | | pleiotropic regulator 1 | pleiotropic regulator 1 |
| 21012 | 2038 | J02592 | h | Glutathione metabolism | Glutathione-S-transferase, mu type 2 (Yb2) | Glutathione-S-transferase, mu type 2 (Yb2) |
| 11372 | 1329 | AI137995 | p | | | ESTs |
| 7582 | 1021 | AI029996 | e | | | ESTs |
| 851 | 2366 | U72497 | c | | fatty acid amide hydrolase | fatty acid amide hydrolase |
| 20082 | 1906 | AI639488 | i | | | EST, Highly similar to A42772 mdm2 protein - rat [R.norvegicus] |
| 17938 | 914 | AI010332 | t | | | ESTs |

TABLE 1-continued

| GLGC ID | SeqID | GenBank Acc | Model Code | Pathway Name | Known Gene Name | Unigene Cluster Title |
|---|---|---|---|---|---|---|
| 2555 | 1922 | D00913 | m,u | | Intercellular adhesion molecule 1 | Intercellular adhesion molecule 1 |
| 17540 | 620 | AA955914 | c | | | EST, EST, Moderately similar to FBRL MOUSE FIBRILLARIN [*M.musculus*], ESTs, Highly similar to FBRL MOUSE FIBRILLARIN [*M.musculus*] |
| 23776 | 1129 | AI060224 | l,General | | | ESTs |
| 15409 | 1918 | D00569 | k,o | | | *Rattus norvegicus* mRNA for 2,4-dienoyl-CoA reductase precursor, complete cds |
| 16767 | 1948 | D16478 | k,n,o | | | Rat mRNA for mitochondrial long-chain enoyl-CoA hydratase/3-hydroxyacyl-CoA dehydrogenase alpha-subunit of mitochondrial trifunctional protein, complete cds |
| 7552 | 1085 | AI045802 | General,y | | | ESTs, Highly similar to PHLD MOUSE PHOSPHATIDYLINOSITOL-GLYCAN-SPECIFIC PHOSPHOLIPASE D 1 PRECURSOR [*M.musculus*] |
| 19143 | 601 | AA946531 | g,t | | Histone H1-0 | ESTs |
| 16024 | 1751 | AI232374 | aa | | Adrenergic, alpha 1B-, receptor | Histone H1-0 |
| 64 | 2206 | M60655 | g,General,z | | | Adrenergic, alpha 1B-, receptor |
| 14595 | 318 | AA892128 | k,o | | | ESTs |
| 24108 | 1701 | AI230728 | General | | | ESTs, Highly similar to S42114 small nuclear ribonucleoprotein U1A - mouse [*M.musculus*] |
| 8872 | 188 | AA851050 | f,l,r,General,x | | | ESTs |
| 21798 | 509 | AA926365 | l,x,aa,cc | | | ESTs, Moderately similar to AF151827 1 CGI-69 protein [*H.sapiens*] |
| 1793 | 1939 | D13912 | f,g,h,o,x,cc | | Cytochrome P450, subfamily IIIA, polypeptide 3 | Cytochrome P450, subfamily IIIA, polypeptide 3 |
| 13353 | 1478 | AI175508 | General | | | ESTs |
| 9905 | 301 | AA891774 | o,w | | carnitine octanoyltransferase | ESTs |
| 20554 | 2049 | J02844 | k | | | carnitine octanoyltransferase |
| 13282 | 2086 | K03041 | General | Arginine and proline metabolism, Urea cycle and metabolism of amino groups | Ornithine carbamoyl-transferase | Ornithine carbamoyltransferase |
| 21015 | 2399 | X04229 | a,h,t,x,cc | Glutathione metabolism | Glutathione-S-transferase, mu type 2 (Yb2) | Glutathione-S-transferase, mu type 2 (Yb2) |
| 19302 | 1099 | AI058968 | bb | | | EST, Moderately similar to CPT2 RAT CARNITINE O-PALMITOYLTRANSFERASE II, MITOCHONDRIAL PRECURSOR [*R.norvegicus*] |
| 15487 | 1503 | AI176351 | v | | tripeptidylpeptidase II | tripeptidylpeptidase II |

Document Number 1740956

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 7586 | 1022 | AI030024 | d | | | ESTs |
| 19769 | 1221 | AI102570 | b,m | | | EST, Weakly similar to A607 16 somatotropin intron-related protein RDE.25 - rat [*R.norvegicus*] |
| 179 | 1955 | D17809 | p | Sphingoglycolipid metabolism | beta-4N-acetylgalactosaminyltransferase | beta-4N-acetylgalactosaminyltransferase |
| 1919 | 1324 | AI137856 | g,General | | P450 (cytochrome) oxidoreductase | P450 (cytochrome) oxidoreductase |
| 22310 | 1214 | AI102194 | General | | | EST |
| 9015 | 1820 | AI234810 | l | | | ESTs |
| 9135 | 1977 | D45247 | c,h | Proteasome | proteasome beta type subunit 5 | ESTs, Highly similar to PRCE RAT PROTEASOME EPSILON CHAIN PRECURSOR [*R.norvegicus*] |
| 10659 | 1238 | AI103059 | m | | | ESTs |
| 13364 | 1392 | AI170606 | v | | | ESTs, Weakly similar to DRNG RAT DEOXYRIBONUCLEASE GAMMA PRECURSOR [*R.norvegicus*] |
| 3925 | 186 | AA851017 | j | | beta-galactoside-binding lectin | ESTs, Highly similar to molybdopterin-synthase large subunit [*M.musculus*] beta-galactoside-binding lectin |
| 20709 | 1447 | AI172064 | i | | | ESTs |
| 11828 | 1386 | AI170418 | t | | | |
| 9598 | 2031 | H33832 | k,v,aa | | | |
| 25805 | 2007 | E01050 | t | | | |
| 2484 | 1273 | AI104675 | e | | | ESTs |
| 4229 | 590 | AA946057 | General | | RAB7, member RAS oncogene family | RAB7, member RAS oncogene family |
| 10887 | 2534 | Z83757 | o,General | | Growth hormone receptor | Growth hormone receptor |
| 1968 | 2224 | M83745 | y | | Protein convertase subtilisin/kexin, type I | Protein convertase subtilisin/kexin, type I |
| 10200 | 1111 | AI059444 | f | | | ESTs |
| 4383 | 1542 | AI177056 | d,General | Proteasome | proteasome (prosome, macropain) subunit, alpha type 6 | ESTs |
| 15535 | 1928 | D10755 | General | | | proteasome (prosome, macropain) subunit, alpha type 6 |
| 25500 | 2258 | S63458 | o | | | ESTs |
| 14425 | 1568 | AI177755 | b,v | | | ESTs |
| 1901 | 71 | AA817849 | General | | Guanine nucleotide-binding protein beta 1 | Guanine nucleotide-binding protein beta 1 |
| 21803 | 857 | AI008284 | z | | | |
| 12157 | 2080 | K01721 | f,g,o,x,cc,dd | Fatty acid metabolism, Tryptophan metabolism | cytochrome P450, 2b19 | cytochrome P450, 2b19 |
| 6018 | 117 | AA819140 | m | Nitrogen metabolism | carbonic anhydrase 3 | carbonic anhydrase 3 |
| 21353 | 175 | AA850247 | b,j,n,General | | | ESTs |
| 20698 | 2502 | X86561 | b,w | | complement factor I | complement factor I |
| 22079 | 554 | AA945094 | bb | | | ESTs |
| 2107 | 314 | AA892006 | aa | | | ESTs |
| 23030 | 457 | AA924763 | e | | | |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 12313 | 558 | AA945418 | r | | cytochrome P450, 8b1, sterol 12 alpha-hydrolase | cytochrome P450, 8b1, sterol 12 alpha-hydrolase |
| 9096 | 1357 | AI169127 | bb | | hypothetical protein LOC56728 | hypothetical protein LOC56728 |
| 17766 | 196 | AA851299 | General,x | | | ESTs |
| 6975 | 1499 | AI176229 | z | | | ESTs |
| 22336 | 382 | AA893924 | v | | | ESTs, Highly similar to AF132599 1 RANTES factor of late activated T lymphocytes-1 [*H.sapiens*] |
| 17130 | 2209 | M62992 | i,dd | | nuclear pore glycoprotein 62 | nuclear pore glycoprotein 62 |
| 15926 | 776 | AB012933 | e,z | | | *Rattus norvegicus* mRNA for acyl-CoA synthetase 5, complete cds |
| 18525 | 1523 | AI176792 | p,r | | | ESTs |
| 20380 | 1946 | D16102 | General | Glycerolipid metabolism | ATP-stimulated gluco-corticoid-receptor translocaton promoter | ATP-stimulated glucocorticoid-receptor translocaton promoter |
| 23710 | 1695 | AI230614 | t | | ATPase Na+/K+ transporting beta 1 polypeptide | ATPase Na+/K+ transporting beta 1 polypeptide |
| 18727 | 1941 | D13978 | g,t | Alanine and aspartate metabolism, Arginine and proline metabolism, Urea cycle and metabolism of amino groups | argininosuccinate lyase | argininosuccinate lyase |
| 15695 | 1932 | D10891 | x | | Glutamate receptor, metabotropic 5 | Glutamate receptor, metabotropic 5 |
| 19258 | 421 | AA900613 | n | | | ESTs |
| 15190 | 1220 | AI102562 | b,g | | | Rat metallothionein-i (mt-1) mrna |
| 960 | 1923 | D10026 | General,y | Glutathione metabolism | glutathione S-transfer-ase, theta 2 | glutathione S-transferase, theta 2 |
| 412 | 2388 | V01216 | b | | | Rat messenger encoding alpha-1-acid glycoprotein |
| 3433 | 1027 | AI030339 | General | | | ESTs |
| 19012 | 1446 | AI172056 | n | | | ESTs |
| 21192 | 897 | AI009732 | q | | | ESTs |
| 10396 | 1138 | AI070294 | General | | | ESTs |
| 25686 | 2434 | X51536 | w | | | ESTs, Highly similar to hypothetical protein [*H.sapiens*] |
| 2084 | 739 | AA998151 | General,cc | | | ESTs |
| 23783 | 345 | AA892773 | General | | | ESTs, Weakly similar to CALMODULIN [*R.norvegicus*] |
| 24233 | 687 | AA964756 | j,General | | | ESTs |
| 21765 | 1787 | AI233696 | i,w | | | ESTs, Weakly similar to GPV RAT PLATELET GLYCOPROTEIN V PRECURSOR [*R.norvegicus*] |
| 7122 | 1318 | AI137468 | b | | | ESTs, Highly similar to ORF3, splicevariant b [*H.sapiens*] |
| 6164 | 1391 | AI170597 | General | | farnesoid X activated receptor | farnesoid X activated receptor |
| 19712 | 2312 | U18374 | General | | | |
| 22992 | 704 | AA996880 | x,z | | | ESTs |
| 10281 | 1122 | AI059947 | General | | | EST |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 18886 | 526 | AA943785 | General | | | ESTs, Highly similar to AF157028 1 protein phosphatase methylesterase-1 [H.sapiens] |
| 6801 | 913 | AI010316 | i | | | ESTs |
| 21391 | 1003 | AI013902 | General | | | ESTs, Weakly similar to ANX4 RAT ANNEXIN IV [R.norvegicus] |
| 6477 | 2035 | J00735 | t | | Fibrinogen, gamma polypeptide | Fibrinogen, gamma polypeptide |
| 8053 | 1470 | AI175033 | b | | | ESTs |
| 18038 | 2339 | U39943 | General,u | | | Rattus norvegicus cytochrome P450 pseudogene (CYP2I3P1) mRNA |
| 19053 | 1934 | D12770 | o,u | | solute carrier family 25 (mitochondrial adenine nucleotide translocator) member 4 | Rattus norvegicus mRNA for mitochondrial adenine nucleotide translocator |
| 17066 | 1998 | D89070 | d | Prostaglandin and leukotriene metabolism | carbonyl reductase | carbonyl reductase |
| 17292 | 2212 | M67465 | f | Androgen and estrogen metabolism, C21-Steroid hormone metabolism | Hydroxy-delta-5-steroid dehydrogenase, 3 beta- and steroid delta-isomerase | Hydroxy-delta-5-steroid dehydrogenase, 3 beta- and steroid delta-isomerase |
| 12276 | 336 | AA892541 | General | | | ESTs |
| 6071 | 344 | AA892675 | f,g,General | | | ESTs, Weakly similar to T20360 hypothetical protein D2030.9b - Caenorhabditis elegans [C.elegans] |
| 172 | 2170 | M27886 | r | Fructose and mannose metabolism | 6-Phosphofructo-2-kinase/fructose-2,6-bisphosphatase 1 (liver and muscle) | 6-Phosphofructo-2-kinaselfrucl bisphosphatase 1 (liver and muscle) |
| 11693 | 1351 | AI68953 | l | | | Rattus norvegicus mRNA for Sulfotransferase K2 |
| 23032 | 1516 | AI176596 | l | | | ESTs |
| 794 | 2363 | U68168 | u | Tryptophan metabolism | HHs:kynureninase (L-kynurenine hydrolase) | Rattus norvegicus L-kynurenin hydrolase mRNA, complete cds |
| 22634 | 577 | AA945722 | General | | | ESTs |
| 3121 | 855 | AI008160 | h,u | | | ESTs, Moderately similar to AF151841 1 CGI-83 protein [H.sapiens] |
| 2505 | 2146 | M16235 | c,e,u | Glycerolipid metabolism | Lipase, hepatic | Lipase, hepatic |
| 15542 | 1239 | AI103095 | d | | | Rattus norvegicus brain Na++/Ca++ exchanger-associated protein mRNA, complete cds |
| 6501 | 896 | AI009724 | General | | | ESTs |
| 22503 | 544 | AA944823 | General | | | ESTs |
| 23521 | 143 | AA848407 | c | | | ESTs |
| 3504 | 1272 | AI104659 | m,v | | B-cell CLL/lymphoma 10 | B-cell CLL/lymphoma 10 |
| 25052 | 2108 | L22190 | b,w | | | |
| 17380 | 25 | AA799612 | t | | ubiquitin conjugating enzyme | ubiquitin conjugating enzyme |
| 1653 | 1797 | AI233806 | General | | Peptidylglycine alpha-amidating monooxygenase | Peptidylglycine alpha-amidating monooxygenase |
| 19992 | 1407 | AI170777 | General | | mitochondrial aconitase (nuclear aco2 gene) | mitochondrial aconitase (nuclear aco2 gene) |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 18939 | 580 | AA945875 | x | | | ESTs, Weakly similar to S12207 hypothetical protein [*M.musculus*] |
| 12677 | 848 | AI007889 | c | | | ESTs, Weakly similar to SNXC_MOUSE SORTING NEXIN 12 (SDP8 PROTEIN) [*M.musculus*] |
| 11235 | 1614 | AI17909 | aa | | | ESTs, Weakly similar to similar to *C.elegans* hypothetical protein CE01H8.1, CEC05C12.3, CEF54D1.5. similar to trp and trp-like proteins [*H.sapiens*] |
| 20755 | 2483 | X70871 | r | | Cyclin G1 | Cyclin G1 |
| 2190 | 672 | AA964004 | k | | resiniferatoxin-binding, phosphotriesterase-related protein | resiniferatoxin-binding, phosphotriesterase related protein |
| 8521 | 1126 | AI060064 | n | | | ESTs |
| 1540 | 2166 | M25073 | General | | kidney aminopeptidase M | kidney aminopeptidase M |
| 20233 | 2461 | X59290 | b | | eph and elk-related kinase | eph and elk-related kinase |
| 18714 | 985 | AI013194 | y | | eukaryotic initiation factor 5 (eIF-5) | eukaryotic initiation factor 5 (eIF-5) |
| 6686 | 1496 | AI176130 | General | | | ESTs |
| 15154 | 335 | AA892532 | e | | | *R.norvegicus* (Wistar) CaBP1 mRNA |
| 15933 | 281 | AA875253 | v | | ADP-ribosylation factor-like 1 | ADP-ribosylation factor-like 1 |
| 20945 | 1411 | AI171085 | t | | Ribosomal protein L39 | Ribosomal protein L39 |
| 192 | 2500 | X83367 | p | Fatty acid metabolism, Tryptophan metabolism | Cytochrome P450 1b1 | Cytochrome P450 1b1 |
| 22586 | 561 | AA945454 | g | | | *Rattus norvegicus* prohepcidin (Hepc) mRNA, complete cds |
| 13684 | 105 | AA818770 | d | | | *Rattus norvegicus* serine protease gene, complete cds |
| 21757 | 841 | AI007656 | t | | | ESTs |
| 1347 | 157 | AA849038 | f | | ribosomal protein L31 | ribosomal protein L31 |
| 6329 | 121 | AA819259 | a | | | ESTs, Moderately similar to APC2 MOUSE APOLIPOPROTEIN C-II PRECURSOR [*M.musculus*] |
| 25814 | 2203 | M59460 | General | Starch and sucrose metabolism | liver glycogen phosphorylase | liver glycogen phosphorylase |
| 5920 | 1360 | AI169163 | General | | | ESTs |
| 22765 | 1501 | AI176265 | m | | | ESTs |
| 22196 | 2315 | U21719 | General,y | | | ESTs |
| 3606 | 1495 | AI176077 | aa | | | ESTs |
| 6788 | 1649 | AI228646 | v | | | ESTs |
| 14528 | 1890 | AI237718 | General | | | ESTs, Highly similar to UDP1_HUMAN UTP-GLUCOSE-1-PHOSPHATE URIDYLYLTRANSFERASE 1 [*H.sapiens*] |
| 17027 | 1398 | AI170679 | bb | | | |
| 25643 | 2375 | U77829 | j | Methionine metabolism, Selenoamino acid metabolism | HMm:methionine adenosyltransferase II, alpha | Rat S-adenosylmethionine synthetase mRNA |
| 24690 | 2076 | J05571 | v | | | |
| 5887 | 1599 | AI179099 | k,z | | | ESTs, Moderately similar to Vanin-1 [*M.musculus*] |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 16610 | 1961 | D28557 | a,General,v | | muscle Y-box protein YB2 | muscle Y-box protein YB2 |
| 211 | 560 | AA945453 | General | | solute carrier family 28 (sodium-coupled nucleoside transporter) | solute carrier family 28 (sodium-coupled nucleoside transporter), member 2 |
| 15189 | 2129 | M11794 | b,g | | | ESTs |
| 3371 | 738 | AA998124 | bb | | | ESTs |
| 7182 | 916 | AI010450 | General | | | ESTs |
| 23451 | 474 | AA925243 | y | | | ESTs, Weakly similar to Ste20-like kinase [*M.musculus*] |
| 3427 | 321 | AA892246 | q | | heterogeneous nuclear ribonucleoprotein L | heterogeneous nuclear ribonucleoprotein L |
| 16945 | 485 | AA925541 | z | | | |
| 53 | 2310 | U16253 | f | | corticotropin-releasing factor receptor subtype 2 | corticotropin-releasing factor receptor subtype 2 |
| 23682 | 1826 | AI234973 | q,General | | | *Rattus norvegicus* protein phosphatase 2A B regulatory subunit delta isoform mRNA, complete cds |
| 11137 | 2078 | K00750 | t | | Cytochrome C, expressed in somatic tissues | Cytochrome C, expressed in somatic tissues |
| 7537 | 1018 | AI029829 | General | | | ESTs |
| 22351 | 579 | AA945867 | e,r,General | | | ESTs |
| 11849 | 2508 | X93352 | w | | ribosomal protein L10a | ribosomal protein L10a |
| 22930 | 1162 | AI071578 | d,m | | | ESTs, Moderately similar to NEURONAL PROTEIN 3.1 [*M.musculus*] |
| 16178 | 803 | AF035387 | r | Oxidative phosphorylation, Type III rotein secretion system | ATPase, H+ transporting, lysosomal (vacuolar proton pump), subun | ATPase, H+ transporting, lysosomal (vacuolar proton pump), subunit 1 |
| 1279 | 2372 | U75916 | General | | | *Rattus norvegicus* zonula occludens 2 protein (ZO-2) mRNA, partial cds |
| 3842 | 817 | AF061242 | bb | | fracture callus 1 | fracture callus 1 |
| 22491 | 394 | AA899289 | z | | | ESTs, Moderately similar to KIAA1049 protein [*H.sapiens*] |
| 8210 | 2256 | S61960 | General,y | | ferritin light chain 1 | ferritin light chain 1 |
| 1460 | 2269 | S76054 | General | | | ESTs, Highly similar to K2C8 RAT KERATIN, TYPE II CYTOSKELETAL 8 [*R.norvegicus*] |
| 14424 | 1142 | AI070421 | i | | oxidative stress induced | oxidative stress induced |
| 25777 | 2519 | Y08355 | g | | | ESTs, Moderately similar to BHMT RAT BETAINE-HOMOCYSTEINE S-METHYLTRANSFERASE [*R.norvegicus*] |
| 23261 | 469 | AA925145 | e | | | |
| 23230 | 1854 | AI236146 | aa | | | ESTs |
| 19617 | 1043 | AI043664 | a | | | EST |
| 17473 | 903 | AI009806 | General | | | *Rattus norvegicus* protein inhibitor of neuronal nitric oxide synthase (PIN) mRNA, complete cds |
| 11050 | 626 | AA956164 | General | | | ESTs, Weakly similar to TCPA RAT T-COMPLEX PROTEIN 1, ALPHA SUBUNIT [*R.norvegicus*] |
| 18315 | 822 | AF072411 | c | | CD36 antigen (collagen type I receptor, thrombospondin receptor) | CD36 antigen (collagen type I receptor, thrombospondin receptor) |
| 23189 | 497 | AA925844 | n | | | ESTs |

TABLE 1-continued

Document Number 1740956

| GLGC ID | SeqID | GenBank Acc | Model Code | Pathway Name | Known Gene Name | Unigene Cluster Title |
|---|---|---|---|---|---|---|
| 2653 | 678 | AA964319 | General | | | ESTs |
| 25069 | 2279 | S82820 | f,General,cc | | | |
| 2818 | 1601 | AI179144 | General | | | ESTs |
| 14670 | 1480 | AI175528 | General | | | RAN, member RAS oncogene family |
| 20714 | 2141 | M14972 | k,o | Fatty acid metabolism, Tryptophan metabolism | RAN, member RAS oncogene family | Cytochrome P450, subfamily IVB, polypeptide 1 |
| 14591 | 355 | AA892847 | General | Sphingoglycolipid metabolism | Cytochrome P450, subfamily IVB, polypeptide 1 | ESTs, Moderately similar to alpha-N-acetylgalactosaminidase [*M.musculus*] |
| 8515 | 170 | AA849917 | General | | HHs:N-acetylgalactosaminidase, alpha- | ESTs |
| 6862 | 167 | AA849729 | n | | | ESTs, Weakly similar to T28096 hypothetical protein ZK909.3 - *Caenorhabditis elegans* [*C.elegans*] |
| 9012 | 1150 | AI070879 | r | | | EST |
| 13575 | 340 | AA892557 | a | | | ESTs |
| 24181 | 1244 | AI103320 | General | | | ESTs, Moderately similar to T26785 hypothetical protein Y40B1B.7 - *Caenorhabditis elegans* [*C.elegans*] |
| 2838 | 1143 | AI070511 | d | Aminoacyl-tRNA biosynthesis, Valine, leucine and isoleucine biosynthesis | HHs:valyl-tRNA synthetase 2 | ESTs, Highly similar to G7A [*M.musculus*] |
| 21328 | 171 | AA850130 | j | | | ESTs, Weakly similar to NB8M_HUMAN NADH-UBIQUINONE OXIDOREDUCTASE B18 SUBUNIT |
| 24433 | 2147 | M16407 | General | | Cholinergic receptor, muscarinic 3 | Cholinergic receptor, muscarinic 3 |
| 17553 | 1253 | AI103643 | General | | | ESTs |
| 22011 | 1498 | AI176212 | General | | | ESTs, Weakly similar to T25165 hypothetical protein T23D8.3 - *Caenorhabditis elegans* [*C.elegans*] |
| 18571 | 1868 | AI236612 | j | | | ESTs, Weakly similar to T08433 helicase homolog hlc - fruit fly [*D.melanogaster*] |
| 2140 | 1456 | AI172272 | General,z | | | ESTs, Moderately similar to A53004 transcription elongation factor S-II - rat [*R.norvegicus*] |
| 16680 | 696 | AA965190 | n,y | | | ESTs |
| 17175 | 2457 | X58389 | h,w | | | *R.norvegicus* ASI mRNA for mammalian equivalent of bacterial large ribosomal subunit protein L22 |
| 18795 | 2386 | U95001 | b | | | *Rattus norvegicus* diphosphoinositol polyphosphate phosphohydrolase type II (Nudt4) mRNA, complete cds |
| 2702 | 647 | AA957307 | General | Aminoacyl-tRNA biosynthesis, Glycine, serine and threonine metabolism | HHs:seryl-tRNA synthetase | ESTs, Moderately similar to SYS_HUMAN SERYL-TRNA SYNTHETASE [*H.sapiens*] |
| 875 | 2353 | U60416 | bb | | Myosin of the dilute-myosin-V family | Myosin of the dilute-myosin-V family |
| 18495 | 1899 | AI639042 | v | | | ESTs |
| 15042 | 1606 | AI179422 | c | | | ESTs |

TABLE 1-continued

| GLGC ID | SeqID | GenBank Acc | Model Code | Pathway Name | Known Gene Name | Unigene Cluster Title | Document Number 1740956 |
|---|---|---|---|---|---|---|---|
| 12614 | 1474 | AI175294 | j | | | ESTs, Weakly similar to GROWTH FACTOR RECEPTOR-BOUND PROTEIN 2 [*R.norvegicus*] | |
| 13095 | 1468 | AI172595 | n | | | ESTs | |
| 13203 | 1651 | AI228728 | r | | | ESTs | |
| 3411 | 746 | AA998638 | General | | | ESTs | |
| 17158 | 2390 | V01227 | i | | alpha-tubulin | alpha-tubulin | |
| 25108 | 137 | AA848268 | j | | | | |
| 4355 | 1248 | AI103410 | t | | | ESTs | |

TABLE 2

U.S. Document No. 17,409,56.1

| Model Code | Compound |
|---|---|
| a | Acyclovir |
| b | Acyclovir |
| c | ANIT |
| d | Acetaminophen |
| e | Acetaminophen |
| f | AY-25329 |
| g | AY-25329 |
| h | Bicalutamide |
| i | Carbon Tetrachloride |
| j | Carbon Tetrachloride |
| k | Clofibrate |
| l | Cyproterone Acetate |
| m | Diclofenac |
| n | Diclofenac |
| o | Diflunisal |
| p | Dioxin |
| q | Dioxin |
| r | Estradiol |
| General | General |
| t | Hydrazine |
| u | Indomethacin |
| v | Indomethacin |
| w | Lipopolysaccharide |
| x | Phenobarbital |
| y | Tacrine |
| z | Valproate |
| aa | Valproate |
| bb | WY-14643 |
| cc | Zileuton |
| dd | Zileuton |

TABLE 3A

ACYCLOVIR
Timepoints (hrs): 24, 168

| GLGC ID | GenBank Acc | Group Mean | Group SD | Non-Group Mean | Non-Group SD | Discriminant Score |
|---|---|---|---|---|---|---|
| 1069 | X15096 | 2345 | 251 | 1100 | 520 | 95 |
| 8983 | L10652 | 376 | 46 | 236 | 52 | 96 |
| 3393 | AA998209 | 178 | 25 | 86 | 101 | 94 |
| 9423 | S61868 | 1189 | 205 | 599 | 225 | 95 |
| 23578 | AA955042 | 366 | 56 | 227 | 67 | 94 |
| 18705 | M30691 | 163 | 25 | 104 | 26 | 95 |
| 25078 | U33540 | 502 | 83 | 302 | 86 | 94 |
| 26330 | AI235911 | 206 | 34 | 47 | 93 | 94 |
| 5573 | AI059063 | 11708 | 1461 | 4834 | 1824 | 98 |
| 16538 | AA799449 | 10 | 8 | 51 | 23 | 94 |
| 8864 | AI070319 | 239 | 42 | 52 | 74 | 97 |
| 563 | Z50051 | 2358 | 334 | 953 | 443 | 97 |
| 23260 | AI169617 | -50 | 11 | 25 | 42 | 97 |
| 21013 | J02810 | 2169 | 464 | 1859 | 1482 | 96 |
| 18356 | R47042 | 115 | 20 | 56 | 25 | 96 |
| 3918 | AA801333 | 27 | 11 | 1 | 14 | 95 |
| 9214 | AA925116 | 410 | 64 | 232 | 86 | 94 |
| 7782 | AI234515 | 383 | 79 | 162 | 49 | 98 |
| 19392 | X02918 | 2263 | 176 | 1035 | 520 | 96 |
| 4017 | AA818287 | 28 | 5 | 75 | 33 | 93 |
| 21657 | X61381 | 1279 | 511 | 546 | 196 | 97 |
| 3882 | AI010191 | 1119 | 115 | 659 | 194 | 96 |
| 18417 | AI230166 | -165 | 84 | 90 | 129 | 94 |
| 24091 | AA957612 | 118 | 16 | 47 | 26 | 96 |
| 20716 | M94548 | 1538 | 187 | 1183 | 663 | 94 |
| 25091 | X65190 | 149 | 22 | 88 | 29 | 94 |
| 22187 | AA943229 | 1896 | 340 | 859 | 391 | 96 |
| 15711 | AF077354 | 0 | 8 | 44 | 26 | 95 |
| 9422 | AI072888 | 113 | 22 | 54 | 17 | 97 |
| 9591 | AI178769 | -64 | 44 | 79 | 87 | 93 |
| 21204 | AF095927 | 26 | 6 | 74 | 30 | 95 |
| 23709 | AI112173 | 279 | 72 | 158 | 144 | 94 |

TABLE 3A-continued

ACYCLOVIR
Timepoints (hrs): 24, 168

| GLGC ID | GenBank Acc | Group Mean | Group SD | Non-Group Mean | Non-Group SD | Discriminant Score |
|---|---|---|---|---|---|---|
| 16458 | AA944956 | 1411 | 180 | 843 | 237 | 94 |
| 20236 | AF091570 | 224 | 32 | 143 | 37 | 94 |
| 6532 | AI234105 | 195 | 16 | 137 | 41 | 94 |
| 12092 | AA848618 | 116 | 19 | 49 | 30 | 95 |
| 7684 | AI030242 | 643 | 110 | 338 | 142 | 93 |
| 2047 | AA963366 | 247 | 18 | 151 | 71 | 93 |
| 671 | U04808 | 5 | 4 | 26 | 19 | 93 |
| 9162 | AI072392 | 353 | 68 | 183 | 61 | 95 |
| 22978 | AA859931 | 58 | 12 | 123 | 37 | 95 |
| 11066 | AI071602 | 452 | 68 | 286 | 79 | 94 |
| 1854 | K02814 | 5990 | 1068 | 1322 | 953 | 99 |
| 24825 | X02741 | 1477 | 213 | 630 | 288 | 96 |
| 25679 | X15013 | 1272 | 80 | 636 | 245 | 98 |
| 18770 | AI233362 | 469 | 17 | 375 | 91 | 94 |
| 19560 | AI030921 | 617 | 63 | 300 | 102 | 98 |
| 11097 | AI071749 | 193 | 24 | 107 | 42 | 95 |
| 15965 | AA866404 | -16 | 14 | 31 | 25 | 94 |
| 24437 | M22357 | 133 | 10 | 70 | 23 | 99 |
| 23933 | AI236376 | 190 | 21 | 128 | 39 | 93 |
| 15419 | AI010476 | 822 | 97 | 529 | 163 | 93 |
| 6873 | AI010055 | 36 | 51 | 37 | 24 | 94 |
| 8232 | AI059122 | 71 | 22 | 23 | 20 | 94 |
| 20971 | AA799576 | 37 | 6 | 71 | 21 | 93 |
| 21010 | AA925306 | 928 | 81 | 624 | 288 | 94 |
| 23637 | AA955587 | -151 | 67 | 41 | 81 | 94 |
| 23826 | U38180 | 205 | 26 | 140 | 27 | 95 |
| 9349 | AI012143 | 227 | 39 | 426 | 126 | 93 |
| 1850 | K02814 | 7440 | 1201 | 1601 | 1106 | 99 |
| 4592 | J02646 | 97 | 6 | 149 | 39 | 94 |
| 16304 | AB008424 | 1395 | 143 | 1074 | 555 | 94 |
| 9469 | AI073023 | 109 | 26 | 39 | 38 | 96 |
| 15141 | D90265 | 83 | 5 | 141 | 39 | 96 |
| 575 | X15734 | 1410 | 308 | 666 | 275 | 95 |
| 11467 | AA901069 | 277 | 30 | 131 | 53 | 97 |
| 24654 | AA819333 | 128 | 24 | 54 | 25 | 96 |
| 1371 | U27319 | 170 | 36 | 47 | 43 | 97 |
| 1818 | Y11283 | 4293 | 562 | 1501 | 1043 | 96 |
| 10190 | AI059342 | 64 | 21 | 0 | 22 | 97 |
| 9795 | AI071989 | 83 | 8 | 32 | 26 | 96 |
| 12577 | AI111344 | 1084 | 451 | 152 | 142 | 98 |
| 228 | U20194 | 665 | 75 | 398 | 111 | 94 |
| 21822 | AI228642 | 221 | 22 | 344 | 91 | 94 |
| 24801 | M35270 | 568 | 78 | 368 | 126 | 95 |
| 3431 | AI176595 | 1349 | 106 | 739 | 288 | 95 |
| 16420 | AA800191 | 652 | 65 | 436 | 106 | 93 |
| 23775 | AA956483 | 269 | 44 | 118 | 48 | 96 |
| 21015 | X04229 | 2415 | 285 | 2058 | 1470 | 98 |
| 6329 | AI059259 | 6595 | 350 | 4869 | 2920 | 94 |
| 16610 | D28557 | 38 | 13 | 141 | 57 | 96 |
| 19617 | AI043664 | 123 | 17 | 57 | 32 | 96 |
| 13575 | AA892557 | 47 | 13 | 119 | 43 | 93 |

TABLE 3B

ACYCLOVIR
Timepoints (hrs): 6

| GLGC ID | GenBank Acc | Group Mean | Group SD | Non-Group Mean | Non-Group SD | Discriminant Score |
|---|---|---|---|---|---|---|
| 2515 | D17512 | 1144 | 3 | 483 | 168 | 100 |
| 20233 | X59290 | 27 | 0 | -32 | 27 | 100 |
| 5616 | L00191 | 2570 | 93 | 898 | 431 | 100 |
| 13332 | AA893080 | 55 | 3 | 210 | 70 | 100 |
| 3292 | D00753 | 9836 | 699 | 1665 | 1260 | 100 |
| 14425 | AI177755 | 4152 | 152 | 427 | 370 | 100 |
| 20698 | X86561 | 3759 | 477 | 659 | 319 | 100 |
| 15190 | AI102562 | 8433 | 274 | 1311 | 1491 | 100 |

TABLE 3B-continued

ACYCLOVIR
Timepoints (hrs): 6

| GLGC ID | GenBank Acc | Group Mean | Group SD | Non-Group Mean | Non-Group SD | Discriminant Score |
|---|---|---|---|---|---|---|
| 2010 | U05675 | 8061 | 658 | 1897 | 1486 | 100 |
| 4199 | M83143 | 1568 | 104 | 660 | 228 | 100 |
| 20701 | AA875097 | 2765 | 300 | 633 | 258 | 100 |
| 19011 | AI102618 | 636 | 16 | 276 | 83 | 100 |
| 4066 | AI013782 | 703 | 15 | 292 | 117 | 100 |
| 21975 | AI172247 | 557 | 37 | 235 | 60 | 100 |
| 11504 | AI171652 | 292 | 6 | 719 | 237 | 100 |
| 19057 | AI235094 | 167 | 9 | 41 | 347 | 100 |
| 1850 | K02814 | 8072 | 747 | 1620 | 1152 | 100 |
| 5110 | AA925274 | 654 | 12 | 282 | 100 | 100 |
| 23424 | AI180068 | 2447 | 191 | 1204 | 244 | 100 |
| 11904 | D85183 | 262 | 24 | 69 | 48 | 100 |
| 22866 | AI233754 | 723 | 41 | 322 | 91 | 100 |
| 6957 | AI010707 | 84 | 0 | 45 | 33 | 99 |
| 412 | V01216 | 3290 | 187 | 1079 | 706 | 99 |
| 21353 | AA850247 | 591 | 16 | 1380 | 349 | 99 |
| 1854 | K02814 | 7031 | 854 | 1336 | 979 | 99 |
| 7047 | AI171172 | −161 | 45 | 38 | 108 | 99 |
| 14676 | AI234615 | 189 | 6 | 85 | 32 | 99 |
| 6352 | AA997600 | 232 | 62 | −14 | 27 | 99 |
| 6171 | AA819633 | −26 | 8 | 192 | 128 | 99 |
| 4892 | AI044292 | 517 | 66 | 115 | 252 | 99 |
| 17340 | AI007803 | 4083 | 378 | 1076 | 424 | 99 |
| 14459 | AI137930 | 12046 | 1339 | 4349 | 2071 | 99 |
| 12845 | AI170497 | −33 | 7 | 60 | 38 | 99 |
| 26133 | AI009950 | 1021 | 158 | 163 | 124 | 99 |
| 402 | AA945143 | 2684 | 204 | 861 | 434 | 99 |
| 9795 | AI071989 | 124 | 10 | 32 | 26 | 99 |
| 18795 | U95001 | 1052 | 44 | 415 | 135 | 99 |
| 19411 | AA893667 | 121 | 6 | 43 | 24 | 99 |
| 25317 | J00735 | 3169 | 371 | 1022 | 561 | 99 |
| 5622 | X05834 | 2804 | 276 | 1100 | 486 | 99 |
| 4833 | AI009178 | 79 | 8 | 19 | 21 | 99 |
| 14324 | AA850402 | 190 | 43 | 19 | 22 | 99 |
| 7053 | AI011467 | −131 | 57 | 74 | 36 | 99 |
| 15961 | AI012130 | 181 | 12 | 42 | 38 | 99 |
| 15703 | AB009372 | 258 | 16 | 132 | 40 | 99 |
| 8522 | AI060071 | 439 | 28 | 130 | 72 | 99 |
| 1114 | AI029917 | 1557 | 211 | 514 | 182 | 99 |
| 1561 | Z50052 | 1597 | 176 | 652 | 242 | 99 |
| 24211 | AI111853 | 123 | 5 | 296 | 111 | 99 |
| 16561 | AI137862 | 376 | 28 | 206 | 46 | 99 |
| 22513 | M23566 | 2025 | 1016 | −62 | 601 | 99 |
| 10988 | AA819640 | 103 | 8 | 23 | 42 | 99 |
| 23387 | AA945952 | 207 | 30 | 30 | 37 | 99 |
| 21933 | AI029057 | 10857 | 531 | 5094 | 1865 | 99 |
| 1818 | Y11283 | 4538 | 294 | 1510 | 1053 | 99 |
| 12734 | AI011208 | 194 | 15 | 83 | 33 | 99 |
| 22018 | AI008309 | 462 | 83 | 144 | 63 | 99 |
| 3589 | AA998590 | 140 | 27 | 24 | 23 | 99 |
| 169 | AI045171 | 238 | 33 | 70 | 31 | 99 |
| 4998 | AA924683 | 49 | 11 | −10 | 18 | 99 |
| 19769 | AI102570 | 1925 | 204 | 764 | 265 | 99 |
| 21980 | AA893454 | 1043 | 153 | 403 | 111 | 99 |
| 6057 | AI172102 | 473 | 102 | 101 | 82 | 99 |
| 15191 | AI176456 | 7523 | 1193 | 835 | 957 | 99 |
| 21740 | AI176810 | 2273 | 287 | 734 | 283 | 99 |
| 26368 | H34047 | 116 | 1 | 152 | 87 | 99 |
| 5579 | AI176863 | 389 | 65 | 131 | 41 | 99 |
| 20524 | AI045201 | 224 | 59 | 17 | 35 | 99 |
| 15189 | M11794 | 9904 | 1521 | 1143 | 1306 | 99 |
| 20088 | AA892666 | 87 | 4 | 163 | 35 | 99 |
| 24012 | AA957335 | 1633 | 214 | 373 | 315 | 99 |
| 24200 | AI012356 | 1653 | 218 | 380 | 222 | 99 |
| 8053 | AI175033 | 128 | 1 | 166 | 95 | 99 |
| 11424 | AI010936 | 247 | 20 | 98 | 62 | 99 |
| 4198 | M83143 | 1635 | 122 | 772 | 252 | 99 |
| 21917 | AA891220 | 479 | 139 | 78 | 47 | 99 |
| 25052 | L22190 | 192 | 54 | 28 | 117 | 99 |
| 1809 | AA946503 | 311 | 125 | 63 | 434 | 99 |
| 17844 | AA955927 | 440 | 31 | 152 | 76 | 99 |
| 640 | S82229 | 73 | 4 | −11 | 40 | 99 |
| 2310 | AI029969 | 731 | 232 | 78 | 86 | 99 |
| 3773 | AA998356 | 344 | 43 | 57 | 46 | 99 |
| 23368 | AA800678 | 20 | 3 | 85 | 37 | 99 |
| 3095 | AA997077 | −49 | 14 | 119 | 57 | 99 |
| 7122 | AI137468 | 1044 | 130 | 416 | 118 | 99 |
| 13932 | AI230988 | −202 | 36 | 69 | 53 | 99 |
| 5675 | AI045026 | 220 | 7 | 111 | 44 | 99 |
| 2532 | AI176590 | −71 | 20 | 112 | 83 | 99 |
| 6544 | AI102064 | −139 | 12 | 61 | 112 | 99 |

TABLE 3C

ANIT
Timepoints (hrs): 24, 48

| GLGC ID | GenBank Acc | Group Mean | Group SD | Non-Group Mean | Non-Group SD | Discriminant Score |
|---|---|---|---|---|---|---|
| 25743 | X80130 | 145 | 20 | 72 | 28 | 96 |
| 7918 | AI179750 | 150 | 46 | 59 | 28 | 96 |
| 20299 | D14564 | 249 | 38 | 572 | 222 | 96 |
| 25137 | AB005540 | 50 | 9 | 17 | 13 | 96 |
| 6017 | AF037072 | 78 | 29 | 613 | 452 | 96 |
| 8344 | AI059511 | 1138 | 194 | 468 | 269 | 96 |
| 10886 | S49003 | 357 | 37 | 734 | 301 | 96 |
| 17540 | AA955914 | 1192 | 180 | 588 | 232 | 96 |
| 22667 | AA945069 | 75 | 20 | 6 | 36 | 96 |
| 18902 | AA875390 | 295 | 37 | 185 | 46 | 96 |
| 3254 | D10756 | 336 | 27 | 222 | 56 | 96 |
| 22927 | AA859920 | 94 | 21 | 37 | 22 | 95 |
| 9191 | AI072107 | 204 | 68 | 711 | 277 | 95 |
| 9032 | AI179950 | 907 | 91 | 603 | 146 | 95 |
| 15029 | AI170696 | 619 | 223 | 1648 | 491 | 95 |
| 3665 | AI009376 | 356 | 83 | 172 | 71 | 95 |
| 9866 | AJ005424 | 47 | 12 | −1 | 27 | 94 |
| 13645 | AI232694 | 295 | 83 | 165 | 53 | 94 |
| 18315 | AF072411 | 134 | 35 | 55 | 37 | 94 |
| 2799 | AI013778 | 107 | 26 | 465 | 226 | 94 |
| 15042 | AI179422 | 310 | 137 | 31 | 67 | 94 |
| 1291 | AB000491 | 207 | 32 | 129 | 34 | 94 |
| 22849 | D10754 | 300 | 27 | 202 | 52 | 94 |
| 24582 | X16554 | 77 | 21 | 31 | 20 | 94 |
| 14353 | AA859585 | 89 | 20 | 46 | 22 | 94 |
| 18393 | AI230632 | 183 | 30 | 113 | 34 | 94 |
| 4330 | AA818747 | 827 | 229 | 1634 | 439 | 93 |
| 7697 | AI176942 | 202 | 67 | 469 | 138 | 93 |
| 21471 | AA851343 | 27 | 47 | −59 | 54 | 93 |
| 9754 | AI112194 | 25 | 24 | 222 | 130 | 93 |
| 17049 | AI172417 | 187 | 39 | 339 | 91 | 93 |
| 4242 | AA893325 | 171 | 58 | 427 | 161 | 93 |
| 8490 | AI059962 | 102 | 25 | 248 | 99 | 93 |
| 16883 | AA997345 | 1259 | 184 | 2012 | 506 | 93 |
| 16205 | X06423 | 777 | 53 | 771 | 268 | 93 |
| 24577 | X55153 | 625 | 46 | 667 | 263 | 93 |
| 3265 | AA997784 | 93 | 24 | 196 | 74 | 93 |
| 11422 | AA799812 | 27 | 6 | 11 | 11 | 93 |
| 9583 | AI071185 | 506 | 265 | 50 | 61 | 93 |
| 22929 | AI071578 | 59 | 145 | 1346 | 799 | 93 |
| 1246 | M57507 | 40 | 14 | 88 | 27 | 93 |
| 22582 | AA945442 | 184 | 33 | 375 | 134 | 93 |
| 1409 | AI012802 | 203 | 33 | 348 | 91 | 92 |
| 15469 | AJ006340 | 144 | 19 | 89 | 31 | 92 |
| 2505 | M16235 | 315 | 51 | 584 | 206 | 92 |
| 1903 | AI177377 | 60 | 23 | 146 | 51 | 92 |
| 22387 | AI230753 | 535 | 81 | 902 | 244 | 92 |
| 347 | U01914 | 72 | 14 | 33 | 20 | 92 |
| 20123 | AI072214 | 153 | 46 | 313 | 109 | 92 |
| 12551 | AI230056 | 123 | 37 | 239 | 79 | 92 |

TABLE 3C-continued

ANIT
Timepoints (hrs): 24, 48

| GLGC ID | GenBank Acc | Group Mean | Group SD | Non-Group Mean | Non-Group SD | Discriminant Score |
|---|---|---|---|---|---|---|
| 7516 | AI072183 | 58 | 24 | 27 | 118 | 92 |
| 10544 | D63411 | 232 | 26 | 164 | 53 | 92 |
| 14492 | AI030091 | 325 | 52 | 215 | 89 | 92 |
| 20848 | X54617 | 405 | 97 | 222 | 57 | 92 |
| 5936 | AA964214 | 56 | 13 | 18 | 24 | 92 |
| 62 | E06822 | 76 | 11 | 124 | 31 | 92 |
| 9135 | D45247 | 563 | 32 | 558 | 160 | 92 |
| 7403 | AI029212 | 796 | 189 | 1509 | 478 | 92 |
| 8984 | L10652 | 238 | 29 | 166 | 44 | 92 |
| 4486 | AA892298 | 51 | 10 | 21 | 16 | 92 |
| 16984 | AI013161 | 769 | 84 | 465 | 207 | 92 |
| 5046 | AI237855 | 247 | 81 | 77 | 43 | 92 |
| 21683 | M65149 | 77 | 20 | 16 | 27 | 92 |
| 11635 | AA859645 | 175 | 21 | 259 | 62 | 92 |
| 851 | U72497 | 245 | 26 | 370 | 86 | 92 |
| 573 | AI232087 | 344 | 58 | 678 | 284 | 92 |
| 9498 | AI073164 | 79 | 14 | 44 | 19 | 92 |
| 17837 | AA893641 | 78 | 13 | 46 | 18 | 92 |
| 17591 | AI171354 | 252 | 70 | 124 | 46 | 91 |
| 6554 | AF097723 | 309 | 34 | 489 | 143 | 91 |
| 17664 | AI234496 | 706 | 197 | 263 | 149 | 91 |
| 9016 | AI070903 | 1304 | 338 | 2773 | 995 | 91 |
| 20169 | X03347 | 61 | 33 | 9 | 33 | 91 |
| 18239 | AI179942 | 159 | 67 | 31 | 30 | 91 |
| 17524 | AI010568 | 1543 | 351 | 2716 | 734 | 91 |
| 15301 | M60921 | 140 | 30 | 12 | 58 | 91 |
| 10015 | AF083269 | 226 | 43 | 137 | 41 | 91 |
| 4527 | AA892774 | 75 | 15 | 43 | 18 | 91 |
| 3404 | D30740 | 204 | 35 | 125 | 30 | 91 |
| 12933 | AA963682 | 34 | 17 | −4 | 23 | 91 |
| 23521 | AA848407 | 562 | 183 | 169 | 115 | 91 |
| 11416 | AI172185 | 163 | 21 | 110 | 38 | 91 |
| 2161 | AI176592 | 1203 | 479 | 371 | 278 | 91 |
| 2013 | AA892390 | 95 | 27 | 32 | 27 | 91 |
| 12677 | AI007889 | 21 | 11 | −4 | 17 | 91 |
| 4444 | AI100882 | 144 | 74 | 608 | 320 | 91 |
| 650 | X55286 | 153 | 50 | 45 | 36 | 91 |
| 21066 | D10587 | 116 | 13 | 68 | 21 | 91 |
| 22566 | AI177122 | 137 | 54 | 45 | 32 | 91 |
| 12542 | AA997499 | 189 | 43 | 395 | 153 | 91 |
| 16700 | AI008838 | 54 | 22 | 176 | 100 | 91 |
| 1475 | L16764 | 193 | 80 | 53 | 110 | 91 |
| 25480 | S46785 | 227 | 102 | 497 | 178 | 91 |
| 14171 | AI178073 | 139 | 55 | 57 | 30 | 91 |

TABLE 3D

ACETAMINOPHEN
Timepoints (hrs): 24

| GLGC ID | GenBank Acc | Group Mean | Group SD | Non-Group Mean | Non-Group SD | Discriminant Score |
|---|---|---|---|---|---|---|
| 16756 | AA818089 | 464 | 42 | 257 | 113 | 98 |
| 588 | X69834 | 253 | 49 | 727 | 329 | 98 |
| 32 | L27651 | 124 | 25 | 270 | 81 | 98 |
| 10886 | S49003 | 232 | 50 | 736 | 299 | 99 |
| 12365 | AI180013 | 328 | 33 | 613 | 161 | 98 |
| 2150 | D90404 | 289 | 34 | 595 | 187 | 98 |
| 20983 | AI044900 | 273 | 46 | 754 | 332 | 98 |
| 229 | U20194 | 238 | 37 | 548 | 178 | 98 |
| 8898 | AI103957 | 233 | 25 | 612 | 210 | 100 |
| 8899 | AI103957 | 233 | 40 | 667 | 232 | 99 |
| 12312 | AA893453 | 246 | 50 | 732 | 287 | 98 |
| 405 | X70223 | 258 | 48 | 708 | 239 | 99 |
| 17066 | D89070 | 76 | 20 | 15 | 25 | 98 |
| 16311 | AA943735 | 1375 | 532 | 191 | 138 | 99 |
| 16217 | U75928 | 166 | 18 | 376 | 97 | 99 |
| 10503 | D21215 | 243 | 26 | 468 | 110 | 98 |
| 6554 | AF097723 | 209 | 38 | 490 | 142 | 97 |
| 811 | D63704 | 245 | 18 | 534 | 161 | 99 |
| 4242 | AA893325 | 98 | 31 | 428 | 160 | 99 |
| 25204 | AF080507 | 151 | 29 | 423 | 122 | 99 |
| 3062 | AA998857 | 1290 | 298 | 3326 | 938 | 98 |
| 24458 | AB003515 | 289 | 26 | 489 | 109 | 97 |
| 24234 | U63923 | 414 | 119 | 130 | 52 | 99 |
| 18095 | AI177482 | 1807 | 208 | 869 | 191 | 99 |
| 16993 | AA799560 | 264 | 39 | 814 | 375 | 98 |
| 228 | U20194 | 183 | 22 | 401 | 112 | 98 |
| 14509 | AA955871 | 1298 | 285 | 4936 | 2339 | 97 |
| 21078 | J02791 | 283 | 23 | 539 | 148 | 98 |
| 17469 | AA892549 | 146 | 19 | 334 | 77 | 99 |
| 16426 | X70369 | 160 | 18 | 347 | 98 | 98 |
| 6911 | D85035 | 87 | 26 | 220 | 51 | 98 |
| 21052 | M15481 | 68 | 27 | 269 | 90 | 98 |
| 11966 | AA891800 | 130 | 17 | 256 | 58 | 98 |
| 6237 | AA819288 | 188 | 80 | 643 | 205 | 98 |
| 6108 | AA891873 | 197 | 31 | 110 | 31 | 98 |
| 17849 | AA900460 | 2016 | 463 | 970 | 259 | 97 |
| 9254 | AA892470 | 94 | 5 | 175 | 36 | 99 |
| 15465 | AI236280 | 235 | 54 | 682 | 174 | 99 |
| 20705 | E01184 | 170 | 38 | 863 | 1122 | 98 |
| 7872 | M86912 | 115 | 22 | 259 | 55 | 98 |
| 17897 | AA893905 | 141 | 21 | 384 | 132 | 98 |
| 3803 | AI170773 | 1384 | 107 | 868 | 193 | 98 |
| 19254 | AF014009 | 335 | 65 | 148 | 39 | 99 |
| 3256 | AI169479 | 2232 | 469 | 1017 | 240 | 99 |
| 6945 | AI229467 | 47 | 15 | 146 | 34 | 99 |
| 16883 | AA997345 | 704 | 181 | 2017 | 495 | 99 |
| 812 | D63704 | 182 | 16 | 375 | 113 | 98 |
| 13684 | AA818770 | 1109 | 202 | 527 | 143 | 98 |
| 16427 | M21354 | 88 | 9 | 209 | 56 | 98 |
| 20601 | X52625 | 147 | 27 | 725 | 394 | 98 |
| 9842 | U94856 | 449 | 35 | 1176 | 635 | 98 |
| 6132 | AA819055 | 216 | 58 | 547 | 125 | 98 |
| 6107 | D13122 | 224 | 46 | 94 | 38 | 98 |
| 9212 | AI071098 | 1855 | 430 | 822 | 234 | 98 |
| 8283 | AI059290 | 372 | 141 | 99 | 50 | 98 |
| 6016 | AA818163 | 598 | 185 | 2266 | 777 | 98 |
| 18036 | U40004 | 69 | 28 | 248 | 72 | 98 |
| 22370 | AA944158 | 63 | 18 | 248 | 110 | 98 |
| 17092 | AA893189 | 200 | 33 | 86 | 33 | 98 |
| 24368 | AI180392 | 360 | 49 | 170 | 71 | 97 |
| 2838 | AI070511 | 154 | 31 | 36 | 41 | 97 |
| 3131 | AA893032 | 122 | 12 | 371 | 131 | 98 |
| 1478 | U32314 | 165 | 23 | 362 | 89 | 98 |
| 7384 | AI029143 | 144 | 74 | 661 | 247 | 98 |
| 22183 | AA943217 | 3965 | 376 | 1948 | 497 | 99 |
| 4383 | AI177056 | 27 | 4 | 82 | 33 | 98 |
| 15542 | AI103095 | 785 | 110 | 397 | 106 | 98 |
| 6824 | AA819709 | 1416 | 370 | 396 | 186 | 98 |
| 15374 | H34186 | 253 | 25 | 136 | 38 | 98 |
| 3822 | AA900863 | 2637 | 354 | 1223 | 359 | 98 |
| 6743 | AI231219 | 526 | 79 | 1119 | 265 | 97 |
| 9032 | AI179950 | 1119 | 161 | 601 | 140 | 98 |
| 19252 | AA892041 | 665 | 95 | 390 | 89 | 97 |
| 7586 | AI030024 | 67 | 17 | 297 | 125 | 98 |
| 12071 | AI009456 | 203 | 48 | 588 | 167 | 97 |
| 6826 | AI009493 | 92 | 34 | 491 | 195 | 98 |
| 16364 | AA892251 | 28 | 17 | 173 | 68 | 98 |
| 28 | D31662 | 154 | 44 | 628 | 259 | 97 |
| 20735 | X89225 | 433 | 85 | 169 | 74 | 98 |
| 10310 | AI176961 | 550 | 73 | 259 | 86 | 97 |
| 23860 | AI237684 | 141 | 23 | 64 | 23 | 98 |
| 17049 | AI172417 | 100 | 41 | 339 | 89 | 98 |
| 18507 | AI175551 | 1459 | 217 | 692 | 197 | 97 |
| 17155 | AI172090 | 377 | 73 | 132 | 58 | 98 |
| 2057 | AI102579 | 777 | 88 | 396 | 124 | 98 |
| 20600 | AI177004 | 64 | 20 | 478 | 262 | 98 |
| 4330 | AA818747 | 381 | 140 | 1638 | 429 | 98 |

TABLE 3D-continued

ACETAMINOPHEN
Timepoints (hrs): 24

| GLGC ID | GenBank Acc | Group Mean | Group SD | Non-Group Mean | Non-Group SD | Discriminant Score |
|---|---|---|---|---|---|---|
| 13294 | AI233731 | 709 | 64 | 345 | 100 | 98 |
| 20123 | AI072214 | 51 | 27 | 314 | 108 | 98 |
| 15543 | AI231800 | 488 | 73 | 212 | 65 | 98 |
| 6614 | AA848389 | 275 | 94 | 974 | 265 | 98 |
| 14083 | AI177181 | 176 | 44 | 579 | 165 | 97 |
| 4590 | AA892778 | −4 | 11 | 64 | 26 | 97 |
| 11404 | AI237002 | 782 | 144 | 210 | 115 | 98 |
| 5460 | AI176944 | 13 | 9 | 103 | 33 | 98 |
| 4730 | AA900326 | 74 | 36 | 1510 | 957 | 98 |
| 22930 | AI071578 | 11 | 12 | 575 | 356 | 98 |
| 3916 | AI169947 | 546 | 126 | 1626 | 405 | 98 |
| 11403 | AI171088 | 824 | 108 | 178 | 176 | 98 |
| 22929 | AI071578 | −33 | 28 | 1348 | 797 | 98 |

TABLE 3E

ACETAMINOPHEN
Timepoints (hrs): 3, 6

| GLGC ID | GenBank Acc | Group Mean | Group SD | Non-Group Mean | Non-Group SD | Discriminant Score |
|---|---|---|---|---|---|---|
| 309 | AA866460 | 318 | 31 | 527 | 135 | 96 |
| 17897 | AA893905 | 163 | 33 | 386 | 131 | 93 |
| 1312 | M31788 | 269 | 27 | 499 | 153 | 95 |
| 28 | D31662 | 230 | 53 | 631 | 259 | 93 |
| 8899 | AI103957 | 323 | 42 | 670 | 232 | 93 |
| 22705 | AA946032 | 8 | 11 | 67 | 34 | 93 |
| 2677 | AA963443 | 18 | 11 | 90 | 43 | 93 |
| 2505 | M16235 | 332 | 31 | 587 | 206 | 92 |
| 10695 | AA819679 | 76 | 32 | 246 | 96 | 95 |
| 25460 | M89945 | 219 | 58 | 853 | 515 | 94 |
| 14191 | AA858924 | 19 | 8 | 66 | 27 | 95 |
| 18867 | D88250 | 303 | 49 | 638 | 242 | 92 |
| 10636 | AI011634 | 82 | 28 | 222 | 87 | 92 |
| 4003 | D10757 | 69 | 21 | 166 | 54 | 94 |
| 11478 | AA926231 | 77 | 25 | 179 | 55 | 92 |
| 135 | D87839 | 123 | 31 | 268 | 80 | 94 |
| 21657 | X61381 | 275 | 48 | 556 | 206 | 94 |
| 20931 | U17697 | 116 | 34 | 357 | 146 | 94 |
| 21742 | AI176172 | 42 | 16 | 157 | 81 | 94 |
| 21916 | AI013627 | 257 | 30 | 445 | 123 | 93 |
| 22635 | AA964289 | 7 | 6 | 36 | 19 | 94 |
| 8898 | AI103957 | 335 | 36 | 613 | 210 | 93 |
| 12331 | AA946466 | 106 | 32 | 295 | 122 | 93 |
| 15926 | AB012933 | 215 | 40 | 475 | 185 | 93 |
| 19408 | X02610 | 453 | 35 | 737 | 232 | 93 |
| 19335 | X05300 | 150 | 22 | 258 | 68 | 93 |
| 2484 | AI104675 | 71 | 37 | 346 | 196 | 93 |
| 1430 | M84648 | −7 | 18 | 99 | 66 | 93 |
| 811 | D63704 | 308 | 42 | 536 | 161 | 93 |
| 2901 | AI043752 | 40 | 12 | 90 | 29 | 93 |
| 25370 | L16995 | 24 | 26 | 149 | 70 | 93 |
| 24170 | AI145601 | 33 | 13 | 114 | 52 | 92 |
| 6365 | AA899163 | 12 | 6 | 54 | 39 | 93 |
| 13670 | AI227734 | 46 | 12 | 107 | 37 | 93 |
| 17533 | D00636 | 121 | 24 | 263 | 94 | 93 |
| 3934 | AI011510 | 921 | 227 | 1914 | 567 | 93 |
| 9633 | AI007768 | 24 | 13 | 95 | 48 | 92 |
| 18978 | AI639208 | 132 | 17 | 223 | 58 | 92 |
| 23261 | AA925145 | 1364 | 279 | 2452 | 721 | 92 |
| 17409 | AI172417 | 195 | 42 | 340 | 90 | 92 |
| 14258 | AI229902 | 33 | 14 | 82 | 34 | 93 |
| 4199 | M83143 | 348 | 63 | 668 | 230 | 93 |
| 16039 | AA799452 | 127 | 23 | 207 | 47 | 93 |
| 7650 | AI230142 | 38 | 17 | 103 | 71 | 92 |
| 4879 | AA923852 | 14 | 22 | 115 | 54 | 92 |
| 1529 | M81687 | 252 | 43 | 458 | 111 | 93 |

TABLE 3E-continued

ACETAMINOPHEN
Timepoints (hrs): 3, 6

| GLGC ID | GenBank Acc | Group Mean | Group SD | Non-Group Mean | Non-Group SD | Discriminant Score |
|---|---|---|---|---|---|---|
| 20146 | M22926 | 95 | 11 | 51 | 24 | 92 |
| 17468 | AA892545 | 247 | 34 | 445 | 107 | 93 |
| 20895 | AI230549 | 50 | 32 | 173 | 64 | 92 |
| 6387 | AI234664 | 49 | 17 | 102 | 25 | 93 |
| 23068 | AA926036 | 161 | 90 | 535 | 192 | 92 |
| 23029 | AA944935 | 27 | 77 | 724 | 448 | 92 |
| 18564 | AA800745 | 182 | 31 | 322 | 74 | 94 |
| 7872 | M86912 | 155 | 27 | 260 | 55 | 94 |
| 23031 | AA963661 | −9 | 8 | 79 | 65 | 95 |
| 25204 | AF080507 | 202 | 28 | 424 | 122 | 97 |
| 23030 | AA924763 | 22 | 40 | 448 | 303 | 92 |
| 1973 | M60103 | 161 | 33 | 335 | 87 | 93 |
| 5597 | AI101622 | 85 | 27 | 173 | 42 | 92 |
| 3537 | AI101690 | 184 | 75 | 461 | 110 | 94 |
| 19069 | AA943737 | 170 | 69 | 715 | 303 | 93 |
| 22351 | AA945867 | 117 | 82 | 20 | 26 | 93 |
| 15154 | AA892532 | 243 | 29 | 488 | 142 | 96 |
| 7225 | AI013657 | 106 | 48 | 317 | 95 | 93 |
| 7069 | AI010301 | 122 | 36 | 278 | 78 | 94 |
| 15599 | X75253 | 260 | 23 | 504 | 152 | 97 |
| 21502 | AI010483 | 82 | 37 | 213 | 66 | 92 |
| 15995 | S74351 | 318 | 121 | 79 | 77 | 93 |
| 23452 | AA925289 | 74 | 33 | 175 | 46 | 92 |
| 3131 | AA893032 | 125 | 30 | 373 | 130 | 96 |
| 12946 | AI228291 | 184 | 36 | 363 | 91 | 93 |
| 24161 | AA858588 | 207 | 23 | 378 | 96 | 92 |
| 14970 | AA891738 | 101 | 25 | 179 | 34 | 92 |
| 16450 | M95591 | 71 | 21 | 226 | 72 | 94 |
| 5952 | AA963102 | 359 | 132 | 79 | 73 | 93 |
| 24321 | AI232340 | 347 | 101 | 854 | 254 | 92 |
| 11021 | AA819767 | 72 | 36 | 267 | 96 | 93 |
| 8387 | AI176365 | 121 | 36 | 292 | 66 | 94 |
| 7582 | AI029996 | 119 | 41 | 483 | 203 | 95 |
| 11726 | AA849518 | 808 | 365 | 110 | 130 | 94 |
| 6135 | AA819065 | 46 | 16 | 168 | 65 | 95 |
| 15996 | S81478 | 322 | 80 | 89 | 81 | 93 |
| 22352 | AI175959 | 367 | 146 | 89 | 81 | 95 |
| 2536 | AI176616 | 126 | 39 | 600 | 338 | 94 |
| 11727 | AA849518 | 1153 | 467 | 145 | 172 | 92 |
| 2911 | AI030835 | 355 | 150 | 1140 | 352 | 94 |
| 15997 | U02553 | 438 | 132 | 102 | 93 | 95 |
| 10184 | H33426 | 21 | 12 | 125 | 48 | 97 |
| 20513 | X05684 | 18 | 10 | 129 | 66 | 94 |
| 5934 | AA817695 | 85 | 35 | 383 | 158 | 95 |
| 25799 | E12625 | 12 | 20 | 196 | 117 | 92 |
| 5141 | AA925393 | 136 | 57 | 795 | 473 | 93 |
| 4360 | H31813 | 60 | 17 | 236 | 99 | 95 |
| 16982 | M58634 | 747 | 131 | 221 | 253 | 95 |
| 21842 | AI172293 | 82 | 26 | 445 | 218 | 93 |
| 8344 | AI059511 | 9 | 22 | 482 | 271 | 96 |
| 15069 | M89945 | 159 | 42 | 690 | 376 | 95 |
| 24249 | AI009273 | 119 | 34 | 1369 | 1280 | 94 |

TABLE 3F

AY 25329
Timepoints (hrs): 24

| GLGC ID | GenBank Acc | Group Mean | Group SD | Non-Group Mean | Non-Group SD | Discriminant Score |
|---|---|---|---|---|---|---|
| 15127 | A56937 | 2229 | 144 | 524 | 247 | 100 |
| 5493 | S56936 | 334 | 20 | 61 | 64 | 100 |
| 5492 | D38061 | 334 | 36 | 38 | 64 | 100 |
| 15126 | D83796 | 3088 | 202 | 886 | 463 | 99 |
| 6143 | AI105167 | 1557 | 120 | 872 | 532 | 99 |
| 18989 | K00136 | 3688 | 219 | 1071 | 818 | 99 |
| 9134 | D45247 | 548 | 6 | 378 | 85 | 99 |

TABLE 3F-continued

AY 25329
Timepoints (hrs): 24

| GLGC ID | GenBank Acc | Group Mean | Group SD | Non-Group Mean | Non-Group SD | Discriminant Score |
|---|---|---|---|---|---|---|
| 1876 | AI030175 | 1170 | 65 | 582 | 186 | 99 |
| 1354 | D38065 | 904 | 94 | 218 | 129 | 99 |
| 1795 | L24207 | 1864 | 163 | 427 | 332 | 99 |
| 15124 | J02612 | 3500 | 356 | 993 | 548 | 99 |
| 20705 | E01184 | 6054 | 567 | 838 | 1077 | 99 |
| 20703 | K03241 | 2972 | 408 | 395 | 536 | 99 |
| 1462 | AI235585 | 282 | 17 | 170 | 47 | 99 |
| 20707 | U88036 | 1649 | 165 | 474 | 224 | 99 |
| 1793 | D13912 | 4009 | 413 | 867 | 622 | 99 |
| 18401 | AI104300 | 1193 | 20 | 807 | 175 | 99 |
| 2424 | AA964617 | 1545 | 110 | 854 | 200 | 99 |
| 24860 | M13506 | 1209 | 232 | 318 | 242 | 99 |
| 1794 | X64401 | 8294 | 1002 | 1520 | 1355 | 99 |
| 22953 | AA946509 | 625 | 121 | 194 | 114 | 99 |
| 1797 | X62086 | 5434 | 614 | 1266 | 1027 | 98 |
| 7246 | AI013331 | 78 | 5 | −44 | 67 | 98 |
| 20704 | M26127 | 5184 | 583 | 1023 | 969 | 98 |
| 3816 | AI233729 | 575 | 20 | 376 | 99 | 98 |
| 25056 | M13234 | 3665 | 860 | 757 | 833 | 98 |
| 12156 | K00996 | 3317 | 1192 | 452 | 965 | 98 |
| 53 | U16253 | 22 | 9 | 81 | 19 | 98 |
| 1796 | L24207 | 1015 | 217 | 218 | 127 | 98 |
| 12155 | J00728 | 3106 | 814 | 542 | 761 | 98 |
| 8872 | AA851050 | 1236 | 271 | 494 | 236 | 98 |
| 6735 | AI172497 | 147 | 3 | 100 | 39 | 98 |
| 12447 | AA956769 | 135 | 6 | 53 | 34 | 98 |
| 21957 | AF087437 | 128 | 1 | 164 | 42 | 98 |
| 12157 | K01721 | 4168 | 1215 | 498 | 1077 | 98 |
| 8661 | AA818604 | 94 | 32 | 13 | 64 | 98 |
| 25928 | AI639236 | 20 | 0 | 39 | 21 | 98 |
| 6236 | AA818627 | 2654 | 311 | 971 | 438 | 98 |
| 7926 | AI043913 | 305 | 95 | 82 | 55 | 98 |
| 2388 | AI011806 | 2353 | 69 | 1625 | 379 | 98 |
| 8864 | AI070319 | 127 | 6 | 53 | 75 | 98 |
| 13330 | AA997716 | 139 | 14 | 50 | 42 | 98 |
| 1792 | AF004218 | 353 | 4 | 267 | 76 | 98 |
| 23321 | AA892821 | 327 | 12 | 219 | 53 | 98 |
| 25069 | S82820 | 726 | 121 | 167 | 149 | 98 |
| 17091 | U73174 | 148 | 27 | 53 | 34 | 98 |
| 18293 | X05341 | 1589 | 35 | 949 | 478 | 98 |
| 25281 | D30804 | 245 | 21 | 149 | 34 | 98 |
| 5824 | AI045555 | 150 | 9 | 70 | 45 | 98 |
| 8283 | AI059290 | 240 | 31 | 100 | 57 | 98 |
| 1347 | AA849038 | 1065 | 13 | 838 | 338 | 98 |
| 15879 | AI228313 | 535 | 74 | 310 | 84 | 97 |
| 15125 | J05132 | 3467 | 402 | 1181 | 765 | 97 |
| 20872 | X51707 | 778 | 9 | 567 | 190 | 97 |
| 16320 | AA859899 | 53 | 4 | 107 | 31 | 97 |
| 17256 | AA891739 | 751 | 37 | 426 | 136 | 97 |
| 16345 | AI013250 | 839 | 33 | 560 | 134 | 97 |
| 16703 | AI179300 | 1660 | 29 | 1207 | 374 | 97 |
| 15623 | AA849769 | 43 | 4 | 82 | 24 | 97 |
| 20842 | AA849722 | 439 | 18 | 302 | 68 | 97 |
| 19501 | AA850601 | 60 | 5 | 0 | 32 | 97 |
| 21040 | AI011734 | 914 | 236 | 97 | 210 | 97 |
| 21039 | J03190 | 680 | 189 | 203 | 125 | 97 |
| 2569 | AA965122 | 1540 | 243 | 875 | 272 | 97 |
| 20153 | K02817 | 557 | 10 | 469 | 139 | 97 |
| 15850 | AI236795 | 1790 | 202 | 857 | 300 | 97 |
| 10152 | AI059110 | 52 | 12 | 13 | 21 | 97 |
| 22884 | AI010755 | 327 | 43 | 168 | 52 | 97 |
| 20864 | AF045464 | 897 | 188 | 344 | 214 | 97 |
| 6071 | AA892675 | 391 | 41 | 228 | 65 | 97 |
| 17292 | M67465 | 878 | 19 | 572 | 226 | 97 |
| 24163 | AI169430 | 488 | 32 | 298 | 90 | 97 |
| 15848 | AI007820 | 2127 | 293 | 929 | 381 | 97 |
| 6072 | AI228630 | 3160 | 286 | 2015 | 464 | 97 |
| 9931 | S83279 | 715 | 37 | 473 | 124 | 97 |
| 8527 | AA996461 | 198 | 9 | 152 | 190 | 97 |
| 22052 | AA899498 | 587 | 22 | 337 | 137 | 97 |
| 21053 | M15481 | 1571 | 197 | 1391 | 955 | 97 |
| 2615 | AI229318 | 119 | 4 | 198 | 59 | 97 |
| 357 | U04835 | 38 | 3 | 80 | 33 | 97 |
| 17092 | AA893189 | 167 | 25 | 86 | 34 | 97 |
| 17117 | AI228042 | 1571 | 154 | 1015 | 208 | 97 |
| 25064 | S45392 | 2030 | 389 | 842 | 315 | 97 |
| 3945 | AI232719 | 44 | 6 | −2 | 25 | 97 |
| 18027 | AF039212 | 105 | 21 | 59 | 37 | 97 |
| 2350 | AA964368 | 955 | 129 | 585 | 129 | 97 |
| 17305 | X59051 | 2631 | 128 | 1670 | 1263 | 97 |
| 17999 | U19485 | 1613 | 27 | 1099 | 525 | 97 |
| 17154 | M15883 | 293 | 23 | 175 | 49 | 97 |
| 21038 | J03190 | 755 | 242 | 245 | 132 | 97 |
| 18368 | AA799645 | 496 | 10 | 360 | 92 | 97 |
| 3645 | AI235362 | 261 | 14 | 172 | 41 | 97 |
| 16272 | X76456 | 1646 | 137 | 1307 | 732 | 97 |
| 1853 | X12367 | 3639 | 291 | 2196 | 1985 | 97 |
| 10200 | AI059444 | 74 | 22 | 21 | 19 | 97 |
| 22883 | AA924028 | 125 | 15 | 62 | 28 | 97 |

TABLE 3G

AY-25329   Document Number 1740956.1

Timepoints (hrs): 6

| GLGC ID | GenBank Acc | Group Mean | Group SD | Non-Group Mean | Non-Group SD | Discriminant Score |
|---|---|---|---|---|---|---|
| 1920 | M10068 | 1515 | 112 | 349 | 166 | 100 |
| 6071 | AA892675 | 531 | 43 | 227 | 62 | 100 |
| 9128 | AI171611 | 354 | 42 | 103 | 36 | 100 |
| 20705 | E01184 | 3201 | 243 | 846 | 1110 | 100 |
| 20703 | K03241 | 1366 | 204 | 399 | 554 | 99 |
| 14737 | AI008416 | 3685 | 157 | 1922 | 515 | 99 |
| 9423 | S61868 | 1314 | 45 | 600 | 225 | 99 |
| 489 | E00778 | 888 | 258 | 46 | 402 | 99 |
| 14738 | AI176993 | 2449 | 139 | 1343 | 320 | 99 |
| 575 | X15734 | 1703 | 109 | 666 | 273 | 99 |
| 20704 | M26127 | 3555 | 254 | 1027 | 987 | 99 |
| 488 | E00717 | 2924 | 441 | 180 | 850 | 99 |
| 15644 | AI010256 | 1914 | 51 | 1266 | 340 | 99 |
| 7281 | AI013755 | 442 | 31 | 204 | 65 | 99 |
| 1921 | E01524 | 762 | 85 | 188 | 106 | 99 |
| 23033 | AA859938 | 628 | 74 | 294 | 66 | 99 |
| 1919 | AI137856 | 698 | 65 | 205 | 102 | 99 |
| 3302 | AA997905 | 430 | 30 | 229 | 81 | 99 |
| 16510 | AI137583 | 72 | 15 | 218 | 72 | 99 |
| 6072 | AI228630 | 3707 | 408 | 2011 | 455 | 99 |
| 20735 | X89225 | 265 | 8 | 171 | 78 | 99 |
| 1794 | X64401 | 6518 | 730 | 1522 | 1375 | 99 |
| 64 | M60655 | 58 | 4 | 134 | 36 | 99 |
| 15126 | D83796 | 2209 | 97 | 888 | 473 | 99 |
| 23448 | AA925167 | 4428 | 562 | 976 | 822 | 99 |
| 15127 | S56937 | 1369 | 119 | 526 | 262 | 99 |
| 8438 | AA892986 | 20 | 6 | 102 | 40 | 99 |
| 23449 | AI176828 | 4318 | 803 | 834 | 691 | 99 |
| 1795 | L24207 | 1240 | 163 | 428 | 338 | 98 |
| 1793 | D13912 | 2717 | 270 | 870 | 639 | 98 |
| 1321 | L37333 | 2755 | 229 | 692 | 542 | 98 |
| 18727 | D13978 | 1448 | 123 | 560 | 243 | 98 |
| 8384 | M32167 | 15 | 1 | 48 | 21 | 98 |
| 356 | S66024 | 273 | 16 | 142 | 56 | 98 |
| 4234 | AB016536 | 956 | 63 | 454 | 172 | 98 |
| 1125 | D82071 | 8 | 3 | 46 | 20 | 98 |
| 12157 | K01721 | 3317 | 1174 | 499 | 1083 | 98 |
| 22534 | AA925045 | 840 | 23 | 549 | 154 | 98 |
| 15190 | AI102562 | 5334 | 244 | 1313 | 1514 | 98 |
| 12155 | J00728 | 2255 | 580 | 543 | 768 | 98 |
| 15189 | M11794 | 4996 | 266 | 1149 | 1361 | 98 |

TABLE 3G-continued

AY-25329　　　　　　　　　　Document Number 1740956.1

Timepoints (hrs): 6

| GLGC ID | GenBank Acc | Group Mean | Group SD | Non-Group Mean | Non-Group SD | Discriminant Score |
|---|---|---|---|---|---|---|
| 20914 | M23995 | 744 | 261 | 218 | 322 | 98 |
| 19938 | AA955980 | 293 | 22 | 169 | 64 | 98 |
| 15125 | J05132 | 3096 | 169 | 1181 | 767 | 98 |
| 22993 | AI007872 | 256 | 9 | 159 | 43 | 98 |
| 20984 | D90109 | 950 | 59 | 881 | 397 | 98 |
| 2424 | AA964617 | 1417 | 87 | 854 | 200 | 98 |
| 15191 | AI176456 | 3613 | 253 | 840 | 1002 | 98 |
| 2354 | AA997763 | 1555 | 147 | 753 | 302 | 98 |
| 5990 | AA956907 | 528 | 23 | 334 | 94 | 98 |
| 15124 | J02612 | 2553 | 199 | 995 | 559 | 98 |
| 24163 | AI169430 | 497 | 28 | 297 | 90 | 98 |
| 20088 | AA892666 | 104 | 3 | 163 | 35 | 98 |
| 21601 | AA943997 | 217 | 24 | 108 | 54 | 98 |
| 9424 | S61868 | 1644 | 131 | 724 | 316 | 98 |
| 21816 | AI231217 | 1775 | 47 | 1260 | 275 | 98 |
| 5684 | AI045056 | 968 | 82 | 527 | 140 | 98 |
| 22586 | AA945454 | 127 | 110 | 4139 | 3514 | 97 |
| 19367 | AI058745 | −11 | 41 | 1391 | 1147 | 97 |
| 15879 | AI228313 | 504 | 54 | 310 | 84 | 97 |
| 20778 | D85844 | 41 | 4 | 84 | 23 | 97 |
| 24219 | L27843 | 661 | 108 | 301 | 108 | 97 |
| 17506 | AI070068 | 112 | 36 | 25 | 64 | 97 |
| 20789 | X12355 | 778 | 23 | 503 | 149 | 97 |
| 5497 | AF080468 | 1000 | 88 | 490 | 169 | 97 |
| 12000 | AA957319 | 666 | 128 | 267 | 136 | 97 |
| 22952 | AA892831 | 628 | 73 | 352 | 87 | 97 |
| 23243 | AA851803 | 4622 | 853 | 1693 | 773 | 97 |
| 21040 | AI011734 | 748 | 128 | 97 | 211 | 97 |
| 9079 | AI071251 | 206 | 5 | 312 | 106 | 97 |
| 9349 | AI012143 | 730 | 61 | 423 | 125 | 97 |
| 19186 | AA851226 | 265 | 23 | 137 | 50 | 97 |
| 16993 | AA799560 | 933 | 86 | 808 | 378 | 97 |
| 23612 | AI170751 | 574 | 71 | 267 | 138 | 97 |
| 16496 | AA996955 | 2003 | 150 | 1134 | 357 | 97 |
| 1796 | L24207 | 444 | 63 | 220 | 135 | 97 |
| 12060 | AA799890 | 48 | 6 | 97 | 23 | 97 |
| 4314 | AF010597 | 582 | 19 | 375 | 96 | 97 |
| 9514 | AA850978 | 1514 | 191 | 882 | 219 | 97 |
| 23515 | AI179498 | 724 | 81 | 368 | 138 | 97 |
| 956 | L21711 | 485 | 70 | 257 | 86 | 97 |
| 17091 | U73174 | 99 | 8 | 54 | 34 | 97 |
| 22250 | AA943541 | 261 | 16 | 124 | 68 | 97 |
| 5496 | AF080468 | 737 | 73 | 391 | 124 | 97 |
| 5256 | AA926088 | 239 | 43 | 82 | 57 | 97 |
| 23322 | AA892821 | 532 | 9 | 439 | 129 | 97 |
| 19783 | AI179388 | 509 | 8 | 401 | 83 | 97 |
| 13799 | AI175871 | 269 | 23 | 138 | 51 | 97 |
| 2468 | AA964807 | 390 | 21 | 233 | 77 | 97 |
| 5593 | AI230698 | 145 | 10 | 91 | 33 | 97 |
| 9150 | AI009198 | 742 | 43 | 488 | 121 | 97 |
| 2242 | AI012635 | 4821 | 661 | 2337 | 861 | 97 |
| 6236 | AA818627 | 2165 | 282 | 972 | 442 | 97 |
| 11708 | AI171807 | 1694 | 180 | 1010 | 237 | 97 |
| 25777 | Y08355 | 1042 | 119 | 508 | 178 | 97 |
| 4050 | AI008094 | 117 | 9 | 63 | 54 | 97 |
| 22490 | AA899289 | 916 | 47 | 621 | 133 | 97 |
| 19143 | AA946531 | 665 | 66 | 408 | 136 | 97 |
| 23874 | AI103556 | 493 | 89 | 209 | 106 | 97 |
| 17560 | AA963674 | 868 | 35 | 530 | 177 | 96 |

TABLE 3H

BICALUTAMIDE　　　　　　　　Document Number 1740956.1

Timepoints (hrs): 24, 168

| GLGC ID | GenBank Acc | Group Mean | Group SD | Non-Group Mean | Non-Group SD | Discriminant Score |
|---|---|---|---|---|---|---|
| 1794 | X64401 | 7428 | 2544 | 1475 | 1241 | 98 |
| 1793 | D13912 | 3556 | 1203 | 847 | 571 | 98 |
| 18717 | AA945050 | 1561 | 356 | 634 | 307 | 95 |
| 1795 | L24207 | 1878 | 801 | 415 | 294 | 95 |
| 9135 | D45247 | 805 | 34 | 555 | 158 | 94 |
| 3121 | AI008160 | 1224 | 179 | 746 | 242 | 94 |
| 20707 | U88036 | 1302 | 271 | 469 | 217 | 94 |
| 15126 | D83796 | 2079 | 356 | 880 | 464 | 93 |
| 15125 | J05132 | 2887 | 471 | 1170 | 757 | 92 |
| 25216 | AF091563 | 33 | 9 | 63 | 18 | 92 |
| 15879 | AI228313 | 424 | 48 | 310 | 84 | 92 |
| 15124 | J02612 | 2185 | 297 | 988 | 555 | 92 |
| 12299 | AI172017 | 1595 | 119 | 850 | 401 | 92 |
| 10626 | D14988 | 3006 | 592 | 1230 | 813 | 92 |
| 20308 | X56327 | 34 | 7 | 65 | 20 | 92 |
| 9313 | AA799681 | 22 | 9 | 47 | 13 | 91 |
| 25574 | U06752 | 41 | 6 | 66 | 16 | 91 |
| 21623 | V01217 | 1768 | 145 | 1045 | 437 | 91 |
| 1682 | AA943555 | 31 | 7 | 54 | 17 | 91 |
| 18719 | X63410 | 2529 | 425 | 980 | 567 | 91 |
| 17958 | M34176 | 12 | 7 | 60 | 35 | 91 |
| 19287 | AI232379 | 41 | 7 | 74 | 23 | 90 |
| 16762 | AF059530 | 41 | 6 | 69 | 46 | 90 |
| 20704 | M26127 | 1523 | 197 | 1032 | 1003 | 90 |
| 25563 | S81497 | 1870 | 301 | 970 | 372 | 89 |
| 2970 | M14775 | 4173 | 740 | 1672 | 1351 | 89 |
| 18728 | AI170776 | 68 | 10 | 105 | 26 | 89 |
| 17175 | X58389 | 583 | 39 | 467 | 136 | 89 |
| 25754 | X89696 | 26 | 5 | 50 | 18 | 89 |
| 19665 | AF022819 | 23 | 6 | 45 | 15 | 89 |
| 25608 | U53927 | 12 | 3 | 35 | 21 | 89 |
| 145 | AF064541 | 45 | 8 | 83 | 20 | 89 |
| 6985 | AI010862 | 1285 | 268 | 733 | 507 | 89 |
| 17541 | M26125 | 2661 | 404 | 1139 | 746 | 89 |
| 16953 | E01534 | 808 | 67 | 660 | 228 | 89 |
| 20427 | X53378 | 819 | 60 | 577 | 175 | 89 |
| 24693 | J02720 | 1480 | 222 | 919 | 434 | 89 |
| 634 | K01932 | 2197 | 379 | 1107 | 600 | 89 |
| 22582 | AA945442 | 523 | 53 | 372 | 134 | 89 |
| 14252 | AA799457 | 28 | 5 | 52 | 13 | 89 |
| 20716 | M94548 | 2022 | 150 | 1176 | 659 | 89 |
| 21904 | M24239 | 5411 | 848 | 2166 | 1962 | 89 |
| 15471 | AA859869 | 341 | 31 | 270 | 58 | 89 |
| 22927 | AA859920 | 11 | 5 | 38 | 22 | 89 |
| 17427 | AA892314 | 1305 | 92 | 824 | 345 | 89 |
| 3406 | AI045083 | 272 | 57 | 143 | 63 | 89 |
| 5907 | AI104261 | 480 | 34 | 378 | 86 | 88 |
| 534 | M58041 | 2737 | 458 | 1320 | 867 | 88 |
| 18952 | AA924006 | 42 | 19 | 18 | 37 | 88 |
| 4441 | X62146 | 859 | 46 | 627 | 199 | 88 |
| 5175 | AA818951 | 10 | 10 | 50 | 56 | 88 |
| 25525 | S72505 | 1894 | 315 | 979 | 511 | 88 |
| 21015 | X04229 | 4631 | 765 | 2030 | 1445 | 88 |
| 5667 | X58200 | 790 | 47 | 593 | 177 | 88 |
| 7266 | AI112237 | 553 | 83 | 364 | 96 | 88 |
| 7351 | D83036 | 26 | 7 | 48 | 18 | 88 |
| 17921 | AI176422 | 441 | 38 | 346 | 106 | 88 |
| 20984 | D90109 | 1342 | 93 | 876 | 395 | 88 |
| 16922 | S45663 | 1024 | 88 | 640 | 236 | 88 |
| 20523 | AA891842 | 25 | 4 | 56 | 52 | 88 |
| 20810 | X14181 | 1205 | 67 | 818 | 323 | 88 |
| 18627 | AI232284 | 11 | 5 | 32 | 19 | 88 |
| 17105 | M29358 | 895 | 71 | 693 | 231 | 88 |
| 21882 | M83740 | 1234 | 108 | 761 | 301 | 88 |
| 16204 | X06423 | 727 | 47 | 564 | 164 | 88 |
| 21663 | D50436 | 574 | 106 | 374 | 117 | 88 |
| 4434 | AA685221 | 28 | 8 | 52 | 14 | 88 |
| 16947 | X08056 | 1621 | 179 | 837 | 392 | 88 |
| 25479 | S45663 | 1444 | 177 | 854 | 331 | 88 |
| 24646 | M23264 | 5 | 6 | 22 | 12 | 88 |
| 9620 | X53377 | 545 | 50 | 415 | 118 | 88 |

TABLE 3H-continued

BICALUTAMIDE  Document Number 1740956.1

Timepoints (hrs): 24, 168

| GLGC ID | GenBank Acc | Group Mean | Group SD | Non-Group Mean | Non-Group SD | Discriminant Score |
|---|---|---|---|---|---|---|
| 15106 | X57529 | 2334 | 201 | 1277 | 700 | 88 |
| 538 | X94246 | 44 | 8 | 72 | 17 | 88 |
| 10109 | X58465 | 1024 | 51 | 742 | 253 | 88 |
| 21012 | J02592 | 2658 | 672 | 1093 | 663 | 88 |
| 15875 | X62145 | 1321 | 105 | 799 | 364 | 88 |
| 21772 | AI011179 | 40 | 4 | 62 | 21 | 88 |
| 10503 | D21215 | 571 | 37 | 464 | 111 | 88 |
| 25768 | X94769 | 90 | 14 | 131 | 34 | 88 |
| 8212 | AI231807 | 2735 | 304 | 1398 | 914 | 88 |
| 23348 | AA874813 | 51 | 14 | 85 | 23 | 88 |
| 17577 | AA799566 | 40 | 14 | 82 | 25 | 88 |
| 18299 | AA799369 | 79 | 11 | 110 | 22 | 88 |
| 25400 | M14776 | 2864 | 395 | 1289 | 1125 | 88 |
| 8597 | AA818593 | 69 | 19 | 109 | 39 | 88 |
| 20385 | X54793 | 976 | 117 | 667 | 201 | 88 |
| 25675 | X14181 | 702 | 64 | 564 | 198 | 88 |
| 23665 | AA852055 | 31 | 4 | 52 | 13 | 88 |
| 11665 | AI102585 | −83 | 37 | −24 | 22 | 88 |
| 16726 | M86235 | 822 | 93 | 592 | 194 | 88 |
| 635 | X78848 | 2330 | 398 | 1130 | 674 | 88 |
| 358 | U52948 | 1798 | 278 | 1045 | 564 | 87 |

TABLE 3I

Carbon Tetrachloride  Document Number 1240956.1

Timepoints (hrs): 24, 48

| GLGC ID | GenBank Acc | Group Mean | Group SD | Non-Group Mean | Non-Group SD | Discriminant Score |
|---|---|---|---|---|---|---|
| 14424 | AI070421 | 296 | 60 | 65 | 244 | 99 |
| 15787 | AF095576 | 87 | 8 | 29 | 14 | 100 |
| 669 | K03039 | 75 | 8 | 7 | 7 | 100 |
| 20523 | AA891842 | 169 | 18 | 55 | 52 | 99 |
| 15174 | U59809 | 197 | 67 | 18 | 42 | 99 |
| 18712 | AA818894 | 79 | 4 | 23 | 15 | 100 |
| 7893 | AI043761 | 108 | 31 | 1187 | 397 | 100 |
| 8025 | AI058365 | 879 | 66 | 363 | 99 | 100 |
| 4375 | AA893869 | 112 | 23 | 3 | 15 | 100 |
| 515 | X63854 | 140 | 13 | 57 | 20 | 100 |
| 3909 | AI169903 | 227 | 57 | 28 | 19 | 99 |
| 926 | AB003042 | 220 | 81 | 45 | 24 | 99 |
| 8119 | AI179974 | 25 | 6 | −23 | 22 | 100 |
| 23171 | AI230190 | 791 | 46 | 423 | 101 | 99 |
| 17119 | U25746 | 138 | 12 | 51 | 24 | 99 |
| 11376 | AI112863 | 175 | 42 | 28 | 20 | 99 |
| 15213 | AA800908 | 78 | 32 | −1 | 10 | 100 |
| 4226 | AI177752 | 138 | 57 | 12 | 10 | 99 |
| 22023 | AI233822 | 176 | 68 | 17 | 30 | 99 |
| 17130 | M62992 | 243 | 41 | 93 | 29 | 99 |
| 3910 | AA894345 | 106 | 19 | 43 | 14 | 99 |
| 20788 | AI236053 | 123 | 76 | 4 | 8 | 99 |
| 21128 | AA848555 | 140 | 82 | −4 | 24 | 99 |
| 16457 | AA944856 | 401 | 44 | 153 | 40 | 100 |
| 2242 | AI012635 | 318 | 137 | 2359 | 866 | 100 |
| 1045 | AB000280 | 105 | 4 | 57 | 17 | 99 |
| 15832 | S68589 | 241 | 22 | 99 | 32 | 100 |
| 12306 | AA944898 | 146 | 49 | 1084 | 501 | 99 |
| 17158 | V01227 | 325 | 81 | 65 | 35 | 99 |
| 5541 | AI111707 | 363 | 318 | −16 | 14 | 99 |
| 19275 | AI009460 | 1432 | 635 | 291 | 84 | 99 |
| 15075 | AA875269 | 167 | 83 | 17 | 18 | 99 |
| 14199 | AI234133 | 499 | 208 | 119 | 44 | 99 |
| 20709 | AI172064 | 249 | 195 | 10 | 19 | 99 |
| 18002 | AI043655 | 228 | 111 | 2224 | 858 | 100 |
| 16346 | AA799824 | 210 | 23 | 78 | 30 | 100 |

TABLE 3I-continued

Carbon Tetrachloride  Document Number 1240956.1

Timepoints (hrs): 24, 48

| GLGC ID | GenBank Acc | Group Mean | Group SD | Non-Group Mean | Non-Group SD | Discriminant Score |
|---|---|---|---|---|---|---|
| 22903 | AA892250 | 235 | 17 | 117 | 27 | 99 |
| 23889 | AA892520 | 397 | 53 | 172 | 41 | 99 |
| 12581 | AI145235 | 136 | 22 | 37 | 19 | 99 |
| 25581 | U13396 | 44 | 16 | −4 | 7 | 99 |
| 23035 | AA945712 | 79 | 31 | 586 | 202 | 100 |
| 23312 | AA891920 | 87 | 7 | 27 | 15 | 99 |
| 8715 | AI069920 | 283 | 99 | 1535 | 676 | 99 |
| 4491 | AA818798 | 682 | 187 | 143 | 50 | 99 |
| 19456 | AA997841 | 1572 | 1400 | 9 | 20 | 99 |
| 20421 | L19699 | 114 | 21 | 40 | 22 | 99 |
| 2736 | AA894330 | 120 | 33 | 23 | 14 | 99 |
| 16214 | M57276 | 316 | 115 | 42 | 21 | 99 |
| 14656 | AI237820 | 122 | 34 | 29 | 14 | 99 |
| 5780 | AI177869 | 182 | 106 | −58 | 40 | 100 |
| 1061 | AF009329 | 70 | 34 | −3 | 7 | 99 |
| 15920 | AI178938 | 321 | 10 | 184 | 43 | 99 |
| 24598 | M25758 | 320 | 31 | 171 | 30 | 99 |
| 23243 | AA851803 | 231 | 79 | 1714 | 792 | 99 |
| 21696 | AA944324 | 382 | 52 | 164 | 44 | 99 |
| 19191 | AA849525 | 3023 | 519 | 1028 | 306 | 99 |
| 17167 | AI013690 | 5932 | 960 | 2628 | 613 | 99 |
| 3895 | AA894029 | 238 | 76 | 35 | 23 | 99 |
| 20082 | AI639488 | 176 | 51 | 45 | 28 | 99 |
| 4989 | AI175087 | 392 | 250 | 31 | 25 | 99 |
| 6107 | D13122 | 324 | 37 | 94 | 37 | 99 |
| 14421 | AA942751 | 327 | 22 | 144 | 46 | 99 |
| 16701 | AI008838 | 451 | 121 | 2226 | 694 | 99 |
| 16006 | AF062594 | 148 | 26 | 15 | 23 | 99 |
| 16007 | AF062594 | 98 | 15 | 14 | 13 | 99 |
| 4395 | H33149 | 185 | 16 | 87 | 27 | 99 |
| 17502 | M12156 | 325 | 62 | 87 | 40 | 99 |
| 910 | S76511 | 106 | 21 | 19 | 16 | 99 |
| 3831 | Y12635 | 168 | 44 | 41 | 22 | 99 |
| 23678 | AF087037 | 116 | 56 | 18 | 13 | 99 |
| 19319 | AA891937 | 295 | 23 | 122 | 40 | 99 |
| 58 | U09870 | 172 | 18 | 54 | 25 | 99 |
| 16267 | AI103977 | 484 | 75 | 188 | 54 | 100 |
| 15500 | AI229337 | 926 | 97 | 423 | 100 | 99 |
| 5884 | AJ223184 | 80 | 23 | 8 | 11 | 99 |
| 25279 | D30740 | 418 | 73 | 169 | 44 | 99 |
| 1386 | L08505 | 208 | 44 | 85 | 26 | 99 |
| 11893 | AI230951 | 513 | 329 | −2 | 38 | 99 |
| 3690 | AA999006 | 25 | 4 | 229 | 129 | 99 |
| 12694 | AA957906 | 29 | 18 | 261 | 86 | 99 |
| 16012 | X62875 | 134 | 31 | 28 | 18 | 99 |
| 5421 | AI101270 | 827 | 333 | 197 | 68 | 99 |
| 20448 | X17053 | 279 | 161 | 44 | 21 | 99 |
| 23538 | AI102727 | 589 | 495 | 86 | 89 | 99 |
| 14258 | AI229902 | 269 | 27 | 80 | 31 | 99 |
| 4317 | AI071531 | 86 | 20 | 8 | 11 | 99 |
| 23781 | AI639012 | 128 | 32 | 12 | 13 | 99 |
| 7161 | AI233407 | 142 | 18 | 46 | 27 | 99 |
| 5175 | AA818951 | 453 | 151 | 47 | 46 | 99 |
| 14840 | AI237698 | 457 | 145 | 71 | 34 | 99 |
| 21765 | AI233696 | 178 | 28 | 36 | 23 | 99 |
| 23275 | X97443 | 304 | 22 | 146 | 41 | 99 |
| 7414 | AI137586 | 440 | 59 | 174 | 76 | 99 |
| 18387 | AI237731 | 250 | 95 | 25 | 20 | 99 |
| 14929 | AI170353 | 795 | 322 | 112 | 49 | 99 |
| 20651 | U36992 | 150 | 59 | 21 | 28 | 99 |
| 2855 | AI236707 | 1124 | 197 | 418 | 86 | 99 |
| 5733 | M81855 | 315 | 55 | 7 | 35 | 99 |
| 18386 | L03294 | 177 | 40 | 42 | 22 | 99 |
| 18385 | L03294 | 271 | 84 | 28 | 26 | 99 |

TABLE 3J

Carbon Tetrachloride  Document Number 1740956.1

Timepoints (hrs): 3, 6

| GLGC ID | GenBank Acc | Group Mean | Group SD | Non-Group Mean | Non-Group SD | Discriminant Score |
|---|---|---|---|---|---|---|
| 1397 | AA817787 | 111 | 10 | 34 | 62 | 99 |
| 19221 | AI103374 | 96 | 18 | −66 | 29 | 100 |
| 5926 | AI177638 | 131 | 5 | 41 | 18 | 100 |
| 24019 | X77235 | 168 | 13 | 32 | 25 | 100 |
| 22870 | AA926360 | 73 | 22 | 842 | 258 | 100 |
| 23878 | AA799686 | 68 | 12 | 7 | 30 | 99 |
| 21326 | AI230013 | 111 | 11 | 11 | 20 | 100 |
| 2250 | AI012354 | 112 | 53 | 1790 | 682 | 100 |
| 2501 | AI112343 | 437 | 52 | 100 | 36 | 100 |
| 8795 | AI172618 | 184 | 23 | 18 | 17 | 100 |
| 14664 | AI232081 | 436 | 35 | 128 | 46 | 100 |
| 22266 | AA945601 | 199 | 57 | 1644 | 337 | 100 |
| 24179 | AA893091 | 84 | 10 | 16 | 11 | 100 |
| 23157 | AI172489 | 294 | 35 | 75 | 29 | 100 |
| 22283 | AA945172 | 46 | 12 | 438 | 162 | 100 |
| 22612 | AA945624 | 44 | 9 | 309 | 92 | 100 |
| 1923 | AI170754 | 875 | 109 | 248 | 81 | 100 |
| 18777 | AI102788 | 123 | 25 | −32 | 39 | 100 |
| 23595 | AI236834 | 187 | 30 | 35 | 22 | 100 |
| 22958 | AI171374 | 500 | 95 | 76 | 35 | 100 |
| 7268 | AI013541 | 242 | 51 | 774 | 174 | 99 |
| 22039 | U13176 | 130 | 7 | 50 | 21 | 100 |
| 12437 | H33686 | 149 | 12 | 37 | 18 | 100 |
| 22631 | AA849030 | 227 | 35 | 908 | 226 | 100 |
| 21353 | AA850247 | 143 | 66 | 1384 | 340 | 100 |
| 24225 | AA925490 | 67 | 18 | 343 | 88 | 100 |
| 17407 | AI012145 | 385 | 149 | 1979 | 556 | 100 |
| 10533 | AI058430 | 65 | 39 | 457 | 168 | 99 |
| 606 | X71898 | 150 | 66 | −51 | 21 | 100 |
| 23435 | AI229502 | 286 | 80 | 2 | 48 | 99 |
| 14004 | AI233261 | 276 | 47 | 77 | 42 | 99 |
| 25108 | AA848268 | 212 | 111 | 20 | 17 | 99 |
| 8715 | AI069920 | 141 | 63 | 1536 | 675 | 100 |
| 12542 | AA997499 | 56 | 20 | 395 | 152 | 100 |
| 12343 | AI231433 | 200 | 20 | 47 | 23 | 100 |
| 19069 | AA943737 | 58 | 19 | 709 | 306 | 100 |
| 1600 | AA686470 | 554 | 169 | 29 | 87 | 100 |
| 2897 | AA818039 | 204 | 32 | 41 | 21 | 100 |
| 10110 | AI058863 | 23 | 7 | 189 | 80 | 99 |
| 21328 | AA850130 | 127 | 41 | 610 | 167 | 99 |
| 15376 | AA875206 | 374 | 31 | 170 | 45 | 99 |
| 24146 | AI169668 | 375 | 33 | 175 | 56 | 100 |
| 18396 | AA799330 | 223 | 51 | 50 | 25 | 99 |
| 1813 | M19651 | 141 | 72 | −53 | 20 | 100 |
| 16576 | AA799570 | 274 | 128 | 33 | 18 | 99 |
| 3674 | AA945587 | 48 | 24 | 505 | 130 | 100 |
| 16579 | AA957143 | 37 | 7 | 206 | 63 | 100 |
| 3963 | AA923955 | 35 | 12 | 394 | 116 | 100 |
| 18192 | AF000899 | 76 | 9 | 10 | 11 | 100 |
| 3925 | AA851017 | 74 | 31 | 768 | 296 | 100 |
| 1599 | AA686470 | 201 | 52 | 14 | 25 | 100 |
| 17339 | AA849497 | 23 | 18 | 787 | 408 | 100 |
| 4954 | AA924444 | 28 | 7 | 319 | 143 | 100 |
| 17721 | AA945762 | 42 | 12 | 305 | 89 | 100 |
| 24233 | AA964756 | 125 | 42 | 827 | 237 | 100 |
| 22957 | AI104897 | 1485 | 294 | 251 | 113 | 100 |
| 16618 | AI168967 | 182 | 27 | 29 | 22 | 100 |
| 25643 | U77829 | 302 | 33 | 125 | 27 | 100 |
| 13286 | AI030790 | 57 | 20 | 456 | 127 | 99 |
| 10108 | AI007857 | 196 | 24 | 72 | 26 | 100 |
| 8834 | AI145899 | 142 | 29 | 4 | 32 | 99 |
| 5200 | AI178699 | 175 | 54 | 26 | 12 | 99 |
| 3833 | AA851255 | 83 | 24 | 403 | 103 | 100 |
| 8808 | AI070132 | 42 | 8 | 385 | 122 | 100 |
| 18571 | AI236612 | 115 | 10 | −7 | 32 | 100 |
| 11431 | AI236120 | 318 | 48 | 66 | 29 | 100 |
| 13694 | AI230538 | 243 | 17 | 106 | 35 | 100 |
| 3062 | AA998857 | 716 | 180 | 3322 | 937 | 99 |
| 20988 | AA900562 | 243 | 58 | 906 | 210 | 99 |
| 10636 | AI011634 | 21 | 12 | 221 | 87 | 99 |
| 11608 | AA859633 | 92 | 9 | 30 | 16 | 99 |

TABLE 3J-continued

Carbon Tetrachloride  Document Number 1740956.1

Timepoints (hrs): 3, 6

| GLGC ID | GenBank Acc | Group Mean | Group SD | Non-Group Mean | Non-Group SD | Discriminant Score |
|---|---|---|---|---|---|---|
| 18002 | AI043655 | 348 | 112 | 2223 | 859 | 99 |
| 23137 | AI070408 | 1152 | 264 | 239 | 84 | 99 |
| 20708 | AB006461 | 114 | 14 | 43 | 17 | 99 |
| 8850 | AI235059 | 322 | 73 | 67 | 30 | 99 |
| 5780 | AI177869 | 269 | 169 | −58 | 35 | 99 |
| 11549 | AI232174 | 500 | 42 | 200 | 55 | 100 |
| 16492 | AI070315 | 77 | 24 | 930 | 254 | 99 |
| 13911 | AI236262 | 126 | 18 | 29 | 15 | 100 |
| 23802 | AA956535 | 45 | 12 | 252 | 72 | 99 |
| 13796 | AI229056 | 101 | 21 | 12 | 8 | 99 |
| 7161 | AI233407 | 260 | 49 | 46 | 23 | 99 |
| 15427 | AI178951 | 211 | 17 | 79 | 30 | 99 |
| 12792 | AI176883 | 214 | 38 | 39 | 27 | 99 |
| 4900 | AA924024 | 65 | 16 | 383 | 92 | 99 |
| 16267 | AI103977 | 597 | 105 | 187 | 50 | 100 |
| 23678 | AF087037 | 131 | 35 | 18 | 13 | 100 |
| 12999 | AI176276 | 527 | 101 | 138 | 41 | 99 |
| 24388 | AI236772 | 781 | 387 | 135 | 62 | 99 |
| 23538 | AI102727 | 765 | 127 | 85 | 89 | 100 |
| 17580 | AI010145 | 31 | 9 | 201 | 63 | 99 |
| 17514 | AA925554 | 105 | 23 | 486 | 137 | 99 |
| 8759 | AI237646 | 493 | 216 | 5 | 35 | 99 |
| 12614 | AI175294 | 187 | 47 | 36 | 20 | 99 |
| 19031 | AI070532 | 1122 | 714 | 14 | 52 | 99 |
| 13619 | AI179464 | 375 | 131 | 78 | 71 | 99 |
| 9963 | AI045144 | 30 | 17 | 702 | 282 | 99 |
| 17734 | AA998683 | 862 | 224 | 63 | 87 | 99 |

TABLE 3K

CLOFIBRATE  Document Number 1740956.1

Timepoints (hrs): 24, 72

| GLGC ID | GenBank Acc | Group Mean | Group SD | Non-Group Mean | Non-Group SD | Discriminant Score |
|---|---|---|---|---|---|---|
| 21078 | J02791 | 1327 | 78 | 533 | 138 | 100 |
| 16148 | J02752 | 4832 | 272 | 737 | 283 | 100 |
| 17758 | K03249 | 4343 | 266 | 287 | 183 | 100 |
| 20711 | AA924267 | 1749 | 109 | 119 | 122 | 100 |
| 18687 | AI170568 | 4931 | 383 | 467 | 323 | 100 |
| 20713 | M57718 | 4038 | 187 | 519 | 319 | 100 |
| 18686 | D00729 | 4823 | 404 | 502 | 372 | 100 |
| 25070 | S83279 | 1030 | 80 | 401 | 98 | 100 |
| 9929 | AI013834 | 1402 | 96 | 510 | 127 | 100 |
| 20714 | M14972 | 3691 | 389 | 405 | 274 | 100 |
| 22603 | AF044574 | 825 | 96 | 228 | 67 | 100 |
| 23699 | J02749 | 3688 | 615 | 497 | 189 | 100 |
| 18293 | X05341 | 3928 | 315 | 935 | 426 | 100 |
| 20925 | U08976 | 3531 | 358 | 319 | 265 | 100 |
| 22370 | AA944158 | 640 | 35 | 244 | 108 | 100 |
| 23698 | J02749 | 4629 | 847 | 277 | 171 | 100 |
| 20555 | U26033 | 1569 | 202 | 290 | 125 | 100 |
| 16768 | D16478 | 1245 | 139 | 389 | 91 | 100 |
| 20554 | J02844 | 1139 | 262 | 230 | 80 | 100 |
| 14987 | AA858640 | 1229 | 106 | 469 | 132 | 100 |
| 20715 | X07259 | 3851 | 506 | 295 | 236 | 100 |
| 18175 | J03621 | 1053 | 95 | 390 | 87 | 100 |
| 16767 | D16478 | 1355 | 126 | 470 | 113 | 100 |
| 16150 | AA799489 | 2967 | 456 | 496 | 162 | 100 |
| 1857 | AB010428 | 1920 | 490 | 12 | 57 | 99 |
| 18890 | AA899964 | 3058 | 535 | 677 | 266 | 99 |
| 1858 | Y09333 | 2312 | 667 | 14 | 71 | 99 |
| 18891 | AA924598 | 1311 | 273 | 268 | 147 | 99 |
| 20385 | X54793 | 1723 | 212 | 665 | 187 | 99 |
| 16701 | AI008838 | 5434 | 639 | 2199 | 664 | 99 |

TABLE 3K-continued

CLOFIBRATE  Document Number 1740956.1

Timepoints (hrs): 24, 72

| GLGC ID | GenBank Acc | Group Mean | Group SD | Non-Group Mean | Non-Group SD | Discriminant Score |
|---|---|---|---|---|---|---|
| 1728 | D16479 | 783 | 129 | 217 | 67 | 99 |
| 22602 | AF044574 | 509 | 79 | 126 | 64 | 99 |
| 12094 | AA899681 | 13551 | 2053 | 4611 | 1687 | 99 |
| 26109 | AA997009 | 2653 | 537 | 141 | 224 | 99 |
| 16190 | AI104482 | 2284 | 349 | 771 | 205 | 99 |
| 22416 | AA944380 | 755 | 165 | 130 | 103 | 99 |
| 16703 | AI179300 | 2964 | 393 | 1200 | 351 | 99 |
| 9889 | AI044621 | 3585 | 392 | 1705 | 553 | 99 |
| 6613 | AA848758 | 1728 | 232 | 671 | 221 | 99 |
| 4271 | AA925603 | 922 | 197 | 55 | 132 | 99 |
| 4272 | AI231309 | 644 | 137 | 37 | 77 | 99 |
| 18742 | AI105131 | 1761 | 373 | 347 | 162 | 99 |
| 9598 | H33832 | 731 | 295 | 154 | 112 | 99 |
| 862 | U62940 | 429 | 29 | 263 | 43 | 99 |
| 6780 | J05029 | 1479 | 242 | 571 | 141 | 99 |
| 22604 | AA945578 | 3218 | 516 | 980 | 420 | 99 |
| 1977 | J05470 | 1020 | 171 | 298 | 102 | 99 |
| 11228 | AI102871 | 2002 | 325 | 784 | 238 | 99 |
| 21010 | AA925306 | 2684 | 544 | 615 | 244 | 99 |
| 17933 | AA891916 | 388 | 45 | 127 | 55 | 99 |
| 10909 | AI180425 | 3622 | 389 | 1962 | 356 | 99 |
| 15610 | L27075 | −1 | 7 | 64 | 22 | 99 |
| 18958 | D13921 | 1064 | 328 | 274 | 71 | 99 |
| 17554 | D85100 | 3433 | 275 | 1151 | 748 | 99 |
| 9931 | S83279 | 1121 | 160 | 470 | 115 | 99 |
| 18029 | M38759 | 166 | 79 | −8 | 27 | 99 |
| 12158 | L00320 | 828 | 313 | 231 | 631 | 99 |
| 23884 | M73714 | 926 | 122 | 391 | 97 | 99 |
| 15601 | AI169631 | 542 | 78 | 267 | 60 | 99 |
| 17626 | S78556 | 721 | 58 | 396 | 83 | 99 |
| 16546 | AA800120 | 483 | 76 | 177 | 59 | 99 |
| 17549 | AA892776 | 795 | 23 | 489 | 116 | 99 |
| 15409 | D00569 | 1695 | 436 | 451 | 174 | 99 |
| 18957 | D00512 | 1062 | 325 | 308 | 81 | 99 |
| 20915 | AF001898 | 1875 | 547 | 401 | 254 | 99 |
| 9268 | AI072375 | 456 | 154 | 150 | 58 | 99 |
| 2190 | AA964004 | 200 | 17 | 92 | 64 | 99 |
| 5887 | AI179099 | 947 | 183 | 81 | 156 | 99 |
| 26258 | AI177501 | 185 | 28 | 58 | 32 | 99 |
| 15582 | AI232320 | 18065 | 3513 | 5849 | 3062 | 99 |
| 12155 | J00728 | 1711 | 405 | 545 | 773 | 99 |
| 17516 | AI176621 | 523 | 142 | 223 | 47 | 99 |
| 15408 | D00569 | 883 | 232 | 247 | 102 | 99 |
| 2457 | AA964752 | 1008 | 198 | 218 | 152 | 99 |
| 22598 | AI137506 | 497 | 55 | 1055 | 346 | 99 |
| 819 | X02284 | 2566 | 199 | 1829 | 1452 | 99 |
| 14595 | AA892128 | 543 | 156 | 73 | 59 | 99 |
| 17601 | X95577 | 23 | 8 | 109 | 37 | 99 |
| 21354 | AA899721 | 3337 | 700 | 374 | 343 | 99 |
| 8944 | AI070597 | 221 | 30 | 42 | 55 | 98 |
| 16721 | D30647 | 539 | 118 | 234 | 45 | 98 |
| 15175 | AA945583 | 355 | 25 | 211 | 44 | 98 |
| 3903 | AA899986 | 77 | 52 | −97 | 58 | 98 |
| 15391 | AI010083 | 1404 | 60 | 721 | 259 | 98 |
| 21341 | AA850195 | 1938 | 242 | 814 | 287 | 98 |
| 15124 | J02612 | 2386 | 98 | 994 | 560 | 98 |
| 1818 | Y11283 | 1723 | 179 | 1517 | 1066 | 98 |
| 15126 | D83796 | 2472 | 193 | 885 | 467 | 98 |
| 21355 | AI105094 | 2421 | 619 | 295 | 266 | 98 |
| 15085 | AI233829 | 3860 | 896 | 1497 | 399 | 98 |
| 9842 | U94856 | 1328 | 163 | 1169 | 637 | 98 |
| 397 | Y09332 | 217 | 70 | 81 | 34 | 98 |
| 7274 | AI013715 | 196 | 35 | 63 | 38 | 98 |
| 21848 | AA957896 | 434 | 31 | 265 | 54 | 98 |
| 4940 | AI178788 | 684 | 132 | 1679 | 447 | 98 |
| 13004 | AI236284 | 511 | 23 | 322 | 83 | 98 |
| 6439 | AI058436 | 553 | 103 | 215 | 80 | 98 |
| 7420 | AI029291 | 1589 | 124 | 793 | 315 | 98 |
| 1448 | X15030 | 1513 | 142 | 727 | 223 | 98 |
| 2888 | AA924902 | 5090 | 1014 | 2588 | 711 | 98 |

TABLE 3L

Cyproterone Acetate  Document Number 1740956.1

Timepoints (hrs): 24, 120

| GLGC ID | GenBank Acc | Group Mean | Group SD | Non-Group Mean | Non-Group SD | Discriminant Score |
|---|---|---|---|---|---|---|
| 12158 | L00320 | 540 | 79 | 233 | 632 | 99 |
| 25055 | M11251 | 544 | 83 | 243 | 630 | 99 |
| 12160 | AA818412 | 2593 | 403 | 1176 | 1532 | 99 |
| 12156 | K00996 | 948 | 169 | 459 | 982 | 98 |
| 19256 | M15562 | 169 | 17 | 306 | 92 | 97 |
| 5074 | AI101695 | 24 | 20 | 161 | 87 | 97 |
| 15127 | S56937 | 912 | 86 | 528 | 266 | 96 |
| 4232 | AI012958 | 35 | 7 | 96 | 52 | 96 |
| 4172 | AA925514 | 10 | 5 | 41 | 18 | 96 |
| 14840 | AI237698 | 26 | 5 | 73 | 45 | 96 |
| 15391 | AI010083 | 749 | 48 | 724 | 264 | 96 |
| 15383 | AA955358 | 55 | 8 | 123 | 47 | 96 |
| 21228 | AI044404 | 60 | 10 | 140 | 54 | 96 |
| 16124 | AI176963 | 60 | 18 | 189 | 95 | 96 |
| 17685 | AI113055 | 18 | 9 | 59 | 33 | 96 |
| 1957 | AI172143 | 452 | 141 | 1540 | 699 | 96 |
| 7317 | AI136123 | 38 | 8 | 90 | 32 | 96 |
| 2125 | AI102519 | 4 | 30 | 173 | 129 | 96 |
| 6842 | AI009764 | 20 | 6 | 63 | 35 | 95 |
| 4234 | AB016536 | 242 | 23 | 458 | 175 | 95 |
| 22914 | AA924335 | 689 | 59 | 1105 | 278 | 95 |
| 3993 | AA925540 | 91 | 17 | 194 | 63 | 95 |
| 18829 | AA818796 | 50 | 9 | 113 | 47 | 95 |
| 6055 | M12337 | 416 | 42 | 794 | 300 | 95 |
| 3997 | AA925771 | 51 | 12 | 132 | 50 | 95 |
| 5241 | AA925986 | 155 | 29 | 316 | 90 | 95 |
| 3866 | AA893074 | 55 | 4 | 32 | 13 | 95 |
| 12155 | J00728 | 849 | 122 | 549 | 778 | 95 |
| 1795 | L24207 | 886 | 169 | 429 | 341 | 95 |
| 1394 | U37099 | 25 | 4 | 10 | 8 | 95 |
| 20707 | U88036 | 836 | 117 | 476 | 234 | 95 |
| 6479 | AI169690 | 447 | 76 | 1116 | 429 | 97 |
| 24860 | M13506 | 763 | 138 | 319 | 246 | 98 |
| 23032 | AI176596 | 175 | 35 | 320 | 78 | 95 |
| 8036 | AI230884 | 61 | 21 | 195 | 74 | 97 |
| 22917 | AI228120 | 151 | 22 | 270 | 64 | 95 |
| 15987 | AA866435 | 364 | 45 | 29 | 29 | 100 |
| 18669 | AA956453 | 68 | 15 | 191 | 75 | 95 |
| 3510 | AI176423 | 7 | 11 | 49 | 21 | 96 |
| 18906 | AA892561 | 165 | 26 | 89 | 28 | 97 |
| 11960 | AA891740 | −22 | 30 | 87 | 33 | 98 |
| 15755 | AB013112 | 214 | 34 | 567 | 179 | 99 |
| 6431 | AA859085 | 45 | 10 | 184 | 196 | 98 |
| 15500 | AI229337 | 239 | 25 | 427 | 106 | 97 |
| 906 | U83112 | 87 | 14 | 43 | 15 | 97 |
| 15032 | U89905 | 171 | 27 | 402 | 146 | 95 |
| 19555 | AA926120 | 820 | 145 | 1434 | 326 | 95 |
| 20804 | AI011684 | 2441 | 676 | 800 | 362 | 98 |
| 17788 | AA899045 | 2319 | 524 | 988 | 260 | 98 |
| 23776 | AI060224 | 22 | 13 | 127 | 64 | 95 |
| 21078 | J02791 | 321 | 18 | 539 | 148 | 97 |
| 1551 | X06150 | 300 | 25 | 743 | 310 | 99 |
| 3381 | AA892993 | 216 | 16 | 118 | 31 | 98 |
| 6801 | AI010316 | 168 | 26 | 420 | 127 | 97 |
| 3143 | AI232408 | 180 | 30 | 360 | 93 | 97 |
| 8872 | AA851050 | 2207 | 222 | 486 | 198 | 99 |
| 17090 | U73174 | 174 | 31 | 68 | 24 | 99 |
| 11724 | AI102812 | 26 | 6 | 101 | 49 | 96 |
| 16319 | AA875047 | 89 | 17 | 33 | 18 | 97 |
| 1478 | U32314 | 192 | 29 | 362 | 89 | 96 |
| 25183 | AF050159 | 58 | 11 | −55 | 37 | 99 |
| 21798 | AA926365 | 2671 | 379 | 1696 | 370 | 96 |
| 17092 | AA893189 | 283 | 56 | 85 | 30 | 99 |
| 20803 | U09256 | 490 | 37 | 240 | 83 | 98 |
| 1479 | U32314 | 143 | 14 | 269 | 67 | 97 |
| 25287 | D38069 | 211 | 40 | 89 | 39 | 97 |
| 15955 | AI232294 | 401 | 65 | 188 | 83 | 96 |
| 17091 | U73174 | 229 | 44 | 53 | 31 | 99 |
| 1749 | M17526 | 37 | 5 | 6 | 10 | 98 |
| 15138 | AI009801 | 184 | 27 | 91 | 37 | 96 |
| 15181 | AI235234 | 25 | 9 | 79 | 29 | 96 |

TABLE 3L-continued

Cyproterone Acetate  Document Number 1740956.1

Timepoints (hrs): 24, 120

| GLGC ID | GenBank Acc | Group Mean | Group SD | Non-Group Mean | Non-Group SD | Discriminant Score |
|---|---|---|---|---|---|---|
| 17117 | AI228042 | 1568 | 192 | 1013 | 206 | 97 |
| 1884 | D50695 | 255 | 40 | 156 | 35 | 96 |
| 11693 | AI168953 | 38 | 37 | 428 | 216 | 98 |
| 25057 | M58495 | 56 | 28 | 2 | 26 | 96 |
| 22715 | AA946120 | 441 | 64 | 752 | 146 | 97 |
| 1888 | E13573 | 109 | 18 | 38 | 29 | 96 |
| 4312 | AB010635 | 459 | 103 | 56 | 77 | 99 |
| 1796 | L24207 | 714 | 125 | 218 | 130 | 98 |
| 11324 | AA964832 | 124 | 23 | 287 | 81 | 96 |
| 21382 | AA945708 | 60 | 11 | 162 | 63 | 96 |
| 17644 | AA924036 | 42 | 6 | 132 | 61 | 96 |
| 5824 | AI045555 | 210 | 52 | 69 | 44 | 96 |
| 23272 | AA955819 | 127 | 19 | 316 | 86 | 98 |
| 12071 | AI009456 | 196 | 66 | 587 | 167 | 97 |
| 25281 | D30804 | 249 | 36 | 149 | 33 | 97 |
| 11039 | AI235465 | 62 | 25 | 176 | 58 | 95 |
| 20864 | AF045464 | 838 | 192 | 343 | 214 | 96 |
| 9015 | AI234810 | 51 | 4 | 110 | 36 | 97 |
| 6263 | AI009666 | 101 | 17 | 266 | 89 | 97 |
| 11644 | AI235282 | 422 | 98 | 907 | 209 | 96 |
| 1354 | D38065 | 595 | 103 | 218 | 132 | 95 |
| 714 | U10279 | 52 | 3 | 14 | 25 | 95 |
| 19363 | AI176247 | 324 | 171 | 1951 | 878 | 95 |

TABLE 3M

DICLOFENAC  Document Number 1740956.1

Timepoints (hrs): 24

| GLGC ID | GenBank Acc | Group Mean | Group SD | Non-Group Mean | Non-Group SD | Discriminant Score |
|---|---|---|---|---|---|---|
| 15003 | AI169327 | 68 | 19 | 0 | 54 | 99 |
| 15860 | AI102868 | 26 | 3 | 2 | 15 | 98 |
| 20707 | U88036 | 76 | 69 | 480 | 234 | 97 |
| 20449 | X17053 | 100 | 36 | 37 | 45 | 98 |
| 19624 | AA998422 | −25 | 15 | 72 | 51 | 98 |
| 2248 | AI170332 | 126 | 21 | 278 | 64 | 99 |
| 3265 | AA997784 | 50 | 15 | 196 | 74 | 98 |
| 899 | U35245 | −14 | 13 | 50 | 22 | 98 |
| 23839 | AA956684 | 113 | 10 | 254 | 78 | 98 |
| 24219 | L27843 | 441 | 10 | 302 | 111 | 98 |
| 23321 | AA892821 | 80 | 32 | 220 | 52 | 98 |
| 6018 | AA819140 | 763 | 205 | 5913 | 4088 | 98 |
| 1173 | M18363 | 304 | 50 | 1173 | 804 | 98 |
| 4444 | AI100882 | 43 | 19 | 607 | 321 | 99 |
| 24712 | E01884 | 36 | 10 | −5 | 20 | 98 |
| 14081 | AI233164 | 747 | 434 | 40 | 133 | 99 |
| 4267 | AA859412 | 898 | 432 | 338 | 138 | 97 |
| 25470 | M95791 | 48 | 1 | 13 | 19 | 99 |
| 891 | U66322 | −34 | 6 | 52 | 51 | 98 |
| 18824 | AI232255 | 32 | 18 | −74 | 41 | 98 |
| 25480 | S46785 | 158 | 51 | 496 | 178 | 97 |
| 13796 | AI229056 | 37 | 7 | 12 | 11 | 97 |
| 10249 | AI059711 | 43 | 6 | −15 | 26 | 98 |
| 7053 | AI011467 | −27 | 24 | 73 | 37 | 98 |
| 22511 | M22670 | 320 | 162 | −2 | 65 | 99 |
| 6431 | AA859085 | 1171 | 691 | 179 | 184 | 99 |
| 16879 | AI169284 | 500 | 45 | 968 | 243 | 98 |
| 5962 | AA817875 | 92 | 46 | 13 | 24 | 98 |
| 12792 | AI176883 | 106 | 11 | 40 | 29 | 98 |
| 2536 | AI176616 | 64 | 31 | 593 | 340 | 97 |
| 21977 | S46785 | 169 | 38 | 560 | 205 | 98 |
| 20162 | X17163 | 38 | 4 | −26 | 52 | 98 |
| 14600 | AA801076 | 324 | 97 | 114 | 62 | 98 |
| 19249 | AA997342 | 551 | 250 | 191 | 73 | 98 |

TABLE 3M-continued

DICLOFENAC  Document Number 1740956.1

Timepoints (hrs): 24

| GLGC ID | GenBank Acc | Group Mean | Group SD | Non-Group Mean | Non-Group SD | Discriminant Score |
|---|---|---|---|---|---|---|
| 12551 | AI230056 | 76 | 15 | 239 | 79 | 98 |
| 12450 | AI103955 | −7 | 13 | 172 | 80 | 98 |
| 1266 | S80631 | 22 | 13 | −17 | 12 | 98 |
| 19769 | AI102570 | 1629 | 487 | 764 | 266 | 97 |
| 5848 | AI168994 | 334 | 22 | 595 | 132 | 98 |
| 6033 | AI233081 | 514 | 32 | 1018 | 258 | 98 |
| 21973 | AA944840 | 87 | 14 | 300 | 128 | 98 |
| 475 | AI233828 | 597 | 57 | 1021 | 200 | 97 |
| 10307 | AI103695 | 142 | 35 | 14 | 44 | 98 |
| 1641 | E03428 | 218 | 31 | 114 | 42 | 97 |
| 23500 | AA860010 | 70 | 19 | 19 | 20 | 98 |
| 6016 | AA818163 | 635 | 214 | 2257 | 785 | 97 |
| 13551 | AI177602 | 100 | 10 | 52 | 18 | 98 |
| 17913 | H31707 | 108 | 15 | 184 | 30 | 97 |
| 1583 | U07201 | 91 | 20 | 38 | 17 | 98 |
| 9166 | AI137406 | 136 | 58 | 27 | 17 | 98 |
| 22929 | AI071578 | −58 | 17 | 1340 | 802 | 98 |
| 6387 | AI234664 | 63 | 2 | 101 | 26 | 98 |
| 21683 | M65149 | 105 | 31 | 16 | 27 | 98 |
| 22619 | AI009825 | 603 | 103 | 258 | 105 | 97 |
| 18354 | X59859 | 122 | 38 | 24 | 33 | 98 |
| 945 | D88666 | 117 | 49 | −32 | 37 | 98 |
| 4026 | AI233835 | 72 | 223 | 377 | 136 | 98 |
| 6532 | AI234105 | 265 | 39 | 136 | 41 | 98 |
| 22765 | AI176265 | 304 | 110 | 73 | 63 | 97 |
| 24366 | AA956246 | 68 | 3 | 167 | 61 | 98 |
| 13762 | AI230326 | 1 | 21 | 153 | 56 | 98 |
| 5197 | AI103376 | 668 | 103 | 336 | 90 | 97 |
| 11720 | AI232273 | 1457 | 246 | 762 | 221 | 98 |
| 22487 | AI102578 | 196 | 55 | 62 | 37 | 97 |
| 3504 | AI104659 | 556 | 112 | 285 | 90 | 97 |
| 6189 | AI178027 | 436 | 244 | 4085 | 2314 | 98 |
| 16809 | X58828 | 139 | 25 | 38 | 29 | 98 |
| 5899 | AI170038 | 304 | 213 | 1263 | 318 | 98 |
| 14996 | X16038 | 120 | 29 | 22 | 39 | 97 |
| 17496 | AA926109 | 41 | 2 | 237 | 171 | 98 |
| 17340 | AI007803 | 2776 | 726 | 1078 | 439 | 98 |
| 20803 | U09256 | 88 | 6 | 242 | 85 | 98 |
| 5791 | AI045423 | −87 | 28 | 27 | 43 | 97 |
| 1690 | AA817829 | 339 | 73 | 146 | 50 | 97 |
| 4374 | AA893869 | 48 | 3 | 16 | 12 | 98 |
| 11762 | AI178631 | 87 | 23 | −9 | 30 | 98 |
| 2555 | D00913 | 307 | 94 | 124 | 51 | 98 |
| 11553 | AI230765 | 267 | 40 | 87 | 48 | 98 |
| 10659 | AI103059 | 651 | 137 | 153 | 154 | 98 |
| 3073 | AI233494 | 27 | 2 | 98 | 80 | 98 |
| 9583 | AI071185 | 307 | 102 | 53 | 75 | 98 |
| 1221 | D11445 | 438 | 73 | 25 | 91 | 98 |
| 3773 | AA998356 | 232 | 48 | 57 | 47 | 97 |
| 21707 | AA859722 | 194 | 45 | 44 | 48 | 97 |
| 2161 | AI176592 | 1614 | 363 | 373 | 280 | 97 |
| 21209 | AI171772 | 419 | 161 | 85 | 86 | 97 |
| 8215 | AI171692 | 924 | 361 | 384 | 128 | 97 |
| 16859 | AI236753 | 550 | 88 | 226 | 101 | 98 |
| 22930 | AI071578 | 13 | 11 | 572 | 357 | 98 |
| 19363 | AI176247 | 245 | 54 | 1947 | 880 | 98 |
| 20354 | M14369 | 289 | 61 | 60 | 54 | 98 |
| 17664 | AI234496 | 793 | 84 | 265 | 151 | 98 |
| 5934 | AA817695 | 33 | 23 | 379 | 160 | 97 |
| 819 | X02284 | 1072 | 24 | 1836 | 1451 | 97 |
| 13932 | AI230988 | −101 | 25 | 68 | 54 | 97 |

TABLE 3N

DICLOFENAC  Document Number 1740956.1

Timepoints (hrs): 3, 6

| GLGC ID | GenBank Acc | Group Mean | Group SD | Non-Group Mean | Non-Group SD | Discriminant Score |
|---|---|---|---|---|---|---|
| 17787 | AI169758 | 1080 | 79 | 1234 | 1075 | 97 |
| 6478 | X05861 | 2135 | 265 | 2343 | 2110 | 97 |
| 818 | X02291 | 1867 | 157 | 2583 | 2537 | 97 |
| 819 | X02284 | 1557 | 112 | 1835 | 1454 | 96 |
| 12792 | AI176883 | 91 | 13 | 40 | 29 | 96 |
| 16274 | D10261 | 2075 | 237 | 3112 | 3332 | 96 |
| 17564 | AA963674 | 252 | 19 | 396 | 89 | 96 |
| 25400 | M14776 | 1031 | 92 | 1309 | 1136 | 95 |
| 6352 | AA997600 | 33 | 12 | −14 | 30 | 96 |
| 16085 | AA874889 | 47 | 6 | 21 | 23 | 95 |
| 3845 | AI011481 | 38 | 7 | 98 | 38 | 95 |
| 2010 | U05675 | 1759 | 242 | 1915 | 1523 | 96 |
| 1877 | X74593 | 284 | 37 | 542 | 174 | 95 |
| 111 | U02506 | 1786 | 177 | 2323 | 2260 | 95 |
| 6862 | AA849729 | 146 | 25 | 287 | 83 | 95 |
| 23512 | AA955282 | 377 | 55 | 776 | 251 | 95 |
| 6373 | AA858726 | 33 | 5 | 70 | 25 | 95 |
| 1684 | X56325 | 1721 | 204 | 2121 | 1936 | 95 |
| 10534 | AI070832 | 20 | 20 | 165 | 97 | 95 |
| 20650 | M12335 | 1141 | 112 | 1298 | 824 | 95 |
| 11080 | AA851330 | 99 | 14 | 191 | 57 | 94 |
| 11576 | AI146177 | 31 | 9 | 83 | 30 | 94 |
| 8211 | AI231807 | 1204 | 76 | 1685 | 1315 | 94 |
| 8521 | AI060064 | 23 | 7 | 72 | 37 | 94 |
| 1818 | Y11283 | 1292 | 119 | 1520 | 1067 | 94 |
| 14390 | AI232385 | 44 | 9 | 83 | 22 | 95 |
| 15755 | AB013112 | 323 | 36 | 567 | 180 | 94 |
| 3019 | AI231218 | 41 | 5 | 97 | 61 | 94 |
| 8549 | AI233639 | 328 | 76 | 720 | 224 | 94 |
| 13757 | AI228676 | 97 | 21 | 195 | 54 | 94 |
| 16767 | D16478 | 304 | 29 | 476 | 130 | 94 |
| 13095 | AI172595 | 32 | 4 | 57 | 16 | 94 |
| 17906 | AA899762 | 227 | 22 | 395 | 136 | 93 |
| 19258 | AA900613 | −5 | 15 | 103 | 96 | 94 |
| 23189 | AA925844 | 131 | 24 | 259 | 75 | 94 |
| 3044 | AA997701 | 104 | 5 | 149 | 54 | 93 |
| 4186 | AA945169 | 1811 | 189 | 2673 | 2390 | 94 |
| 1876 | AI030175 | 306 | 47 | 586 | 188 | 94 |
| 19038 | AA851818 | 91 | 9 | 149 | 39 | 93 |
| 6825 | AI045972 | 224 | 31 | 395 | 125 | 94 |
| 24219 | L27843 | 466 | 49 | 302 | 110 | 94 |
| 2367 | AF095741 | 217 | 25 | 337 | 74 | 94 |
| 7667 | AI233687 | 41 | 9 | 86 | 29 | 94 |
| 18522 | AI145870 | 222 | 52 | 436 | 121 | 94 |
| 22725 | AA900506 | −9 | 12 | 46 | 32 | 93 |
| 14094 | AI235377 | 72 | 7 | 117 | 35 | 93 |
| 6640 | AI101500 | 0 | 14 | 62 | 34 | 94 |
| 3467 | AI237835 | 52 | 17 | 130 | 55 | 93 |
| 10248 | L23148 | 69 | 10 | 32 | 22 | 94 |
| 20911 | AA899901 | 319 | 53 | 561 | 137 | 94 |
| 17903 | AI231083 | 154 | 20 | 236 | 53 | 94 |
| 20850 | AA899956 | −15 | 20 | 74 | 57 | 94 |
| 16680 | AA965190 | 116 | 54 | 363 | 134 | 93 |
| 16565 | U91847 | 60 | 10 | 22 | 21 | 93 |
| 18302 | U33500 | 299 | 54 | 131 | 104 | 94 |
| 25325 | K03045 | 843 | 139 | 1267 | 1228 | 94 |
| 8989 | AI070792 | 40 | 11 | 81 | 24 | 93 |
| 4899 | AA924017 | 72 | 29 | 13 | 49 | 96 |
| 16327 | AA875050 | 203 | 43 | 432 | 126 | 94 |
| 3310 | AA997945 | 55 | 27 | 13 | 22 | 94 |
| 6598 | M58587 | 287 | 31 | 170 | 63 | 94 |
| 21353 | AA850247 | 745 | 187 | 1382 | 347 | 94 |
| 6604 | AI229192 | 6 | 9 | 40 | 18 | 93 |
| 6891 | U53922 | 222 | 23 | 403 | 106 | 97 |
| 14459 | AI137930 | 9574 | 934 | 4333 | 2066 | 97 |
| 24321 | AI232340 | 370 | 85 | 848 | 259 | 95 |
| 15786 | AI013924 | 124 | 36 | 288 | 87 | 94 |
| 25852 | AI638998 | 56 | 9 | 25 | 11 | 97 |
| 7003 | AI030259 | 126 | 36 | 364 | 131 | 96 |
| 6252 | AA819381 | 155 | 19 | 363 | 135 | 97 |
| 25508 | S67620 | 27 | 9 | −6 | 16 | 96 |
| 17676 | V01235 | 1521 | 111 | 2334 | 2060 | 94 |
| 15180 | AI010354 | 511 | 110 | 903 | 199 | 94 |
| 19085 | AA892598 | 160 | 23 | 89 | 37 | 94 |
| 6438 | AA819269 | 60 | 24 | 180 | 64 | 95 |
| 8837 | AI102849 | 99 | 31 | 222 | 57 | 95 |
| 15551 | AI230759 | 204 | 24 | 324 | 61 | 96 |
| 7362 | AI029026 | 392 | 111 | 878 | 238 | 95 |
| 19012 | AI172056 | 934 | 211 | 428 | 152 | 97 |
| 2242 | AI012635 | 4544 | 1011 | 2332 | 856 | 95 |
| 16465 | AA901042 | 196 | 23 | 379 | 102 | 96 |
| 24366 | AA956246 | 60 | 15 | 167 | 60 | 94 |
| 23608 | AI233190 | 1289 | 380 | 392 | 192 | 97 |
| 26335 | AI236460 | 3287 | 771 | 1175 | 863 | 96 |
| 19086 | AA892598 | 220 | 34 | 117 | 49 | 95 |
| 20161 | X54686 | 109 | 30 | 28 | 37 | 95 |
| 16821 | AA999042 | 910 | 193 | 476 | 128 | 97 |
| 13481 | AI235352 | 21 | 8 | 79 | 29 | 96 |
| 16312 | AA875032 | 62 | 18 | 16 | 14 | 96 |
| 15932 | U12402 | 146 | 19 | 92 | 25 | 94 |
| 4868 | AI170763 | 121 | 21 | 280 | 76 | 97 |
| 17709 | U24489 | 134 | 28 | 44 | 35 | 95 |
| 5384 | AA891041 | 146 | 29 | 27 | 42 | 97 |
| 1221 | D11445 | 361 | 71 | 24 | 90 | 98 |
| 3773 | AA998356 | 169 | 47 | 57 | 47 | 96 |
| 17664 | AI234496 | 720 | 107 | 263 | 150 | 97 |

TABLE 3O

DIFLUNISAL  Document Number 1740956.1

Timepoints (hrs): 24

| GLGC ID | GenBank Acc | Group Mean | Group SD | Non-Group Mean | Non-Group SD | Discriminant Score |
|---|---|---|---|---|---|---|
| 15408 | D00569 | 626 | 11 | 249 | 112 | 100 |
| 18687 | AI170568 | 3601 | 172 | 482 | 430 | 100 |
| 20715 | X07259 | 2716 | 163 | 308 | 330 | 100 |
| 14595 | AA892128 | 327 | 5 | 75 | 68 | 100 |
| 20713 | M57718 | 3609 | 313 | 529 | 377 | 100 |
| 22416 | AA944380 | 438 | 24 | 132 | 112 | 100 |
| 3149 | AA894030 | 12 | 0 | 50 | 37 | 100 |
| 23699 | J02749 | 1669 | 186 | 511 | 296 | 100 |
| 24798 | X06357 | 806 | 29 | 442 | 149 | 100 |
| 354 | L32591 | 92 | 0 | 74 | 69 | 100 |
| 1728 | D16479 | 484 | 20 | 219 | 78 | 100 |
| 17758 | K03249 | 2134 | 579 | 304 | 334 | 100 |
| 20711 | AA924267 | 1058 | 208 | 125 | 164 | 100 |
| 1857 | AB010428 | 135 | 35 | 22 | 154 | 99 |
| 8527 | AA996461 | 296 | 2 | 152 | 190 | 99 |
| 16148 | J02752 | 3132 | 593 | 752 | 392 | 99 |
| 15848 | AI007820 | 2281 | 100 | 930 | 382 | 99 |
| 12093 | AA848628 | −1 | 0 | 21 | 22 | 99 |
| 18125 | AI008787 | 880 | 17 | 527 | 153 | 99 |
| 2457 | AA964752 | 963 | 38 | 221 | 158 | 99 |
| 17764 | AI234604 | 2068 | 97 | 801 | 300 | 99 |
| 23698 | J02749 | 1633 | 392 | 297 | 358 | 99 |
| 20925 | U08976 | 2529 | 381 | 330 | 335 | 99 |
| 18685 | AA997746 | 204 | 14 | 13 | 34 | 99 |
| 18293 | X05341 | 3200 | 349 | 945 | 464 | 99 |
| 19053 | D12770 | 18 | 0 | 35 | 33 | 99 |
| 18686 | D00729 | 4182 | 704 | 515 | 449 | 99 |
| 16767 | D16478 | 1099 | 97 | 473 | 127 | 99 |
| 3431 | AI176595 | 1472 | 18 | 741 | 289 | 99 |
| 6919 | AI010461 | 313 | 1 | 282 | 246 | 99 |
| 4271 | AA925603 | 512 | 68 | 59 | 145 | 99 |
| 15409 | D00569 | 1460 | 213 | 455 | 191 | 99 |

TABLE 3O-continued

DIFLUNISAL        Document Number 1740956.1

Timepoints (hrs): 24

| GLGC ID | GenBank Acc | Group Mean | Group SD | Non-Group Mean | Non-Group SD | Discriminant Score |
|---|---|---|---|---|---|---|
| 26109 | AA997009 | 1617 | 209 | 150 | 281 | 99 |
| 4196 | AA899304 | 247 | 45 | 79 | 108 | 99 |
| 20714 | M14972 | 3335 | 869 | 415 | 330 | 99 |
| 22603 | AF044574 | 598 | 90 | 231 | 78 | 99 |
| 16150 | AA799489 | 1574 | 395 | 507 | 237 | 99 |
| 14267 | AI011738 | 2613 | 147 | 1119 | 396 | 99 |
| 15580 | M33648 | 4011 | 142 | 1585 | 942 | 99 |
| 25064 | S45392 | 2088 | 172 | 843 | 316 | 99 |
| 23183 | AI144586 | 516 | 27 | 217 | 88 | 99 |
| 5213 | AA925767 | 627 | 3 | 498 | 171 | 99 |
| 16521 | AI010470 | 470 | 38 | 231 | 65 | 99 |
| 15383 | AA955358 | 201 | 2 | 122 | 47 | 99 |
| 18958 | D13921 | 589 | 58 | 277 | 93 | 99 |
| 2811 | AI171090 | 333 | 12 | 178 | 56 | 99 |
| 8856 | AI072402 | 96 | 3 | 47 | 16 | 99 |
| 16768 | D16478 | 927 | 161 | 392 | 107 | 99 |
| 18742 | AI105131 | 1159 | 155 | 352 | 189 | 99 |
| 25070 | S83279 | 865 | 113 | 404 | 105 | 99 |
| 5602 | AI232611 | 1266 | 120 | 215 | 232 | 99 |
| 9929 | AI013834 | 1157 | 154 | 513 | 138 | 99 |
| 22604 | AA945578 | 3212 | 610 | 986 | 435 | 99 |
| 12157 | K01721 | 1472 | 350 | 509 | 1099 | 99 |
| 15577 | AA924557 | 3114 | 40 | 1835 | 663 | 99 |
| 15850 | AI236795 | 1835 | 108 | 858 | 301 | 99 |
| 1793 | D13912 | 1869 | 112 | 875 | 648 | 99 |
| 21354 | AA899721 | 2463 | 381 | 385 | 393 | 99 |
| 20915 | AF001898 | 1373 | 278 | 406 | 273 | 99 |
| 14763 | AA944481 | 1777 | 110 | 506 | 379 | 99 |
| 21341 | AA850195 | 1507 | 72 | 818 | 296 | 99 |
| 10887 | Z83757 | 65 | 1 | 110 | 28 | 99 |
| 9931 | S83279 | 912 | 81 | 472 | 123 | 98 |
| 1858 | Y09333 | 243 | 90 | 26 | 187 | 98 |
| 21750 | AI009663 | 401 | 55 | 135 | 60 | 98 |
| 20555 | U26033 | 886 | 217 | 295 | 153 | 98 |
| 25500 | S63458 | 78 | 4 | 154 | 37 | 98 |
| 4272 | AI231309 | 327 | 49 | 39 | 88 | 98 |
| 15085 | AI233829 | 3317 | 397 | 1505 | 428 | 98 |
| 24665 | AI009098 | 51 | 9 | 174 | 76 | 98 |
| 22083 | AA850587 | 97 | 8 | 12 | 38 | 98 |
| 21010 | AA925306 | 1495 | 116 | 623 | 285 | 98 |
| 16703 | AI179300 | 2323 | 177 | 1206 | 370 | 98 |
| 19852 | AA946053 | 54 | 1 | 41 | 20 | 98 |
| 6409 | AA858910 | 193 | 5 | 105 | 46 | 98 |
| 1977 | J05470 | 697 | 63 | 300 | 113 | 98 |
| 17847 | AI178214 | 1109 | 68 | 729 | 141 | 98 |
| 18891 | AA924598 | 569 | 65 | 273 | 166 | 98 |
| 16546 | AA800120 | 344 | 20 | 178 | 63 | 98 |
| 16518 | AI176546 | 1353 | 182 | 544 | 195 | 98 |
| 14070 | AI232649 | 180 | 1 | 167 | 56 | 98 |
| 15579 | M33648 | 3552 | 356 | 1231 | 818 | 98 |
| 18957 | D00512 | 670 | 144 | 311 | 98 | 98 |
| 7665 | AI030668 | 279 | 10 | 164 | 73 | 98 |
| 4207 | AA945591 | 186 | 9 | 466 | 244 | 98 |
| 9905 | AA891774 | 769 | 9 | 505 | 140 | 98 |
| 355 | S66024 | 22 | 2 | 70 | 33 | 98 |
| 22851 | AA925204 | 70 | 1 | 97 | 56 | 98 |
| 21729 | AA946532 | 1658 | 628 | 474 | 235 | 98 |
| 4067 | AA924813 | 157 | 1 | 143 | 79 | 98 |
| 12156 | K00996 | 1279 | 410 | 460 | 980 | 98 |
| 40 | U02096 | 830 | 205 | 315 | 129 | 98 |
| 22602 | AF044574 | 373 | 68 | 127 | 69 | 98 |
| 16416 | AA875098 | 62 | 3 | 108 | 39 | 98 |
| 18890 | AA899964 | 1488 | 203 | 688 | 317 | 98 |
| 21355 | AI105094 | 1996 | 627 | 301 | 296 | 98 |
| 20802 | AI059508 | 39 | 6 | 127 | 47 | 98 |

TABLE 3P

DIOXIN        Document Number 1740956.1

Timepoints (hrs): 68

| GLGC ID | GenBank Acc | Group Mean | Group SD | Non-Group Mean | Non-Group SD | Discriminant Score |
|---|---|---|---|---|---|---|
| 15188 | D16302 | 309 | 12 | 181 | 30 | 100 |
| 11724 | AI102812 | 7 | 1 | 100 | 49 | 100 |
| 15599 | X75253 | 987 | 8 | 498 | 152 | 100 |
| 9842 | U94856 | 3961 | 210 | 1162 | 620 | 100 |
| 11372 | AI137995 | 597 | 47 | 12 | 14 | 100 |
| 23192 | AA891107 | 72 | 1 | 192 | 62 | 100 |
| 12306 | AA944898 | 45 | 5 | 1081 | 502 | 100 |
| 4007 | AA926066 | 273 | 8 | 64 | 36 | 100 |
| 13185 | U23055 | 1439 | 190 | 29 | 28 | 100 |
| 9841 | U94856 | 4423 | 113 | 1503 | 852 | 100 |
| 2922 | AA996816 | 133 | 8 | 24 | 22 | 100 |
| 3664 | AI171289 | 450 | 19 | 171 | 46 | 100 |
| 70 | M58308 | 113 | 9 | 389 | 116 | 100 |
| 24644 | J03637 | 1957 | 144 | 47 | 55 | 100 |
| 15703 | AB009372 | 10 | 3 | 133 | 40 | 100 |
| 1559 | U28504 | 237 | 12 | 78 | 32 | 100 |
| 193 | AI176856 | 4147 | 1365 | 25 | 62 | 100 |
| 191 | U09540 | 2495 | 514 | 60 | 52 | 100 |
| 190 | U09540 | 2765 | 442 | -43 | 35 | 100 |
| 15107 | AI233220 | 11779 | 470 | 3744 | 2644 | 100 |
| 13187 | U23056 | 1806 | 345 | 38 | 21 | 100 |
| 23851 | AI136862 | 901 | 55 | 409 | 130 | 100 |
| 20703 | K03241 | 5465 | 178 | 390 | 492 | 100 |
| 15098 | M31837 | 43 | 1 | 124 | 34 | 100 |
| 1869 | J03959 | 2950 | 247 | 888 | 425 | 100 |
| 16366 | AA892888 | 2467 | 161 | 614 | 306 | 100 |
| 21489 | AA851443 | 1024 | 199 | 109 | 98 | 100 |
| 3693 | AI011448 | 927 | 139 | 213 | 97 | 100 |
| 179 | D17809 | 42 | 8 | 147 | 35 | 100 |
| 19129 | AA943990 | 922 | 68 | 439 | 94 | 100 |
| 18027 | AF039212 | 576 | 208 | 57 | 24 | 100 |
| 4245 | AA818692 | 1993 | 270 | 737 | 150 | 100 |
| 23584 | AA955071 | 756 | 55 | 203 | 90 | 100 |
| 588 | X69834 | 1923 | 127 | 720 | 325 | 100 |
| 699 | U55765 | 1173 | 25 | 479 | 160 | 100 |
| 16367 | AA892888 | 5011 | 664 | 1047 | 659 | 100 |
| 14231 | AI072358 | 922 | 159 | 44 | 50 | 100 |
| 18028 | D38062 | 719 | 212 | 10 | 29 | 100 |
| 21488 | U32575 | 362 | 136 | 43 | 21 | 100 |
| 4381 | H33003 | 187 | 31 | -57 | 53 | 100 |
| 9889 | AI044621 | 5330 | 633 | 1705 | 537 | 100 |
| 6143 | AI105167 | 7928 | 967 | 855 | 386 | 100 |
| 20429 | J05035 | 101 | 12 | 499 | 239 | 100 |
| 19443 | AA892832 | 3167 | 255 | 966 | 464 | 100 |
| 15252 | AI178605 | 845 | 59 | 342 | 118 | 100 |
| 1127 | AB003400 | -1 | 1 | 124 | 72 | 100 |
| 10710 | AI030494 | 643 | 119 | 159 | 62 | 100 |
| 24590 | M35299 | -24 | 1 | 34 | 36 | 100 |
| 293 | J05499 | 37 | 7 | 213 | 64 | 100 |
| 10260 | S81497 | 58 | 9 | 190 | 53 | 100 |
| 21288 | AI227935 | 1241 | 311 | 410 | 163 | 100 |
| 17831 | AI012017 | -10 | 1 | 91 | 53 | 100 |
| 4561 | AI102927 | 1118 | 88 | 366 | 103 | 100 |
| 19322 | AA851960 | 964 | 63 | 483 | 118 | 100 |
| 23520 | AA955305 | 251 | 5 | 127 | 48 | 100 |
| 6016 | AA818163 | 9538 | 2790 | 2232 | 685 | 100 |
| 3062 | AA998857 | 10421 | 2703 | 3289 | 873 | 100 |
| 22727 | AA955814 | 8316 | 941 | 3365 | 989 | 100 |
| 16364 | AA892251 | 643 | 144 | 170 | 64 | 100 |
| 24649 | AI234950 | 328 | 40 | 124 | 28 | 100 |
| 15379 | AI639162 | 59 | 11 | 12 | 9 | 99 |
| 5006 | AI229908 | 97 | 54 | -12 | 11 | 99 |
| 25598 | U32575 | 79 | 13 | 9 | 14 | 99 |
| 1698 | J02679 | 1687 | 260 | 182 | 129 | 99 |
| 18588 | AA899635 | 570 | 61 | 207 | 99 | 99 |
| 1822 | AA817843 | 10 | 3 | 67 | 29 | 99 |
| 18525 | AI176792 | 496 | 69 | 198 | 84 | 99 |
| 14495 | AA893658 | 1168 | 310 | 272 | 78 | 99 |
| 12314 | AA945596 | 5617 | 750 | 2132 | 575 | 99 |
| 5007 | AI236229 | 528 | 371 | 8 | 9 | 99 |
| 17324 | AF056031 | 117 | 12 | 315 | 74 | 99 |

TABLE 3P-continued

DIOXIN  Document Number 1740956.1

Timepoints (hrs): 68

| GLGC ID | GenBank Acc | Group Mean | Group SD | Non-Group Mean | Non-Group SD | Discriminant Score |
|---|---|---|---|---|---|---|
| 590 | X53428 | 1 | 0 | 24 | 15 | 99 |
| 2467 | AA964789 | 54 | 6 | −4 | 26 | 99 |
| 17359 | AI007981 | 11372 | 2758 | 3613 | 977 | 99 |
| 8594 | AI012932 | 1014 | 51 | 473 | 141 | 99 |
| 489 | E00778 | 3511 | 550 | 40 | 363 | 99 |
| 21094 | D10354 | 1 | 8 | 205 | 91 | 99 |
| 20311 | U52034 | 88 | 13 | 7 | 19 | 99 |
| 6121 | AA848573 | 114 | 15 | 33 | 15 | 99 |
| 192 | X83867 | 147 | 71 | 11 | 9 | 99 |
| 1174 | J02657 | 2086 | 83 | 1827 | 1623 | 99 |
| 2354 | AA997763 | 2566 | 494 | 752 | 292 | 99 |
| 14479 | AA858969 | 620 | 22 | 361 | 84 | 99 |
| 20430 | J05035 | 91 | 20 | 652 | 376 | 99 |
| 22755 | AA946323 | 436 | 156 | 120 | 70 | 99 |
| 21856 | AA858550 | 4 | 5 | 95 | 50 | 99 |
| 16781 | AI234527 | 1700 | 747 | 323 | 107 | 99 |
| 13563 | AI233773 | 4123 | 999 | 1235 | 347 | 99 |
| 4511 | AA944348 | 460 | 41 | 188 | 67 | 99 |
| 16873 | AI008015 | 84 | 27 | −8 | 18 | 99 |
| 16345 | AI013250 | 816 | 5 | 560 | 135 | 99 |
| 22713 | AA945904 | 73 | 3 | 205 | 74 | 99 |
| 6628 | AI178793 | 635 | 79 | 291 | 76 | 99 |
| 4134 | AA851240 | 1819 | 94 | 859 | 317 | 99 |
| 11791 | AI177843 | 1567 | 284 | 676 | 150 | 99 |
| 23699 | J02749 | 984 | 38 | 513 | 302 | 99 |

TABLE 3Q

DIOXIN  Document Number 1740956.1

Timepoints (hrs): 6, 24

| GLGC ID | GenBank Acc | Group Mean | Group SD | Non-Group Mean | Non-Group SD | Discriminant Score |
|---|---|---|---|---|---|---|
| 6143 | AI105167 | 4317 | 1089 | 850 | 439 | 100 |
| 21288 | AI227935 | 2022 | 619 | 400 | 88 | 100 |
| 19288 | AI231305 | 343 | 55 | −9 | 36 | 100 |
| 22755 | AA946323 | 731 | 197 | 116 | 48 | 100 |
| 13619 | AI179464 | 470 | 210 | 77 | 65 | 99 |
| 24649 | AI234950 | 276 | 48 | 124 | 27 | 99 |
| 489 | E00778 | 3584 | 633 | 24 | 270 | 99 |
| 4561 | AI102927 | 919 | 135 | 364 | 99 | 99 |
| 23584 | AA955071 | 595 | 89 | 201 | 88 | 99 |
| 1698 | J02679 | 1112 | 272 | 180 | 128 | 99 |
| 1169 | AI177161 | 233 | 62 | 71 | 35 | 99 |
| 488 | E00717 | 6373 | 923 | 148 | 691 | 99 |
| 20703 | K03241 | 3973 | 780 | 378 | 465 | 99 |
| 1170 | AI177161 | 382 | 116 | 113 | 50 | 99 |
| 8661 | AA818604 | 189 | 68 | 12 | 63 | 99 |
| 20705 | E01184 | 7144 | 1385 | 811 | 982 | 99 |
| 9527 | D28560 | 629 | 90 | 204 | 91 | 99 |
| 5492 | D38061 | 407 | 264 | 36 | 55 | 99 |
| 5493 | S56936 | 448 | 235 | 59 | 54 | 99 |
| 12314 | AA945596 | 4958 | 1147 | 2121 | 548 | 99 |
| 20704 | M26127 | 5480 | 992 | 1006 | 925 | 98 |
| 15252 | AI178605 | 675 | 118 | 341 | 117 | 98 |
| 9528 | D28560 | 563 | 162 | 187 | 69 | 98 |
| 15127 | S56937 | 1500 | 454 | 523 | 252 | 98 |
| 18989 | K00136 | 4129 | 1154 | 1059 | 788 | 98 |
| 23851 | AI136862 | 703 | 40 | 409 | 130 | 97 |
| 8457 | AI059835 | 115 | 43 | 25 | 24 | 97 |
| 2713 | AA962943 | 514 | 80 | 222 | 90 | 97 |
| 15126 | D83796 | 2608 | 725 | 881 | 456 | 97 |
| 3690 | AA999006 | 806 | 408 | 224 | 115 | 97 |
| 19185 | AI111361 | 91 | 40 | 15 | 21 | 97 |
| 16366 | AA892888 | 1871 | 567 | 610 | 300 | 97 |

TABLE 3Q-continued

DIOXIN  Document Number 1740956.1

Timepoints (hrs): 6, 24

| GLGC ID | GenBank Acc | Group Mean | Group SD | Non-Group Mean | Non-Group SD | Discriminant Score |
|---|---|---|---|---|---|---|
| 23682 | AI234973 | 525 | 136 | 239 | 89 | 97 |
| 23448 | AA925167 | 4473 | 1661 | 966 | 792 | 97 |
| 23449 | AI176828 | 3104 | 739 | 834 | 704 | 97 |
| 3427 | AA892246 | 196 | 43 | 85 | 33 | 97 |
| 15743 | AA996434 | 439 | 132 | 194 | 75 | 97 |
| 15124 | J02612 | 2734 | 593 | 989 | 548 | 97 |
| 16367 | AA892888 | 3316 | 885 | 1041 | 661 | 96 |
| 19443 | AA892832 | 2484 | 509 | 961 | 460 | 95 |
| 22866 | AI233754 | 524 | 59 | 321 | 92 | 95 |
| 23608 | AI233190 | 796 | 113 | 395 | 206 | 95 |
| 18597 | AB013732 | 762 | 126 | 450 | 122 | 95 |
| 21192 | AI009732 | 136 | 45 | 51 | 37 | 95 |
| 20464 | M20406 | 1770 | 185 | 1281 | 780 | 95 |
| 11301 | AI136709 | 635 | 159 | 308 | 140 | 95 |
| 6781 | AA848753 | 315 | 47 | 152 | 73 | 94 |
| 25041 | D14014 | 37 | 8 | 106 | 52 | 94 |
| 3431 | AI176595 | 1437 | 257 | 738 | 285 | 94 |
| 2264 | AI144741 | 254 | 32 | 420 | 99 | 94 |
| 22490 | AA899289 | 848 | 49 | 621 | 134 | 94 |
| 20779 | M15185 | 2030 | 257 | 984 | 440 | 94 |
| 18028 | D38062 | 245 | 187 | 10 | 41 | 93 |
| 18027 | AF039212 | 218 | 140 | 58 | 33 | 93 |
| 18867 | D88250 | 1189 | 214 | 628 | 240 | 93 |
| 17768 | AI105196 | 509 | 108 | 801 | 150 | 93 |
| 21904 | M24239 | 3898 | 318 | 2192 | 1985 | 93 |
| 9157 | AI179947 | 113 | 19 | 42 | 38 | 93 |
| 14231 | AI072358 | 403 | 299 | 44 | 56 | 93 |
| 8212 | AI231807 | 3081 | 205 | 1402 | 913 | 93 |
| 7084 | AI230362 | 811 | 80 | 430 | 203 | 93 |
| 17742 | AA866302 | 2311 | 185 | 1454 | 972 | 93 |
| 9842 | U94856 | 2284 | 132 | 1161 | 631 | 92 |
| 9192 | AI137345 | 2612 | 316 | 1633 | 654 | 92 |
| 19009 | AA850164 | 1499 | 140 | 1100 | 306 | 92 |
| 1529 | M81687 | 661 | 44 | 452 | 113 | 92 |
| 2536 | AI176616 | 1159 | 237 | 587 | 338 | 92 |
| 13563 | AI233773 | 2683 | 602 | 1233 | 357 | 92 |
| 15296 | AI228738 | 94 | 40 | 191 | 56 | 92 |
| 9383 | AI059824 | 114 | 45 | 21 | 20 | 92 |
| 15173 | AI231846 | 1112 | 292 | 360 | 163 | 92 |
| 2354 | AA997763 | 2333 | 966 | 746 | 266 | 92 |
| 8130 | AI008894 | 134 | 48 | 21 | 27 | 91 |
| 12482 | AI144965 | 183 | 11 | 144 | 64 | 91 |
| 25468 | M94918 | 3534 | 445 | 1637 | 1265 | 91 |
| 17614 | AA848306 | 240 | 28 | 155 | 48 | 91 |
| 1850 | K02814 | 2275 | 250 | 1633 | 1201 | 91 |
| 22250 | AA943541 | 236 | 36 | 124 | 68 | 91 |
| 25469 | M94919 | 2398 | 319 | 1165 | 806 | 91 |
| 8438 | AA892986 | 41 | 12 | 102 | 40 | 91 |
| 20311 | U52034 | 69 | 40 | 7 | 19 | 91 |
| 4791 | AI179106 | 144 | 13 | 104 | 31 | 91 |
| 21903 | AA945571 | 1509 | 173 | 1095 | 642 | 91 |
| 17817 | AA892777 | 22 | 4 | 46 | 20 | 91 |
| 23576 | X72757 | 1480 | 70 | 961 | 472 | 91 |
| 25057 | M58495 | 77 | 42 | 2 | 25 | 91 |
| 17236 | AA858903 | −10 | 6 | 27 | 51 | 91 |
| 6619 | AA818743 | 781 | 170 | 406 | 96 | 91 |
| 15357 | AI010803 | 289 | 58 | 84 | 73 | 91 |
| 1262 | AB017044 | 22 | 6 | 62 | 32 | 91 |
| 11563 | AI102560 | −10 | 9 | 35 | 38 | 91 |
| 20055 | AI230762 | −13 | 25 | 70 | 68 | 91 |
| 23606 | U05784 | 786 | 275 | 324 | 138 | 91 |

TABLE 3R

ESTRADIOL  Document Number 1740956.1

Timepoints (hrs): 24, 240

| GLGC ID | GenBank Acc | Group Mean | Group SD | Non-Group Mean | Non-Group SD | Discriminant Score |
|---|---|---|---|---|---|---|
| 7804 | AI233771 | 101 | 41 | −4 | 64 | 94 |
| 12313 | AA945418 | 393 | 636 | 3851 | 1917 | 94 |
| 18525 | AI176792 | 72 | 27 | 201 | 84 | 90 |
| 22604 | AA945578 | 418 | 89 | 1001 | 448 | 88 |
| 2569 | AA965122 | 469 | 128 | 884 | 272 | 91 |
| 7199 | AI013044 | 962 | 171 | 1719 | 472 | 90 |
| 10545 | U21871 | 27 | 32 | 192 | 63 | 88 |
| 8984 | L10652 | 234 | 22 | 166 | 44 | 90 |
| 3458 | AA997861 | 1060 | 134 | 1495 | 269 | 90 |
| 633 | AI231127 | 952 | 161 | 1414 | 277 | 90 |
| 11404 | AI237002 | 335 | 62 | 213 | 127 | 89 |
| 14421 | AA942751 | 218 | 26 | 144 | 47 | 89 |
| 22351 | AA945867 | 57 | 18 | 21 | 31 | 88 |
| 20601 | X52625 | 269 | 82 | 727 | 395 | 88 |
| 20600 | AI177004 | 162 | 57 | 479 | 263 | 88 |
| 14737 | AI008416 | 1290 | 173 | 1941 | 525 | 88 |
| 12958 | AI177155 | 664 | 96 | 1123 | 357 | 87 |
| 24162 | AI169279 | 851 | 77 | 1257 | 313 | 88 |
| 17590 | AA892851 | 150 | 15 | 109 | 43 | 90 |
| 9012 | AI070879 | 277 | 155 | 748 | 270 | 88 |
| 8058 | AA818475 | 460 | 53 | 649 | 145 | 90 |
| 1379 | M83676 | 50 | 9 | 22 | 18 | 87 |
| 20983 | AI044900 | 394 | 51 | 756 | 333 | 88 |
| 1126 | AI231007 | 48 | 8 | 22 | 18 | 87 |
| 13203 | AI228728 | 33 | 32 | −49 | 58 | 89 |
| 16006 | AF062594 | 51 | 15 | 16 | 25 | 88 |
| 1169 | AI177161 | 120 | 22 | 72 | 38 | 89 |
| 3880 | AA893247 | 120 | 14 | 76 | 27 | 91 |
| 15259 | AI178135 | 163 | 27 | 99 | 48 | 88 |
| 570 | X82445 | 183 | 22 | 128 | 34 | 88 |
| 16943 | AI236097 | 1319 | 247 | 2062 | 459 | 88 |
| 10544 | D63411 | 223 | 25 | 164 | 53 | 88 |
| 21772 | AI011179 | 95 | 11 | 61 | 20 | 90 |
| 18524 | AA946017 | 874 | 112 | 1177 | 268 | 87 |
| 14996 | X16038 | 58 | 18 | 22 | 40 | 88 |
| 17431 | AI070521 | 213 | 18 | 158 | 40 | 87 |
| 14545 | AA800456 | 79 | 13 | 46 | 20 | 87 |
| 19590 | D87336 | 105 | 18 | 62 | 30 | 88 |
| 22350 | AA944014 | 31 | 9 | 11 | 14 | 89 |
| 8872 | AA851050 | 697 | 102 | 494 | 241 | 88 |
| 1170 | AI177161 | 179 | 32 | 114 | 55 | 88 |
| 2629 | Y00396 | 66 | 17 | 34 | 32 | 89 |
| 21952 | AA891537 | 86 | 10 | 59 | 20 | 88 |
| 3823 | AI233147 | 747 | 125 | 519 | 183 | 89 |
| 17502 | M12156 | 153 | 32 | 87 | 43 | 88 |
| 20755 | X70871 | 103 | 29 | 54 | 37 | 87 |
| 16416 | AA875098 | 151 | 26 | 107 | 39 | 90 |
| 24779 | J03863 | 473 | 231 | 136 | 284 | 87 |
| 574 | L13039 | 125 | 26 | 91 | 43 | 89 |
| 23299 | AI176839 | 393 | 87 | 186 | 125 | 90 |
| 5711 | AI045151 | 455 | 219 | 1053 | 323 | 87 |
| 16178 | AF035387 | 207 | 20 | 149 | 33 | 87 |
| 1373 | L24907 | 100 | 13 | 65 | 19 | 88 |
| 12358 | AI170661 | 54 | 21 | 15 | 21 | 88 |
| 6536 | AA891834 | 54 | 16 | 25 | 14 | 89 |
| 20781 | U89282 | 72 | 14 | 38 | 17 | 87 |
| 23825 | U38180 | 77 | 12 | 46 | 17 | 89 |
| 5082 | D14015 | 59 | 18 | 18 | 22 | 87 |
| 16649 | AF051895 | 132 | 85 | −4 | 29 | 91 |
| 2587 | AI232103 | 953 | 356 | 1747 | 412 | 90 |
| 3944 | AA900688 | 2029 | 565 | 302 | 119 | 97 |
| 16650 | D42137 | 229 | 100 | 65 | 36 | 96 |
| 24013 | AI229260 | 191 | 51 | 58 | 58 | 91 |
| 23468 | AA926067 | 843 | 175 | 461 | 121 | 91 |
| 14973 | L19180 | 279 | 117 | 79 | 64 | 91 |
| 22972 | AB015946 | 70 | 16 | 37 | 15 | 88 |
| 17956 | AA964379 | 110 | 12 | 67 | 22 | 90 |
| 3905 | AI103403 | 655 | 139 | 385 | 140 | 90 |
| 10002 | AI137988 | 253 | 61 | 135 | 64 | 88 |
| 15056 | U60578 | 57 | 29 | 11 | 17 | 87 |
| 23500 | AA860010 | 53 | 23 | 19 | 19 | 87 |
| 21103 | AF034582 | 308 | 54 | 165 | 51 | 91 |
| 16043 | AA874830 | 279 | 77 | 129 | 27 | 96 |
| 19259 | AA900613 | 530 | 236 | −70 | 199 | 88 |
| 10248 | L23148 | 88 | 32 | 32 | 21 | 87 |
| 21504 | AI137941 | 1572 | 405 | 719 | 300 | 88 |
| 6101 | AI170752 | 74 | 20 | 31 | 23 | 88 |
| 5264 | AA926107 | 776 | 245 | 62 | 100 | 96 |
| 21703 | U82591 | 93 | 18 | 47 | 22 | 91 |
| 18085 | AA858603 | 48 | 31 | −24 | 39 | 88 |
| 172 | M27886 | 87 | 15 | 37 | 23 | 96 |
| 764 | X84210 | 172 | 17 | 104 | 34 | 94 |
| 17894 | U25264 | 126 | 36 | 58 | 21 | 89 |
| 15684 | AI171535 | 655 | 123 | 349 | 129 | 93 |
| 6547 | AI012181 | 836 | 347 | 225 | 137 | 89 |
| 20741 | AF084186 | 92 | 21 | 28 | 32 | 89 |
| 4477 | U77829 | 41 | 9 | 16 | 13 | 89 |
| 13294 | AI233731 | 519 | 86 | 346 | 104 | 87 |
| 15685 | AI233870 | 376 | 119 | 13 | 173 | 92 |
| 174 | J04197 | 128 | 29 | 50 | 31 | 88 |
| 11850 | R46985 | 1714 | 305 | 1117 | 312 | 88 |
| 2230 | AA957643 | 204 | 59 | 64 | 33 | 94 |
| 11830 | AI179093 | 1124 | 215 | 608 | 262 | 87 |
| 23192 | AA891107 | 327 | 63 | 189 | 60 | 90 |
| 173 | X15580 | 253 | 41 | 111 | 63 | 95 |
| 778 | U84410 | 55 | 15 | 19 | 19 | 87 |
| 21115 | AF086624 | 206 | 46 | 70 | 61 | 88 |

TABLE 3

GENERAL  Document Number 1740956.1

| GLGC ID | GenBank Acc | Group Mean | Group SD | Non-Group Mean | Non-Group SD | Discriminant Score |
|---|---|---|---|---|---|---|
| 17887 | AI172414 | 923 | 285 | 1246 | 255 | 74 |
| 4590 | AA892778 | 42 | 29 | 69 | 24 | 73 |
| 9292 | AI072485 | 98 | 32 | 67 | 22 | 72 |
| 17155 | AI172090 | 195 | 86 | 120 | 44 | 72 |
| 3031 | AF079864 | 44 | 25 | 80 | 38 | 72 |
| 8215 | AI171692 | 528 | 204 | 352 | 77 | 71 |
| 20380 | D16102 | 128 | 54 | 176 | 55 | 71 |
| 17703 | AI232498 | 294 | 81 | 375 | 69 | 71 |
| 24290 | AI045040 | 2253 | 694 | 2921 | 640 | 70 |
| 22870 | AA926360 | 631 | 247 | 888 | 243 | 70 |
| 18725 | AF029240 | 154 | 60 | 207 | 55 | 70 |
| 24366 | AA956246 | 124 | 66 | 177 | 55 | 70 |
| 2544 | AA817968 | 166 | 64 | 240 | 70 | 70 |
| 5026 | AA924783 | 48 | 57 | 123 | 83 | 70 |
| 5874 | AI145801 | 90 | 48 | 125 | 42 | 70 |
| 4093 | AI232001 | 677 | 210 | 518 | 113 | 70 |
| 11382 | AI136692 | 308 | 95 | 241 | 54 | 70 |
| 15398 | AI236566 | 120 | 77 | 67 | 37 | 69 |
| 19712 | U18374 | 119 | 47 | 150 | 38 | 69 |
| 18564 | AA800745 | 268 | 82 | 331 | 68 | 69 |
| 23874 | AI103556 | 300 | 167 | 188 | 73 | 69 |
| 62 | E06822 | 103 | 30 | 129 | 30 | 69 |
| 7665 | AI030668 | 234 | 107 | 148 | 50 | 69 |
| 4650 | AI101582 | 91 | 80 | 51 | 46 | 69 |
| 6263 | AI009666 | 201 | 89 | 281 | 83 | 69 |
| 24763 | AI176488 | 78 | 31 | 105 | 38 | 69 |
| 8872 | AA851050 | 673 | 456 | 455 | 113 | 69 |
| 15372 | AA875205 | 205 | 58 | 162 | 29 | 69 |
| 15685 | AI233870 | 127 | 263 | −7 | 139 | 69 |
| 10555 | AA900198 | 203 | 206 | 410 | 212 | 69 |
| 11644 | AI235282 | 804 | 308 | 928 | 174 | 68 |
| 26123 | AI008396 | 362 | 220 | 223 | 83 | 68 |
| 17613 | AA799511 | 297 | 104 | 242 | 47 | 68 |

TABLE 3-continued

Document Number 1740956.1

| GLGC ID | GenBank Acc | Group Mean | Group SD | Non-Group Mean | Non-Group SD | Discriminant Score |
|---|---|---|---|---|---|---|
| 18507 | AI175551 | 870 | 327 | 658 | 142 | 68 |
| 18726 | AF029240 | 259 | 84 | 317 | 71 | 68 |
| 11850 | R46985 | 1391 | 422 | 1063 | 253 | 68 |
| 11830 | AI179093 | 828 | 454 | 565 | 166 | 68 |
| 10887 | Z83757 | 93 | 32 | 114 | 25 | 68 |
| 14521 | AI232350 | 385 | 157 | 501 | 151 | 68 |
| 10087 | AI171803 | 1189 | 319 | 1458 | 299 | 68 |
| 7199 | AI013044 | 1376 | 509 | 1786 | 435 | 68 |
| 6440 | AA859130 | 426 | 234 | 261 | 108 | 68 |
| 11416 | AI172185 | 135 | 57 | 104 | 29 | 68 |
| 11039 | AI235465 | 138 | 70 | 185 | 51 | 68 |
| 6715 | AI228284 | 206 | 50 | 250 | 47 | 68 |
| 4134 | AA851240 | 679 | 364 | 906 | 293 | 68 |
| 1540 | M25073 | 138 | 46 | 159 | 37 | 68 |
| 5711 | AI045151 | 798 | 347 | 1103 | 298 | 68 |
| 2822 | AI233763 | 119 | 54 | 169 | 55 | 68 |
| 15538 | AI112633 | 381 | 107 | 291 | 85 | 68 |
| 21173 | AA848990 | 139 | 92 | 183 | 68 | 68 |
| 20986 | AA893242 | 225 | 110 | 285 | 90 | 68 |
| 1159 | AA891949 | 206 | 87 | 242 | 64 | 68 |
| 10985 | AA818998 | 484 | 163 | 608 | 116 | 67 |
| 12361 | AA965031 | 336 | 273 | 401 | 164 | 67 |
| 15175 | AA945583 | 195 | 60 | 216 | 40 | 67 |
| 17963 | AB012231 | 86 | 39 | 116 | 41 | 67 |
| 23390 | AI172328 | 582 | 252 | 404 | 108 | 67 |
| 6743 | AI231219 | 936 | 295 | 1156 | 245 | 67 |
| 17693 | AA891737 | 171 | 89 | 183 | 59 | 67 |
| 11632 | AI102427 | 533 | 154 | 427 | 104 | 67 |
| 5110 | AA925274 | 368 | 169 | 263 | 63 | 67 |
| 70 | M58308 | 337 | 152 | 401 | 102 | 67 |
| 11561 | AI233182 | 217 | 87 | 162 | 51 | 67 |
| 17532 | J03867 | 347 | 160 | 408 | 121 | 67 |
| 11546 | AI175535 | 153 | 48 | 122 | 33 | 67 |
| 2350 | AA964368 | 690 | 182 | 561 | 100 | 67 |
| 4731 | AI230773 | 113 | 110 | 36 | 29 | 67 |
| 6673 | AI044325 | 595 | 236 | 797 | 256 | 67 |
| 7552 | AI045802 | 747 | 298 | 986 | 237 | 67 |
| 12071 | AI009456 | 461 | 177 | 614 | 154 | 67 |
| 3191 | AI013075 | 299 | 132 | 234 | 67 | 67 |
| 13899 | AI230424 | 111 | 45 | 75 | 33 | 67 |
| 23159 | AA925318 | 354 | 105 | 275 | 80 | 67 |
| 7451 | AI029450 | 1306 | 478 | 1027 | 239 | 67 |
| 18434 | AA924413 | 561 | 238 | 770 | 228 | 67 |
| 1335 | AI169105 | 1126 | 266 | 1315 | 219 | 67 |
| 3411 | AA998638 | 1457 | 464 | 1817 | 408 | 67 |
| 7252 | AI235058 | 112 | 55 | 75 | 25 | 67 |
| 23608 | AI233190 | 587 | 316 | 353 | 139 | 67 |
| 15365 | AI177598 | 890 | 324 | 666 | 131 | 67 |
| 6151 | AA819199 | 24 | 18 | 10 | 20 | 67 |
| 10184 | H33426 | 95 | 55 | 130 | 45 | 67 |
| 9136 | AA891226 | 331 | 88 | 278 | 58 | 67 |
| 22283 | AA945172 | 332 | 136 | 461 | 161 | 67 |
| 20895 | AI230549 | 138 | 77 | 178 | 60 | 67 |
| 17104 | M29358 | 491 | 137 | 397 | 86 | 67 |
| 22604 | AA945578 | 961 | 687 | 1000 | 372 | 67 |
| 18349 | AA799744 | 87 | 43 | 67 | 20 | 67 |
| 21092 | AA800380 | 2322 | 913 | 2692 | 609 | 67 |
| 17997 | AA800671 | 167 | 36 | 197 | 37 | 67 |
| 14191 | AA858924 | 63 | 40 | 66 | 24 | 67 |
| 24225 | AA925490 | 298 | 114 | 351 | 80 | 67 |
| 24654 | AA819333 | 69 | 34 | 51 | 21 | 67 |
| 13874 | AI229832 | 61 | 33 | 39 | 17 | 67 |
| 12958 | AI177155 | 882 | 364 | 1171 | 335 | 67 |
| 5082 | D14015 | 33 | 26 | 15 | 20 | 67 |
| 22914 | AA924335 | 974 | 335 | 1133 | 255 | 67 |
| 15259 | AI178135 | 138 | 72 | 91 | 36 | 66 |
| 6911 | D85035 | 184 | 54 | 228 | 49 | 66 |
| 17896 | AA893905 | 94 | 39 | 122 | 36 | 66 |
| 960 | D10026 | 174 | 62 | 208 | 45 | 66 |
| 23182 | AI230981 | 119 | 70 | 175 | 81 | 66 |
| 17879 | AI230741 | 246 | 80 | 317 | 99 | 66 |
| 1973 | M60103 | 271 | 86 | 347 | 84 | 66 |
| 15089 | AI009752 | 200 | 123 | 126 | 52 | 66 |
| 1602 | U76379 | 348 | 121 | 386 | 81 | 66 |
| 23183 | AI144586 | 177 | 102 | 228 | 83 | 66 |
| 8490 | AI059962 | 185 | 95 | 262 | 94 | 66 |
| 15684 | AI171535 | 461 | 206 | 329 | 94 | 66 |
| 4703 | AI231606 | 644 | 398 | 375 | 163 | 66 |
| 25718 | X62145 | 401 | 101 | 336 | 69 | 66 |
| 6686 | AI176130 | 163 | 62 | 124 | 34 | 66 |
| 23260 | AI169617 | 52 | 62 | 17 | 33 | 66 |
| 293 | J05499 | 179 | 80 | 221 | 57 | 66 |
| 24323 | AI104798 | 444 | 143 | 394 | 65 | 66 |
| 22820 | AA848315 | 363 | 163 | 246 | 80 | 66 |
| 11720 | AI232273 | 817 | 407 | 752 | 150 | 66 |
| 14676 | AI234615 | 104 | 38 | 81 | 30 | 66 |
| 9952 | AA891422 | 205 | 57 | 171 | 33 | 66 |
| 11303 | X12752 | 35 | 54 | 74 | 46 | 66 |
| 14234 | AA858928 | 642 | 187 | 509 | 112 | 66 |
| 7537 | AI029829 | 55 | 27 | 76 | 30 | 66 |
| 14670 | AI175528 | 1517 | 594 | 1164 | 283 | 66 |
| 3433 | AI030339 | 839 | 562 | 1072 | 441 | 66 |
| 25057 | M58495 | 24 | 46 | −3 | 14 | 66 |
| 8728 | AA818615 | 112 | 69 | 72 | 23 | 66 |
| 9032 | AI179950 | 713 | 207 | 580 | 117 | 66 |
| 6471 | AA850706 | 352 | 180 | 478 | 164 | 66 |
| 15535 | D10755 | 466 | 119 | 388 | 85 | 66 |
| 2486 | AA964871 | 420 | 258 | 498 | 150 | 66 |
| 2084 | AA998151 | 548 | 210 | 464 | 108 | 66 |
| 18900 | AI233570 | 956 | 234 | 790 | 136 | 66 |
| 25069 | S82820 | 282 | 263 | 142 | 93 | 66 |
| 9433 | AI072917 | 47 | 96 | 112 | 94 | 66 |
| 4091 | AI169417 | 346 | 115 | 280 | 66 | 66 |
| 10229 | AI059618 | 259 | 164 | 384 | 180 | 66 |
| 19187 | AA851230 | 159 | 88 | 105 | 39 | 66 |
| 15879 | AI228313 | 313 | 150 | 311 | 59 | 66 |
| 2057 | AI102579 | 494 | 194 | 376 | 95 | 66 |
| 5873 | AI045767 | 241 | 103 | 302 | 94 | 66 |
| 11455 | M24604 | 80 | 50 | 50 | 45 | 66 |
| 17419 | AI030524 | 203 | 87 | 158 | 53 | 66 |
| 17533 | D00636 | 221 | 109 | 270 | 89 | 66 |
| 21712 | AI169249 | 163 | 75 | 214 | 78 | 66 |
| 15606 | AA944401 | 494 | 135 | 579 | 117 | 66 |
| 23106 | AI145081 | 39 | 48 | 17 | 12 | 66 |
| 4917 | AA924140 | 184 | 67 | 225 | 53 | 66 |
| 20350 | AI232552 | 203 | 70 | 243 | 58 | 66 |
| 13682 | L38482 | 188 | 60 | 146 | 41 | 66 |
| 1430 | M84648 | 66 | 81 | 104 | 62 | 66 |
| 21078 | J02791 | 499 | 213 | 546 | 128 | 66 |
| 15081 | AA859218 | 758 | 234 | 892 | 176 | 66 |
| 1921 | E01524 | 295 | 165 | 165 | 78 | 66 |
| 13966 | AI231421 | 212 | 78 | 164 | 33 | 66 |
| 2539 | AI111960 | 59 | 66 | 23 | 24 | 66 |
| 2242 | AI012635 | 2285 | 1321 | 2363 | 731 | 66 |
| 17091 | U73174 | 76 | 58 | 48 | 22 | 66 |
| 20862 | E01415 | 220 | 94 | 258 | 69 | 66 |
| 19067 | AA859663 | 110 | 46 | 143 | 40 | 66 |
| 25370 | L16995 | 113 | 74 | 154 | 69 | 66 |
| 4896 | AA924000 | 1526 | 375 | 1699 | 277 | 66 |
| 15759 | AF089825 | 143 | 85 | 170 | 59 | 66 |
| 17962 | AB012230 | 69 | 23 | 84 | 26 | 66 |
| 6791 | AA945613 | 3078 | 1419 | 4013 | 1018 | 66 |
| 4462 | AA866264 | 127 | 84 | 189 | 80 | 66 |
| 7161 | AI233407 | 67 | 46 | 42 | 18 | 66 |
| 2388 | AI011806 | 1904 | 518 | 1562 | 304 | 66 |
| 15098 | M31837 | 104 | 41 | 128 | 31 | 66 |
| 3266 | AI171948 | 179 | 58 | 148 | 32 | 66 |
| 19249 | AA997342 | 244 | 124 | 180 | 53 | 66 |
| 9942 | AA942697 | 390 | 127 | 308 | 72 | 66 |
| 5979 | AA817990 | 94 | 42 | 69 | 20 | 66 |
| 6783 | AA996463 | 82 | 59 | 52 | 23 | 66 |
| 11660 | AI178944 | 112 | 46 | 88 | 25 | 66 |
| 2670 | AI012552 | 132 | 92 | 211 | 93 | 66 |
| 2079 | L14462 | 189 | 52 | 214 | 41 | 66 |
| 11324 | AA964832 | 238 | 86 | 298 | 76 | 66 |
| 24181 | AI103320 | 120 | 64 | 78 | 26 | 66 |

TABLE 3-continued

GENERAL — Document Number 1740956.1

| GLGC ID | GenBank Acc | Group Mean | Group SD | Non-Group Mean | Non-Group SD | Discriminant Score |
|---|---|---|---|---|---|---|
| 8132 | AI060050 | 62 | 32 | 43 | 20 | 66 |
| 19728 | AI170394 | 461 | 205 | 538 | 144 | 66 |
| 13434 | AI172552 | 43 | 42 | 73 | 44 | 66 |
| 1698 | J02679 | 309 | 283 | 157 | 69 | 65 |
| 22196 | U21719 | 79 | 50 | 52 | 24 | 65 |
| 24501 | AI232006 | 630 | 155 | 524 | 92 | 65 |
| 23502 | AA998025 | 95 | 66 | 139 | 61 | 65 |
| 5723 | AI045191 | 822 | 465 | 1146 | 440 | 65 |
| 1884 | D50695 | 185 | 54 | 149 | 26 | 65 |
| 2468 | AA964807 | 292 | 105 | 220 | 62 | 65 |
| 7776 | AI028963 | 119 | 58 | 90 | 41 | 65 |
| 4229 | AA946057 | 1126 | 439 | 1260 | 316 | 65 |
| 16809 | X58828 | 57 | 47 | 34 | 21 | 65 |
| 17107 | AI178582 | 2787 | 1171 | 2426 | 715 | 65 |
| 9963 | AI045144 | 554 | 324 | 733 | 264 | 65 |
| 8339 | AI145761 | 66 | 35 | 89 | 34 | 65 |
| 17530 | AA963839 | 194 | 99 | 241 | 80 | 65 |
| 16216 | AA955392 | 243 | 138 | 162 | 56 | 65 |
| 2913 | AI232272 | 989 | 223 | 1096 | 156 | 65 |
| 21164 | AI137488 | 323 | 225 | 382 | 145 | 65 |
| 4190 | AI177016 | 64 | 42 | 42 | 17 | 65 |
| 23524 | J04792 | 109 | 56 | 69 | 43 | 65 |
| 1920 | M10068 | 511 | 273 | 317 | 129 | 65 |
| 3467 | AI237835 | 107 | 61 | 134 | 52 | 65 |
| 11153 | M91652 | 426 | 172 | 499 | 135 | 65 |
| 23606 | U05784 | 442 | 230 | 300 | 97 | 65 |
| 23297 | AI028953 | 434 | 150 | 345 | 95 | 65 |
| 15007 | AA900236 | 403 | 98 | 470 | 106 | 65 |
| 64 | M60655 | 113 | 37 | 139 | 34 | 65 |
| 16465 | AA901042 | 311 | 104 | 394 | 96 | 65 |
| 13785 | AI228970 | 37 | 30 | 24 | 12 | 65 |
| 8303 | AI059352 | 114 | 88 | 144 | 54 | 65 |
| 5608 | AA819041 | 144 | 68 | 103 | 30 | 65 |
| 22370 | AA944158 | 222 | 188 | 252 | 82 | 65 |
| 11067 | AI012397 | 90 | 46 | 68 | 29 | 65 |
| 21462 | AA851261 | 327 | 90 | 264 | 76 | 65 |
| 10019 | AI178756 | 207 | 112 | 151 | 52 | 65 |
| 211 | AA945453 | 630 | 414 | 1060 | 594 | 65 |
| 17768 | AI105196 | 714 | 169 | 820 | 139 | 65 |
| 25281 | D30804 | 168 | 46 | 145 | 29 | 65 |
| 15188 | D16302 | 173 | 41 | 183 | 27 | 65 |
| 23847 | AA956723 | 97 | 42 | 81 | 54 | 65 |
| 14959 | U03390 | 493 | 139 | 399 | 93 | 65 |
| 6188 | AA818774 | 423 | 135 | 515 | 113 | 65 |
| 9267 | AI072384 | 1670 | 724 | 1829 | 446 | 65 |
| 23035 | AA945712 | 524 | 323 | 597 | 161 | 65 |
| 16704 | AA686132 | 543 | 335 | 619 | 227 | 65 |
| 10018 | AA924622 | 207 | 103 | 157 | 53 | 65 |
| 4444 | AI100882 | 473 | 374 | 636 | 300 | 65 |
| 2161 | AI176592 | 591 | 492 | 327 | 181 | 65 |
| 21510 | AA851620 | 320 | 291 | 164 | 121 | 65 |
| 23596 | AI105435 | 1227 | 462 | 1435 | 313 | 65 |
| 24048 | AI170570 | 554 | 300 | 520 | 127 | 65 |
| 6166 | AI136516 | 67 | 55 | 96 | 46 | 65 |
| 7225 | AI013657 | 290 | 151 | 319 | 80 | 65 |
| 9067 | AI070087 | 776 | 281 | 596 | 159 | 65 |
| 3143 | AI232408 | 309 | 104 | 371 | 87 | 65 |
| 1678 | M96674 | 110 | 38 | 132 | 31 | 65 |
| 2629 | Y00396 | 56 | 63 | 30 | 15 | 65 |
| 2702 | AA957307 | 299 | 157 | 213 | 56 | 65 |
| 6472 | AI175880 | −34 | 87 | 46 | 110 | 65 |
| 12606 | M59861 | 540 | 298 | 583 | 212 | 65 |
| 22634 | AA945722 | 24 | 28 | 38 | 24 | 65 |
| 5920 | AI169163 | 489 | 424 | 455 | 165 | 65 |
| 22840 | AI009676 | 861 | 373 | 799 | 206 | 65 |
| 15097 | AI009405 | 23 | 28 | 42 | 24 | 65 |
| 18990 | S72506 | 55 | 73 | 19 | 22 | 65 |
| 4674 | AA899847 | 405 | 212 | 549 | 196 | 65 |
| 16610 | D28557 | 174 | 85 | 133 | 46 | 65 |
| 25701 | X57986 | 121 | 39 | 150 | 38 | 65 |
| 1523 | D26439 | 183 | 42 | 207 | 36 | 65 |
| 4592 | J02646 | 177 | 62 | 142 | 28 | 65 |
| 6164 | AI170597 | 323 | 120 | 356 | 77 | 65 |
| 22846 | AA923982 | 1091 | 334 | 1226 | 237 | 65 |
| 15283 | AA858548 | 768 | 321 | 608 | 137 | 65 |
| 18886 | AA943785 | 202 | 69 | 165 | 50 | 65 |
| 4232 | AI012958 | 101 | 100 | 94 | 31 | 65 |
| 13229 | AA858760 | 167 | 75 | 187 | 47 | 65 |
| 20123 | AI072214 | 239 | 127 | 329 | 98 | 65 |
| 24648 | M74054 | 87 | 24 | 104 | 24 | 65 |
| 6071 | AA892675 | 220 | 99 | 230 | 54 | 65 |
| 14502 | AI232339 | 198 | 65 | 155 | 39 | 65 |
| 4205 | AI011982 | 235 | 121 | 165 | 57 | 65 |
| 17473 | AI009806 | 235 | 100 | 197 | 49 | 65 |
| 12463 | AI232706 | 426 | 130 | 369 | 63 | 65 |
| 13353 | AI175508 | 236 | 78 | 295 | 56 | 65 |
| 8860 | AA945915 | 255 | 118 | 333 | 104 | 65 |
| 6778 | AA964763 | 65 | 34 | 45 | 29 | 65 |
| 15313 | AA875126 | 57 | 52 | 26 | 18 | 65 |
| 16320 | AA859899 | 87 | 29 | 111 | 29 | 65 |
| 10378 | AI233300 | 1513 | 635 | 1524 | 388 | 65 |
| 3023 | AI170795 | 314 | 124 | 390 | 101 | 65 |
| 3242 | AA997596 | 35 | 52 | 67 | 59 | 65 |
| 19991 | AI103956 | 82 | 43 | 58 | 24 | 65 |
| 9432 | AI072914 | 67 | 45 | 44 | 22 | 65 |
| 19150 | AA799461 | 65 | 31 | 50 | 16 | 65 |
| 22855 | AI236150 | 224 | 113 | 266 | 87 | 65 |
| 3417 | AI012337 | 434 | 148 | 352 | 82 | 65 |
| 6382 | AI009362 | 108 | 76 | 65 | 39 | 65 |
| 10532 | AI009602 | 260 | 128 | 241 | 74 | 65 |
| 23192 | AA891107 | 230 | 96 | 182 | 47 | 65 |
| 21353 | AA850247 | 1169 | 444 | 1428 | 304 | 65 |
| 1447 | X55986 | 236 | 56 | 209 | 35 | 65 |
| 19936 | AA956517 | 482 | 153 | 569 | 142 | 65 |
| 18755 | AI236599 | 196 | 73 | 148 | 51 | 65 |
| 15018 | AA964688 | 76 | 51 | 50 | 36 | 65 |
| 16125 | AF090134 | 95 | 46 | 109 | 33 | 65 |
| 21864 | H31144 | 39 | 21 | 29 | 14 | 65 |
| 12082 | AB016800 | 243 | 138 | 290 | 108 | 65 |
| 8808 | AI070132 | 315 | 148 | 400 | 112 | 65 |
| 7344 | AI028942 | 129 | 65 | 177 | 55 | 65 |
| 22011 | AI176212 | 92 | 41 | 70 | 20 | 65 |
| 4879 | AA923852 | 81 | 54 | 120 | 52 | 65 |
| 19992 | AI170777 | 750 | 274 | 599 | 147 | 65 |
| 4383 | AI177056 | 75 | 48 | 84 | 29 | 65 |
| 6032 | AA818258 | 60 | 37 | 87 | 42 | 65 |
| 15374 | H34186 | 165 | 53 | 130 | 32 | 65 |
| 268 | U67908 | 31 | 31 | 37 | 18 | 65 |
| 6291 | AI144797 | 918 | 288 | 1049 | 226 | 65 |
| 9029 | D30804 | 361 | 97 | 299 | 62 | 65 |
| 410 | AI008974 | 141 | 92 | 176 | 71 | 65 |
| 671 | U04808 | 16 | 19 | 29 | 18 | 65 |
| 21601 | AA943997 | 139 | 90 | 101 | 38 | 65 |
| 16492 | AI070315 | 777 | 326 | 961 | 230 | 65 |
| 1571 | U05014 | 84 | 62 | 50 | 31 | 65 |
| 11485 | AI235348 | 45 | 44 | 23 | 37 | 65 |
| 12523 | D21800 | 183 | 61 | 146 | 36 | 65 |
| 4588 | AB009636 | 47 | 41 | 55 | 16 | 65 |
| 5496 | AF080468 | 339 | 158 | 406 | 113 | 65 |
| 382 | AF080507 | 235 | 78 | 270 | 60 | 64 |
| 22211 | AI104279 | 635 | 209 | 504 | 98 | 64 |
| 3905 | AI103403 | 489 | 236 | 366 | 97 | 64 |
| 18107 | X94242 | 319 | 73 | 276 | 55 | 64 |
| 19269 | AA851785 | 494 | 155 | 398 | 87 | 64 |
| 6108 | AA891873 | 130 | 43 | 106 | 27 | 64 |
| 5696 | AI045116 | 230 | 118 | 283 | 87 | 64 |
| 12314 | AA945596 | 2076 | 993 | 2157 | 463 | 64 |
| 21851 | AA859330 | 378 | 192 | 467 | 160 | 64 |
| 7022 | AI176041 | 64 | 54 | 29 | 27 | 64 |
| 22747 | AI171832 | 34 | 23 | 49 | 24 | 64 |
| 25078 | U33540 | 260 | 84 | 314 | 85 | 64 |
| 17349 | AI179987 | 932 | 384 | 783 | 193 | 64 |
| 18128 | AA891800 | 106 | 30 | 129 | 27 | 64 |
| 3256 | AI169479 | 1227 | 413 | 980 | 192 | 64 |
| 8520 | AI060052 | 291 | 112 | 347 | 87 | 64 |
| 8438 | AA892986 | 82 | 47 | 107 | 37 | 64 |

TABLE 3-continued

Document Number 1740956.1

| GLGC ID | GenBank Acc | Group Mean | Group SD | Non-Group Mean | Non-Group SD | Discriminant Score |
|---|---|---|---|---|---|---|
| 12551 | AI230056 | 214 | 110 | 244 | 69 | 64 |
| 20864 | AF045464 | 439 | 363 | 324 | 156 | 64 |
| 13701 | AI230180 | 84 | 28 | 68 | 20 | 64 |
| 8210 | S61960 | 179 | 98 | 114 | 51 | 64 |
| 475 | AI233828 | 892 | 250 | 1050 | 175 | 64 |
| 23836 | AI105088 | 61 | 55 | 35 | 24 | 64 |
| 20056 | AI639504 | 99 | 28 | 118 | 27 | 64 |
| 18991 | AA945082 | 35 | 35 | 20 | 13 | 64 |
| 9595 | AI136630 | 177 | 91 | 179 | 53 | 64 |
| 5464 | AI044345 | 242 | 163 | 306 | 133 | 64 |
| 9719 | AI071722 | 229 | 119 | 152 | 84 | 64 |
| 4781 | AI233925 | 193 | 91 | 147 | 43 | 64 |
| 11326 | AI029015 | 79 | 47 | 104 | 43 | 64 |
| 23682 | AI234973 | 298 | 112 | 228 | 81 | 64 |
| 2297 | AI103602 | 825 | 331 | 1016 | 290 | 64 |
| 4115 | AI008890 | 106 | 104 | 70 | 67 | 64 |
| 19438 | AA819450 | 248 | 184 | 347 | 170 | 64 |
| 14013 | AI231992 | 83 | 62 | 42 | 47 | 64 |
| 17386 | AI169144 | 233 | 124 | 157 | 61 | 64 |
| 11057 | AI071509 | 71 | 46 | 43 | 31 | 64 |
| 18038 | U39943 | 190 | 72 | 230 | 55 | 64 |
| 13332 | AA893080 | 175 | 78 | 218 | 65 | 64 |
| 21090 | AB005547 | 134 | 60 | 146 | 39 | 64 |
| 23448 | AA925167 | 1502 | 1245 | 869 | 674 | 64 |
| 16007 | AF062594 | 25 | 21 | 12 | 11 | 64 |
| 21305 | AA893082 | 135 | 41 | 161 | 40 | 64 |
| 2818 | AI179144 | 361 | 103 | 298 | 57 | 64 |
| 11050 | AA956164 | 643 | 237 | 504 | 143 | 64 |
| 8283 | AI059290 | 135 | 97 | 93 | 39 | 64 |
| 10281 | AI059947 | 102 | 72 | 147 | 66 | 64 |
| 21604 | AI013913 | 731 | 268 | 895 | 228 | 64 |
| 10667 | AI236366 | 121 | 268 | −32 | 111 | 64 |
| 15663 | AI175566 | 81 | 56 | 56 | 20 | 64 |
| 15312 | AA875126 | 34 | 35 | 13 | 13 | 64 |
| 19370 | AA963797 | 237 | 81 | 282 | 66 | 64 |
| 1496 | U56839 | 171 | 76 | 173 | 46 | 64 |
| 14102 | AI232131 | 425 | 122 | 488 | 95 | 64 |
| 12563 | AA964533 | 118 | 52 | 91 | 29 | 64 |
| 23417 | AB022209 | 235 | 72 | 194 | 34 | 64 |
| 8515 | AA849917 | 726 | 351 | 772 | 207 | 64 |
| 22866 | AI233754 | 389 | 118 | 307 | 78 | 64 |
| 1928 | U10357 | 221 | 88 | 262 | 62 | 64 |
| 18562 | AI175515 | 976 | 255 | 1139 | 267 | 64 |
| 4312 | AB010635 | 122 | 149 | 44 | 46 | 64 |
| 1460 | S76054 | 289 | 133 | 226 | 43 | 64 |
| 19993 | AI170777 | 510 | 206 | 376 | 140 | 64 |
| 13167 | AI145832 | 95 | 40 | 115 | 33 | 64 |
| 2330 | AA964292 | 32 | 19 | 23 | 18 | 64 |
| 20422 | AI111858 | 3 | 34 | 28 | 37 | 64 |
| 1557 | AB000216 | 37 | 24 | 50 | 21 | 64 |
| 14594 | AI236152 | 32 | 44 | 47 | 31 | 64 |
| 18036 | U40004 | 207 | 86 | 256 | 67 | 64 |
| 14987 | AA858640 | 554 | 202 | 454 | 117 | 64 |
| 15465 | AI236280 | 587 | 191 | 700 | 168 | 64 |
| 24170 | AI145601 | 85 | 54 | 120 | 50 | 64 |
| 6390 | AA858821 | 84 | 58 | 50 | 30 | 64 |
| 4107 | AA899109 | 167 | 128 | 180 | 48 | 64 |
| 11876 | AI009321 | 84 | 63 | 51 | 25 | 64 |
| 23299 | AI176839 | 286 | 229 | 166 | 69 | 64 |
| 23080 | AA957423 | 824 | 494 | 1105 | 435 | 64 |
| 2888 | AA924902 | 2379 | 1111 | 2655 | 600 | 64 |
| 1653 | AI233806 | 365 | 104 | 411 | 91 | 64 |
| 11152 | M91652 | 244 | 115 | 291 | 79 | 64 |
| 24138 | AI169160 | 105 | 32 | 90 | 21 | 64 |
| 16126 | AF090134 | 18 | 18 | 24 | 14 | 64 |
| 18927 | AA848813 | 896 | 610 | 551 | 204 | 64 |
| 25814 | M59460 | 98 | 51 | 144 | 59 | 64 |
| 3516 | AI175064 | 175 | 102 | 155 | 52 | 64 |
| 16053 | AI228596 | 374 | 526 | 124 | 61 | 64 |
| 17721 | AA945762 | 256 | 101 | 315 | 84 | 64 |
| 16449 | M95591 | 216 | 163 | 299 | 125 | 64 |
| 14939 | AI228557 | 69 | 54 | 43 | 25 | 64 |
| 22303 | AI179779 | 72 | 42 | 84 | 35 | 64 |
| 4242 | AA893325 | 344 | 172 | 444 | 154 | 64 |
| 3434 | AI232014 | 597 | 380 | 756 | 317 | 64 |
| 14520 | AI178785 | 740 | 289 | 907 | 268 | 64 |
| 24233 | AA964756 | 694 | 294 | 855 | 217 | 64 |
| 17664 | AI234496 | 381 | 271 | 239 | 90 | 64 |
| 20797 | AA924310 | 615 | 243 | 748 | 177 | 64 |
| 11937 | AI137218 | 119 | 36 | 98 | 23 | 64 |
| 5926 | AI177638 | 53 | 24 | 38 | 17 | 64 |
| 13932 | AI230988 | 28 | 85 | 77 | 39 | 64 |
| 15371 | AA875205 | 281 | 74 | 234 | 42 | 64 |
| 17161 | AA892333 | 721 | 318 | 521 | 185 | 64 |
| 5998 | AI639501 | 164 | 55 | 198 | 49 | 64 |
| 13646 | X62166 | 644 | 199 | 526 | 156 | 64 |
| 20090 | AI639353 | 133 | 64 | 108 | 26 | 64 |
| 8784 | AI103007 | 154 | 81 | 182 | 54 | 64 |
| 23068 | AA926036 | 481 | 270 | 540 | 173 | 64 |
| 4511 | AA944348 | 170 | 88 | 194 | 62 | 64 |
| 10187 | AI176781 | 183 | 79 | 233 | 75 | 64 |
| 19035 | AI236576 | 291 | 123 | 220 | 82 | 64 |
| 6945 | AI229467 | 126 | 38 | 149 | 32 | 64 |
| 15088 | AI232613 | 98 | 46 | 74 | 24 | 64 |
| 12108 | AA848963 | 273 | 97 | 317 | 83 | 64 |
| 3233 | AA818105 | 395 | 148 | 317 | 68 | 64 |
| 22592 | AI013740 | 85 | 89 | 36 | 47 | 64 |
| 14738 | AI176993 | 1316 | 501 | 1356 | 269 | 64 |
| 1901 | AA817849 | 583 | 311 | 668 | 214 | 64 |
| 18837 | AI171583 | 242 | 105 | 298 | 88 | 64 |
| 6047 | AI073230 | −33 | 107 | 24 | 91 | 64 |
| 9621 | AI175486 | 280 | 84 | 230 | 47 | 64 |
| 21052 | M15481 | 218 | 94 | 279 | 87 | 64 |
| 21822 | AI228642 | 393 | 143 | 331 | 69 | 64 |
| 6501 | AI009724 | 559 | 254 | 755 | 280 | 64 |
| 14384 | AI177096 | 251 | 82 | 214 | 39 | 64 |
| 13317 | AI103637 | 59 | 37 | 43 | 27 | 64 |
| 22876 | AI172041 | 50 | 21 | 36 | 17 | 64 |
| 3655 | AA818183 | 133 | 71 | 97 | 31 | 64 |
| 17159 | J00797 | 387 | 151 | 293 | 84 | 64 |
| 9254 | AA892470 | 158 | 47 | 178 | 33 | 64 |
| 23224 | AI146033 | 248 | 125 | 179 | 53 | 64 |
| 15654 | AA799501 | 311 | 118 | 265 | 73 | 64 |
| 20880 | L46791 | 295 | 159 | 355 | 118 | 64 |
| 15146 | AI176969 | 177 | 108 | 231 | 100 | 64 |
| 16943 | AI236097 | 1778 | 496 | 2116 | 434 | 64 |
| 16684 | D17445 | 329 | 118 | 276 | 64 | 64 |
| 356 | S66024 | 140 | 99 | 143 | 40 | 64 |
| 9674 | AI178784 | 540 | 497 | 263 | 217 | 64 |
| 14462 | AI100871 | 86 | 52 | 55 | 29 | 64 |
| 14910 | AI177631 | 176 | 50 | 150 | 35 | 64 |
| 18421 | AA945617 | 1189 | 340 | 1255 | 203 | 64 |
| 16321 | AI231506 | 151 | 62 | 115 | 31 | 64 |
| 3082 | AA999172 | 276 | 133 | 208 | 62 | 64 |
| 1521 | M63122 | 173 | 85 | 137 | 43 | 64 |
| 1588 | S61865 | 197 | 80 | 209 | 45 | 64 |
| 15281 | D13623 | 237 | 112 | 182 | 46 | 64 |
| 23579 | AI171802 | 628 | 167 | 685 | 116 | 64 |
| 15907 | AA996422 | 223 | 96 | 281 | 83 | 64 |
| 15193 | AI229508 | 180 | 77 | 134 | 42 | 64 |
| 7870 | AI101319 | 100 | 53 | 120 | 46 | 64 |
| 2578 | D50694 | 173 | 48 | 148 | 28 | 64 |
| 15718 | U75689 | 69 | 31 | 90 | 30 | 64 |
| 3148 | AI007881 | 99 | 55 | 77 | 30 | 64 |
| 7497 | AI169302 | 1700 | 414 | 1792 | 268 | 64 |
| 10710 | AI030494 | 138 | 98 | 165 | 56 | 64 |
| 5339 | AI171727 | 685 | 582 | 454 | 138 | 64 |
| 14003 | S65555 | 144 | 93 | 145 | 46 | 64 |
| 15543 | AI231800 | 269 | 113 | 202 | 47 | 64 |
| 15496 | AI232370 | 77 | 28 | 62 | 17 | 64 |
| 5091 | AI073092 | 212 | 100 | 285 | 115 | 64 |
| 23644 | AA957808 | 61 | 42 | 85 | 39 | 64 |
| 20775 | AI175494 | 309 | 126 | 267 | 79 | 64 |
| 494 | Z24721 | 29 | 41 | 56 | 37 | 64 |
| 22310 | AI102194 | 221 | 77 | 178 | 58 | 64 |
| 13294 | AI233731 | 418 | 150 | 332 | 84 | 64 |

TABLE 3-continued

Document Number 1740956.1

GENERAL

| GLGC ID | GenBank Acc | Group Mean | Group SD | Non-Group Mean | Non-Group SD | Discriminant Score |
|---|---|---|---|---|---|---|
| 5897 | AI045862 | 31 | 30 | 14 | 21 | 64 |
| 2296 | AI112979 | 812 | 292 | 955 | 241 | 64 |
| 17368 | AA900548 | 140 | 73 | 109 | 35 | 64 |
| 2140 | AI172272 | 68 | 54 | 91 | 45 | 64 |
| 15292 | AF012714 | 189 | 79 | 147 | 32 | 64 |
| 23440 | AA924881 | 106 | 119 | 194 | 142 | 64 |
| 16484 | AI169116 | 86 | 57 | 67 | 34 | 64 |
| 5952 | AA963102 | 152 | 146 | 68 | 45 | 64 |
| 4479 | AI111599 | 275 | 173 | 179 | 75 | 64 |
| 4235 | AI104524 | 325 | 110 | 258 | 59 | 64 |
| 13393 | AI234100 | 73 | 66 | 108 | 64 | 64 |
| 1431 | AI044610 | 310 | 236 | 425 | 180 | 64 |
| 4849 | AA901155 | 725 | 204 | 601 | 129 | 64 |
| 2653 | AA964319 | 34 | 33 | 53 | 32 | 64 |
| 6002 | AA818101 | 96 | 36 | 73 | 20 | 64 |
| 9309 | AA963794 | 162 | 96 | 120 | 46 | 64 |
| 12184 | AI170621 | 207 | 69 | 227 | 47 | 64 |
| 10396 | AI070294 | 141 | 71 | 120 | 46 | 64 |
| 11150 | AA852004 | 142 | 78 | 171 | 63 | 64 |
| 23491 | AA944422 | 141 | 79 | 130 | 40 | 64 |
| 7436 | AA848354 | 220 | 130 | 158 | 56 | 64 |
| 18682 | AI059499 | 473 | 180 | 375 | 105 | 64 |
| 12223 | AI171266 | 231 | 66 | 184 | 50 | 64 |
| 6844 | AI009770 | 38 | 47 | 58 | 39 | 64 |
| 18829 | AA818796 | 122 | 78 | 111 | 35 | 64 |
| 23163 | AA925328 | 22 | 19 | 32 | 18 | 64 |
| 14254 | AI103988 | 35 | 24 | 23 | 23 | 64 |
| 13382 | AI101527 | 110 | 84 | 67 | 36 | 64 |
| 22612 | AA945624 | 262 | 114 | 318 | 85 | 64 |
| 13618 | AI230724 | 116 | 52 | 86 | 24 | 64 |
| 23099 | AI112365 | 122 | 60 | 89 | 29 | 64 |
| 43 | L23413 | 325 | 126 | 361 | 73 | 64 |
| 22548 | AA945031 | 506 | 275 | 512 | 189 | 64 |
| 17590 | AA892851 | 137 | 71 | 103 | 30 | 64 |
| 22503 | AA944823 | 121 | 77 | 144 | 54 | 64 |
| 24234 | U63923 | 173 | 105 | 123 | 34 | 64 |
| 1125 | D82071 | 38 | 23 | 48 | 19 | 64 |
| 12524 | D21800 | 370 | 98 | 310 | 65 | 64 |
| 15181 | AI235234 | 69 | 35 | 81 | 26 | 64 |
| 7859 | AI043660 | 78 | 32 | 63 | 28 | 64 |
| 7362 | AI029026 | 747 | 297 | 906 | 214 | 64 |
| 16416 | AA875098 | 132 | 70 | 102 | 23 | 64 |
| 23783 | AA892773 | 383 | 120 | 448 | 103 | 64 |
| 6638 | AI137579 | 67 | 41 | 83 | 27 | 64 |
| 23536 | AI175558 | 61 | 63 | 28 | 35 | 64 |
| 23203 | AA799971 | 99 | 46 | 109 | 34 | 64 |
| 17301 | M69246 | 29 | 44 | 35 | 23 | 64 |
| 17517 | L12383 | 307 | 92 | 271 | 51 | 64 |
| 17514 | AA925554 | 401 | 158 | 504 | 126 | 64 |
| 23547 | AI176734 | 193 | 72 | 156 | 47 | 64 |
| 10310 | AI176961 | 319 | 129 | 248 | 72 | 63 |
| 13282 | K03041 | 169 | 61 | 213 | 60 | 63 |
| 14021 | AA848834 | 422 | 222 | 278 | 162 | 63 |
| 18425 | AI230208 | 814 | 210 | 917 | 157 | 63 |
| 16780 | X62660 | 292 | 197 | 265 | 61 | 63 |
| 14258 | AI229902 | 95 | 57 | 78 | 25 | 63 |
| 8837 | AI102849 | 191 | 69 | 228 | 52 | 63 |
| 5995 | AI232565 | 27 | 20 | 39 | 18 | 63 |
| 17448 | AI229637 | 79 | 48 | 57 | 31 | 63 |
| 25090 | X63594 | 80 | 45 | 57 | 29 | 63 |
| 373 | D86086 | 375 | 190 | 393 | 125 | 63 |
| 23320 | AA955164 | 224 | 123 | 214 | 70 | 63 |
| 13952 | AA858886 | 47 | 32 | 40 | 17 | 63 |
| 23865 | AI102760 | 44 | 31 | 64 | 30 | 63 |
| 22351 | AA945867 | 41 | 55 | 17 | 18 | 63 |
| 11844 | AA859473 | 43 | 40 | 62 | 34 | 63 |
| 14528 | AI237718 | 246 | 104 | 318 | 104 | 63 |
| 15090 | AA859224 | 81 | 33 | 64 | 21 | 63 |
| 17092 | AA893189 | 108 | 56 | 82 | 25 | 63 |
| 5059 | AI236947 | 97 | 107 | 50 | 35 | 63 |
| 21380 | AA800739 | 93 | 37 | 73 | 24 | 63 |
| 23512 | AA955282 | 651 | 271 | 802 | 238 | 63 |
| 22854 | AI112101 | 1301 | 360 | 1458 | 307 | 63 |
| 17549 | AA892776 | 564 | 153 | 473 | 101 | 63 |
| 10533 | AI058430 | 532 | 257 | 437 | 136 | 63 |
| 20529 | L32132 | 216 | 256 | 101 | 53 | 63 |
| 4005 | AI177481 | 153 | 110 | 186 | 84 | 63 |
| 17832 | AI012182 | 2182 | 1181 | 2668 | 985 | 63 |
| 18672 | AI178189 | 105 | 42 | 79 | 28 | 63 |
| 17753 | AI103246 | 210 | 88 | 169 | 47 | 63 |
| 10999 | AI071110 | 43 | 33 | 51 | 23 | 63 |
| 20646 | AI237641 | 345 | 120 | 272 | 83 | 63 |
| 18831 | AI104357 | 2851 | 1127 | 2461 | 635 | 63 |
| 16656 | AI179634 | 389 | 95 | 329 | 85 | 63 |
| 17644 | AA924036 | 119 | 80 | 134 | 55 | 63 |
| 25725 | X62660 | 149 | 109 | 136 | 34 | 63 |
| 21382 | AA945708 | 124 | 55 | 170 | 62 | 63 |
| 23149 | AI171213 | 41 | 20 | 31 | 11 | 63 |
| 11191 | AI013042 | 691 | 655 | 1129 | 739 | 63 |
| 17684 | AA892345 | 251 | 98 | 284 | 64 | 63 |
| 16706 | AI180032 | 218 | 92 | 174 | 43 | 63 |
| 9325 | AI072617 | 202 | 97 | 154 | 45 | 63 |
| 6438 | AA819269 | 145 | 72 | 187 | 60 | 63 |
| 15127 | S56937 | 724 | 460 | 484 | 164 | 63 |
| 21993 | AA943149 | 58 | 36 | 42 | 16 | 63 |
| 6508 | AI013900 | 397 | 149 | 333 | 102 | 63 |
| 9128 | AI171611 | 131 | 63 | 98 | 28 | 63 |
| 23983 | AI229708 | 865 | 282 | 950 | 197 | 63 |
| 13574 | AA892557 | 234 | 72 | 281 | 81 | 63 |
| 21818 | AF036537 | 31 | 30 | 16 | 16 | 63 |
| 21679 | AA799691 | 64 | 32 | 73 | 24 | 63 |
| 23869 | U75397 | 98 | 119 | 53 | 49 | 63 |
| 13563 | AI233773 | 1187 | 620 | 1256 | 293 | 63 |
| 11419 | AI171365 | 41 | 26 | 29 | 15 | 63 |
| 6502 | AI178283 | 533 | 152 | 441 | 105 | 63 |
| 17394 | J03969 | 332 | 112 | 267 | 59 | 63 |
| 1801 | AA858636 | 90 | 37 | 69 | 15 | 63 |
| 18890 | AA899964 | 714 | 568 | 684 | 222 | 63 |
| 12766 | AI012505 | 600 | 223 | 776 | 214 | 63 |
| 10020 | AI045632 | 125 | 99 | 147 | 77 | 63 |
| 15011 | AA799893 | 99 | 39 | 85 | 26 | 63 |
| 355 | S66024 | 67 | 57 | 71 | 25 | 63 |
| 16419 | AA875102 | 226 | 65 | 199 | 35 | 63 |
| 1809 | AA946503 | 304 | 948 | 6 | 46 | 63 |
| 14109 | AI233227 | 31 | 17 | 36 | 13 | 63 |
| 21660 | AI169751 | 1825 | 1048 | 1743 | 480 | 63 |
| 17766 | AA851299 | 433 | 155 | 437 | 99 | 63 |
| 5360 | AI011763 | 621 | 236 | 723 | 199 | 63 |
| 12276 | AA892541 | 24 | 20 | 38 | 21 | 63 |
| 7067 | AI229655 | 260 | 78 | 305 | 66 | 63 |
| 18674 | AA849603 | 123 | 56 | 150 | 43 | 63 |
| 6919 | AI010461 | 451 | 464 | 241 | 123 | 63 |
| 13446 | AI230625 | 55 | 52 | 26 | 19 | 63 |
| 6237 | AA819288 | 579 | 286 | 653 | 182 | 63 |
| 2133 | AA894193 | 48 | 23 | 60 | 23 | 63 |
| 22251 | AA957037 | 90 | 40 | 79 | 32 | 63 |
| 23868 | AF023087 | 269 | 258 | 152 | 134 | 63 |
| 23872 | M18416 | 112 | 138 | 59 | 60 | 63 |
| 19412 | AA849222 | 469 | 190 | 366 | 88 | 63 |
| 2619 | AI231290 | 156 | 79 | 113 | 48 | 63 |
| 11559 | AI030472 | 290 | 118 | 342 | 88 | 63 |
| 21933 | AI029057 | 5110 | 2449 | 5109 | 1727 | 63 |
| 21672 | AA891789 | 381 | 125 | 327 | 71 | 63 |
| 891 | U66322 | 37 | 78 | 55 | 41 | 63 |
| 23776 | AI060224 | 103 | 70 | 132 | 62 | 63 |
| 6826 | AI009493 | 398 | 210 | 509 | 188 | 63 |
| 7584 | AI043724 | 778 | 686 | 889 | 415 | 63 |
| 3106 | AA997109 | 51 | 54 | 25 | 27 | 63 |
| 21066 | D10587 | 79 | 30 | 66 | 17 | 63 |
| 21839 | AI071644 | 212 | 122 | 142 | 40 | 63 |
| 13054 | AI179560 | 65 | 25 | 49 | 20 | 63 |
| 2373 | AA964455 | 340 | 181 | 273 | 91 | 63 |
| 7182 | AI010450 | 175 | 64 | 149 | 44 | 63 |
| 4452 | AI011196 | 875 | 323 | 1089 | 281 | 63 |
| 7913 | AI043849 | 183 | 113 | 132 | 46 | 63 |
| 18401 | AI104300 | 894 | 234 | 788 | 152 | 63 |

TABLE 3-continued

GENERAL — Document Number 1740956.1

| GLGC ID | GenBank Acc | Group Mean | Group SD | Non-Group Mean | Non-Group SD | Discriminant Score |
|---|---|---|---|---|---|---|
| 21321 | AI233902 | 73 | 52 | 105 | 57 | 63 |
| 2691 | AA965075 | 196 | 85 | 145 | 59 | 63 |
| 21748 | AA850777 | 74 | 44 | 102 | 48 | 63 |
| 18718 | M33329 | 599 | 397 | 638 | 274 | 63 |
| 8715 | AI069920 | 1756 | 1298 | 1474 | 396 | 63 |
| 15703 | AB009372 | 138 | 59 | 132 | 35 | 63 |
| 6479 | AI169690 | 1107 | 648 | 1113 | 361 | 63 |
| 8592 | H33491 | 283 | 109 | 319 | 78 | 63 |
| 23494 | AI170967 | 102 | 48 | 123 | 43 | 63 |
| 17849 | AA900460 | 1152 | 408 | 938 | 219 | 63 |
| 16450 | M95591 | 191 | 85 | 231 | 70 | 63 |
| 23768 | AI011709 | 214 | 113 | 159 | 56 | 63 |
| 18369 | AA799645 | 130 | 56 | 164 | 41 | 63 |
| 21683 | M65149 | 36 | 49 | 12 | 15 | 63 |
| 12577 | AI111344 | 273 | 297 | 130 | 88 | 63 |
| 23656 | AI044533 | 147 | 60 | 111 | 51 | 63 |
| 6614 | AA848389 | 771 | 327 | 1015 | 234 | 63 |
| 23229 | AI234038 | 339 | 134 | 324 | 71 | 63 |
| 2587 | AI232103 | 1613 | 575 | 1763 | 372 | 63 |
| 19230 | AI059604 | 204 | 116 | 177 | 82 | 63 |
| 17210 | AI233746 | 98 | 59 | 69 | 23 | 63 |
| 18529 | AI230716 | 89 | 69 | 62 | 25 | 63 |
| 18205 | AI044836 | 341 | 91 | 287 | 73 | 63 |
| 15558 | AA875537 | 296 | 96 | 251 | 50 | 63 |
| 21391 | AI013902 | 154 | 143 | 73 | 60 | 63 |
| 4040 | AI179993 | 39 | 32 | 22 | 18 | 63 |
| 22607 | AA945580 | 779 | 326 | 924 | 225 | 63 |
| 2352 | AI104325 | 472 | 125 | 548 | 119 | 63 |
| 5460 | AI176944 | 80 | 40 | 107 | 30 | 63 |
| 13633 | AI012335 | 524 | 198 | 402 | 139 | 63 |
| 26051 | AA894316 | 78 | 40 | 92 | 31 | 63 |
| 21254 | AI170059 | 145 | 54 | 162 | 42 | 63 |
| 5593 | AI230698 | 105 | 38 | 88 | 31 | 63 |
| 16397 | AA850155 | 34 | 24 | 21 | 21 | 63 |
| 4001 | AI102070 | 656 | 130 | 743 | 123 | 63 |
| 13162 | AI172269 | 41 | 95 | −11 | 62 | 63 |
| 26045 | AA893803 | 25 | 17 | 35 | 14 | 63 |
| 16781 | AI234527 | 345 | 252 | 322 | 80 | 63 |
| 9800 | AI072014 | 128 | 92 | 86 | 53 | 63 |
| 11514 | AI171855 | 239 | 81 | 210 | 49 | 63 |
| 17553 | AI103643 | 83 | 44 | 58 | 39 | 63 |
| 1919 | AI137856 | 296 | 160 | 186 | 77 | 63 |
| 15218 | AI102495 | 1625 | 357 | 1854 | 348 | 63 |
| 15914 | AA997711 | 86 | 49 | 56 | 35 | 63 |
| 7219 | AI232900 | 1043 | 247 | 1189 | 240 | 63 |
| 16561 | AI137862 | 226 | 65 | 202 | 39 | 63 |
| 13369 | D21132 | 179 | 38 | 154 | 29 | 63 |
| 18266 | AI234256 | 873 | 197 | 811 | 127 | 63 |
| 14591 | AA892847 | 70 | 25 | 84 | 25 | 63 |
| 21400 | M36410 | 269 | 62 | 282 | 45 | 63 |
| 5999 | AA819138 | 510 | 220 | 606 | 174 | 63 |
| 1841 | AI113289 | 81 | 74 | 46 | 26 | 63 |
| 15679 | AI011058 | 169 | 87 | 130 | 50 | 63 |
| 11483 | AF020618 | 63 | 83 | 23 | 22 | 63 |
| 24049 | AI177341 | 1819 | 925 | 1499 | 378 | 63 |
| 7403 | AI029212 | 1229 | 567 | 1569 | 433 | 63 |
| 6816 | AI103458 | 153 | 58 | 123 | 34 | 63 |
| 13782 | AI177848 | 56 | 29 | 67 | 24 | 63 |
| 4801 | AA900981 | 201 | 64 | 230 | 50 | 63 |
| 13670 | AI227734 | 87 | 42 | 110 | 35 | 63 |
| 23078 | AI229647 | 81 | 32 | 98 | 27 | 63 |
| 22375 | AI230046 | 77 | 41 | 60 | 24 | 63 |
| 5789 | AI044718 | 90 | 50 | 69 | 58 | 63 |
| 17618 | AI236786 | 178 | 49 | 186 | 38 | 63 |
| 9339 | AI101160 | 322 | 82 | 275 | 58 | 63 |
| 3665 | AI009376 | 214 | 98 | 164 | 62 | 63 |
| 14600 | AA801076 | 151 | 126 | 106 | 28 | 63 |
| 24433 | M16407 | 43 | 30 | 29 | 20 | 63 |
| 18524 | AA946017 | 1036 | 341 | 1204 | 238 | 63 |
| 15401 | AA875257 | 71 | 41 | 52 | 21 | 63 |
| 16898 | AI170249 | 57 | 25 | 64 | 18 | 63 |
| 20431 | S81448 | 212 | 128 | 275 | 121 | 63 |
| 12616 | AA997599 | 44 | 33 | 51 | 25 | 63 |
| 15383 | AA955358 | 100 | 53 | 128 | 44 | 63 |
| 4926 | AI175034 | 352 | 118 | 303 | 89 | 63 |
| 5488 | AI229684 | 735 | 152 | 805 | 112 | 63 |
| 12965 | AI112926 | 84 | 71 | 53 | 28 | 63 |
| 3535 | AA999135 | 21 | 24 | 9 | 23 | 63 |
| 22266 | AA945601 | 1538 | 482 | 1660 | 309 | 63 |
| 2997 | AI030545 | 307 | 166 | 357 | 109 | 63 |
| 12628 | AA998123 | 221 | 124 | 315 | 148 | 63 |
| 23029 | AA944935 | 477 | 364 | 768 | 455 | 63 |
| 21196 | AI044873 | 16 | 26 | 22 | 21 | 63 |
| 16 | AI009426 | 482 | 310 | 407 | 123 | 63 |
| 23245 | AI179570 | 484 | 161 | 438 | 82 | 63 |
| 23355 | AA848530 | 98 | 66 | 61 | 36 | 63 |
| 5953 | AI171231 | 394 | 467 | 140 | 128 | 63 |
| 14933 | H31588 | 52 | 32 | 66 | 27 | 63 |
| 12613 | H31620 | 125 | 80 | 86 | 33 | 63 |
| 22540 | AA924630 | 2418 | 901 | 2801 | 730 | 63 |
| 7171 | AI012761 | 222 | 113 | 231 | 72 | 63 |
| 1279 | U75916 | 49 | 34 | 52 | 19 | 63 |
| 22213 | AI234858 | 364 | 103 | 328 | 58 | 63 |
| 22655 | AA944308 | 58 | 35 | 41 | 33 | 63 |
| 22142 | AA943066 | 30 | 27 | 39 | 21 | 63 |
| 23055 | AA942929 | 62 | 67 | 91 | 71 | 63 |
| 13697 | AI176718 | 50 | 23 | 59 | 19 | 63 |
| 9150 | AI009198 | 556 | 161 | 474 | 104 | 63 |
| 23515 | AI179498 | 459 | 222 | 348 | 100 | 63 |
| 6295 | AA819672 | 1303 | 895 | 1081 | 276 | 63 |
| 26133 | AI009950 | 258 | 198 | 143 | 98 | 63 |
| 2677 | AA963443 | 77 | 49 | 92 | 41 | 63 |
| 21586 | X97772 | 43 | 38 | 24 | 19 | 63 |
| 22081 | AA944818 | 82 | 50 | 88 | 32 | 63 |
| 22867 | AA892353 | 200 | 61 | 236 | 48 | 63 |
| 19105 | AA859230 | 884 | 291 | 757 | 142 | 63 |
| 3917 | AI232970 | 1655 | 690 | 1634 | 422 | 63 |
| 5930 | AA817688 | 23 | 22 | 11 | 13 | 63 |
| 24108 | AI230728 | 185 | 62 | 145 | 43 | 63 |
| 14550 | AI104146 | 40 | 28 | 26 | 22 | 63 |
| 7916 | AI043855 | 537 | 252 | 625 | 177 | 63 |
| 5108 | AA925264 | 16 | 25 | 26 | 24 | 63 |
| 18141 | AI177413 | 436 | 318 | 288 | 95 | 63 |
| 23360 | AA955104 | 158 | 66 | 178 | 49 | 63 |
| 1603 | X78855 | 349 | 142 | 387 | 101 | 63 |
| 25198 | AF069782 | 35 | 35 | 18 | 13 | 63 |
| 15286 | AI169361 | 506 | 108 | 452 | 83 | 63 |
| 6057 | AI172102 | 150 | 150 | 90 | 52 | 63 |
| 20386 | U68562 | 259 | 106 | 200 | 54 | 63 |
| 1962 | AB000199 | 239 | 83 | 286 | 94 | 63 |
| 23344 | AA800034 | 345 | 132 | 301 | 70 | 63 |

TABLE 3T

HYDRAZINE — Document Number 1740956.1

Timepoints (hrs) 3, 6, 24

| GLGC ID | GenBank Acc | Group Mean | Group SD | NonGroup Mean | NonGroup SD | Discriminant Score |
|---|---|---|---|---|---|---|
| 23709 | AI112173 | 1101 | 242 | 149 | 107 | 100 |
| 18383 | AA946421 | 1709 | 389 | 690 | 144 | 99 |
| 24798 | X06357 | 1519 | 253 | 432 | 102 | 99 |
| 24800 | M35270 | 462 | 85 | 135 | 48 | 99 |
| 24799 | E01050 | 1196 | 333 | 259 | 65 | 99 |
| 17380 | AA799612 | 501 | 98 | 228 | 38 | 99 |
| 23710 | AI230614 | 427 | 158 | 42 | 51 | 99 |
| 956 | L21711 | 721 | 156 | 254 | 73 | 99 |
| 23711 | AI176376 | 1639 | 606 | 165 | 173 | 99 |

TABLE 3T-continued

HYDRAZINE  Document Number 1740956.1

Timepoints (hrs) 3, 6, 24

| GLGC ID | GenBank Acc | Group Mean | Group SD | NonGroup Mean | NonGroup SD | Discriminant Score |
|---|---|---|---|---|---|---|
| 20744 | J04171 | 1141 | 158 | 270 | 161 | 99 |
| 8182 | AA945608 | 1203 | 48 | 1049 | 519 | 99 |
| 4154 | AI009467 | 556 | 278 | 69 | 50 | 99 |
| 25567 | S85184 | 546 | 172 | 129 | 66 | 99 |
| 6697 | AI045340 | 179 | 38 | 59 | 21 | 99 |
| 3430 | S85184 | 690 | 199 | 206 | 62 | 99 |
| 21043 | AI237813 | 465 | 225 | 68 | 42 | 99 |
| 17227 | Z36980 | 1414 | 109 | 1206 | 642 | 98 |
| 5339 | AI171727 | 1793 | 478 | 486 | 266 | 98 |
| 6477 | J00735 | 1694 | 106 | 1622 | 1091 | 98 |
| 22204 | AI70820 | 739 | 370 | 97 | 58 | 98 |
| 21153 | AI010632 | 2087 | 214 | 1965 | 1296 | 98 |
| 4155 | AI059014 | 250 | 152 | 22 | 25 | 98 |
| 6408 | AA858902 | 63 | 36 | 7 | 11 | 98 |
| 14997 | J03572 | 814 | 304 | 233 | 136 | 98 |
| 11137 | K00750 | 792 | 145 | 327 | 96 | 98 |
| 4234 | AB016536 | 1161 | 206 | 449 | 160 | 98 |
| 23576 | X72757 | 1115 | 93 | 964 | 474 | 98 |
| 1549 | J05519 | 411 | 141 | 173 | 43 | 98 |
| 12119 | AA849354 | 360 | 104 | 120 | 49 | 98 |
| 15621 | J04473 | 663 | 153 | 309 | 67 | 98 |
| 18727 | D13978 | 1423 | 224 | 555 | 235 | 98 |
| 23544 | AA875233 | 1094 | 73 | 992 | 462 | 98 |
| 15292 | AF012714 | 359 | 103 | 153 | 42 | 98 |
| 15558 | AA875537 | 524 | 125 | 257 | 57 | 98 |
| 16163 | D13309 | 648 | 89 | 364 | 76 | 98 |
| 9841 | U94856 | 1671 | 208 | 1510 | 868 | 98 |
| 5989 | AA956907 | 352 | 40 | 179 | 58 | 98 |
| 24219 | L27843 | 759 | 196 | 298 | 100 | 98 |
| 21757 | AI007656 | 140 | 29 | 45 | 25 | 98 |
| 25805 | E01050 | 133 | 31 | 63 | 18 | 98 |
| 6013 | AA818144 | 1464 | 147 | 1384 | 881 | 98 |
| 13959 | AI236696 | 171 | 45 | 13 | 60 | 97 |
| 4090 | S63233 | 976 | 275 | 457 | 109 | 97 |
| 17394 | J03969 | 593 | 150 | 277 | 69 | 97 |
| 6044 | AI011285 | 1316 | 200 | 695 | 195 | 97 |
| 19407 | X02610 | 894 | 220 | 450 | 116 | 97 |
| 11828 | AI170418 | 81 | 31 | 14 | 17 | 97 |
| 15872 | L28135 | 910 | 170 | 382 | 132 | 97 |
| 5990 | AA956907 | 617 | 95 | 332 | 91 | 97 |
| 15371 | AA875205 | 400 | 39 | 242 | 51 | 97 |
| 19392 | X02918 | 1149 | 106 | 1042 | 530 | 97 |
| 17938 | AI010332 | 430 | 77 | 200 | 81 | 97 |
| 634 | K01932 | 1249 | 142 | 1119 | 612 | 97 |
| 22545 | AI009747 | 610 | 157 | 217 | 105 | 97 |
| 7416 | AI230458 | 820 | 98 | 1219 | 252 | 96 |
| 18000 | U19485 | 1453 | 156 | 1504 | 963 | 96 |
| 21015 | X04229 | 2071 | 311 | 2060 | 1473 | 96 |
| 10055 | AI058291 | 98 | 49 | 31 | 22 | 96 |
| 15106 | X57529 | 1565 | 164 | 1287 | 708 | 96 |
| 17211 | M34331 | 1018 | 118 | 943 | 489 | 96 |
| 15080 | AI102045 | 316 | 55 | 647 | 151 | 96 |
| 17742 | AA866302 | 1381 | 150 | 1461 | 976 | 96 |
| 7864 | D10874 | 1265 | 205 | 687 | 189 | 96 |
| 4355 | AI103410 | 134 | 79 | 416 | 106 | 96 |
| 17507 | J03583 | 525 | 71 | 333 | 74 | 96 |
| 20945 | AI171085 | 968 | 59 | 787 | 349 | 96 |
| 14346 | M31109 | 1194 | 160 | 1090 | 547 | 95 |
| 20716 | MI94548 | 1205 | 166 | 1185 | 665 | 95 |
| 25644 | U77931 | 516 | 79 | 273 | 102 | 95 |
| 24251 | AA955887 | 1038 | 756 | 66 | 93 | 95 |
| 7804 | AI233771 | 208 | 118 | −4 | 61 | 95 |
| 20427 | X53378 | 1014 | 161 | 575 | 171 | 95 |
| 22311 | AI176007 | 512 | 285 | 174 | 63 | 95 |
| 24801 | M35270 | 1207 | 291 | 361 | 92 | 95 |
| 24797 | D13667 | 516 | 309 | 71 | 40 | 94 |
| 958 | U72741 | 807 | 316 | 245 | 62 | 94 |
| 23471 | AA955162 | 296 | 209 | 35 | 40 | 94 |
| 18713 | AI012604 | 538 | 115 | 273 | 102 | 94 |
| 1869 | J03959 | 1049 | 110 | 892 | 439 | 94 |
| 1995 | AF038870 | 1616 | 214 | 1395 | 1100 | 94 |
| 2789 | AI234949 | 318 | 115 | 73 | 44 | 94 |
| 24825 | X02741 | 1177 | 130 | 630 | 292 | 94 |
| 957 | U72741 | 264 | 94 | 99 | 30 | 94 |
| 21042 | AA799814 | 305 | 110 | 64 | 30 | 94 |
| 15642 | AI177503 | 809 | 240 | 294 | 74 | 94 |
| 3498 | AI069912 | 300 | 103 | 63 | 39 | 94 |
| 1597 | AF014503 | 610 | 269 | 104 | 77 | 94 |
| 15599 | X75253 | 796 | 49 | 497 | 152 | 94 |
| 4723 | AF093773 | 1181 | 152 | 623 | 221 | 94 |
| 3302 | AA997905 | 592 | 198 | 227 | 72 | 94 |
| 2040 | AA799700 | 774 | 318 | 192 | 77 | 94 |
| 17908 | AI014163 | 341 | 138 | 65 | 54 | 94 |
| 11314 | AA799656 | 258 | 68 | 101 | 23 | 94 |
| 7913 | AI043849 | 465 | 197 | 138 | 56 | 94 |
| 21625 | AI179012 | 1496 | 262 | 1395 | 819 | 94 |
| 21053 | M15481 | 1262 | 154 | 1393 | 958 | 94 |
| 19143 | AA946531 | 1001 | 270 | 404 | 122 | 94 |
| 2342 | AA964336 | 401 | 137 | 114 | 49 | 94 |
| 5034 | AI170613 | 961 | 188 | 547 | 178 | 94 |

TABLE 3U

INDOMETHACIN  Document Number 1740956.1

Timepoints (hrs): 48, 72

| GLGC ID | GenBank Acc | Group Mean | Group SD | NonGroup Mean | NonGroup SD | Discriminant Score |
|---|---|---|---|---|---|---|
| 1995 | AF038870 | 110 | 119 | 1407 | 1093 | 99 |
| 6381 | AA858768 | 51 | 32 | −2 | 34 | 99 |
| 10071 | AI639058 | 82 | 7 | 40 | 22 | 99 |
| 19053 | D12770 | 110 | 26 | 35 | 33 | 99 |
| 15002 | AI169327 | 296 | 67 | 138 | 54 | 99 |
| 13138 | AI233552 | 95 | 51 | 1 | 23 | 99 |
| 6143 | AI105167 | 128 | 59 | 880 | 531 | 99 |
| 25746 | X80778 | 40 | 9 | 6 | 12 | 99 |
| 17480 | U31598 | 174 | 45 | 76 | 27 | 99 |
| 16993 | AA799560 | 188 | 35 | 813 | 375 | 99 |
| 8597 | AA818593 | 239 | 34 | 108 | 37 | 99 |
| 19438 | AA819450 | 46 | 17 | 330 | 176 | 99 |
| 15872 | L28135 | 120 | 36 | 389 | 140 | 98 |
| 3895 | AA894029 | 131 | 35 | 36 | 27 | 98 |
| 19031 | AI070532 | 442 | 325 | 17 | 98 | 100 |
| 12606 | M59861 | 172 | 30 | 578 | 230 | 99 |
| 5176 | AA998722 | 81 | 47 | −46 | 38 | 99 |
| 26320 | AI234927 | 139 | 43 | 20 | 31 | 98 |
| 1472 | U26356 | 61 | 5 | −5 | 25 | 99 |
| 22515 | AA900582 | 880 | 248 | 114 | 323 | 99 |
| 21092 | AA800380 | 1213 | 119 | 2631 | 685 | 99 |
| 12797 | AA800790 | 100 | 22 | 28 | 18 | 99 |
| 15003 | AI169327 | 179 | 45 | −1 | 52 | 99 |
| 16885 | AI105188 | 574 | 110 | 1678 | 449 | 99 |
| 12551 | AI230056 | 51 | 13 | 240 | 78 | 99 |
| 13283 | M11266 | 188 | 36 | 695 | 303 | 99 |
| 1175 | X79081 | −8 | 33 | 506 | 321 | 99 |
| 15517 | D42145 | 135 | 32 | 43 | 18 | 99 |
| 5175 | AA818951 | 220 | 62 | 48 | 54 | 99 |
| 19004 | AI175875 | 474 | 124 | 147 | 60 | 99 |
| 20783 | AI171966 | 229 | 65 | 61 | 40 | 99 |
| 14840 | AI237698 | 247 | 79 | 71 | 42 | 99 |

TABLE 3U-continued

INDOMETHACIN  Document Number 1740956.1

Timepoints (hrs): 48, 72

| GLGC ID | GenBank Acc | Group Mean | Group SD | NonGroup Mean | NonGroup SD | Discriminant Score |
|---|---|---|---|---|---|---|
| 12736 | AI233972 | 228 | 74 | 70 | 35 | 98 |
| 17684 | AA892345 | 113 | 8 | 279 | 72 | 99 |
| 8317 | AA892234 | 130 | 16 | 488 | 178 | 99 |
| 9267 | AI072384 | 560 | 104 | 1807 | 506 | 99 |
| 2005 | D269646 | 109 | 19 | 28 | 18 | 99 |
| 2505 | M16235 | 171 | 53 | 585 | 205 | 99 |
| 11465 | AI236084 | 414 | 60 | 142 | 109 | 98 |
| 20869 | M32062 | 243 | 64 | 67 | 38 | 99 |
| 20816 | M58404 | 555 | 123 | 207 | 90 | 99 |
| 9223 | M36151 | 291 | 100 | 98 | 37 | 98 |
| 23321 | AA892821 | 94 | 11 | 221 | 52 | 99 |
| 20668 | M32062 | 195 | 53 | 51 | 31 | 99 |
| 22511 | M22670 | 558 | 189 | −5 | 48 | 99 |
| 4914 | AI112086 | 76 | 41 | 500 | 154 | 99 |
| 18453 | D17370 | 107 | 15 | 491 | 212 | 99 |
| 1748 | M84488 | 73 | 14 | 8 | 12 | 99 |
| 11422 | AA799812 | 68 | 16 | 11 | 10 | 99 |
| 18387 | AI237731 | 107 | 28 | 26 | 26 | 99 |
| 6366 | AA858716 | 832 | 207 | 280 | 109 | 98 |
| 4207 | AA945591 | 1424 | 533 | 459 | 227 | 98 |
| 21066 | D10587 | 141 | 11 | 68 | 20 | 99 |
| 794 | U68168 | 158 | 36 | 606 | 227 | 99 |
| 1572 | AI178828 | 175 | 18 | 81 | 29 | 99 |
| 666 | M10072 | 60 | 11 | 12 | 13 | 99 |
| 14311 | U10699 | 61 | 19 | 8 | 10 | 99 |
| 6614 | AA848389 | 141 | 45 | 974 | 264 | 99 |
| 3121 | AI008160 | 137 | 55 | 756 | 242 | 98 |
| 6322 | AA818801 | 147 | 47 | 16 | 22 | 99 |
| 24712 | E01884 | 116 | 53 | −6 | 17 | 99 |
| 6189 | AI178027 | 190 | 109 | 4100 | 2305 | 99 |
| 6615 | AA942889 | 90 | 34 | 440 | 120 | 99 |
| 2555 | D00913 | 420 | 58 | 123 | 45 | 99 |
| 7427 | J05122 | 167 | 27 | 38 | 30 | 99 |
| 475 | AI233828 | 441 | 87 | 1024 | 196 | 99 |
| 10015 | AF083269 | 287 | 43 | 137 | 40 | 99 |
| 6532 | AI234105 | 322 | 59 | 136 | 38 | 99 |
| 15185 | X62952 | 216 | 57 | 64 | 43 | 99 |
| 72 | M57263 | 175 | 97 | −21 | 23 | 99 |
| 18354 | X59859 | 151 | 28 | 23 | 31 | 99 |
| 4318 | AB005900 | 46 | 17 | 5 | 6 | 99 |
| 4439 | AA685175 | 444 | 86 | 202 | 46 | 99 |
| 14600 | AA801076 | 564 | 219 | 111 | 48 | 99 |
| 18709 | M32397 | 31 | 8 | −5 | 10 | 99 |
| 22690 | AA945970 | 75 | 47 | 589 | 217 | 99 |
| 9191 | AI072107 | 66 | 33 | 711 | 275 | 99 |
| 6365 | AA899163 | 193 | 37 | 52 | 37 | 99 |
| 4636 | AA899491 | 362 | 74 | 52 | 60 | 99 |
| 20879 | X65296 | 64 | 40 | 500 | 220 | 99 |
| 16809 | X58828 | 176 | 31 | 38 | 27 | 99 |
| 18352 | Z12298 | 99 | 25 | 12 | 18 | 99 |
| 16416 | AA875098 | 251 | 57 | 107 | 37 | 98 |
| 20123 | AI072214 | 15 | 20 | 314 | 107 | 99 |
| 10016 | AF083269 | 255 | 41 | 96 | 42 | 99 |
| 18038 | U39943 | 86 | 12 | 223 | 60 | 98 |
| 25471 | M96630 | 255 | 36 | 99 | 45 | 98 |
| 4026 | AI233835 | 958 | 174 | 375 | 132 | 98 |
| 24237 | AA817726 | 943 | 204 | 186 | 113 | 99 |
| 5899 | AI170038 | 257 | 102 | 1267 | 313 | 99 |
| 2799 | AI013778 | 56 | 8 | 465 | 225 | 98 |
| 12118 | AA892775 | 544 | 71 | 221 | 91 | 99 |
| 9583 | AI071185 | 435 | 105 | 51 | 69 | 98 |
| 3916 | AI169947 | 466 | 88 | 1624 | 405 | 98 |
| 20354 | M14369 | 319 | 34 | 59 | 51 | 98 |
| 24219 | L27843 | 697 | 69 | 300 | 106 | 98 |
| 1221 | D11445 | 551 | 80 | 23 | 83 | 99 |

TABLE 3V

INDOMETHACIN  Document Number 1740956.1

Timepoints (hrs): 6, 24

| GLGC ID | GenBank Acc | Group Mean | Group SD | NonGroup Mean | NonGroup SD | Discriminant Score |
|---|---|---|---|---|---|---|
| 17588 | AA892849 | 61 | 9 | 14 | 27 | 93 |
| 9712 | AI176836 | 22 | 14 | 81 | 33 | 93 |
| 17908 | AI014163 | 142 | 31 | 67 | 62 | 93 |
| 16579 | AA957143 | 122 | 15 | 205 | 64 | 92 |
| 21488 | U32575 | 75 | 9 | 44 | 27 | 92 |
| 12191 | D26073 | 62 | 7 | 27 | 28 | 91 |
| 13768 | AA819792 | 83 | 32 | −16 | 58 | 92 |
| 19584 | X13905 | 195 | 25 | 116 | 44 | 92 |
| 16684 | D17445 | 368 | 32 | 285 | 80 | 91 |
| 10245 | AI059701 | 62 | 19 | 135 | 52 | 91 |
| 24596 | X16044 | 116 | 8 | 83 | 33 | 90 |
| 20652 | L14463 | 49 | 4 | 29 | 14 | 90 |
| 17379 | M62388 | 214 | 33 | 115 | 61 | 90 |
| 17573 | AI013132 | 29 | 19 | 148 | 100 | 90 |
| 8274 | AI059270 | 78 | 17 | 152 | 59 | 91 |
| 18908 | AA849426 | 116 | 27 | 252 | 157 | 90 |
| 10829 | AI044467 | 28 | 6 | 53 | 25 | 90 |
| 24219 | L27843 | 469 | 76 | 301 | 110 | 92 |
| 11842 | AA858617 | 48 | 7 | 26 | 13 | 90 |
| 3847 | AA892036 | 75 | 10 | 46 | 20 | 90 |
| 1822 | AA817843 | 102 | 9 | 66 | 29 | 89 |
| 25644 | U77931 | 403 | 39 | 275 | 104 | 90 |
| 515 | X63854 | 87 | 9 | 58 | 21 | 89 |
| 21524 | AI012014 | −6 | 12 | 33 | 28 | 90 |
| 18165 | AA892259 | 50 | 7 | 30 | 13 | 89 |
| 14827 | AI237404 | 31 | 20 | 97 | 48 | 90 |
| 1427 | L38644 | 69 | 8 | 39 | 22 | 89 |
| 18002 | AI043655 | 1223 | 230 | 2221 | 867 | 89 |
| 19942 | AF008554 | 207 | 25 | 137 | 45 | 90 |
| 9598 | H33832 | 247 | 39 | 156 | 121 | 89 |
| 21491 | AF040954 | 114 | 9 | 88 | 22 | 89 |
| 3365 | AI008919 | 424 | 128 | 765 | 232 | 90 |
| 17214 | AI639008 | 179 | 29 | 119 | 40 | 91 |
| 22069 | AA946349 | 337 | 57 | 516 | 129 | 89 |
| 6537 | AI233817 | 56 | 46 | −59 | 112 | 90 |
| 24508 | M34643 | 174 | 25 | 116 | 36 | 90 |
| 20819 | M81225 | 114 | 14 | 82 | 25 | 89 |
| 16610 | D28557 | 213 | 31 | 140 | 58 | 89 |
| 6788 | AI228646 | 241 | 42 | 138 | 75 | 89 |
| 9498 | AI073164 | 75 | 13 | 44 | 19 | 90 |
| 6016 | AA818163 | 1277 | 406 | 2259 | 787 | 89 |
| 7063 | M12919 | 147 | 30 | 92 | 65 | 90 |
| 24690 | J05571 | 58 | 11 | 35 | 17 | 89 |
| 25670 | X07648 | 170 | 48 | 108 | 53 | 91 |
| 959 | D38072 | 60 | 18 | 28 | 19 | 89 |
| 353 | L32591 | 151 | 44 | 54 | 60 | 90 |
| 14303 | AI231159 | 450 | 110 | 225 | 75 | 90 |
| 870 | U66478 | 58 | 11 | 29 | 16 | 91 |
| 14768 | AI235912 | 263 | 64 | 137 | 77 | 90 |
| 4250 | AA818700 | 218 | 31 | 135 | 44 | 92 |
| 13364 | AI170606 | 208 | 27 | 134 | 41 | 93 |
| 21708 | AA956930 | 129 | 18 | 71 | 29 | 93 |
| 4527 | AA892774 | 82 | 15 | 43 | 18 | 95 |
| 18327 | AA799537 | 125 | 32 | 54 | 26 | 89 |
| 2554 | D00913 | 117 | 24 | 66 | 20 | 89 |
| 18068 | S79676 | 91 | 21 | 52 | 18 | 90 |
| 7197 | AI171962 | 74 | 20 | 34 | 21 | 89 |
| 25508 | S67620 | 36 | 18 | −6 | 15 | 91 |
| 18400 | AA799991 | 122 | 35 | 59 | 27 | 89 |
| 24570 | M95578 | 64 | 41 | −22 | 30 | 91 |
| 11827 | AA859468 | 97 | 20 | 47 | 21 | 89 |
| 155 | U32681 | 116 | 35 | 52 | 28 | 91 |
| 9866 | AJ005424 | 73 | 49 | −1 | 27 | 90 |
| 17953 | AA894090 | 232 | 44 | 151 | 38 | 93 |
| 23587 | AI176598 | 123 | 29 | 62 | 29 | 90 |
| 15487 | AI176351 | 145 | 35 | 74 | 33 | 89 |
| 4043 | AI227852 | 110 | 38 | 56 | 28 | 90 |
| 17634 | AJ223355 | 325 | 71 | 157 | 54 | 90 |
| 15933 | AA875253 | 245 | 45 | 153 | 44 | 93 |

TABLE 3V-continued

INDOMETHACIN  Document Number 1740956.1

Timepoints (hrs): 6, 24

| GLGC ID | GenBank Acc | Group Mean | Group SD | NonGroup Mean | NonGroup SD | Discriminant Score |
|---|---|---|---|---|---|---|
| 22336 | AA893924 | 91 | 18 | 9 | 38 | 95 |
| 21683 | M65149 | 137 | 67 | 15 | 24 | 93 |
| 17377 | X13058 | 173 | 56 | 81 | 46 | 89 |
| 9821 | AI180114 | 141 | 24 | 70 | 31 | 91 |
| 1379 | M83676 | 61 | 10 | 22 | 18 | 94 |
| 19411 | AA893667 | 137 | 55 | 42 | 23 | 92 |
| 1641 | E03428 | 203 | 35 | 113 | 41 | 89 |
| 2005 | D29646 | 71 | 18 | 29 | 19 | 90 |
| 20161 | X54686 | 127 | 54 | 28 | 37 | 90 |
| 11203 | AA892554 | 112 | 32 | 52 | 22 | 90 |
| 2557 | AI176820 | 92 | 29 | 34 | 16 | 92 |
| 14425 | AI177755 | 1447 | 556 | 428 | 405 | 92 |
| 20090 | AI639353 | 209 | 62 | 112 | 37 | 91 |
| 6085 | AI171990 | 162 | 50 | 54 | 50 | 90 |
| 3504 | AI104659 | 476 | 77 | 285 | 90 | 91 |
| 14501 | AI175778 | 109 | 30 | 41 | 23 | 90 |
| 21111 | AI227832 | 84 | 40 | 14 | 27 | 91 |
| 19884 | AI170501 | 2331 | 266 | 5485 | 2830 | 90 |
| 5384 | AA891041 | 140 | 48 | 27 | 41 | 90 |
| 18495 | AI639042 | 51 | 15 | 18 | 16 | 93 |
| 13166 | AI178736 | 244 | 92 | 80 | 56 | 91 |
| 1844 | M33962 | 234 | 74 | 114 | 44 | 91 |
| 22566 | AI177122 | 113 | 35 | 46 | 33 | 89 |
| 1841 | AI113289 | 188 | 61 | 52 | 40 | 92 |
| 17589 | AA892851 | 143 | 49 | 41 | 36 | 91 |
| 6226 | AA818521 | 70 | 25 | 25 | 20 | 91 |
| 3773 | AA998356 | 192 | 81 | 56 | 47 | 91 |
| 23855 | AI236773 | 343 | 68 | 164 | 68 | 96 |

TABLE 3W

Lipopolysaccharide  Document Number 1740956.1

Timepoints (hrs): 24

| GLGC ID | GenBank Acc | Group Mean | Group SD | NonGroup Mean | NonGroup SD | Discriminant Score |
|---|---|---|---|---|---|---|
| 20872 | X51707 | 1346 | 39 | 565 | 185 | 100 |
| 309 | AA866460 | 1271 | 75 | 521 | 129 | 100 |
| 14495 | AA893658 | 78 | 13 | 275 | 91 | 100 |
| 20810 | X14181 | 2038 | 83 | 818 | 316 | 100 |
| 9214 | AA925116 | 881 | 98 | 231 | 78 | 100 |
| 20462 | M20156 | 1387 | 54 | 608 | 172 | 100 |
| 10109 | X58465 | 1938 | 117 | 741 | 244 | 100 |
| 24728 | M55532 | 29 | 8 | 234 | 58 | 100 |
| 22042 | AA946476 | 6154 | 992 | 110 | 57 | 100 |
| 25802 | E02315 | 516 | 16 | 223 | 57 | 100 |
| 5969 | AI102520 | 363 | 62 | 1269 | 487 | 100 |
| 20707 | U88036 | 9 | 10 | 480 | 234 | 100 |
| 634 | K01932 | 225 | 44 | 1123 | 608 | 100 |
| 25084 | X06769 | 44 | 4 | 149 | 45 | 100 |
| 15004 | AI235224 | 1695 | 241 | 223 | 88 | 100 |
| 15098 | M31837 | 25 | 6 | 124 | 34 | 100 |
| 25525 | S72505 | 173 | 36 | 992 | 517 | 100 |
| 18618 | M24026 | 1838 | 88 | 807 | 300 | 100 |
| 21522 | AA944449 | 766 | 53 | 152 | 160 | 100 |
| 21660 | AI169751 | 5231 | 324 | 1747 | 597 | 100 |
| 18244 | AA848776 | 1182 | 48 | 498 | 138 | 100 |
| 18205 | AI044836 | 540 | 12 | 297 | 78 | 100 |
| 19438 | AA819450 | 18 | 8 | 329 | 177 | 100 |
| 24860 | M13506 | 32 | 5 | 323 | 248 | 100 |
| 1501 | AI072634 | 1189 | 106 | 377 | 125 | 100 |

TABLE 3W-continued

Lipopolysaccharide  Document Number 1740956.1

Timepoints (hrs): 24

| GLGC ID | GenBank Acc | Group Mean | Group SD | NonGroup Mean | NonGroup SD | Discriminant Score |
|---|---|---|---|---|---|---|
| 20944 | X82396 | 1456 | 146 | 463 | 118 | 100 |
| 574 | L13039 | 252 | 19 | 91 | 42 | 100 |
| 5967 | AI102520 | 203 | 34 | 931 | 449 | 100 |
| 11849 | X93352 | 1292 | 27 | 561 | 179 | 100 |
| 20701 | AA875097 | 2699 | 266 | 631 | 252 | 100 |
| 25675 | X14181 | 1146 | 19 | 564 | 195 | 100 |
| 18250 | X51706 | 1694 | 101 | 683 | 230 | 100 |
| 21643 | AI104544 | 1667 | 167 | 644 | 209 | 100 |
| 23005 | AA942770 | 271 | 18 | 100 | 65 | 100 |
| 25687 | X51706 | 2035 | 160 | 865 | 301 | 100 |
| 20698 | X86561 | 3388 | 619 | 657 | 317 | 100 |
| 18580 | AA851963 | 1020 | 40 | 193 | 144 | 100 |
| 1599 | AA686470 | 53 | 4 | 14 | 29 | 100 |
| 17758 | K03249 | 17 | 8 | 310 | 348 | 100 |
| 22598 | AI137506 | 3246 | 213 | 1045 | 322 | 100 |
| 1069 | X15096 | 2982 | 294 | 1101 | 517 | 100 |
| 20589 | X06916 | 125 | 14 | 32 | 25 | 100 |
| 1561 | Z50052 | 1985 | 196 | 649 | 233 | 100 |
| 11904 | D85183 | 269 | 17 | 69 | 47 | 100 |
| 6911 | D85035 | 57 | 7 | 220 | 52 | 100 |
| 14384 | AI77096 | 542 | 33 | 220 | 49 | 100 |
| 3134 | AI180292 | 375 | 108 | 34 | 28 | 100 |
| 18541 | X14671 | 1651 | 44 | 766 | 292 | 100 |
| 5667 | X58200 | 1364 | 112 | 592 | 172 | 100 |
| 1600 | AA686470 | 80 | 4 | 31 | 96 | 100 |
| 635 | X78848 | 188 | 85 | 1148 | 682 | 100 |
| 21285 | AA849898 | 1158 | 138 | 80 | 129 | 100 |
| 15002 | AI169327 | 813 | 201 | 137 | 37 | 100 |
| 18611 | X58200 | 2091 | 199 | 792 | 282 | 100 |
| 20915 | AF001898 | 99 | 6 | 410 | 277 | 100 |
| 22006 | U96490 | 516 | 40 | 262 | 47 | 100 |
| 20529 | L32132 | 1181 | 95 | 120 | 114 | 100 |
| 18750 | D45250 | 373 | 9 | 216 | 43 | 100 |
| 9905 | AA891774 | 166 | 21 | 507 | 139 | 100 |
| 25686 | X51536 | 1038 | 43 | 539 | 158 | 100 |
| 15135 | S71021 | 1406 | 112 | 578 | 180 | 100 |
| 713 | X91234 | −62 | 12 | 380 | 485 | 100 |
| 20839 | AA891729 | 1945 | 203 | 799 | 289 | 100 |
| 13563 | AI233773 | 455 | 25 | 1246 | 377 | 99 |
| 19018 | M86870 | 644 | 29 | 297 | 82 | 99 |
| 12320 | AA946149 | 1193 | 1266 | 5 | 21 | 99 |
| 18606 | X53504 | 1203 | 88 | 543 | 169 | 99 |
| 25679 | X15013 | 1526 | 95 | 637 | 244 | 99 |
| 154 | U32681 | 502 | 58 | 160 | 45 | 99 |
| 25719 | X62146 | 1680 | 122 | 783 | 273 | 99 |
| 17324 | AF056031 | 82 | 19 | 316 | 73 | 99 |
| 25052 | L22190 | 1614 | 302 | 23 | 68 | 99 |
| 24577 | X155153 | 1617 | 106 | 664 | 256 | 99 |
| 21657 | X61381 | 2029 | 431 | 546 | 187 | 99 |
| 1641 | E03428 | 275 | 15 | 113 | 41 | 99 |
| 23651 | M14656 | 66 | 17 | 19 | 47 | 99 |
| 6614 | AA848389 | 119 | 27 | 971 | 268 | 99 |
| 1598 | U30186 | 101 | 15 | 15 | 34 | 99 |
| 17284 | J02827 | 66 | 7 | 179 | 39 | 99 |
| 7858 | AI043654 | 149 | 52 | −2 | 22 | 99 |
| 25747 | X81448 | 932 | 89 | 321 | 98 | 99 |
| 16204 | X06423 | 1325 | 135 | 563 | 158 | 99 |
| 21765 | AI233696 | 134 | 12 | 37 | 25 | 99 |
| 11416 | AI172185 | 283 | 21 | 109 | 37 | 99 |
| 2997 | AI030545 | 88 | 6 | 348 | 123 | 99 |
| 17175 | X58389 | 1068 | 83 | 466 | 131 | 99 |
| 21074 | AI013890 | 1007 | 95 | 404 | 136 | 99 |
| 9215 | AA925116 | 1095 | 215 | 269 | 109 | 99 |
| 4914 | AI112086 | 49 | 19 | 499 | 155 | 99 |
| 22515 | AA900582 | 4184 | 1045 | 105 | 215 | 99 |
| 16173 | AA957003 | 286 | 72 | 20 | 26 | 99 |
| 14929 | AI170353 | 373 | 82 | 114 | 71 | 99 |
| 5175 | AA818951 | 345 | 77 | 48 | 53 | 99 |
| 4365 | AI070200 | 724 | 67 | 259 | 120 | 99 |

TABLE 3W-continued

Lipopolysaccharide     Document Number 1740956.1

Timepoints (hrs): 24

| GLGC ID | GenBank Acc | Group Mean | Group SD | NonGroup Mean | NonGroup SD | Discriminant Score |
|---|---|---|---|---|---|---|
| 1678 | M96674 | 22 | 13 | 128 | 33 | 99 |
| 15872 | L28135 | 73 | 25 | 388 | 141 | 99 |
| 20862 | E01415 | 62 | 16 | 251 | 75 | 99 |
| 2744 | D87991 | 510 | 37 | 187 | 54 | 99 |

TABLE 3X

PHENOBARBITAL     Document Number 1740956.1

Timepoints (hrs): 24, 48

| GLGC ID | GenBank Acc | Group Mean | Group SD | NonGroup Mean | NonGroup SD | Discriminant Score |
|---|---|---|---|---|---|---|
| 20913 | M23995 | 2689 | 2126 | 225 | 221 | 99 |
| 12160 | AA818412 | 14509 | 1800 | 1065 | 855 | 99 |
| 20384 | D17349 | 2702 | 410 | 145 | 137 | 99 |
| 25055 | M11251 | 5930 | 1086 | 194 | 310 | 99 |
| 20914 | M23995 | 2652 | 1037 | 198 | 208 | 99 |
| 16619 | AA997544 | 713 | 246 | 33 | 26 | 99 |
| 12158 | L00320 | 5925 | 1168 | 183 | 311 | 99 |
| 24860 | M13506 | 2060 | 460 | 306 | 181 | 99 |
| 5102 | AA925211 | 617 | 308 | −41 | 23 | 99 |
| 25056 | M13234 | 7387 | 1370 | 708 | 563 | 99 |
| 12155 | J00728 | 6863 | 1252 | 494 | 483 | 99 |
| 15695 | D10891 | 38 | 11 | −15 | 15 | 99 |
| 12156 | K00996 | 8592 | 2033 | 389 | 580 | 99 |
| 12157 | K01721 | 9008 | 1943 | 435 | 730 | 99 |
| 18989 | K00136 | 4513 | 610 | 1050 | 766 | 99 |
| 20915 | AF001898 | 1965 | 773 | 395 | 225 | 99 |
| 17541 | M26125 | 4034 | 521 | 1130 | 712 | 99 |
| 10152 | AI059110 | 136 | 41 | 12 | 17 | 99 |
| 1795 | L24207 | 2240 | 704 | 416 | 290 | 98 |
| 15879 | AI228313 | 611 | 118 | 308 | 80 | 98 |
| 1794 | X64401 | 8381 | 2185 | 1483 | 1246 | 98 |
| 20707 | U88036 | 1399 | 196 | 470 | 218 | 98 |
| 2486 | AA964871 | 1196 | 262 | 477 | 164 | 98 |
| 4312 | AB010635 | 521 | 267 | 55 | 67 | 98 |
| 1793 | D13912 | 4172 | 1131 | 848 | 563 | 98 |
| 12556 | AI180376 | 472 | 169 | 61 | 83 | 98 |
| 21903 | AA945571 | 3644 | 730 | 1075 | 593 | 98 |
| 1797 | X62086 | 6145 | 1635 | 1237 | 942 | 98 |
| 1796 | L24207 | 882 | 339 | 215 | 117 | 98 |
| 16310 | L13600 | 70 | 34 | −92 | 67 | 97 |
| 23930 | AA997182 | 237 | 60 | 47 | 38 | 97 |
| 1603 | X78855 | 707 | 83 | 376 | 107 | 97 |
| 15127 | S56937 | 1093 | 113 | 525 | 263 | 97 |
| 11152 | M91652 | 99 | 23 | 283 | 88 | 97 |
| 17766 | AA851299 | 689 | 57 | 434 | 110 | 97 |
| 15125 | J05132 | 3096 | 530 | 1172 | 757 | 97 |
| 2446 | AA965241 | 90 | 34 | 11 | 22 | 96 |
| 11150 | AA852004 | 44 | 14 | 166 | 66 | 96 |
| 15124 | J02612 | 2406 | 354 | 989 | 553 | 96 |
| 18588 | AA899635 | 404 | 65 | 207 | 99 | 96 |
| 11988 | AA819193 | 140 | 38 | 55 | 26 | 96 |
| 1602 | U76379 | 629 | 75 | 376 | 88 | 96 |
| 21011 | H32189 | 5333 | 1153 | 1599 | 1167 | 96 |
| 25400 | M14776 | 4569 | 802 | 1278 | 1091 | 96 |
| 21904 | M24239 | 8157 | 1553 | 2150 | 1904 | 96 |
| 21260 | AI233885 | 300 | 54 | 126 | 67 | 96 |
| 22979 | AA851372 | 446 | 46 | 271 | 79 | 95 |
| 4751 | AA900481 | 159 | 38 | 75 | 35 | 95 |
| 17995 | M13646 | 3548 | 564 | 1234 | 775 | 95 |

TABLE 3X-continued

PHENOBARBITAL     Document Number 1740956.1

Timepoints (hrs): 24, 48

| GLGC ID | GenBank Acc | Group Mean | Group SD | NonGroup Mean | NonGroup SD | Discriminant Score |
|---|---|---|---|---|---|---|
| 12060 | AA799890 | 51 | 9 | 98 | 23 | 95 |
| 762 | AF007107 | 3039 | 634 | 1148 | 704 | 95 |
| 16703 | AI179300 | 1966 | 255 | 1202 | 368 | 95 |
| 373 | D86086 | 742 | 146 | 387 | 136 | 95 |
| 21029 | AA799981 | 1 | 14 | 49 | 24 | 94 |
| 23243 | AA851803 | 3388 | 494 | 1691 | 783 | 94 |
| 20650 | M12335 | 1856 | 205 | 1291 | 823 | 94 |
| 24849 | S60953 | −13 | 8 | 21 | 20 | 94 |
| 634 | K01932 | 2522 | 315 | 1107 | 597 | 94 |
| 21014 | J03914 | 1545 | 206 | 768 | 344 | 94 |
| 6633 | AI2288931 | 759 | 173 | 1285 | 315 | 94 |
| 21798 | AA926365 | 2455 | 327 | 1695 | 371 | 94 |
| 17805 | U06274 | 1809 | 191 | 898 | 401 | 94 |
| 23322 | AA892821 | 693 | 66 | 437 | 127 | 94 |
| 22884 | AI010755 | 274 | 45 | 167 | 52 | 94 |
| 4314 | AF010597 | 571 | 52 | 374 | 95 | 94 |
| 15955 | AI232294 | 331 | 30 | 189 | 84 | 93 |
| 5622 | X05834 | 1262 | 148 | 1103 | 496 | 93 |
| 25725 | X62660 | 270 | 57 | 137 | 56 | 93 |
| 20090 | AI639353 | 63 | 7 | 113 | 38 | 93 |
| 21015 | X04229 | 5744 | 999 | 2027 | 1427 | 93 |
| 24112 | AI008773 | 2164 | 366 | 1154 | 537 | 93 |
| 6000 | AA818088 | 55 | 39 | −23 | 26 | 93 |
| 21013 | J02810 | 5831 | 1552 | 1826 | 1429 | 93 |
| 25525 | S72505 | 2250 | 465 | 978 | 505 | 93 |
| 18473 | AI168975 | 942 | 242 | 419 | 137 | 93 |
| 21039 | J03190 | 721 | 176 | 200 | 118 | 93 |
| 16274 | D10261 | 6084 | 624 | 3078 | 3324 | 93 |
| 23445 | M84719 | 78 | 29 | 212 | 88 | 93 |
| 17676 | V01235 | 4545 | 318 | 2308 | 2052 | 93 |
| 8872 | AA851050 | 998 | 282 | 492 | 235 | 92 |
| 22992 | AA996880 | 359 | 38 | 231 | 73 | 92 |
| 4573 | AI179613 | 1044 | 136 | 896 | 359 | 92 |
| 19040 | J03627 | 18 | 3 | 46 | 36 | 92 |
| 16019 | AI008498 | 483 | 156 | 147 | 90 | 92 |
| 7926 | AI043913 | 163 | 37 | 82 | 56 | 92 |
| 4186 | AA945169 | 5001 | 445 | 2646 | 2383 | 92 |
| 2681 | AA901043 | 127 | 21 | 73 | 36 | 92 |
| 21038 | J03190 | 734 | 178 | 243 | 128 | 92 |
| 9697 | AI071642 | 82 | 27 | 15 | 19 | 92 |
| 1354 | D38065 | 373 | 55 | 219 | 135 | 92 |
| 19271 | AI231566 | 135 | 36 | 271 | 92 | 92 |
| 3143 | AI232408 | 250 | 20 | 360 | 94 | 92 |
| 20385 | X54793 | 939 | 76 | 669 | 202 | 92 |
| 18939 | AA945875 | 673 | 205 | 176 | 110 | 92 |
| 9841 | U94856 | 2341 | 150 | 1504 | 864 | 92 |

TABLE 3Y

TACRINE     Document Number: 1740956.1

Timepoints (hrs): 6

| GLGC ID | GenBank Acc | Group Mean | Group SD | NonGroup Mean | NonGroup SD | Discriminant Score |
|---|---|---|---|---|---|---|
| 18389 | AA799498 | 108 | 8 | 26 | 33 | 99 |
| 6236 | AA818627 | 241 | 53 | 981 | 447 | 98 |
| 6919 | AI010461 | 972 | 168 | 279 | 242 | 98 |
| 14996 | X16038 | 184 | 86 | 21 | 38 | 98 |
| 14997 | J03572 | 612 | 134 | 237 | 147 | 98 |
| 17050 | AA799466 | 279 | 31 | 175 | 34 | 98 |
| 8210 | S61960 | 308 | 33 | 125 | 67 | 98 |

TABLE 3Y-continued

TACRINE  Document Number: 1740956.1

Timepoints (hrs): 6

| GLGC ID | GenBank Acc | Group Mean | Group SD | NonGroup Mean | NonGroup SD | Discriminant Score |
|---|---|---|---|---|---|---|
| 12704 | AI009194 | 3250 | 993 | 1446 | 335 | 97 |
| 20744 | J04171 | 577 | 60 | 277 | 181 | 97 |
| 22513 | M23566 | 425 | 292 | −59 | 611 | 97 |
| 21063 | D89983 | 134 | 25 | 55 | 25 | 97 |
| 21209 | AI171772 | 364 | 116 | 85 | 87 | 97 |
| 13369 | D21132 | 242 | 14 | 158 | 32 | 97 |
| 22512 | M22670 | 101 | 24 | 39 | 58 | 97 |
| 373 | D86086 | 189 | 21 | 391 | 139 | 97 |
| 23606 | U05784 | 571 | 57 | 326 | 144 | 97 |
| 344 | AI008865 | 2955 | 653 | 1139 | 500 | 97 |
| 11215 | AA817921 | −95 | 39 | 114 | 86 | 97 |
| 21923 | AA891260 | 55 | 7 | 20 | 16 | 97 |
| 2939 | AA996885 | 36 | 22 | 188 | 82 | 97 |
| 19410 | AA893667 | 153 | 10 | 95 | 26 | 96 |
| 2899 | AA996698 | 8 | 2 | 45 | 37 | 96 |
| 24284 | M94287 | 94 | 28 | 39 | 18 | 96 |
| 26190 | AI072578 | 126 | 139 | −166 | 107 | 96 |
| 4107 | AA899109 | 82 | 9 | 178 | 71 | 96 |
| 20772 | U60882 | 107 | 9 | 63 | 27 | 96 |
| 22396 | AA859806 | 146 | 4 | 104 | 29 | 96 |
| 16701 | AI008838 | 1112 | 132 | 2221 | 702 | 96 |
| 633 | AI231127 | 880 | 67 | 1409 | 280 | 96 |
| 6263 | AI009666 | 132 | 11 | 266 | 89 | 96 |
| 21980 | AA893454 | 577 | 23 | 404 | 115 | 96 |
| 19412 | AA849222 | 641 | 70 | 385 | 121 | 96 |
| 1968 | M83745 | 34 | 6 | 13 | 8 | 96 |
| 12516 | AI179651 | 1418 | 164 | 893 | 195 | 96 |
| 7552 | AI045802 | 684 | 24 | 941 | 267 | 96 |
| 14393 | AI011367 | 39 | 6 | 88 | 30 | 96 |
| 5020 | AA924768 | 160 | 9 | 251 | 72 | 96 |
| 10545 | U21871 | 304 | 28 | 193 | 63 | 96 |
| 13932 | AI230988 | −49 | 35 | 68 | 54 | 96 |
| 2569 | AA965122 | 183 | 114 | 881 | 271 | 95 |
| 1843 | M33962 | 83 | 12 | 40 | 19 | 95 |
| 9432 | AI072914 | 114 | 27 | 48 | 29 | 95 |
| 798 | U38253 | 48 | 6 | 22 | 11 | 95 |
| 6352 | AA997600 | 30 | 10 | −14 | 30 | 95 |
| 6060 | AA818702 | 313 | 32 | 500 | 107 | 95 |
| 25567 | S85184 | 286 | 68 | 133 | 78 | 95 |
| 5696 | AI045116 | 142 | 15 | 273 | 96 | 95 |
| 20850 | AA899956 | 4 | 7 | 74 | 57 | 95 |
| 17449 | AI237258 | 95 | 6 | 57 | 23 | 95 |
| 21341 | AA850195 | 393 | 77 | 822 | 297 | 95 |
| 2242 | AI012635 | 4504 | 962 | 2338 | 864 | 95 |
| 23243 | AA851803 | 512 | 138 | 1711 | 795 | 95 |
| 15786 | AI013924 | 136 | 24 | 287 | 87 | 95 |
| 1991 | M83196 | 68 | 11 | 37 | 14 | 95 |
| 410 | AI008974 | 40 | 20 | 169 | 77 | 95 |
| 22514 | X13983 | 124 | 32 | 63 | 70 | 95 |
| 13975 | AA850450 | 69 | 14 | 162 | 68 | 95 |
| 17590 | AA892851 | 186 | 31 | 109 | 43 | 95 |
| 1426 | Z48225 | 194 | 15 | 133 | 30 | 95 |
| 21799 | AI102576 | −15 | 5 | 24 | 23 | 95 |
| 19575 | AA850814 | 130 | 23 | 288 | 98 | 95 |
| 2250 | AI012354 | 733 | 201 | 1786 | 689 | 95 |
| 3145 | AA997237 | 278 | 49 | 607 | 196 | 95 |
| 16703 | AI179300 | 591 | 122 | 1212 | 373 | 95 |
| 10573 | AI101003 | 164 | 22 | 80 | 48 | 94 |
| 960 | D10026 | 120 | 14 | 202 | 50 | 94 |
| 10555 | AA900198 | 29 | 28 | 371 | 225 | 94 |
| 6072 | AI228630 | 1091 | 273 | 2023 | 465 | 94 |
| 19370 | AA963797 | 136 | 43 | 274 | 71 | 94 |
| 4592 | J02646 | 211 | 20 | 149 | 39 | 94 |
| 4879 | AA923852 | 25 | 13 | 113 | 55 | 94 |
| 24427 | J03170 | 155 | 15 | 114 | 20 | 94 |
| 4232 | AI012958 | 25 | 17 | 95 | 52 | 94 |
| 7063 | M12919 | 151 | 22 | 92 | 65 | 94 |
| 22196 | U21719 | 117 | 24 | 57 | 32 | 94 |
| 19085 | AA892598 | 168 | 29 | 90 | 37 | 94 |
| 4183 | AI102789 | 95 | 16 | 167 | 44 | 94 |
| 16680 | AA965190 | 120 | 44 | 362 | 136 | 94 |
| 21062 | AI043631 | 101 | 18 | 31 | 160 | 94 |
| 20 | L26268 | 406 | 32 | 284 | 90 | 94 |
| 18507 | AI175551 | 1005 | 111 | 697 | 209 | 94 |
| 11166 | AA801346 | 266 | 78 | 530 | 135 | 94 |
| 1583 | U07201 | 65 | 9 | 38 | 17 | 94 |
| 18910 | AI232419 | 426 | 128 | 1198 | 431 | 94 |
| 18714 | AI013194 | 281 | 7 | 238 | 93 | 94 |
| 10176 | AA819530 | 242 | 77 | 447 | 99 | 94 |
| 2486 | AA964871 | 162 | 74 | 485 | 178 | 94 |
| 23451 | AA925243 | 191 | 4 | 241 | 59 | 94 |
| 23577 | AA955513 | 18 | 3 | 51 | 26 | 94 |
| 3282 | AA818113 | 90 | 27 | 207 | 70 | 94 |

TABLE 3Z

VALPROATE  Document Number 1740956.1

Timepoints (hrs): 24, 96

| GLGC ID | GenBank Acc | Group Mean | Group SD | NonGroup Mean | NonGroup SD | Discriminant Score |
|---|---|---|---|---|---|---|
| 12829 | AA858695 | 547 | 24 | 393 | 93 | 96 |
| 23698 | J02749 | 491 | 47 | 299 | 365 | 95 |
| 1774 | J03754 | 24 | 3 | 8 | 10 | 95 |
| 12698 | AI170665 | 164 | 17 | 74 | 303 | 94 |
| 2179 | AA848270 | 592 | 105 | 352 | 102 | 94 |
| 14937 | AI237159 | 196 | 21 | 120 | 38 | 94 |
| 22604 | AA945578 | 1839 | 334 | 987 | 446 | 94 |
| 19358 | AI009675 | 269 | 199 | 993 | 439 | 93 |
| 5887 | AI179099 | 165 | 51 | 86 | 168 | 93 |
| 20711 | AA824267 | 291 | 45 | 127 | 170 | 93 |
| 15907 | AA996422 | 182 | 13 | 270 | 89 | 93 |
| 23203 | AA799971 | 170 | 21 | 107 | 36 | 93 |
| 21656 | AA800202 | 66 | 5 | 36 | 21 | 93 |
| 3362 | AA998092 | 27 | 8 | 81 | 39 | 93 |
| 23579 | AI171802 | 801 | 21 | 673 | 130 | 92 |
| 26109 | AA997009 | 394 | 109 | 153 | 291 | 92 |
| 3279 | AI103224 | 1011 | 116 | 716 | 202 | 92 |
| 17290 | AA891785 | 257 | 43 | 166 | 60 | 92 |
| 17237 | X16145 | 280 | 31 | 208 | 44 | 92 |
| 12964 | AI236227 | 395 | 31 | 241 | 96 | 92 |
| 64 | M60655 | 205 | 28 | 134 | 36 | 92 |
| 4914 | AI112086 | 727 | 59 | 496 | 157 | 92 |
| 21094 | D10354 | 342 | 45 | 204 | 91 | 92 |
| 20715 | X07259 | 522 | 82 | 313 | 353 | 91 |
| 2373 | AA964455 | 145 | 31 | 287 | 116 | 91 |
| 23228 | AI235446 | 1110 | 63 | 1557 | 574 | 91 |
| 17289 | AA891785 | 196 | 17 | 128 | 53 | 91 |
| 2140 | AI172272 | 165 | 29 | 86 | 47 | 91 |
| 18637 | AA858651 | 1105 | 182 | 2045 | 614 | 91 |
| 19433 | AA819776 | 200 | 32 | 105 | 79 | 91 |
| 17529 | AI171460 | 205 | 39 | 136 | 41 | 91 |
| 17758 | K03249 | 411 | 53 | 308 | 349 | 91 |
| 21068 | AI175675 | 283 | 101 | 21 | 135 | 91 |
| 3848 | AA892306 | 34 | 12 | 11 | 13 | 91 |
| 1301 | J02585 | 425 | 58 | 1016 | 906 | 91 |
| 17187 | AA800315 | 80 | 12 | 43 | 23 | 91 |
| 22379 | AI231448 | 254 | 55 | 479 | 205 | 91 |
| 15148 | AA859325 | 702 | 111 | 483 | 132 | 91 |
| 7756 | AA892864 | 88 | 15 | 41 | 35 | 91 |

TABLE 3Z-continued

VALPROATE  Document Number 1740956.1

Timepoints (hrs): 24, 96

| GLGC ID | GenBank Acc | Group Mean | Group SD | NonGroup Mean | NonGroup SD | Discriminant Score |
|---|---|---|---|---|---|---|
| 23886 | AA963008 | 118 | 9 | 181 | 62 | 91 |
| 9644 | AI071410 | 28 | 12 | −13 | 27 | 91 |
| 10073 | AI058515 | 39 | 5 | 56 | 51 | 91 |
| 15926 | AB012933 | 363 | 18 | 471 | 187 | 90 |
| 16780 | X62660 | 339 | 20 | 269 | 103 | 90 |
| 725 | U62316 | 96 | 17 | 53 | 25 | 90 |
| 14332 | AJ001044 | 48 | 2 | 35 | 24 | 90 |
| 17107 | AI178582 | 1275 | 313 | 2504 | 831 | 90 |
| 21285 | AA849898 | −76 | 42 | 85 | 144 | 90 |
| 7381 | AI029132 | 76 | 12 | 127 | 41 | 90 |
| 18168 | AA942995 | 0 | 6 | 31 | 33 | 90 |
| 15980 | AA866426 | 104 | 6 | 73 | 28 | 90 |
| 15849 | AI008074 | 228 | 26 | 157 | 69 | 90 |
| 9192 | AI137345 | 836 | 128 | 1645 | 656 | 90 |
| 15041 | AB016532 | 32 | 12 | 10 | 28 | 90 |
| 4312 | AB010635 | 98 | 21 | 59 | 84 | 90 |
| 5712 | AI045154 | 39 | 8 | 95 | 48 | 90 |
| 15638 | AA875633 | 89 | 10 | 51 | 29 | 90 |
| 20795 | AA944397 | 194 | 34 | 123 | 86 | 90 |
| 11998 | AA892828 | 61 | 7 | 39 | 26 | 90 |
| 20980 | AA799633 | 102 | 17 | 67 | 22 | 90 |
| 14504 | AA799804 | 177 | 18 | 131 | 107 | 90 |
| 18002 | AI043655 | 1397 | 127 | 2219 | 868 | 90 |
| 7186 | AI072833 | 498 | 36 | 377 | 122 | 90 |
| 16721 | D30647 | 293 | 28 | 235 | 50 | 89 |
| 5094 | AA925165 | 50 | 8 | 94 | 45 | 89 |
| 9754 | AI112194 | 380 | 48 | 220 | 130 | 89 |
| 11162 | AI008183 | 28 | 5 | 59 | 36 | 89 |
| 25725 | X62660 | 183 | 16 | 138 | 57 | 89 |
| 20846 | AI231140 | 1579 | 283 | 2762 | 796 | 89 |
| 22308 | AA899535 | 482 | 85 | 778 | 273 | 89 |
| 2337 | AA964307 | 83 | 8 | 122 | 41 | 89 |
| 22491 | AA899289 | 167 | 16 | 243 | 94 | 89 |
| 17809 | AA686461 | 63 | 7 | 43 | 24 | 89 |
| 6912 | D85035 | 231 | 14 | 180 | 45 | 89 |
| 14506 | H32584 | 298 | 12 | 253 | 71 | 89 |
| 16945 | AA925541 | 460 | 93 | 669 | 153 | 89 |
| 4360 | H31813 | 130 | 25 | 233 | 101 | 89 |
| 7784 | J04591 | 168 | 18 | 124 | 35 | 89 |
| 22077 | AI177099 | 96 | 19 | 58 | 26 | 89 |
| 8977 | AA799741 | 62 | 5 | 41 | 17 | 89 |
| 22992 | AA996880 | 147 | 19 | 233 | 73 | 89 |
| 4271 | AA925603 | 249 | 78 | 59 | 146 | 89 |
| 1728 | D16479 | 249 | 17 | 220 | 80 | 89 |
| 21785 | AI177312 | 146 | 20 | 218 | 56 | 89 |
| 21531 | M91595 | 35 | 9 | 26 | 41 | 89 |
| 21803 | AI008284 | 204 | 51 | 374 | 129 | 89 |
| 6975 | AI176229 | 391 | 39 | 329 | 162 | 89 |
| 12233 | AI013474 | 243 | 32 | 393 | 135 | 89 |
| 811 | D63704 | 453 | 12 | 532 | 163 | 89 |
| 1391 | X66366 | 141 | 7 | 104 | 29 | 89 |
| 2103 | AA851135 | 1356 | 415 | 2464 | 709 | 89 |
| 7783 | AA892069 | 94 | 10 | 60 | 30 | 89 |

TABLE 3AA

VALPROATE  Document Number 1740956.1

Timepoints (hrs): 6

| GLGC ID | GenBank Acc | Group Mean | Group SD | NonGroup Mean | NonGroup SD | Discriminant Score |
|---|---|---|---|---|---|---|
| 14619 | AI236989 | 24 | 3 | −1 | 15 | 98 |
| 11528 | AI170766 | 43 | 3 | 19 | 19 | 98 |
| 16025 | AI232374 | 215 | 102 | 60 | 25 | 98 |
| 2153 | U75404 | 110 | 51 | 37 | 19 | 98 |
| 3091 | AI236027 | 212 | 31 | 102 | 46 | 98 |
| 16026 | AA874802 | 250 | 78 | 74 | 25 | 99 |
| 7806 | AA818421 | 100 | 13 | 49 | 26 | 98 |
| 12248 | AA942829 | 178 | 16 | 23 | 51 | 99 |
| 14275 | AI177748 | 347 | 70 | 109 | 29 | 100 |
| 9598 | H33832 | 392 | 52 | 156 | 121 | 98 |
| 2107 | AA892006 | 243 | 65 | 102 | 39 | 98 |
| 19463 | AI103915 | 908 | 119 | 424 | 89 | 99 |
| 11542 | AI170664 | 484 | 60 | 238 | 57 | 99 |
| 7161 | AI233407 | 104 | 11 | 47 | 27 | 98 |
| 14697 | AI234834 | 77 | 25 | 1 | 24 | 98 |
| 3467 | AI237835 | 325 | 79 | 128 | 53 | 98 |
| 16024 | AI232374 | 254 | 85 | 101 | 25 | 98 |
| 11235 | AI179709 | 295 | 76 | 145 | 45 | 98 |
| 5186 | AA925674 | 179 | 33 | 79 | 26 | 98 |
| 13171 | AI144722 | 307 | 68 | 123 | 57 | 98 |
| 2519 | AI010770 | 135 | 23 | 50 | 21 | 99 |
| 12164 | AA851029 | 371 | 100 | 85 | 38 | 99 |
| 8850 | AI235059 | 154 | 14 | 68 | 35 | 98 |
| 11256 | AA945898 | 191 | 72 | 28 | 27 | 99 |
| 5921 | AI178556 | 251 | 50 | 70 | 33 | 99 |
| 9410 | AI072842 | 86 | 10 | 35 | 20 | 98 |
| 5944 | AI227892 | 169 | 30 | 68 | 31 | 98 |
| 23331 | AI233457 | 307 | 36 | 198 | 39 | 98 |
| 22689 | AA945962 | 137 | 46 | 36 | 25 | 98 |
| 22396 | AA859806 | 185 | 10 | 104 | 29 | 99 |
| 9322 | AI177333 | 35 | 10 | −3 | 12 | 98 |
| 23862 | AA891933 | 107 | 25 | 14 | 28 | 98 |
| 22081 | AA944818 | 225 | 50 | 86 | 35 | 98 |
| 22311 | AI176007 | 555 | 206 | 175 | 71 | 99 |
| 6408 | AA858902 | 84 | 15 | 7 | 11 | 99 |
| 11331 | AI145556 | 274 | 45 | 109 | 37 | 99 |
| 22866 | AI233754 | 482 | 18 | 322 | 93 | 98 |
| 22966 | AI230320 | 65 | 12 | 13 | 17 | 98 |
| 14033 | AI012979 | 566 | 55 | 311 | 96 | 98 |
| 7937 | AI235414 | 691 | 123 | 233 | 172 | 98 |
| 6895 | AI170067 | 222 | 52 | 97 | 31 | 98 |
| 22130 | AA943020 | 174 | 43 | 31 | 25 | 99 |
| 26147 | AI013387 | 921 | 74 | 1611 | 372 | 98 |
| 22686 | AI233753 | 251 | 23 | 150 | 37 | 98 |
| 3705 | AA999054 | 152 | 33 | 51 | 25 | 98 |
| 11431 | AI236120 | 202 | 58 | 67 | 33 | 98 |
| 21229 | AI008371 | 76 | 51 | 2 | 17 | 98 |
| 2789 | AI234949 | 273 | 36 | 75 | 49 | 99 |
| 15476 | AA944426 | 334 | 26 | 135 | 63 | 99 |
| 5074 | AI101695 | 555 | 102 | 159 | 83 | 99 |
| 15090 | AA859224 | 157 | 21 | 67 | 24 | 98 |
| 13458 | AI175338 | 61 | 17 | 0 | 19 | 99 |
| 17903 | AI231083 | 369 | 30 | 235 | 53 | 98 |
| 16618 | AI168967 | 137 | 40 | 29 | 23 | 98 |
| 14616 | AA925559 | 132 | 27 | 36 | 31 | 98 |
| 14939 | AI228557 | 150 | 26 | 47 | 33 | 99 |
| 3606 | AI176077 | 37 | 4 | −29 | 44 | 98 |
| 3148 | AI007881 | 193 | 23 | 81 | 37 | 98 |
| 13911 | AI236262 | 87 | 17 | 29 | 17 | 98 |
| 5916 | AI172078 | 487 | 92 | 132 | 84 | 98 |
| 9524 | AI073249 | 255 | 62 | 51 | 51 | 98 |
| 14256 | AI176845 | 551 | 144 | 275 | 73 | 98 |
| 18002 | AI043655 | 866 | 103 | 2219 | 865 | 98 |
| 11660 | AI178944 | 205 | 23 | 92 | 31 | 98 |
| 19271 | AI231566 | 624 | 97 | 268 | 89 | 98 |
| 24256 | AI228256 | 586 | 38 | 368 | 86 | 98 |
| 12287 | AI102751 | 109 | 14 | 43 | 23 | 98 |
| 9325 | AI072617 | 424 | 92 | 162 | 59 | 98 |
| 3516 | AI175064 | 380 | 69 | 158 | 64 | 98 |

TABLE 3AA-continued

VALPROATE                                                   Document Number 1740956.1

Timepoints (hrs): 6

| GLGC ID | GenBank Acc | Group Mean | Group SD | NonGroup Mean | NonGroup SD | Discriminant Score |
|---|---|---|---|---|---|---|
| 19187 | AA851230 | 314 | 76 | 115 | 55 | 98 |
| 3655 | AA818183 | 239 | 52 | 103 | 44 | 98 |
| 23679 | AF087037 | 100 | 28 | 10 | 19 | 99 |
| 5937 | AI171684 | 376 | 34 | 200 | 50 | 99 |
| 13945 | U09793 | 93 | 12 | 27 | 18 | 99 |
| 21798 | AA926365 | 910 | 70 | 1706 | 375 | 98 |
| 1843 | M33962 | 95 | 9 | 40 | 19 | 98 |
| 23230 | AI236146 | 825 | 183 | 295 | 97 | 99 |
| 5193 | AA925693 | 906 | 68 | 1639 | 402 | 98 |
| 23099 | AI112365 | 244 | 53 | 95 | 38 | 98 |
| 14766 | AI235886 | 263 | 27 | 502 | 117 | 98 |
| 23469 | AI103282 | 66 | 26 | -2 | 20 | 98 |
| 15888 | AA875225 | 313 | 71 | 156 | 52 | 98 |
| 8808 | AI070132 | 84 | 20 | 385 | 123 | 99 |
| 9288 | AI072458 | 50 | 6 | 19 | 11 | 98 |
| 3718 | AI229643 | 67 | 6 | 33 | 14 | 98 |
| 10937 | AI230131 | 94 | 17 | -1 | 43 | 98 |
| 17334 | AA858704 | 479 | 63 | 171 | 80 | 98 |
| 21274 | AI236726 | 204 | 26 | 87 | 28 | 98 |
| 23347 | AA860015 | 66 | 17 | 14 | 14 | 98 |
| 20899 | X65948 | 155 | 11 | 78 | 28 | 98 |
| 13467 | AI138034 | 124 | 27 | 22 | 36 | 98 |
| 13167 | AI145832 | 65 | 2 | 111 | 35 | 98 |
| 6234 | AA818612 | 177 | 11 | 73 | 39 | 98 |
| 14677 | AI234620 | 111 | 43 | 21 | 17 | 98 |
| 11516 | AI103962 | 154 | 15 | 77 | 30 | 98 |
| 9889 | AI044621 | 511 | 107 | 1720 | 564 | 98 |
| 911 | U49729 | 52 | 11 | 0 | 14 | 98 |
| 1844 | M33962 | 269 | 51 | 114 | 44 | 98 |
| 1841 | AI113289 | 196 | 52 | 52 | 41 | 98 |

TABLE 3BB

WY-14643                                                    Document Number 1740956.1

Timepoints (hrs): 24, 168

| GLGC ID | GenBank Acc | Group Mean | Group SD | NonGroup Mean | NonGroup SD | Discriminant Score |
|---|---|---|---|---|---|---|
| 17736 | M86389 | 166 | 32 | 30 | 90 | 98 |
| 48 | D17310 | 238 | 33 | 538 | 213 | 97 |
| 5497 | AF080468 | 216 | 39 | 494 | 171 | 97 |
| 373 | D86086 | 204 | 18 | 391 | 139 | 97 |
| 5496 | AF080468 | 193 | 28 | 395 | 125 | 96 |
| 20705 | E01184 | 162 | 76 | 862 | 1122 | 96 |
| 18719 | X63410 | 319 | 73 | 1004 | 588 | 96 |
| 24722 | M30282 | 305 | 38 | 626 | 206 | 98 |
| 12094 | AA899681 | 1632 | 400 | 4683 | 1796 | 96 |
| 1857 | AB010428 | 560 | 89 | 18 | 146 | 100 |
| 6055 | M12337 | 400 | 35 | 795 | 300 | 97 |
| 4950 | AJ005046 | 63 | 18 | 3 | 12 | 99 |
| 22119 | AA859661 | 26 | 13 | -5 | 5 | 99 |
| 17805 | U06274 | 419 | 40 | 910 | 408 | 97 |
| 17127 | AI012213 | 106 | 47 | -103 | 70 | 99 |
| 20711 | AA924267 | 446 | 58 | 125 | 169 | 97 |
| 8784 | AI103007 | 349 | 60 | 175 | 59 | 97 |
| 17644 | AA924036 | 324 | 48 | 130 | 59 | 98 |
| 22603 | AF044574 | 411 | 33 | 230 | 78 | 98 |
| 21812 | AA997588 | 623 | 91 | 330 | 106 | 97 |
| 7031 | AI011291 | 365 | 78 | 174 | 60 | 97 |
| 3903 | AA899986 | 98 | 41 | -98 | 57 | 99 |
| 22139 | AI176548 | 1089 | 89 | 642 | 133 | 99 |

TABLE 3BB-continued

WY-14643                                                    Document Number 1740956.1

Timepoints (hrs): 24, 168

| GLGC ID | GenBank Acc | Group Mean | Group SD | NonGroup Mean | NonGroup SD | Discriminant Score |
|---|---|---|---|---|---|---|
| 17187 | AA800315 | 127 | 27 | 42 | 22 | 98 |
| 20851 | D88890 | 266 | 64 | 75 | 56 | 97 |
| 4196 | AA899304 | 952 | 220 | 73 | 73 | 100 |
| 3568 | AA899821 | 370 | 45 | 190 | 54 | 98 |
| 21995 | AI008955 | 336 | 49 | 172 | 56 | 98 |
| 11520 | AA997068 | 543 | 133 | 225 | 93 | 97 |
| 20859 | M92074 | 107 | 10 | 51 | 20 | 98 |
| 14021 | AA848834 | 899 | 165 | 301 | 177 | 98 |
| 268 | U67908 | -17 | 12 | 36 | 21 | 98 |
| 8182 | AA945608 | 446 | 47 | 1055 | 516 | 96 |
| 875 | U60416 | 64 | 16 | 7 | 19 | 97 |
| 3842 | AF061242 | 186 | 40 | 77 | 30 | 97 |
| 20853 | AF063302 | 58 | 25 | -10 | 19 | 97 |
| 20980 | AA799633 | 133 | 16 | 67 | 22 | 97 |
| 19302 | AI058968 | 281 | 43 | 34 | 34 | 99 |
| 17999 | U19485 | 455 | 36 | 1106 | 524 | 97 |
| 10636 | AI011634 | 555 | 122 | 217 | 82 | 98 |
| 2997 | AI030545 | 700 | 125 | 345 | 119 | 97 |
| 6512 | AI235898 | 280 | 50 | 136 | 49 | 97 |
| 9096 | AI169127 | 906 | 159 | 350 | 119 | 99 |
| 22847 | AA923982 | 1749 | 125 | 1098 | 233 | 98 |
| 15829 | AF034577 | 145 | 41 | 28 | 38 | 98 |
| 23305 | AA957451 | 200 | 38 | 79 | 44 | 97 |
| 2811 | AI171090 | 345 | 60 | 177 | 54 | 97 |
| 5027 | AA924793 | 374 | 63 | 209 | 57 | 96 |
| 17044 | AI010173 | 221 | 52 | 95 | 42 | 96 |
| 16411 | AI058647 | 127 | 32 | -2 | 42 | 98 |
| 6791 | AA945613 | 1843 | 230 | 3849 | 1156 | 97 |
| 12829 | AA858695 | 653 | 79 | 392 | 91 | 96 |
| 11488 | AI176477 | 835 | 128 | 513 | 112 | 97 |
| 6943 | AI010637 | 343 | 31 | 183 | 59 | 97 |
| 4174 | AI011613 | 229 | 30 | 111 | 41 | 97 |
| 23285 | AA955976 | 608 | 64 | 325 | 118 | 96 |
| 2267 | AI009450 | 223 | 28 | 127 | 37 | 97 |
| 10596 | AA956405 | 195 | 49 | 74 | 34 | 97 |
| 4199 | M83143 | 381 | 21 | 665 | 232 | 97 |
| 16721 | D30647 | 368 | 42 | 235 | 49 | 97 |
| 23968 | AI172260 | 752 | 89 | 465 | 101 | 97 |
| 16769 | X98225 | 262 | 53 | 123 | 45 | 96 |
| 25139 | AB005743 | 70 | 11 | 16 | 14 | 98 |
| 18317 | AA799326 | 92 | 24 | -17 | 36 | 97 |
| 23566 | AA955482 | 73 | 19 | 19 | 17 | 97 |
| 9180 | AI043694 | 148 | 24 | 69 | 30 | 96 |
| 17027 | AI170679 | 378 | 93 | 1232 | 445 | 98 |
| 3860 | AI232703 | 1027 | 172 | 400 | 146 | 98 |
| 3371 | AA998124 | 330 | 41 | 151 | 68 | 97 |
| 1197 | J05470 | 534 | 61 | 300 | 113 | 97 |
| 4428 | AI171362 | 433 | 75 | 232 | 71 | 96 |
| 25693 | X53949 | 73 | 12 | 25 | 15 | 97 |
| 5451 | AI044322 | 375 | 21 | 233 | 65 | 97 |
| 17662 | AI103774 | 618 | 73 | 399 | 78 | 97 |
| 5902 | AI045871 | 176 | 49 | 58 | 29 | 97 |
| 23320 | AA955164 | 461 | 41 | 214 | 80 | 98 |
| 5215 | AA925774 | 151 | 29 | 53 | 25 | 97 |
| 14621 | AA859529 | 227 | 16 | 138 | 36 | 97 |
| 19259 | AA900613 | 484 | 116 | -65 | 208 | 97 |
| 18726 | AF029240 | 155 | 21 | 307 | 76 | 97 |
| 17489 | AI012566 | 257 | 63 | 99 | 66 | 97 |
| 17349 | AI179987 | 1359 | 129 | 807 | 245 | 96 |
| 22602 | AF044574 | 298 | 45 | 126 | 68 | 96 |
| 11525 | AI172286 | 658 | 98 | 382 | 88 | 97 |
| 22051 | AA899498 | 318 | 72 | 131 | 58 | 97 |
| 3264 | AA997779 | 194 | 29 | 71 | 35 | 98 |
| 14881 | M20629 | 429 | 39 | 1306 | 850 | 97 |
| 21895 | AI008971 | 500 | 110 | 155 | 106 | 97 |
| 3167 | AI031012 | 553 | 84 | 228 | 92 | 97 |
| 22079 | AA945094 | 1807 | 234 | 4647 | 1469 | 97 |
| 17353 | AI008020 | 248 | 76 | 44 | 46 | 98 |
| 18319 | AA925752 | 187 | 47 | 46 | 36 | 97 |

TABLE 3BB-continued

WY-14643      Document Number 1740956.1

Timepoints (hrs): 24, 168

| GLGC ID | GenBank Acc | Group Mean | Group SD | NonGroup Mean | NonGroup SD | Discriminant Score |
|---|---|---|---|---|---|---|
| 17064 | X95986 | 48 | 25 | −8 | 15 | 98 |
| 20888 | AI145680 | 355 | 41 | 151 | 71 | 97 |
| 18316 | AF072411 | 265 | 39 | 79 | 51 | 98 |
| 15052 | M34043 | 440 | 30 | 1034 | 535 | 97 |
| 7665 | AI030668 | 363 | 53 | 163 | 71 | 97 |
| 21355 | AI105094 | 1202 | 308 | 299 | 299 | 97 |
| 3665 | AI009376 | 373 | 45 | 172 | 71 | 97 |

TABLE 3CC

ZILEUTON      Document Number 1740956.1

Timepoints (hrs): 24, 336

| GLGC ID | GenBank Acc | Group Mean | Group SD | NonGroup Mean | NonGroup SD | Discriminant Score |
|---|---|---|---|---|---|---|
| 20384 | D17349 | 1259 | 451 | 161 | 266 | 99 |
| 12158 | L00320 | 2623 | 1125 | 222 | 603 | 99 |
| 20705 | E01184 | 2761 | 603 | 846 | 1113 | 99 |
| 24860 | M13506 | 1534 | 436 | 315 | 230 | 99 |
| 12156 | K00996 | 4726 | 1494 | 439 | 926 | 99 |
| 25056 | M13234 | 4347 | 1048 | 748 | 808 | 99 |
| 12157 | K01721 | 5418 | 1701 | 485 | 1035 | 99 |
| 12155 | J00728 | 3997 | 1348 | 532 | 730 | 99 |
| 20864 | AF045464 | 1812 | 558 | 339 | 185 | 98 |
| 17541 | M26125 | 4122 | 645 | 1140 | 729 | 98 |
| 1794 | X64401 | 5922 | 880 | 1521 | 1378 | 98 |
| 488 | E00717 | 113 | 13 | 193 | 870 | 97 |
| 1793 | D13912 | 2578 | 462 | 869 | 638 | 97 |
| 25069 | S82820 | 917 | 428 | 165 | 140 | 97 |
| 11997 | AA892828 | 114 | 3 | 182 | 64 | 97 |
| 1797 | X62086 | 4276 | 726 | 1264 | 1034 | 97 |
| 1802 | AA817841 | 209 | 6 | 324 | 100 | 97 |
| 24323 | AI104798 | 625 | 84 | 403 | 86 | 96 |
| 18597 | AB013732 | 774 | 66 | 450 | 122 | 96 |
| 20704 | M26127 | 3006 | 696 | 1027 | 990 | 96 |
| 1995 | AF038870 | 1943 | 157 | 1394 | 1097 | 96 |
| 17104 | M29358 | 588 | 28 | 414 | 104 | 96 |
| 12447 | AA956769 | 154 | 32 | 53 | 33 | 96 |
| 21798 | AA926365 | 2543 | 181 | 1698 | 373 | 96 |
| 2084 | AA998151 | 810 | 101 | 478 | 136 | 96 |
| 10093 | AI058746 | 716 | 96 | 364 | 147 | 96 |
| 23766 | AA956456 | 199 | 16 | 96 | 51 | 96 |
| 11153 | M91652 | 302 | 18 | 486 | 146 | 96 |
| 10109 | X58465 | 1186 | 51 | 743 | 252 | 96 |
| 15193 | AI229508 | 275 | 66 | 142 | 53 | 96 |
| 4689 | AA899899 | 92 | 26 | 23 | 29 | 96 |
| 6941 | AI044892 | 165 | 46 | 35 | 52 | 95 |
| 15615 | AA944316 | 7738 | 707 | 4513 | 1439 | 95 |
| 17382 | AA858607 | 398 | 45 | 243 | 67 | 95 |
| 762 | AF007107 | 3386 | 989 | 1153 | 706 | 95 |
| 23699 | J02749 | 853 | 73 | 512 | 302 | 95 |
| 12060 | AA799890 | 53 | 6 | 98 | 23 | 95 |
| 12094 | AA899681 | 7548 | 429 | 4643 | 1801 | 95 |
| 25691 | X53504 | 1076 | 63 | 645 | 214 | 95 |
| 4441 | X62146 | 1001 | 54 | 628 | 198 | 95 |
| 15382 | AI172302 | 175 | 18 | 140 | 275 | 95 |
| 16125 | AF090134 | 52 | 106 | 36 | | 95 |
| 25679 | X15013 | 1192 | 98 | 637 | 246 | 95 |
| 21903 | AA945571 | 2861 | 698 | 1088 | 628 | 95 |
| 635 | X78848 | 2637 | 225 | 1136 | 676 | 95 |
| 25687 | X51706 | 1530 | 144 | 865 | 306 | 94 |

TABLE 3CC-continued

ZILEUTON      Document Number 1740956.1

Timepoints (hrs): 24, 336

| GLGC ID | GenBank Acc | Group Mean | Group SD | NonGroup Mean | NonGroup SD | Discriminant Score |
|---|---|---|---|---|---|---|
| 15987 | AA866435 | 69 | 9 | 31 | 39 | 94 |
| 21013 | J02810 | 5773 | 1056 | 1840 | 1452 | 94 |
| 15126 | D83796 | 1733 | 375 | 889 | 477 | 94 |
| 23698 | J02749 | 542 | 79 | 299 | 365 | 94 |
| 634 | K01932 | 2302 | 161 | 1114 | 605 | 94 |
| 18606 | X53504 | 887 | 71 | 544 | 171 | 94 |
| 15955 | AI232294 | 365 | 53 | 189 | 84 | 94 |
| 24771 | M77479 | 1101 | 88 | 835 | 393 | 94 |
| 17092 | AA893189 | 149 | 32 | 86 | 34 | 94 |
| 20803 | U09256 | 400 | 43 | 241 | 84 | 94 |
| 17729 | X52619 | 1102 | 57 | 678 | 228 | 94 |
| 12606 | M59861 | 1178 | 231 | 571 | 228 | 94 |
| 21746 | L02896 | 50 | 2 | 63 | 18 | 94 |
| 3924 | AA851017 | 73 | 288 | 118 | | 94 |
| 18991 | AA945082 | 56 | 14 | 22 | 20 | 94 |
| 12312 | AA893453 | 902 | 61 | 726 | 290 | 94 |
| 15052 | M34043 | 1412 | 96 | 1028 | 536 | 94 |
| 4091 | AI69417 | 426 | 39 | 292 | 82 | 94 |
| 17531 | AI229440 | 853 | 41 | 590 | 233 | 94 |
| 18588 | AA899635 | 331 | 32 | 208 | 101 | 94 |
| 21015 | X04229 | 5834 | 1057 | 2040 | 1441 | 93 |
| 9143 | AA998450 | 147 | 31 | 50 | 40 | 93 |
| 13118 | AI137292 | 128 | 49 | 0 | 63 | 93 |
| 1175 | X79081 | 1228 | 290 | 498 | 319 | 93 |
| 24521 | AA945636 | 5658 | 409 | 3577 | 1264 | 93 |
| 16367 | AA892888 | 2207 | 158 | 1051 | 686 | 93 |
| 16272 | X76456 | 2086 | 93 | 1304 | 730 | 93 |
| 26030 | M34331 | 937 | 65 | 549 | 236 | 93 |
| 1877 | X74593 | 802 | 49 | 539 | 174 | 93 |
| 20810 | X14181 | 1478 | 139 | 819 | 321 | 93 |
| 15124 | J02612 | 2056 | 528 | 996 | 562 | 93 |
| 16164 | S83025 | 607 | 23 | 520 | 139 | 93 |
| 2939 | AA996885 | 347 | 59 | 187 | 81 | 93 |
| 25170 | AF030087 | 31 | 3 | 62 | 26 | 93 |
| 21904 | M24239 | 6866 | 1206 | 2179 | 1957 | 93 |
| 16696 | AA799607 | 61 | 5 | 107 | 33 | 93 |
| 1876 | AI030175 | 910 | 63 | 582 | 188 | 93 |
| 25702 | X58465 | 571 | 46 | 390 | 109 | 93 |
| 4093 | AI232001 | 812 | 113 | 547 | 150 | 93 |
| 11798 | AI059337 | 128 | 7 | 98 | 36 | 93 |
| 14882 | D00362 | 2042 | 188 | 969 | 519 | 93 |
| 17281 | U10697 | 871 | 121 | 497 | 175 | 93 |
| 16701 | AI008838 | 3476 | 509 | 2210 | 699 | 93 |
| 2480 | AA893471 | 126 | 28 | 217 | 52 | 93 |
| 15135 | S71021 | 918 | 79 | 579 | 185 | 93 |
| 20464 | M20406 | 1857 | 191 | 1282 | 779 | 93 |
| 11152 | M91652 | 130 | 42 | 283 | 89 | 93 |
| 8212 | AI231807 | 3634 | 607 | 1402 | 908 | 93 |

TABLE 3DD

ZILEUTON      Document Number 1740956.1

Timepoints (hrs): 6

| GLGC ID | GenBank Acc | Group Mean | Group SD | NonGroup Mean | NonGroup SD | Discriminant Score |
|---|---|---|---|---|---|---|
| 488 | E00717 | 1109 | 140 | 190 | 867 | 100 |
| 489 | E00778 | 247 | 38 | 49 | 406 | 100 |
| 16619 | AA997544 | 157 | 10 | 38 | 72 | 100 |
| 20384 | D17349 | 1161 | 103 | 165 | 274 | 100 |
| 20705 | E01184 | 2561 | 241 | 852 | 1117 | 99 |

TABLE 3DD-continued

ZILEUTON  Document Number 1740956.1

Timepoints (hrs): 6

| GLGC ID | GenBank Acc | Group Mean | Group SD | NonGroup Mean | NonGroup SD | Discriminant Score |
|---|---|---|---|---|---|---|
| 12158 | L00320 | 2465 | 317 | 229 | 621 | 99 |
| 2666 | AA962942 | 8 | 2 | 61 | 29 | 99 |
| 20443 | U14192 | 131 | 0 | 130 | 36 | 99 |
| 20703 | K03241 | 1002 | 195 | 402 | 557 | 99 |
| 23417 | AB022209 | 117 | 8 | 202 | 47 | 99 |
| 25055 | M11251 | 2332 | 477 | 239 | 620 | 99 |
| 25056 | M13234 | 3559 | 444 | 760 | 839 | 99 |
| 12160 | AA818412 | 6636 | 1338 | 1170 | 1506 | 99 |
| 2096 | AI233801 | 1867 | 7 | 1663 | 377 | 99 |
| 14051 | AI232489 | 169 | 0 | 161 | 49 | 99 |
| 1797 | X62086 | 4428 | 238 | 1272 | 1044 | 99 |
| 12156 | K00996 | 5096 | 1174 | 450 | 950 | 99 |
| 16310 | L13600 | 25 | 8 | −91 | 68 | 99 |
| 12155 | J00728 | 3548 | 642 | 543 | 761 | 99 |
| 12157 | K01721 | 6086 | 1523 | 496 | 1059 | 99 |
| 1764 | X83399 | 50 | 0 | 73 | 28 | 99 |
| 5046 | AI237855 | 30 | 1 | 79 | 46 | 98 |
| 1794 | X64401 | 3199 | 114 | 1540 | 1412 | 98 |
| 7312 | AI177543 | 71 | 1 | 55 | 22 | 98 |
| 21904 | M24239 | 6286 | 173 | 2193 | 1974 | 98 |
| 3723 | AI012599 | 181 | 5 | 94 | 48 | 98 |
| 1818 | Y11283 | 2279 | 73 | 1516 | 1064 | 98 |
| 21011 | H32189 | 4404 | 237 | 1625 | 1211 | 98 |
| 3114 | AI176018 | 57 | 0 | 55 | 29 | 98 |
| 20704 | M26127 | 3288 | 475 | 1032 | 993 | 98 |
| 7225 | AI013657 | 167 | 5 | 314 | 98 | 98 |
| 22802 | AI179291 | 54 | 1 | 107 | 59 | 98 |
| 21065 | AA800179 | 6 | 0 | 24 | 27 | 98 |
| 5497 | AF080468 | 881 | 27 | 491 | 171 | 98 |
| 16538 | AA799449 | 30 | 1 | 51 | 23 | 98 |
| 20795 | AA944397 | 29 | 3 | 123 | 85 | 98 |
| 10152 | AI059110 | 63 | 14 | 13 | 21 | 98 |
| 25066 | S75280 | 115 | 2 | 150 | 48 | 98 |
| 341 | X89383 | 22 | 0 | 31 | 13 | 98 |
| 10245 | AI059701 | 203 | 4 | 134 | 52 | 97 |
| 10348 | AI069934 | 47 | 2 | 26 | 17 | 97 |
| 10161 | AI059168 | 76 | 5 | 39 | 26 | 97 |
| 1175 | X79081 | 1521 | 131 | 499 | 319 | 97 |
| 15906 | AI233425 | 1162 | 10 | 1421 | 456 | 97 |
| 16724 | AA850987 | 280 | 16 | 150 | 50 | 97 |
| 22042 | AA946476 | 146 | 3 | 131 | 369 | 97 |
| 19371 | AI100841 | 95 | 2 | 72 | 22 | 97 |
| 6472 | AI175880 | −125 | 9 | 31 | 110 | 97 |
| 23863 | AA955628 | 60 | 3 | 35 | 24 | 97 |
| 9143 | AA998450 | 118 | 4 | 50 | 41 | 97 |
| 20808 | AA851281 | 322 | 10 | 206 | 65 | 97 |
| 20926 | S81353 | 595 | 10 | 439 | 146 | 97 |
| 2123 | AI229746 | 85 | 7 | 204 | 84 | 97 |
| 17130 | M62992 | 49 | 2 | 94 | 31 | 97 |
| 8999 | AI070839 | 41 | 1 | 67 | 31 | 97 |
| 16034 | AI008701 | 344 | 18 | 190 | 74 | 97 |
| 17333 | AA891940 | 47 | 0 | 61 | 23 | 97 |
| 11876 | AI009321 | 97 | 6 | 57 | 38 | 97 |
| 23243 | AA851803 | 3631 | 253 | 1701 | 792 | 97 |
| 1262 | AB017044 | 36 | 1 | 62 | 32 | 97 |
| 22804 | AI011194 | 1011 | 29 | 718 | 153 | 97 |
| 10153 | AI059110 | 25 | 11 | −8 | 39 | 97 |
| 670 | X54096 | 1225 | 35 | 898 | 412 | 97 |
| 22235 | AA924152 | 371 | 2 | 336 | 94 | 97 |
| 9195 | AI072118 | 27 | 13 | −6 | 11 | 97 |
| 21588 | AA899160 | 175 | 6 | 122 | 34 | 97 |
| 347 | U01914 | 10 | 1 | 34 | 20 | 97 |
| 8597 | AA818593 | 74 | 3 | 109 | 39 | 97 |
| 16278 | D38381 | 853 | 37 | 493 | 230 | 97 |
| 11514 | AI171855 | 305 | 10 | 216 | 57 | 97 |
| 21903 | AA945571 | 2599 | 240 | 1094 | 637 | 97 |
| 18704 | AI171562 | 24 | 1 | 40 | 19 | 97 |
| 8310 | AI178868 | 334 | 20 | 224 | 47 | 97 |
| 6791 | AA945613 | 4663 | 55 | 3830 | 1167 | 97 |
| 18301 | U33500 | 362 | 166 | 139 | 71 | 97 |
| 25406 | M18330 | 50 | 1 | 73 | 17 | 96 |
| 25479 | S45663 | 1145 | 29 | 860 | 336 | 96 |
| 14267 | AI011738 | 867 | 10 | 1124 | 404 | 96 |
| 19775 | AA900590 | 229 | 5 | 174 | 45 | 96 |
| 12371 | AA924752 | 597 | 26 | 386 | 107 | 96 |
| 18588 | AA899635 | 367 | 26 | 208 | 101 | 96 |
| 15252 | AI178605 | 329 | 2 | 344 | 121 | 96 |
| 14651 | AI235919 | 30 | 28 | 25 | 15 | 96 |
| 19732 | AI236066 | 1409 | 25 | 1044 | 461 | 96 |
| 9053 | AA892861 | 31 | 5 | 85 | 33 | 96 |
| 20897 | AI175812 | 269 | 2 | 298 | 78 | 96 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07590493B2). An electronic copy of the "Sequence Listing" will also be available from the USPTO upon request and payment of the fee set forth in 37 CFR 1.19(b)(3).

We claim:

1. A method for determining whether a test compound is a hepatotoxin, comprising:
   (a) exposing liver tissue or liver cells to the test compound;
   (b) preparing a normalized gene expression profile of at least ten genes for said liver tissue or liver cells, wherein the gene expression profile contains the differential gene expression levels for said at least ten genes upon exposure to the test compound, and wherein said at least ten genes are listed in one of Tables 3-3DD;
   (c) comparing the gene expression profile to a hepatotoxicity model, the hepatotoxicity model comprising:
      (i) the normalized mean expression levels of said at least ten genes in liver tissue or liver cells exposed to a known hepatotoxin, (ii) the normalized mean expression levels of said at least ten genes in liver tissue or liver cells not exposed to a hepatotoxin, and (iii) information from one or more of Tables 3-3DD; and (d) scoring the comparison to determine whether the test compound is a hepatotoxin.

2. The method of claim 1, wherein the gene expression profile contains the differential gene expression levels for at least 20 genes listed in one of Tables 3-3DD, and wherein the hepatotoxicity model comprises the gene expression levels in said one of Tables 3-3DD.

3. The method of claim 1, wherein said gene expression profile is generated by hybridization of nucleic acids to a microarray, and is normalized for hybridization conditions, label intensity, and reading efficiency prior to comparison.

4. The method of claim 1, wherein the hepatotoxicity model comprises all the information in one of Tables 3-3DD.

5. The method of claim 1, wherein the liver tissue or liver cells are exposed to the test compound in vivo and the hepatotoxicity model is generated by exposure of liver tissue or liver cells to the known hepatotoxin in vivo.

6. The method of claim 1, wherein the known hepatotoxin is associated with at least one of hepatitis, liver necrosis, protein adduct formation and fatty liver.

7. The method of claim 1, wherein the known hepatotoxin is one or more of acetominophen, acyclovir, ANIT, AY-25329, bicalutamide, carbon tetrachloride, clofibrate, cyproterone acetate, diclofenac, diflunisal, dioxin, estradiol, hydrazine, indomethacin, LPS, phenobarbitol, tacrine, valproate, WY-14643, and zileuton.

8. The method of claim 1, wherein the gene expression profile contains the differential gene expression levels for at least 30 genes listed in one of Tables 3-3DD, and wherein the hepatotoxicity model comprises the gene expression levels in said one of Tables 3-3DD.

9. The method of claim 1, wherein the gene expression profile contains the differential gene expression levels for at least 50 genes listed in one of Tables 3-3DD, and wherein the hepatotoxicity model comprises the gene expression levels in said one of Tables 3-3DD.

10. The method of claim 1, wherein the comparison is scored by determining whether the test compound induces a change in expression of the at least 10 genes in the same direction as the known hepatotoxin.

\* \* \* \* \*